US008039588B2

(12) United States Patent
Pancer et al.

(10) Patent No.: US 8,039,588 B2
(45) Date of Patent: Oct. 18, 2011

(54) VARIABLE LYMPHOCYTE RECEPTORS

(75) Inventors: Zeev Pancer, Baltimore, MD (US); Max D. Cooper, Birmingham, AL (US); Chris Amemiya, Seattle, WA (US); G. Larry Gartland, Birmingham, AL (US); Goetz R. A. Ehrhardt, Birmingham, AL (US)

(73) Assignees: The UAB Research Foundation, Birmingham, AL (US); Benaroya Research Institute, Seattle, WA (US)

( * ) Notice: Subject to any disclaimer, the term of this patent is extended or adjusted under 35 U.S.C. 154(b) by 1162 days.

(21) Appl. No.: 11/568,601

(22) PCT Filed: May 23, 2005

(86) PCT No.: PCT/US2005/017901

§ 371 (c)(1), (2), (4) Date: Jun. 12, 2007

(87) PCT Pub. No.: WO2006/083275

PCT Pub. Date: Aug. 10, 2006

(65) Prior Publication Data

US 2011/0165584 A1 Jul. 7, 2011

Related U.S. Application Data

(60) Provisional application No. 60/573,563, filed on May 21, 2004.

(51) Int. Cl.
*C07K 14/00* (2006.01)

(52) U.S. Cl. ........................................ 530/350

(58) Field of Classification Search .................... None
See application file for complete search history.

(56) References Cited

U.S. PATENT DOCUMENTS

2003/0175733 A1 9/2003 Kirst et al.

OTHER PUBLICATIONS

Kajava, "Structural diversity of leucine-rich repeat proteins" *Journal of Molecular Biology* 277(3):519-27 (1998).

Kobe and Deisenhofer, "The leucine-rich repeat: A versatile binding motif" *Trends in Biochemical Sciences* 19(10):415-421 (1994).

Kobe and Kajava, "The leucine-rich repeat as a protein recognition motif" *Current Opinion in Structural Biology* 11(6):725-732 (2001).

Lopez et al., "The alpha and beta chains of human platelet glycoprotein IB are both transmembrane proteins containing a leucine-rich amino acid sequence" *PNAS* 85(7):2135-9 (1988).

Pignot et al., "Characterization of two novel proteins, NgRH1 and NgRH2, structurally and biochemically homologous to the Nogo-66 receptor" *Journal of Neurochemistry* 85(3):717-728 (2003).

Rogozin et al., "Evolution and diversification of lamprey antigen receptors: evidence for involvement of AID-APOBEC family cytosine deaminase" *Nature Immunology* 8(6):647-656 (2007).

Rogozin, Igor et al, "Evolution and Diversification of Lamprey Antigen Receptors: Evidence for Involvement of an Aid-Apobec Family Cytosine Deaminase." *Nature Immunology*, Jun. 2007, vol. 8, No. 6, Jun. 2007, pp. 647-656, XP002503283 ISSN: 1529-2908.

Pancer, Zeev et al. "Somatic Diversification of Variable Lymphocyte Receptors in the Agnathan Sea Lamprey" *Nature* (London), vol. 430, No. 6996, Jul. 8, 2004, pp. 174-180, XP002503284, ISSN: 0028-0836.

Kobe B and Deisenhofer J., The Leucine-Rich Repeat: A Versatile Binding Motif: *Trends in Biochemical Sciences*, Elsevier, Haywards, GB, vol. 19, No. 10, Oct. 1, 1994, pp. 415-421, XP001074045, ISSN: 0968-0004.

Communication from Related European Application No. 05 856 742.1 (European Examination Report) dated Feb. 11, 2010.

Anderson MK, et al. (2001) Evolution of hematopoiesis: Three members of the PU.1 transcription factor family in a cartilaginous fish, Raja eglanteria. Proc. Natl. Acad. Sci. USA 98:553-8.

Ardavin CF and Zapata A (1987) Ultrastructure and changes during metamorphosis of the lympho-hemopoietic tissue of the larval anadromous sea lamprey Petromyzon marinus. Dev. Comp. Immunol., 11:79-93.

Azumi K et al., Genomic analysis of immunity in a Urochordate and the emergence of the vertebrate immune system: "waiting for Godot", Immunogenetics 55: 570-81, 2001.

Bell, JK., et al. Leucine-rich repeats and pathogen recognition in Toll-like receptors. Trends in Immunology 2003, 24: 528-533.

Beutler, B. Innate immunity: an overview, Molecular Immunology 40 (2004) 845-859.

Binz, HK, et al., "High affinity binders selected from designed ankyrin repeat protein libraries" *Nature Biotechnology* 22(5):575-82 (2004).

Bryan, M.B., et al. Polymorphic microsatellite markers for the land-locked sea lamprey, Petromyzon marinus. Conservation Genetics 4: 113-116, 2003.

Bottaro, A., et al. S region transcription per se promotes basal IgE class switch recombination but additional factors regulate the efficiency of the process. (1994) EMBO J. 13, 665-674.

Chamaillard, M., et al. Nods, Nalps and Naip: intracellular regulators of bacterial-induced inflammation. Cellular Microbiology (2003) 5: 581-592.

Cooper AJ (1971) Ammocoete lymphoid cell populations in vitro. In: 4th Leukocyte Culture Conference. O.R. McIntyre (Ed). New York Appleton Century-Crofts. pp. 137-147.

Donelson JE. Antigenic variation and the African trypanosome genome. Acta Trop. 2003, 85: 391-404.

Finstad J and Good RA (1964) The evolution of the immune response. III. Immunologic responses in the lamprey. J. Exp. Med., 120: 1151-67.

Finstad J, et al. (1964) Evolution of the immune response. II. Morphologic studies of the thymus and organized lymphoid tissue. Lab Invest., 13:490-512.

Flajnik MF and Kasahara M (2001) Comparative genomics of the MHC: glimpses into the evolution of the adaptive immune system. Immunity 15:351-62.

Flajnik MF (2002) Comparative analyses of immunoglobulin genes: surprises and portents. Nat. Rev. Immunol., 2:688-98.

Forey PL and Janvier P (1993) Agnathans and the origin of jawed vertebrates. Nature 361:129-134.

(Continued)

*Primary Examiner* — Michael Pak

(74) *Attorney, Agent, or Firm* — McKeon, Meunier, Carlin & Curfman, LLC

(57) ABSTRACT

Disclosed are compositions and methods related to variable lymphocyte receptors (VLRs).

33 Claims, 14 Drawing Sheets

OTHER PUBLICATIONS

Fujii T (1982) Electron microscopy of the leukocytes of the typhlosole in ammocoetes, with special attention to the antibody-producing cells. J. Morphol., 173:87-100.
Fujii T and Hayakawa I (1983) A histological and electron-microscopic study of the cell types involved in rejection of the skin allografts in ammocoetes. Cell Tissue Res., 231:301-12.
Good, R. A., Finstad, J. & Litman, G. W. in The biology of lampreys II: Immunology (Eds Hardisty, M.V. & Potter, I.C.) 405-432 (Academic Press, London 1972).
Grimholt U, et al., MHC polymorphism and disease resistance in Atlantic salmon (Salmo salar); facing pathogens with single expressed major histocompatibility class I and class II loci. Immunogenetics. 55:210-9, 2003.
Hagen M, et al. (1985) The immune response in adult sea lamprey (*Petromyzon marinus* L.): the effect of temperature. Comp. Biochem. Physiol., 82:207-10.
Haire RN, et al. (2000) Members of the Ikaros gene family are present in early representative vertebrates. J. Immunol., 165:306-12.
Hamrick TS, et al. Antigenic variation of gonococcal pilin expression in vivo: analysis of the strain FA1090 pilin repertoire and identification of the pilS gene copies recombining with pilE during experimental human infection. Microbiology 2001, 147:839-49.
Hein, K., et al. Processing of switch transcripts is required for targeting of antibody class switch recombination. (1998) J. Exp. Med. 188, 2369-2374.
Ikezawa, H. Glycosylphosphatidylinositol (GPI)—Anchored Proteins. Biol. Pharm. Bull. 25: 409-417 (2002).
Jones, D.A. and Takemoto, D. Plant innate immunity—direct and indirect recognition of general and specific pathogen-associated molecules. Current Opinion in Immunology 2004, 16:48-62.
Kaufman J (2002) The origins of the adaptive immune system: whatever next? Nat. Immunol., 3:1124-5.
Kilarski W and Plytyez B (1981) The presence of plasma cells in the lamprey (Agnatha). Dev. Comp. Immunol., 5:361-6.
Kumar, S., et al. MEGA3: Integrated software for molecular evolutionary genetics analysis and sequence alignment. (2004) Brief. Bioinform. 5, 150-163.
Laird DJ, et al. (2000) 50 million years of chordate evolution: seeking the origins of adaptive immunity. Proc. Natl. Acad. Sci., USA 97:6924-6.
Landmann, R., et al. CD14, new aspects of ligand and signal diversity. Microbes and Infection, 2, 2000, 295-304.
Litman GW, et al. (1970) The evolution of the immune response. VIII. Structural studies of the lamprey immunoglobulin. J. Immunol., 105:1278-85.
Mallatt, J. & Chen, J. Y. Fossil sister group of craniates: predicted and found. (2003) J. Morphol. 258:1-31.
Marchalonis JJ and Edelman GM (1968) Phylogenetic origins of antibody structure. 3. Antibodies in the primary immune response of the sea lamprey, *Petromyzon marinus*. J. Exp. Med., 127:891-914.
Mayer WE, et al. (2002) Isolation and characterization of lymphocyte-like cells from a lamprey. Proc. Natl. Acad. Sci., USA 99: 14350-5.
Mayer WE, et al. (2002) Identification of two Ikaros-like transcription factors in lamprey, Scand. J. Immunol., 55:162-70.
Meyer, A. & Zardoya, R. Recent advances in the molecular phylogeny of vertebrates. (2003) Annu. Rev. Ecol. Evol. Syst. 34:311-338.
Newton, R. A., et al. Chemotactic responses of hagfish Vertebrata, Agnatha leucocytes. (1994) Dev. Comp. Immunol. 18:295-303.
Pancer, Z., et al. Prototypic T cell receptor and CD4-like coreceptor are expressed by lymphocytes in the agnathan sea lamprey. (2004) Proc. Natl. Acad. Sci. USA 101. 13272-13278.
Pancer et al., Somatic diversification of variable lymphocyte receptors in the agnathan sea lamprey. *Nature* 430(8):174-180 (2004).
Penn DJ, et al. MHC heterozygosity confers a selective advantage against multiple-strain infections Proc Natl Acad Sci 99: 11260-4 (2002).
Perey DY, et al. (1968) Evolution of the immune response. VI. First and second set skin homograft rejections in primitive fishes. Lab. Invest., 19:591-7.
Piavis GW and Hiatt JL. (1971) Blood cell lineage in the sea lamprey *Petromyzon marinus* (Pisces: Petromyzontidae). Copeia 4:722-8.
Pollara B, et al. (1970) The evolution of the immune response. VII. Antibody to human "O" cells and properties of the immunoglobulin in lamprey. J. Immunol., 105:738-45.
Raison, R. L., et al. A cell surface opsonic receptor on leucocytes from the phylogenetically primitive vertebrate, Eptatretus stouti. (1994) Immunol. Cell Biol. 72, 326-332.
Rast, J.P., et al. α, β, g, and δ T Cell Antigen Receptor Genes Arose Early in Vertebrate Phylogeny. Immunity, 6:1-11, 1997.
Schluter SF, et al. (1999) 'Big Bang' emergence of the combinatorial immune system. Dev. Comp. Immunol., 23:107-11.
Schwede, T., et al. Protein structure computing in the genomic era. Research in Microbiology 151: 107-112 (2000).
Shintani S, et al. (2000) Do lampreys have lymphocytes? The Spi evidence Proc. Natl. Acad. Sci., USA 97:7417-22.
Suzuki, T., et al. Construction of a bacterial artificial chromosome library from the inshore hagfish, Eptatretus burgeri: A resource for the analysis of the agnathan genome. (2004A) Genes Genet. Syst. 79, 251-253.
Suzuki, T., et al. Transcriptone analysis of hagfish leukocytes: a framework for understanding the immune system of jawless fishes. (2004B) Dev. Comp. Immunol. 28, 993-1003.
Uinuk-Ool T, et al. (2002) Lamprey lymphocyte-like cells express homologs of genes involved in immunologically relevant activities of mammalian lymphocytes. Proc. Natl. Acad. Sci., USA 99:14356-61.
Uinuk-Ool TS, et al. (2003) Identification and characterization of a TAP-family gene in the lamprey. Immunogenetics 55:38-48.
Wang D, et al. Characterization of the vls antigenic variation loci of the Lyme disease *spirochaetes Borrelia garinii* 1p90 and *Borrelia afzelii* ACAI. Mol. Microbiol. 2003, 47: 1407-17.
Zapata A, et al. (1981) Plasma cells in the ammocoete of *Petromyzon marinus*. Cell Tissue Res., 221:203-8.

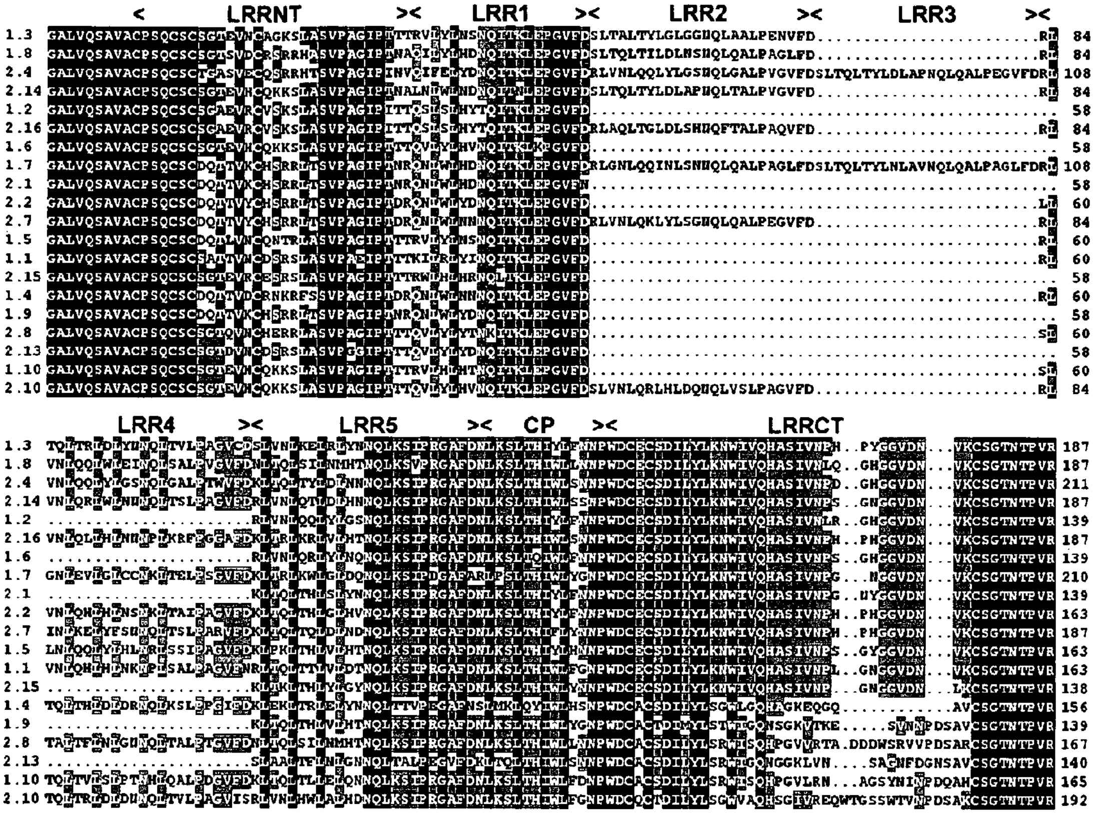

Figure 2

```
            <    LRRNT    ><    LRR1    ><    LRR2    ><    LRR3    ><
1.3   GALVQSAVACPSQCSCSGTEVHCAGKSLASVPAGIPTTTRVLYLNSNQITKLEPGVFDSLTALTYLGLGGHQLAALPENVFD........................RL  84
1.8   GALVQSAVACPSQCSCSGTSVDCRSRRHASVPAGIPLNASILYLHDNQITKLEPGVFDSLTQLTILDLNSHQLQALPAGLFD........................RL  84
2.4   GALVQSAVACPSQCSCTCASVECQSRRHTSVPAGIPLNVCIFELYDNQLTKLEPGVFDRLVNLQQLYLGSHQLGALPVGVFDSLTQLTYLDLAPNQLQALPEGVFDRL 108
2.14  GALVQSAVACPSQCSCSGTEVHCQKKSLASVPAGIPLNALNLWLNDNQLTNLEPGVFDSLTQLTYLDLAPHQLTALPVGVFD........................RL  84
1.2   GALVQSAVACPSQCSCSGAEVRCVSKSLASVPAGIPTTTCSLSLHYTQLTKLEPGVFD.................................................  58
2.16  GALVQSAVACPSQCSCSGAEVRCVSKSLASVPAGIPTTTCSLSLHYTQLTKLEPGVFDRLAQLTGLDLSHUQFTALPAQVFD........................RL  84
1.6   GALVQSAVACPSQCSCSGTEVHCQKKSLASVPAGIPTTCVLYLHVNQITKLEPGVFD.................................................  58
1.7   GALVQSAVACPSQCSCDQNTVKCHSRRLTSVPAGIPLNRCNLWLHDNQITKLEPGVFDRLGNLQQINLSNHQLQALPAGLFDSLTQLTYLNLAVNQLQALPAGLFDRL 108
2.1   GALVQSAVACPSQCSCDQNTVKCHSRRLTSVPAGIPLNRCNLWLHDNQITKLEPGVFD.................................................  58
2.2   GALVQSAVACPSQCSCDQNTVYCHSRRLTSVPAGIPTDRCNLWLYDNQITKLEPGVFD................................................LL  60
2.7   GALVQSAVACPSQCSCDQNTVVCHSRRLTSVPAGIPTDRCNLWLNNNQITKLEPGVFDRLVNLQKLYLSGHQLQALPEGVFD........................RL  84
1.5   GALVQSAVACPSQCSCDQLVLNCONTRLASVPAGIPTTTRVLYLMSNQITKLEPGVFD................................................RL  60
1.1   GALVQSAVACPSQCSCSATTVLCDSRSLASVPAGIPTTTKIVRLYINQITKLEPGVFD................................................RL  60
2.15  GALVQSAVACPSQCSCSGTEVRCESRSLASVPAGIPTTTRWLHLHRNQLTKLEPGVFD.................................................  58
1.4   GALVQSAVACPSQCSCDQNTVDCRNKRFSSVPAGIPTDRCNLWLNNNQITKLEPGVFD................................................RL  60
1.9   GALVQSAVACPSQCSCDQNTVVCHSRRLTSVPAGIPLNRCNLWLYDNQITKLEPGVFD.................................................  58
2.8   GALVQSAVACPSQCSCSGTQVNCHERRLASVPAGIPLNTCVLYTNKITKLEPGVFD..................................................SL  60
2.13  GALVQSAVACPSQCSCSGTDVNCDSRSLASVPGGIPLTCVLYLYDNQITKLEPGVFD..................................................  58
1.10  GALVQSAVACPSQCSCSGTEVHCQKKSLASVPAGIPTTTRVLHLMTNQLTKLEPGVFD................................................SL  60
2.10  GALVQSAVACPSQCSCSGTEVHCQKKSLASVPAGIPTTTCVLYLHVNQITKLEPGVFDSLVNLQRLHLDQHQLVSLPAGVFD........................RL  84

            LRR4    ><    LRR5    ><    CP    ><            LRRCT
1.3   TQLTRLDLYLNQLTVLJAGVCDSLVNLKELRLYNQLKSIPRGAFDNLKSLTHIVLFNPWDCECSDILYLKNWIVQHASIVNLH..PYGGVDN...VKCSGTNTPVR 187
1.8   VNLQQLWLELNQLSALJVGVFDNLLQLSILNMHTNQLKSVPRGAFDNLKSLTHIWLNNPWDCECSDILYLKNWIVQHASIVNLQ..GHGGVDN...VKCSGTNTPVR 187
2.4   VNLQQLYLGSNQLGALLTWLEDKLLQLTYLDLPNNNQLKSIPRGAFDNLKSLTHIWLSNPWDCECSDILYLKNWIVQHASIVNPD..GHGGVDN...VKCSGTNTPVR 211
2.14  VNLQRLWLNDLQLTSLJAGVERLVNLQTLDLHNNQLKSIPRGAFDNLKSLTHIWLSNPWDCECSDILYLKNWIVQHASIVNPS..GHGGVDN...VKCSGTNTPVR 187
1.2   ......................RLVNLQQLYLGSNQLGALTHIVLNPWDCECSDILYLKNWIVQHASIVNLR..GHGGVDN...VKCSGTNTPVR 139
2.16  VNLQLTHLNHLPLKRFLGLADKLLRLKRLVLHTNQLKSIPRGAFDNLKSLTHIWLSNPWDCECSDILYLKNWIVQHASIVNPH..PHGGVDN...VKCSGTNTPVR 187
1.6   ......................RLVNLQRLYLNQNQLKSIPRGAFDNLKSLTQLWLNNPWDCECSDILYLKNWIVQHASIVNPS..GHGGVDN...VKCSGTNTPVR 139
1.7   GNLEVLGLCCLKLTELLSLVEDKLTRLKWLGLDQNQLKSIPDGAFDLPSLTHIWLYGNPWDCECSDILYLKNWIVQHASIVNPC...NGGVDN...VKCSGTNTPVR 210
2.1   ......................KLLKLQQLTHLSLSLYNNQLKSIPRGAFDNLKSLTHIVLGNPWDCECSDILYLKNWIVQHASIVNPC...UYGGVDN...VKCSGTNTPVR 139
2.2   VNLQHLHLNSLKLTAILAGVEDKLLQLTHLGLHVNQLKSIPRGAFDNLKSLTHIWLFNPWDCECSDILYLKNWIVQHASIVNPH..PHGGVDN...VKCSGTNTPVR 163
2.7   INLKELTYFSHLQLTSLJARVEDKLLQLTQLDLNDNQLKSIPRGAFDNLKSLTHIWLSNPWDCECSDILYLKNWIVQHASIVNPH..PHGGVDN...VKCSGTNTPVR 187
1.5   LNLQQLTYLHLRLSSIELAGVEDKLPRLTHLDVLTNQLKSIPRGAFDNLKSLTHIYLHNPWDCECSDILYLKNWIVQHASIVNPS..GYGGVDN...VKCSGTNTPVR 163
1.1   VNLQHLHLNKLPISALJAGVERLVLQLTTRVLDTNQLKSIPRGAFDNLKSLTHIWLFGNPWDCECSDILYLKNWIVQHASIVNPH..GNGGVDN...VKCSGTNTPVR 163
2.15  ......................KLLKLHILYLYGYNNQLKSIPRGAFDNLKSLTHIWLFNPWDCECSDILYLKNWIVQHASIVNLF..GNGGVDN...LKCSGTNTPVR 138
1.4   TQLTHLDLDRLQLKSLLPLGLSDKLDEKLTRLELYNNQLTTVPEGASNSMKLDYLLHSNPWDCACSDILYLSGLLQHAGKEQGQ.........AVCSGTNTPVR 156
1.9   ......................KLLKLQHLTHLDVLTHTNQLKSIPRGAFDNLKSLTHIWLYGNPWDCACDILYLASLTWLFQNSGKLTKE.....SLNNPDSAVCSGTNTPVR 139
2.8   TALQTFLNLGLDQLTALLTGVEDNLLQLSILNMHTNQLKSIPRGAFDNLKSLTHIWLFNPWDCECSDILYLSRLHLSQHPGVLRTA.DDDWSRVVPDSARCSGTNTPVR 167
2.13  ......................SLPALYLFNLTGNNQLTALLFGVEDKLTQLHILSNPWDCACDILYLSRLTGQNGGKLVN...SACNFDGNSAVCSGTNTPVR 140
1.10  TQLTVLSLPLTLHLQALLDLGVEDKLLQLTLLEMQNNQLKSIPRGAFDNLKSLTHIWLFDNPWDCECSDILYLSRLTSQLLPGVLRN...AGSYNILPDQAHCSGTNTPVR 165
2.10  TQLTRLDLDDLLQLTVLJACVISRLVNLHWLADHDNQLKSIPRGAFDNLKSLTHIWLFGNPWDCQCDILYLSGLVAQHSGLVREQWTGSSWTVNPDSAKCSGTNTPVR 192
```

```
                                 Signal peptide                                       >   <                 LRRNT
1     M  W  I  K  W  I  A  T  L  V  A  F  G  A  L  V  Q  S  A  V  A  C  P  S  Q  C  S  C  D  Q
118  ATGTGGATCAAGTGGATCGCCACGCTGGTCGCCTTTGGCGCCCTGGTGCAAAGTGCGGTAGCATGTCCCTCGCAGTGTTCGTGCGATCAG
                                                 Exon 2
                                      LRRNT                                  >  <           LRR1
31    T  L  V  N  C  Q  N  I  R  L  A  S  V  P  A  G  I  P  T  D  K  Q  R  L  W  L  N  N  N  Q
208  ACACTTGTGAACTGCCAGAATATACGCCTCGCATCTGTGCCTGCGGGAATCCCCACCGACAAGCAGAGGCTGTGGTTGAACAACAATCAG

               LRR1                   >  <                       LRR2
61    I  T  K  L  E  P  G  V  F  D  H  L  V  N  L  Q  Q  L  Y  F  N  S  N  K  L  T  A  I  P  T
298  ATCACGAAGCTTGAGCCCGGGGTGTTTGACCATCTGGTGAATCTGCAGCAGCTCTATTTTAACAGCAACAAGCTAACAGCTATACCCACT

                 >  <                                LRR3                                 >  <
91    G  V  F  D  K  L  T  Q  L  T  Q  L  D  L  N  D  N  H  L  K  S  I  P  R  G  A  F  D  N  L
388  GGGGTGTTTGACAAACTCACCCAGCTCACTCAACTGGATTTGAATGACAACCATCTGAAGAGCATTCCCAGGGGCGCCTTTGACAACCTC

              Connecting peptide            >  <                                LRRCT
121   K  S  L  T  H  I  Y  L  Y  N  N  P  W  D  C  E  C  R  D  I  M  Y  L  R  N  W  V  A  D  H
478  AAGAGCCTAACTCACATCTATCTGTACAACAACCCATGGGATTGCGAGTGCAGGGACATTATGTACCTCAGGAACTGGGTCGCAGACCAC
                                                                                Exon 3
                                                            LRRCT
151   T  S  I  V  M  R  W  D  G  K  A  V  N  D  P  D  S  A  K  C  A  G  T  N  T  P  V  R  A  V
568  ACTTCTATTGTAATGCGCTGGGATGGGAAGGCCGTTAACGACCCCGACTCTGCCAAGTGCGCTGGTACCAATACCCCCGTCCGTGCGGTC
                                                                                            Exon 4
                LRRCT                     >  <                ********** Threonine/Proline rich Stalk ***
181   T  E  A  S  T  S  P  S  K  C  P  G  Y  V  A  T  T  T  T  P  T  T  T  T  P  E  F  I  P  E
658  ACCGAGGCCAGCACTAGCCCCTCGAAATGCCCAGGCTACGTTGCTACGACCACGACGCCGACGACGACCACGCCCGAATTCATCCCTGAG

     ********************
211   T  T  T  S  P  Q  P  V  I  T  T  Q  K  P  K  P  L  W  N  F  N  C  T  S  I  Q  E  R  K  N
748  ACCACCACCTCGCCGCAGCCCGTGATCACAACCCAGAAACCCAAGCCTCTGTGGAATTTCAACTGCACCTCAATTCAGGAGAGGAAGAAC

   GPI cleavage                            ******************** Hydrophobic tail ********************
241   D  G  G  D  C  G  K  P  A  C  T  T  L  L  N  C  A  N  F  L  S  C  L  C  S  T  C  A  L  C
838  GACGGTGGCGACTGCGGAAAGCCCGCCTGCACAACTCTCCTGAACTGCGCGAATTTCCTCAGCTGCCTCTGCTCGACCTGCGCCCTCTGC

      *******
271   R  K  R  *
928  AGGAAACGTTGA
```

Figure 7

|                | Signal peptide           >      <                              LRRNT                        ><           LRR1        ><           LRR2         >  |
|---|---|
| Eb_VLR-B | MKPALRGTCVLLALLLCCRHGKACPSRCSCSG........TKVECYSEGCTSVITGIPAQTTYCDLCCCKLQSCPHGVCDKCTSCTYCDCGGCKFQSIPHGVFD |
| Es_VLR-B | MKFALRGTCVLLALLLCCRHGKACPSRCSCSG........TEVYCGSRSCTHVCSGIPSSATRCGLESCKFQSCPHGVCDBCTQLTKCCNCHHCQLQSLPSGVFD |
| Pm_VLR | MCIKNIATLVAEGALVQSAVACPSQCSCSG........TTVNCDSRSCASVCGGCIPTTCQCVLYLYDCQTTKCEPGVCDSLTACTFLCCAVCQLTCLPVGVFD |
| La_VLR | MCIKNIATLVAEGALVQSAVACPAQCSCSG........TSVNCQGRSCTSVCAGCIPTTQCNLMVCQTTKCEPGVCDSLTACTFLCCGHCQLTCLSTGVFD |
| If_VLR | MCIKNIATLVAEGALVQSAVACPSQCSCGKESWAAG..LQATCCAGKCLSSVCAGCIPDHTCACSVGSNCKESCPEGVCDRLCVHCQWCSCDSCQLKCLPAWVFD |
| Es_VLR-A | IMCGPVLAACCLIILSTAWISQCNGATCKKDGGVCTCHDNTKCVDCSSKGCTVICSNCIPCTDTDHCCKLDYCKLSSCPSKACHHCSKCCTCLSSTCQLQTLPPGVFD |
| Eb_VLR-A | IMCGPVLAACCLIILSTAWISQCHEALCKKDGGVCSCHHHKMCVDCSSKRCTAICCNCIPCTDTERCCKLDYCKLSSCPSKACHECSCKCTCLCTGCKLQTLPPGVFD |

|                | <        LRR3        ><          LRR4         ><       CP      ><              LRRCT                |
|---|---|
| Eb_VLR-B | KCTSCTKLYCCCCKFQSCCHGVCDKCTKCTILGCCDKCCQLKSVPDGICDRCCTSLQKIWCYSCPWDCTCPGCRCYCSQCIHKHCGIIKD.....CSCHPDSAKCSGC |
| Es_VLR-B | QCSKCTGLCCCTCQLQSCCHGVCDKCTKCTALGCCTNCQLKSVPDGIEDRCCTSLQKIYCCSCPWDCTCPGCRCYCSECIHKMCGVVVNAY....GTATPDSAKCSGC |
| Pm_VLR | SCCCCTICLAPERCCQLPALCAGVCHKCTCCTQLGCCHDNQLKSIPRGAFDCCCKSLCQIYCCCNPWDCACCSDCCLCYCSRCCISCHPGVPRTADDHW.TRCVPDSARCSGT |
| La_VLR | SCAHCCQRICCCHCCQLTSCCTGVCDKCTQCTHLVCCHDNQLKSIPRGAFDCCCKSLCYIYCCNPWDCACCSDCCLCYCSRCCISCHPGVPRTADDHW.TRCVPDSARCSGT |
| If_VLR | KCCQCTGLCDCHRCCQLQACCTGMCDRCGHCCQRFDCSRNQLKSVTCAEDCCCKSLTHIWCYCNPWDCCCTDCCLCYCSCCVADHCCIVRGHWDGSSYACNPDSAKCSGT |
| Es_VLR-A | HCVACCTUYCHNCQLQRCCEGVCDHCAKCCTRLECCNICQLRSVPHGACDNCSHIKTLMCNCNPWDCSCCNDCLCCCDAKCCLATHLE............RHAGRNCDQS |
| Eb_VLR-A | HCVACCTCHCHKCQLQSCCEPRVCDSCTTKCTYLSCRNCQLRSVPHRACDSCCSHLNLLYCCRSCNPCDCSCCKDCLCCRDCIDDNKDKVTG.........AQDAACGDQQ |

|                | LRRCT    >< Threonine/Proline-rich Stalk                                            Hydrophobic Tail             |      |
|---|---|---|
| Eb_VLR-B | GKPCR........SIICP..TTCCCTTTTTTCHPTTTTLPTT......TKMSHVKVPLVPPEAFGRVHCACACTPSYIFLHLVHGLAAVPLVYLICHASQLL | 280 |
| Es_VLR-B | GKPCR........SIICPTTTTCTCCCCCCHPTTTTLPTT......TKMSHVKVPLVPPETFGRVHCACACVEPSYIFLHLVHGLAAVPLVYLVCHASQLL | 283 |
| Pm_VLR | CTPCRAVTEASTSPSKCPGYVACTTTPTTTTPEFIPETTTSPQPVITTQKEXPCLMHFHCCECIQERKCDGGDCGKPACCTLLNCANFLSCLCSTCALCRKR | 294 |
| La_VLR | CTPCRAVTEASTSPSKCPGYVACTTTPTTTTPEIIEETTTLPQPVITTQKPRSCLMHFNCSCIQERKCDGGDCGKPACCTLLNCANFLSCLCSTCALCKKR | 298 |
| If_VLR | CTPCRAVTEASTSPSKCPGYVACTTTPTTTTPEFIPETTTSPQPVITTQKEXHCLMHFHCCECLLERKCDGGDCGKPACCTLLNCANFLSCLCSTCALCRKR | 306 |
| Es_VLR-A | SKPCLDVTE.EEAAEDCVPHTCCCAIPTTIITTLASSHDDDIPELPVPQENFQKFLGYQEPDHLPTQPQCLMCSISGYLGICMSCVLTSAAILYVIHELKKA | 296 |
| Eb_VLR-A | SKPCLEITE.KDAASDCVSPHTCCAIPIGTCCT.PASVIYDDIHEIKVPQENFQKFLGYQEPDHLPTQPQCLMCSISGYLGICMSCMLTSAALLYVEHEDKKA | 299 |

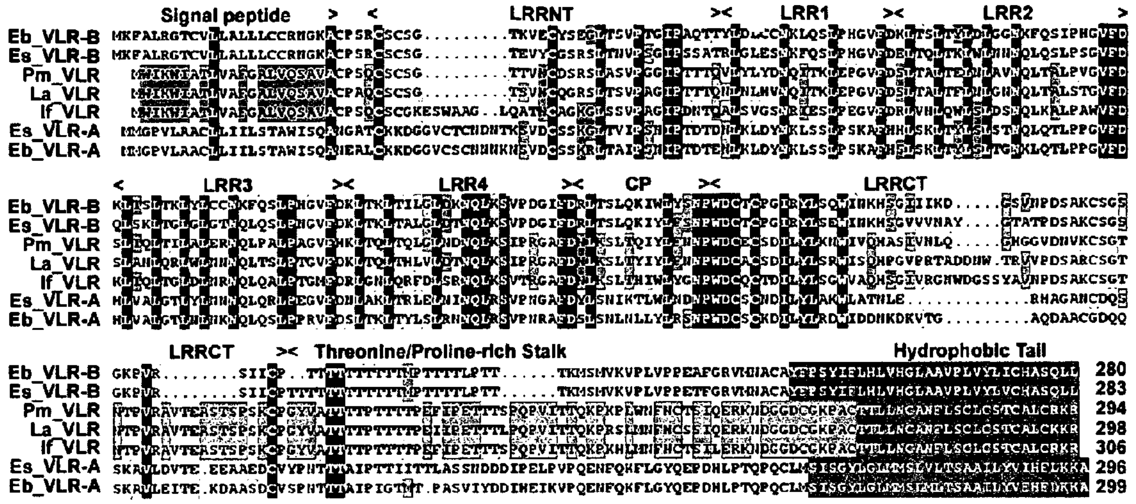

Figure 9

SEQUENCE LISTING

```
<160> NUMBER OF SEQ ID NOS: 333

<210> SEQ ID NO 1
<211> LENGTH: 187
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

Gly Ala Leu Val Gln Ser Ala Val Ala Cys Pro Ser Gln Cys Ser Cys
1               5                   10                  15

Ser Gly Thr Glu Val Asn Cys Ala Gly Lys Ser Leu Ala Ser Val Pro
            20                  25                  30

Ala Gly Ile Pro Thr Thr Thr Arg Val Leu Tyr Leu Asn Ser Asn Gln
        35                  40                  45

Ile Thr Lys Leu Glu Pro Gly Val Phe Asp Ser Leu Thr Ala Leu Thr
    50                  55                  60

Tyr Leu Gly Leu Gly Gly Asn Gln Leu Ala Ala Leu Pro Glu Asn Val
65                  70                  75                  80

Phe Asp Arg Leu Thr Gln Leu Thr Arg Leu Asp Leu Tyr Asn Asn Gln
                85                  90                  95

Leu Thr Val Leu Pro Ala Gly Val Cys Asp Ser Leu Val Asn Leu Lys
            100                 105                 110

Glu Leu Arg Leu Tyr Asn Asn Gln Leu Lys Ser Ile Pro Arg Gly Ala
        115                 120                 125
```

-continued

```
Phe Asp Asn Leu Lys Ser Leu Thr His Ile Tyr Leu Phe Asn Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Pro His Pro Tyr Gly Gly Val Asp Asn
                165                 170                 175

Val Lys Cys Ser Gly Thr Asn Thr Pro Val Arg
            180                 185


<210> SEQ ID NO 2
<211> LENGTH: 187
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Gly Ala Leu Val Gln Ser Ala Val Ala Cys Pro Ser Gln Cys Ser Cys
 1               5                  10                  15

Ser Gly Thr Ser Val Asp Cys Arg Ser Arg Arg His Ala Ser Val Pro
            20                  25                  30

Ala Gly Ile Pro Thr Asn Ala Gln Ile Leu Tyr Leu His Asp Asn Gln
        35                  40                  45

Ile Thr Lys Leu Glu Pro Gly Val Phe Asp Ser Leu Thr Gln Leu Thr
    50                  55                  60

Ile Leu Asp Leu Asn Ser Asn Gln Leu Gln Ala Leu Pro Ala Gly Leu
65                  70                  75                  80

Phe Asp Arg Leu Val Asn Leu Gln Gln Leu Trp Leu Glu Ile Asn Gln
                85                  90                  95

Leu Ser Ala Leu Pro Val Gly Val Phe Asp Asn Leu Thr Gln Leu Ser
            100                 105                 110

Ile Leu Asn Met His Thr Asn Gln Leu Lys Ser Val Pro Arg Gly Ala
        115                 120                 125

Phe Asp Asn Leu Lys Ser Leu Thr His Ile Trp Leu Leu Asn Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Leu Gln Gly His Gly Gly Val Asp Asn
                165                 170                 175

Val Lys Cys Ser Gly Thr Asn Thr Pro Val Arg
            180                 185


<210> SEQ ID NO 3
<211> LENGTH: 211
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Gly Ala Leu Val Gln Ser Ala Val Ala Cys Pro Ser Gln Cys Ser Cys
 1               5                  10                  15

Thr Gly Ala Ser Val Glu Cys Gln Ser Arg Arg His Thr Ser Val Pro
            20                  25                  30

Ala Gly Ile Pro Ile Asn Val Gln Ile Phe Glu Leu Tyr Asp Asn Gln
        35                  40                  45

Ile Thr Lys Leu Glu Pro Gly Val Phe Asp Arg Leu Val Asn Leu Gln
```

-continued

```
    50                  55                  60

Gln Leu Tyr Leu Gly Ser Asn Gln Leu Gly Ala Leu Pro Val Gly Val
65                  70                  75                  80

Phe Asp Ser Leu Thr Gln Leu Thr Tyr Leu Asp Leu Ala Pro Asn Gln
                85                  90                  95

Leu Gln Ala Leu Pro Glu Gly Val Phe Asp Arg Leu Val Asn Leu Gln
            100                 105                 110

Gln Leu Tyr Leu Gly Ser Asn Gln Leu Gly Ala Leu Pro Thr Trp Val
        115                 120                 125

Phe Asp Lys Leu Thr Gln Leu Thr Tyr Leu Asp Leu Asn Asn Asn Gln
    130                 135                 140

Leu Lys Ser Ile Pro Arg Gly Ala Phe Asp Asn Leu Lys Ser Leu Thr
145                 150                 155                 160

His Ile Trp Leu Ser Asn Asn Pro Trp Asp Cys Glu Cys Ser Asp Ile
                165                 170                 175

Leu Tyr Leu Lys Asn Trp Ile Val Gln His Ala Ser Ile Val Asn Pro
            180                 185                 190

Asp Gly His Gly Gly Val Asp Asn Val Lys Cys Ser Gly Thr Asn Thr
        195                 200                 205

Pro Val Arg
    210


<210> SEQ ID NO 4
<211> LENGTH: 187
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Gly Ala Leu Val Gln Ser Ala Val Ala Cys Pro Ser Gln Cys Ser Cys
 1               5                  10                  15

Ser Gly Thr Glu Val His Cys Gln Lys Lys Ser Leu Ala Ser Val Pro
            20                  25                  30

Ala Gly Ile Pro Thr Asn Ala Leu Asn Leu Trp Leu Asn Asp Asn Gln
        35                  40                  45

Ile Thr Asn Leu Glu Pro Gly Val Phe Asp Ser Leu Thr Gln Leu Thr
    50                  55                  60

Tyr Leu Asp Leu Ala Pro Asn Gln Leu Thr Ala Leu Pro Val Gly Val
65                  70                  75                  80

Phe Asp Arg Leu Val Asn Leu Gln Arg Leu Trp Leu Asn Asn Asn Gln
                85                  90                  95

Leu Thr Ser Leu Pro Ala Gly Val Phe Asp Arg Leu Val Asn Leu Gln
            100                 105                 110

Thr Leu Asp Leu His Asn Asn Gln Leu Lys Ser Ile Pro Arg Gly Ala
        115                 120                 125

Phe Asp Asn Leu Lys Ser Leu Thr His Ile Trp Leu Ser Ser Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Pro Ser Gly Asn Gly Gly Val Asp Asn
                165                 170                 175

Val Lys Cys Ser Gly Thr Asn Thr Pro Val Arg
            180                 185
```

<210> SEQ ID NO 5
<211> LENGTH: 139
<212> TYPE: PRT
<213> ORGANISM: Artificial Sequence
<220> FEATURE:
<223> OTHER INFORMATION: Description of Artificial Sequence; note = synthetic construct

<400> SEQUENCE: 5

```
Gly Ala Leu Val Gln Ser Ala Val Ala Cys Pro Ser Gln Cys Ser Cys
 1               5                  10                  15

Ser Gly Ala Glu Val Arg Cys Val Ser Lys Ser Leu Ala Ser Val Pro
            20                  25                  30

Ala Gly Ile Pro Ile Thr Thr Gln Ser Leu Ser Leu His Tyr Thr Gln
        35                  40                  45

Ile Thr Lys Leu Glu Pro Gly Val Phe Asp Arg Leu Val Asn Leu Gln
    50                  55                  60

Gln Leu Tyr Leu Gly Ser Asn Gln Leu Lys Ser Ile Pro Arg Gly Ala
65                  70                  75                  80

Phe Asp Asn Leu Lys Ser Leu Thr His Ile Tyr Leu Phe Asn Asn Pro
                85                  90                  95

Trp Asp Cys Glu Cys Ser Asp Ile Leu Tyr Leu Lys Asn Trp Ile Val
            100                 105                 110

Gln His Ala Ser Ile Val Asn Leu Arg Gly His Gly Gly Val Asp Asn
        115                 120                 125

Val Lys Cys Ser Gly Thr Asn Thr Pro Val Arg
    130                 135
```

<210> SEQ ID NO 6
<211> LENGTH: 187
<212> TYPE: PRT
<213> ORGANISM: Artificial Sequence
<220> FEATURE:
<223> OTHER INFORMATION: Description of Artificial Sequence; note = synthetic construct

<400> SEQUENCE: 6

```
Gly Ala Leu Val Gln Ser Ala Val Ala Cys Pro Ser Gln Cys Ser Cys
 1               5                  10                  15

Ser Gly Ala Glu Val Arg Cys Val Ser Lys Ser Leu Ala Ser Val Pro
            20                  25                  30

Ala Gly Ile Pro Ile Thr Thr Gln Ser Leu Ser Leu His Tyr Thr Gln
        35                  40                  45

Ile Thr Lys Leu Glu Pro Gly Val Phe Asp Arg Leu Ala Gln Leu Thr
    50                  55                  60

Gly Leu Asp Leu Ser His Asn Gln Phe Thr Ala Leu Pro Ala Gln Val
65                  70                  75                  80

Phe Asp Arg Leu Val Asn Leu Gln Leu Leu His Leu Asn Asn Asn Pro
                85                  90                  95

Leu Lys Arg Phe Pro Gly Gly Ala Phe Asp Lys Leu Thr Arg Leu Lys
            100                 105                 110

Arg Leu Val Leu His Thr Asn Gln Leu Lys Ser Ile Pro Arg Gly Ala
        115                 120                 125

Phe Asp Asn Leu Lys Ser Leu Thr His Ile Trp Leu Ser Asn Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Pro His Pro His Gly Gly Val Asp Asn
                165                 170                 175
```

```
Val Lys Cys Ser Gly Thr Asn Thr Pro Val Arg
            180                 185


<210> SEQ ID NO 7
<211> LENGTH: 139
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Gly Ala Leu Val Gln Ser Ala Val Ala Cys Pro Ser Gln Cys Ser Cys
 1               5                  10                  15

Ser Gly Thr Glu Val His Cys Gln Lys Lys Ser Leu Ala Ser Val Pro
            20                  25                  30

Ala Gly Ile Pro Thr Thr Thr Gln Val Leu Tyr Leu His Val Asn Gln
        35                  40                  45

Ile Thr Lys Leu Lys Pro Gly Val Phe Asp Arg Leu Val Asn Leu Gln
    50                  55                  60

Arg Leu Tyr Leu Asn Gln Asn Gln Leu Lys Ser Ile Pro Arg Gly Ala
65                  70                  75                  80

Phe Asp Asn Leu Lys Ser Leu Thr Gln Ile Trp Leu Phe Asn Asn Pro
                85                  90                  95

Trp Asp Cys Glu Cys Ser Asp Ile Leu Tyr Leu Lys Asn Trp Ile Val
            100                 105                 110

Gln His Ala Ser Ile Val Asn Pro Ser Gly His Gly Gly Val Asp Asn
        115                 120                 125

Val Lys Cys Ser Gly Thr Asn Thr Pro Val Arg
    130                 135


<210> SEQ ID NO 8
<211> LENGTH: 210
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Gly Ala Leu Val Gln Ser Ala Val Ala Cys Pro Ser Gln Cys Ser Cys
 1               5                  10                  15

Asp Gln Thr Thr Val Lys Cys His Ser Arg Arg Leu Thr Ser Val Pro
            20                  25                  30

Ala Gly Ile Pro Thr Asn Arg Gln Asn Leu Trp Leu His Asp Asn Gln
        35                  40                  45

Ile Thr Lys Leu Glu Pro Gly Val Phe Asp Arg Leu Gly Asn Leu Gln
    50                  55                  60

Gln Ile Asn Leu Ser Asn Asn Gln Leu Gln Ala Leu Pro Ala Gly Leu
65                  70                  75                  80

Phe Asp Ser Leu Thr Gln Leu Thr Tyr Leu Asn Leu Ala Val Asn Gln
                85                  90                  95

Leu Gln Ala Leu Pro Ala Gly Leu Phe Asp Arg Leu Gly Asn Leu Glu
            100                 105                 110

Val Leu Gly Leu Cys Cys Asn Lys Leu Thr Glu Leu Pro Ser Gly Val
        115                 120                 125

Phe Asp Lys Leu Thr Arg Leu Lys Trp Leu Gly Leu Asp Gln Asn Gln
    130                 135                 140
```

```
Leu Lys Ser Ile Pro Asp Gly Ala Phe Ala Arg Leu Pro Ser Leu Thr
145                 150                 155                 160

His Ile Trp Leu Tyr Gly Asn Pro Trp Asp Cys Glu Cys Ser Asp Ile
                165                 170                 175

Leu Tyr Leu Lys Asn Trp Ile Val Gln His Ala Ser Ile Val Asn Pro
            180                 185                 190

Gly Asn Gly Gly Val Asp Asn Val Lys Cys Ser Gly Thr Asn Thr Pro
        195                 200                 205

Val Arg
    210


<210> SEQ ID NO 9
<211> LENGTH: 139
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Gly Ala Leu Val Gln Ser Ala Val Ala Cys Pro Ser Gln Cys Ser Cys
 1               5                  10                  15

Asp Gln Thr Thr Val Lys Cys His Ser Arg Arg Leu Thr Ser Val Pro
            20                  25                  30

Ala Gly Ile Pro Thr Asn Arg Gln Asn Leu Trp Leu His Asp Asn Gln
        35                  40                  45

Ile Thr Lys Leu Glu Pro Gly Val Phe Asn Lys Leu Thr Gln Leu Thr
    50                  55                  60

His Leu Ser Leu Tyr Asn Asn Gln Leu Lys Ser Ile Pro Arg Gly Ala
65                  70                  75                  80

Phe Asp Asn Leu Lys Ser Leu Thr His Ile Tyr Leu Phe Asn Asn Pro
                85                  90                  95

Trp Asp Cys Glu Cys Ser Asp Ile Leu Tyr Leu Lys Asn Trp Ile Val
            100                 105                 110

Gln His Ala Ser Ile Val Asn Pro Gly Asn Tyr Gly Gly Val Asp Asn
        115                 120                 125

Val Lys Cys Ser Gly Thr Asn Thr Pro Val Arg
    130                 135


<210> SEQ ID NO 10
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 10

Gly Ala Leu Val Gln Ser Ala Val Ala Cys Pro Ser Gln Cys Ser Cys
 1               5                  10                  15

Asp Gln Thr Thr Val Tyr Cys His Ser Arg Arg Leu Thr Ser Val Pro
            20                  25                  30

Ala Gly Ile Pro Thr Asp Arg Gln Asn Leu Trp Leu Tyr Asp Asn Gln
        35                  40                  45

Ile Thr Lys Leu Glu Pro Gly Val Phe Asp Leu Leu Val Asn Leu Gln
    50                  55                  60

His Leu His Leu Asn Ser Asn Lys Leu Thr Ala Ile Pro Ala Gly Val
65                  70                  75                  80

Phe Asp Lys Leu Thr Gln Leu Thr His Leu Gly Leu His Val Asn Gln
```

-continued

```
                85                  90                  95

Leu Lys Ser Ile Pro Arg Gly Ala Phe Asp Asn Leu Lys Ser Leu Thr
            100                 105                 110

His Ile Tyr Leu Phe Asn Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

His Pro His Gly Gly Val Asp Asn Val Lys Cys Ser Gly Thr Asn Thr
145                 150                 155                 160

Pro Val Arg


<210> SEQ ID NO 11
<211> LENGTH: 187
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 11

Gly Ala Leu Val Gln Ser Ala Val Ala Cys Pro Ser Gln Cys Ser Cys
 1               5                  10                  15

Asp Gln Thr Thr Val Tyr Cys His Ser Arg Arg Leu Thr Ser Val Pro
            20                  25                  30

Ala Gly Ile Pro Thr Asp Arg Gln Asn Leu Trp Leu Asn Asn Asn Gln
        35                  40                  45

Ile Thr Lys Leu Glu Pro Gly Val Phe Asp Arg Leu Val Asn Leu Gln
    50                  55                  60

Lys Leu Tyr Leu Ser Gly Asn Gln Leu Gln Ala Leu Pro Glu Gly Val
65                  70                  75                  80

Phe Asp Arg Leu Ile Asn Leu Lys Glu Leu Tyr Phe Ser Asn Asn Gln
                85                  90                  95

Leu Thr Ser Leu Pro Ala Arg Val Phe Asp Lys Leu Thr Gln Leu Thr
            100                 105                 110

Gln Leu Asp Leu Asn Asp Asn Gln Leu Lys Ser Ile Pro Arg Gly Ala
        115                 120                 125

Phe Asp Asn Leu Lys Ser Leu Thr His Ile Phe Leu Tyr Asn Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Pro His Pro His Gly Gly Val Asp Asn
                165                 170                 175

Val Lys Cys Ser Gly Thr Asn Thr Pro Val Arg
            180                 185


<210> SEQ ID NO 12
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 12

Gly Ala Leu Val Gln Ser Ala Val Ala Cys Pro Ser Gln Cys Ser Cys
 1               5                  10                  15

Asp Gln Thr Leu Val Asn Cys Gln Asn Thr Arg Leu Ala Ser Val Pro
            20                  25                  30
```

```
Ala Gly Ile Pro Thr Thr Thr Arg Val Leu Tyr Leu Asn Ser Asn Gln
        35                  40                  45

Ile Thr Lys Leu Glu Pro Gly Val Phe Asp Arg Leu Leu Asn Leu Gln
    50                  55                  60

Gln Leu Tyr Leu His Leu Asn Arg Leu Ser Ser Ile Pro Ala Gly Val
65                  70                  75                  80

Phe Asp Lys Leu Pro Lys Leu Thr His Leu Val Leu His Thr Asn Gln
                85                  90                  95

Leu Lys Ser Ile Pro Arg Gly Ala Phe Asp Asn Leu Lys Ser Leu Thr
            100                 105                 110

His Ile Tyr Leu His Asn Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

Ser Gly Tyr Gly Gly Val Asp Asn Val Lys Cys Ser Gly Thr Asn Thr
145                 150                 155                 160

Pro Val Arg


<210> SEQ ID NO 13
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 13

Gly Ala Leu Val Gln Ser Ala Val Ala Cys Pro Ser Gln Cys Ser Cys
 1               5                  10                  15

Ser Ala Thr Thr Val Asn Cys Asp Ser Arg Ser Leu Ala Ser Val Pro
            20                  25                  30

Ala Glu Ile Pro Thr Thr Thr Lys Ile Leu Arg Leu Tyr Ile Asn Gln
        35                  40                  45

Ile Thr Lys Leu Glu Pro Gly Val Phe Asp Arg Leu Val Asn Leu Gln
    50                  55                  60

His Leu His Leu Asn Lys Asn Pro Leu Ser Ala Leu Pro Ala Gly Val
65                  70                  75                  80

Phe Asn Arg Leu Thr Gln Leu Thr Thr Leu Val Leu Asp Thr Asn Gln
                85                  90                  95

Leu Lys Ser Ile Pro Arg Gly Ala Phe Asp Asn Leu Lys Ser Leu Thr
            100                 105                 110

His Ile Trp Leu Phe Gly Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

Leu Gly Asn Gly Gly Val Asp Asn Val Lys Cys Ser Gly Thr Asn Thr
145                 150                 155                 160

Pro Val Arg


<210> SEQ ID NO 14
<211> LENGTH: 138
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 14
```

```
Gly Ala Leu Val Gln Ser Ala Val Ala Cys Pro Ser Gln Cys Ser Cys
 1               5                  10                  15

Ser Gly Thr Glu Val Arg Cys Glu Ser Arg Ser Leu Ala Ser Val Pro
            20                  25                  30

Ala Gly Ile Pro Thr Thr Thr Arg Trp Leu His Leu His Arg Asn Gln
        35                  40                  45

Leu Thr Lys Leu Glu Pro Gly Val Phe Asp Lys Leu Thr Lys Leu Thr
    50                  55                  60

His Leu Tyr Leu Gly Tyr Asn Gln Leu Lys Ser Ile Pro Arg Gly Ala
65                  70                  75                  80

Phe Asp Asn Leu Lys Ser Leu Thr His Ile Trp Leu Tyr Asn Asn Pro
                85                  90                  95

Trp Asp Cys Glu Cys Ser Asp Ile Leu Tyr Leu Lys Asn Trp Ile Val
            100                 105                 110

Gln His Ala Ser Ile Val Asn Pro Gly Asn Gly Gly Val Asp Asn Leu
        115                 120                 125

Lys Cys Ser Gly Thr Asn Thr Pro Val Arg
    130                 135


<210> SEQ ID NO 15
<211> LENGTH: 156
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 15

Gly Ala Leu Val Gln Ser Ala Val Ala Cys Pro Ser Gln Cys Ser Cys
 1               5                  10                  15

Asp Gln Thr Thr Val Asp Cys Arg Asn Lys Arg Phe Ser Ser Val Pro
            20                  25                  30

Ala Gly Ile Pro Thr Asp Arg Gln Asn Leu Trp Leu Asn Asn Asn Gln
        35                  40                  45

Ile Thr Lys Leu Glu Pro Gly Val Phe Asp Arg Leu Thr Gln Leu Thr
    50                  55                  60

His Leu Asp Leu Asp Arg Asn Gln Leu Lys Ser Leu Pro Pro Gly Ile
65                  70                  75                  80

Phe Asp Lys Leu Glu Lys Leu Thr Arg Leu Glu Leu Tyr Asn Asn Gln
                85                  90                  95

Leu Thr Thr Val Pro Glu Gly Ala Phe Asn Ser Leu Met Lys Leu Gln
            100                 105                 110

Tyr Ile Trp Leu His Ser Asn Pro Trp Asp Cys Ala Cys Ser Asp Ile
        115                 120                 125

Leu Tyr Leu Ser Gly Trp Leu Gly Gln His Ala Gly Lys Glu Gln Gly
    130                 135                 140

Gln Ala Val Cys Ser Gly Thr Asn Thr Pro Val Arg
145                 150                 155


<210> SEQ ID NO 16
<211> LENGTH: 139
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 16

Gly Ala Leu Val Gln Ser Ala Val Ala Cys Pro Ser Gln Cys Ser Cys
```

-continued

```
 1               5                   10                  15

Asp Gln Thr Thr Val Lys Cys His Ser Arg Arg Leu Thr Ser Val Pro
            20                  25                  30

Ala Gly Ile Pro Thr Asn Arg Gln Asn Leu Trp Leu Tyr Asp Asn Gln
        35                  40                  45

Ile Thr Lys Leu Glu Pro Gly Val Phe Asp Lys Leu Thr Gln Leu Thr
    50                  55                  60

His Leu Val Leu His Thr Asn Gln Leu Lys Ser Ile Pro Arg Gly Ala
65                  70                  75                  80

Phe Asp Asn Leu Lys Ser Leu Thr His Ile Trp Leu Tyr Gly Asn Pro
                85                  90                  95

Trp Asp Cys Ala Cys Thr Asp Ile Met Tyr Leu Ser Thr Trp Ile Gly
            100                 105                 110

Gln Asn Ser Gly Lys Val Thr Lys Glu Ser Val Asn Asn Pro Asp Ser
        115                 120                 125

Ala Val Cys Ser Gly Thr Asn Thr Pro Val Arg
    130                 135
```

```
<210> SEQ ID NO 17
<211> LENGTH: 167
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 17

Gly Ala Leu Val Gln Ser Ala Val Ala Cys Pro Ser Gln Cys Ser Cys
 1               5                   10                  15

Ser Gly Thr Gln Val Asn Cys His Glu Arg Arg Leu Ala Ser Val Pro
            20                  25                  30

Ala Gly Ile Pro Thr Thr Thr Gln Val Leu Tyr Leu Tyr Thr Asn Lys
        35                  40                  45

Ile Thr Lys Leu Glu Pro Gly Val Phe Asp Ser Leu Thr Ala Leu Thr
    50                  55                  60

Phe Leu Asn Leu Gly Asn Asn Gln Leu Thr Ala Leu Pro Thr Gly Val
65                  70                  75                  80

Phe Asp Asn Leu Thr Gln Leu Ser Ile Leu Asn Met His Thr Asn Gln
                85                  90                  95

Leu Lys Ser Ile Pro Arg Gly Ala Phe Asp Asn Leu Lys Ser Leu Thr
            100                 105                 110

His Ile Trp Leu Leu Asn Asn Pro Trp Asp Cys Ala Cys Ser Asp Ile
        115                 120                 125

Leu Tyr Leu Ser Arg Trp Ile Ser Gln His Pro Gly Val Val Arg Thr
    130                 135                 140

Ala Asp Asp Asp Trp Ser Arg Val Val Pro Asp Ser Ala Arg Cys Ser
145                 150                 155                 160

Gly Thr Asn Thr Pro Val Arg
                165
```

```
<210> SEQ ID NO 18
<211> LENGTH: 140
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 18
```

```
Gly Ala Leu Val Gln Ser Ala Val Ala Cys Pro Ser Gln Cys Ser Cys
 1               5                  10                  15

Ser Gly Thr Asp Val Asn Cys Asp Ser Arg Ser Leu Ala Ser Val Pro
            20                  25                  30

Gly Gly Ile Pro Thr Thr Thr Gln Val Leu Tyr Leu Tyr Asp Asn Gln
        35                  40                  45

Ile Thr Lys Leu Glu Pro Gly Val Phe Asp Ser Leu Ala Ala Leu Thr
    50                  55                  60

Phe Leu Asn Leu Gly Asn Asn Gln Leu Thr Ala Leu Pro Glu Gly Val
65                  70                  75                  80

Phe Asp Lys Leu Thr Gln Leu Thr His Ile Trp Leu Ser Asn Asn Pro
                85                  90                  95

Trp Asp Cys Ala Cys Ser Asp Ile Leu Tyr Leu Ser Arg Trp Ile Gly
            100                 105                 110

Gln Asn Gly Gly Lys Leu Val Asn Ser Ala Gly Asn Phe Asp Gly Asn
        115                 120                 125

Ser Ala Val Cys Ser Gly Thr Asn Thr Pro Val Arg
    130                 135                 140
```

<210> SEQ ID NO 19
<211> LENGTH: 165
<212> TYPE: PRT
<213> ORGANISM: Artificial Sequence
<220> FEATURE:
<223> OTHER INFORMATION: Description of Artificial Sequence; note = synthetic construct

<400> SEQUENCE: 19

```
Gly Ala Leu Val Gln Ser Ala Val Ala Cys Pro Ser Gln Cys Ser Cys
 1               5                  10                  15

Ser Gly Thr Glu Val His Cys Gln Lys Lys Ser Leu Ala Ser Val Pro
            20                  25                  30

Ala Gly Ile Pro Thr Thr Thr Arg Val Leu His Leu His Thr Asn Gln
        35                  40                  45

Ile Thr Lys Leu Glu Pro Gly Val Phe Asp Ser Leu Thr Gln Leu Thr
    50                  55                  60

Val Leu Ser Leu Pro Thr Asn His Leu Gln Ala Leu Pro Asp Gly Val
65                  70                  75                  80

Phe Asp Lys Leu Thr Gln Leu Thr Leu Leu Glu Leu Gln Asn Asn Gln
                85                  90                  95

Leu Lys Ser Ile Pro Arg Gly Ala Phe Asp Asn Leu Lys Ser Leu Thr
            100                 105                 110

His Ile Trp Leu Phe Asp Asn Pro Trp Asp Cys Ala Cys Ser Asp Ile
        115                 120                 125

Leu Tyr Leu Ser Arg Trp Ile Ser Gln His Pro Gly Val Leu Arg Asn
    130                 135                 140

Ala Gly Ser Tyr Asn Ile Asn Pro Asp Gln Ala His Cys Ser Gly Thr
145                 150                 155                 160

Asn Thr Pro Val Arg
                165
```

<210> SEQ ID NO 20
<211> LENGTH: 192
<212> TYPE: PRT
<213> ORGANISM: Artificial Sequence
<220> FEATURE:
<223> OTHER INFORMATION: Description of Artificial Sequence; note = synthetic construct

<400> SEQUENCE: 20

Gly Ala Leu Val Gln Ser Ala Val Ala Cys Pro Ser Gln Cys Ser Cys
1 5 10 15

Ser Gly Thr Glu Val His Cys Gln Lys Lys Ser Leu Ala Ser Val Pro
20 25 30

Ala Gly Ile Pro Thr Thr Thr Gln Val Leu Tyr Leu His Val Asn Gln
35 40 45

Ile Thr Lys Leu Glu Pro Gly Val Phe Asp Ser Leu Val Asn Leu Gln
50 55 60

Arg Leu His Leu Asp Gln Asn Gln Leu Val Ser Leu Pro Ala Gly Val
65 70 75 80

Phe Asp Arg Leu Thr Gln Leu Thr Arg Leu Asp Leu Asp Asn Asn Gln
85 90 95

Leu Thr Val Leu Pro Ala Gly Val Ile Ser Arg Leu Val Asn Leu His
100 105 110

Trp Leu Ala Leu His Asp Asn Gln Leu Lys Ser Ile Pro Arg Gly Ala
115 120 125

Phe Asp Asn Leu Lys Ser Leu Thr His Ile Trp Leu Phe Gly Asn Pro
130 135 140

Trp Asp Cys Gln Cys Thr Asp Ile Leu Tyr Leu Ser Gly Trp Val Ala
145 150 155 160

Gln His Ser Gly Ile Val Arg Glu Gln Trp Thr Gly Ser Ser Trp Thr
165 170 175

Val Asn Pro Asp Ser Ala Lys Cys Ser Gly Thr Asn Thr Pro Val Arg
180 185 190

<210> SEQ ID NO 21
<211> LENGTH: 239
<212> TYPE: PRT
<213> ORGANISM: Artificial Sequence
<220> FEATURE:
<223> OTHER INFORMATION: Description of Artificial Sequence; note = synthetic construct

<400> SEQUENCE: 21

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Ser Gly Thr Thr
20 25 30

Val Asn Cys Asp Ser Arg Ser Leu Ala Ser Val Pro Gly Gly Ile Pro
35 40 45

Thr Thr Thr Gln Val Leu Tyr Leu Tyr Asp Asn Gln Ile Thr Lys Leu
50 55 60

Gly Pro Gly Val Phe Asp Arg Leu Val Asn Leu Gln His Leu His Leu
65 70 75 80

Tyr Asn Asn Gln Leu Thr Ser Ile Pro Arg Gly Ala Phe Asp Asn Leu
85 90 95

Lys Ser Leu Thr His Ile Trp Leu Tyr Asn Asn Pro Trp Asp Cys Ala
100 105 110

Cys Ser Asp Ile Leu Tyr Leu Ser Gly Trp Leu Gly Gln His Ala Gly
115 120 125

Lys Glu Gln Gly Gln Ala Val Cys Ser Gly Thr Asn Thr Pro Val Arg
130 135 140

Ala Val Thr Glu Ala Ser Thr Ser Pro Ser Lys Cys Pro Gly Tyr Val
145 150 155 160

```
Ala Thr Thr Thr Thr Pro Thr Thr Thr Thr Pro Glu Phe Ile Pro Glu
                165                 170                 175

Thr Thr Thr Ser Pro Gln Pro Val Ile Thr Thr Gln Lys Pro Lys Pro
            180                 185                 190

Leu Trp Asn Phe Asn Cys Thr Ser Ile Gln Glu Arg Lys Asn Asp Gly
        195                 200                 205

Gly Asp Cys Gly Lys Pro Ala Cys Thr Thr Leu Leu Asn Cys Ala Asn
    210                 215                 220

Phe Leu Ser Cys Leu Cys Ser Thr Cys Ala Leu Cys Arg Lys Arg
225                 230                 235
```

<210> SEQ ID NO 22
<211> LENGTH: 241
<212> TYPE: PRT
<213> ORGANISM: Artificial Sequence
<220> FEATURE:
<223> OTHER INFORMATION: Description of Artificial Sequence; note = synthetic construct

<400> SEQUENCE: 22

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Leu Cys Ser Gly Thr Asp
            20                  25                  30

Val His Cys His Ser Arg Ser Leu Ala Ser Val Pro Ala Gly Ile Pro
        35                  40                  45

Thr Asn Ser Lys Phe Leu Asn Leu Asn Tyr Asn Gln Ile Thr Lys Leu
    50                  55                  60

Glu Pro Gly Val Phe Asp Arg Leu Val Asn Leu Gln Arg Leu Tyr Leu
65                  70                  75                  80

Asn Gln Asn Gln Leu Lys Ser Ile Pro Arg Gly Ala Phe Asp Asn Leu
                85                  90                  95

Lys Ser Leu Thr His Ile Trp Leu Phe Gly Asn Pro Trp Asp Cys Glu
            100                 105                 110

Cys Ser Asp Ile Leu Tyr Leu Lys Asn Trp Ile Val Gln His Ala Ser
        115                 120                 125

Ile Val Asn Pro Ser Gly His Gly Gly Val Asp Asn Val Lys Cys Ser
    130                 135                 140

Gly Thr Asn Thr Pro Val Arg Ala Val Thr Glu Ala Ser Thr Ser Pro
145                 150                 155                 160

Ser Lys Cys Pro Gly Tyr Val Ala Thr Thr Thr Thr Pro Thr Thr Thr
                165                 170                 175

Thr Pro Glu Phe Ile Pro Glu Thr Thr Thr Ser Pro Gln Pro Val Ile
            180                 185                 190

Thr Thr Gln Lys Pro Lys Pro Leu Trp Asn Phe Asn Cys Thr Ser Ile
        195                 200                 205

Gln Glu Arg Lys Asn Asp Gly Gly Asp Cys Gly Lys Pro Ala Cys Thr
    210                 215                 220

Thr Leu Leu Asn Cys Ala Asn Phe Leu Ser Cys Leu Cys Ser Thr Cys
225                 230                 235                 240

Ala
```

<210> SEQ ID NO 23
<211> LENGTH: 254
<212> TYPE: PRT
<213> ORGANISM: Artificial Sequence
<220> FEATURE:
<223> OTHER INFORMATION: Description of Artificial Sequence; note = synthetic construct

<400> SEQUENCE: 23

Met Trp Ile Lys Trp Ile Ala Thr Leu Val Ala Phe Gly Ala Leu Val
1 5 10 15

Gln Ser Ala Val Ala Cys Pro Ser Gln Cys Leu Cys Ser Gly Thr Glu
20 25 30

Leu His Cys Ala Gly Lys Ser Leu Ala Ser Val Pro Ala Gly Ile Pro
35 40 45

Thr Thr Thr His Tyr Leu Asn Leu Asn Ser Asn Gln Ile Thr Lys Leu
50 55 60

Glu Pro Gly Val Phe Asp Arg Leu Val Asn Leu Gln Arg Leu Trp Leu
65 70 75 80

Asn Asn Asn Gln Leu Thr Ser Leu Pro Ala Gly Val Phe Asp Lys Leu
85 90 95

Thr Gln Leu Thr His Ile Val Leu Ser Thr Asn Pro Trp Asp Cys Ala
100 105 110

Cys Ser Asp Ile Leu Tyr Leu Ser Arg Trp Ile Ser Gln His Pro Gly
115 120 125

Ile Val Arg Thr Ala Asp Asp Gly Trp Asn Arg Val Asp Pro Asp Ser
130 135 140

Ala Arg Cys Ser Ala Val Cys Ser Gly Thr Asn Thr Pro Val Arg Ala
145 150 155 160

Val Thr Glu Ala Ser Thr Ser Pro Ser Lys Cys Pro Gly Tyr Val Ala
165 170 175

Thr Thr Thr Thr Pro Thr Thr Thr Thr Pro Glu Phe Ile Pro Glu Thr
180 185 190

Thr Thr Ser Pro Gln Pro Val Ile Thr Thr Gln Lys Pro Lys Pro Leu
195 200 205

Trp Asn Phe Asn Cys Thr Ser Ile Gln Glu Arg Lys Asn Asp Gly Gly
210 215 220

Asp Cys Gly Lys Pro Ala Cys Thr Thr Leu Leu Asn Cys Ala Asn Phe
225 230 235 240

Leu Ser Cys Leu Cys Ser Thr Cys Ala Leu Cys Arg Lys Arg
245 250

<210> SEQ ID NO 24
<211> LENGTH: 147
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 24

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Ser Gly Thr Glu
20 25 30

Val His Cys Gln Lys Lys Ser Leu Ala Ser Val Pro Ala Gly Ile Pro
35 40 45

Thr Thr Thr Gln Val Leu Tyr Leu His Val Asn Gln Ile Thr Lys Leu
50 55 60

Glu Pro Gly Val Phe Asp Arg Leu Val Asn Leu Lys Glu Leu His Leu
65 70 75 80

Tyr Gly Asn Trp Gly Thr Asn Thr Pro Val Arg Ala Val Thr Glu Ala
85 90 95

```
Ser Thr Ser Pro Ser Lys Cys Pro Gly Tyr Val Ala Thr Thr Thr Thr
            100                 105                 110

Pro Thr Thr Thr Thr Pro Glu Phe Ile Pro Glu Thr Thr Thr Ser Pro
        115                 120                 125

Gln Pro Val Ile Thr Thr Gln Lys Pro Lys Pro Leu Trp Asn Phe Asn
    130                 135                 140

Cys Thr Ser
145
```

```
<210> SEQ ID NO 25
<211> LENGTH: 272
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 25

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Lys Thr
            20                  25                  30

Val Asp Cys Arg Ser Leu Ala Ser Val Pro Ala Gly Ile Pro Thr Thr
        35                  40                  45

Thr Gln Val Leu Gly Leu Ser Ser Asn Gln Ile Thr Lys Leu Glu Pro
    50                  55                  60

Gly Val Phe Asp Arg Leu Val Asn Leu Gln Gln Leu Tyr Ile Ser Trp
65                  70                  75                  80

Asn Gln Leu Gln Ala Leu Pro Thr Gly Val Leu Asp Lys Leu Thr Gln
                85                  90                  95

Leu Thr Tyr Leu Asp Leu Asn Asn Asn Gln Leu Lys Ser Ile Pro Arg
            100                 105                 110

Gly Ala Phe Asp Asn Leu Lys Ser Leu Thr His Ile Trp Leu Phe Gly
        115                 120                 125

Asn Pro Trp Asp Cys Gln Cys Thr Asp Ile Leu Tyr Leu Ser Gly Trp
    130                 135                 140

Val Ala Gln His Ser Gly Ile Val Gly Glu Gly Trp Leu Arg Ser Trp
145                 150                 155                 160

Thr Val Asn Pro Asp Asn Val Lys Cys Ser Gly Thr Asn Thr Pro Val
                165                 170                 175

Arg Ala Val Thr Glu Ala Ser Thr Ser Pro Ser Lys Cys Pro Gly Tyr
            180                 185                 190

Val Ala Thr Thr Thr Thr Pro Thr Thr Thr Thr Pro Glu Phe Ile Pro
        195                 200                 205

Glu Thr Thr Thr Ser Pro Gln Pro Val Ile Thr Thr Gln Lys Pro Lys
    210                 215                 220

Pro Leu Trp Asn Phe Asn Cys Thr Ser Ile Gln Glu Arg Lys Asn Asp
225                 230                 235                 240

Gly Gly Asp Cys Gly Lys Pro Ala Cys Thr Thr Leu Leu Asn Cys Ala
                245                 250                 255

Asn Phe Leu Ser Cys Leu Cys Ser Thr Cys Ala Leu Cys Arg Lys Arg
            260                 265                 270
```

```
<210> SEQ ID NO 26
<211> LENGTH: 233
<212> TYPE: PRT
<213> ORGANISM: Artificial Sequence
```

<220> FEATURE:
<223> OTHER INFORMATION: Description of Artificial Sequence; note =
synthetic construct

<400> SEQUENCE: 26

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asn Cys Asp Ser Arg Ser Leu Ala Ser Val Pro Ala Gly Ile Pro
        35                  40                  45

Thr Asp Arg Gln Asn Leu Trp Leu Asn Asn Asn Gln Ile Thr Lys Leu
    50                  55                  60

Glu Pro Gly Val Phe Asp Ser Leu Val Asn Leu Gln Thr Leu Tyr Leu
65                  70                  75                  80

His Gln Asn Glu Leu Thr Thr Leu Pro Ala Gly Val Phe Asp Asn Leu
                85                  90                  95

Thr Gln Leu Ser Ile Leu Asn Met His Thr Asn Gln Leu Lys Ser Ile
            100                 105                 110

Pro Arg Gly Ala Phe Asp Asn Leu Lys Ser Leu Thr His Ile Trp Leu
        115                 120                 125

Leu Asn Asn Pro Trp Asp Cys Glu Cys Ser Asp Ile Leu Tyr Leu Lys
    130                 135                 140

Asn Trp Ile Val Gln His Ala Ser Ile Val Asn Pro Leu Gly Asn Gly
145                 150                 155                 160

Gly Val Asp Asn Val Lys Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln
225                 230
```

<210> SEQ ID NO 27
<211> LENGTH: 263
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 27

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Asp Gln Thr Thr
            20                  25                  30

Val Tyr Cys His Ser Arg Arg Leu Thr Ser Val Pro Ala Gly Ile Pro
        35                  40                  45

Thr Asp Arg Gln Asn Leu Trp Leu Asn Asp Asn Gln Ile Thr Lys Leu
    50                  55                  60

Glu Pro Gly Val Phe Asp Arg Leu Ala Gln Leu Thr Arg Leu Gly Leu
65                  70                  75                  80

Ser His Asn Gln Phe Thr Ala Leu Pro Ala Arg Val Phe Asp Arg Leu
                85                  90                  95
```

-continued

```
Gly Asn Leu Gln Trp Leu Gly Leu His Val Asn Gln Leu Lys Ser Ile
            100                 105                 110

Pro Arg Gly Ala Phe Asp Asn Leu Lys Ser Leu Thr His Ile Trp Leu
        115                 120                 125

His Thr Asn Pro Trp Asp Cys Glu Cys Ser Asp Ile Leu Tyr Leu Lys
    130                 135                 140

Asn Trp Ile Val Gln His Ala Ser Ile Val Asn Leu Arg Gly His Gly
145                 150                 155                 160

Gly Val Asp Asn Val Lys Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln Glu Arg Lys Asn Asp Gly Gly
225                 230                 235                 240

Asp Cys Gly Lys Pro Ala Cys Thr Thr Leu Leu Asn Cys Ala Asn Phe
                245                 250                 255

Leu Ser Cys Leu Cys Ser Thr
            260


<210> SEQ ID NO 28
<211> LENGTH: 270
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 28

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asn Cys Asp Ser Arg Ser Leu Ala Ser Val Pro Thr Gly Ile Pro
        35                  40                  45

Thr Thr Thr Gln Val Leu Tyr Leu His Val Asn Gln Ile Thr Lys Leu
    50                  55                  60

Glu Pro Gly Val Phe Asp Arg Leu Ile Asn Leu Lys Glu Leu Tyr Phe
65                  70                  75                  80

Ser Asn Asn Gln Leu Thr Ser Leu Pro Ala Gly Arg Phe Asp Lys Leu
                85                  90                  95

Thr Lys Leu Met Thr Leu Gly Leu His Asn Asn Gln Leu Lys Ser Ile
            100                 105                 110

Pro Arg Gly Ala Phe Asp Asn Leu Lys Ser Leu Thr His Ile Tyr Leu
        115                 120                 125

Phe Asn Asn Pro Trp Asp Cys Glu Cys Ser Asp Ile Leu Tyr Leu Lys
    130                 135                 140

Asn Trp Ile Val Gln His Ala Ser Ile Val Asn Leu Gln Gly His Gly
145                 150                 155                 160

Gly Val Asp Asn Val Lys Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190
```

```
Thr Thr Thr Thr Pro Thr Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln Glu Arg Lys Asn Asp Gly Gly
225                 230                 235                 240

Asp Cys Gly Lys Pro Ala Cys Thr Thr Leu Leu Asn Cys Ala Asn Phe
                245                 250                 255

Leu Ser Cys Leu Cys Ser Thr Cys Ala Leu Cys Arg Lys Arg
            260                 265                 270


<210> SEQ ID NO 29
<211> LENGTH: 270
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 29

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asp Cys Ser Gly Lys Ser Leu Ala Ser Val Pro Ala Gly Ile Pro
        35                  40                  45

Thr Thr Thr Gln Arg Leu Trp Leu Asn Asn Asn Gln Ile Thr Lys Leu
    50                  55                  60

Asp Pro Gly Val Phe Asp Arg Leu Ile Asn Leu Lys Glu Leu Tyr Phe
65                  70                  75                  80

Ser Asn Asn Gln Leu Thr Ser Leu Pro Ala Gly Val Phe Asp Arg Leu
                85                  90                  95

Val Asn Leu Gln Ser Leu Val Leu Asn Ile Asn Gln Leu Lys Ser Ile
            100                 105                 110

Pro Arg Gly Ala Phe Asp Asn Leu Lys Ser Leu Thr His Ile Tyr Leu
        115                 120                 125

Phe Asn Asn Pro Trp Asp Cys Glu Cys Ser Asp Ile Leu Tyr Leu Lys
    130                 135                 140

Asn Trp Ile Val Gln His Ala Ser Ile Val Asn Leu Arg Gly His Gly
145                 150                 155                 160

Gly Val Asp Asn Val Lys Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln Glu Arg Lys Asn Asp Gly Gly
225                 230                 235                 240

Asp Cys Gly Lys Pro Ala Cys Thr Thr Leu Leu Asn Cys Ala Asn Phe
                245                 250                 255

Leu Ser Cys Leu Cys Ser Thr Cys Ala Leu Cys Arg Lys Arg
            260                 265                 270


<210> SEQ ID NO 30
<211> LENGTH: 274
```

<212> TYPE: PRT
<213> ORGANISM: Artificial Sequence
<220> FEATURE:
<223> OTHER INFORMATION: Description of Artificial Sequence; note =
synthetic construct

<400> SEQUENCE: 30

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Ser
            20                  25                  30

Val Asp Cys Asn Ser Arg Arg His Ala Ser Val Pro Ala Gly Ile Pro
        35                  40                  45

Thr Asn Val Gln Ile Leu Asn Leu Tyr Asn Asn Gln Ile Thr Asn Leu
    50                  55                  60

Glu Pro Gly Val Phe Asp Ser Leu Thr Gln Leu Thr Ala Leu His Leu
65                  70                  75                  80

Ser Val Asn Gln Leu Thr Ala Leu Pro Glu Gly Val Phe Asp Arg Leu
                85                  90                  95

Val Asn Leu Gln Thr Leu Leu Leu Tyr Lys Asn Gln Leu Lys Ser Ile
            100                 105                 110

Pro Arg Gly Ala Phe Asp Asn Leu Lys Ser Leu Thr His Ile Trp Leu
        115                 120                 125

Ser Ser Asn Pro Trp Asp Cys Ala Cys Ser Asp Ile Leu Tyr Leu Ser
    130                 135                 140

Arg Trp Ile Ser Gln His Pro Gly Val Val Arg Thr Ala Asp Asp Asp
145                 150                 155                 160

Trp Ser Arg Val Val Pro Asp Ser Ala Arg Cys Ser Gly Thr Asn Thr
                165                 170                 175

Pro Val Arg Ala Val Thr Glu Ala Ser Thr Ser Pro Ser Lys Cys Pro
            180                 185                 190

Gly Tyr Val Ala Thr Thr Thr Thr Pro Thr Thr Thr Thr Pro Glu Phe
        195                 200                 205

Ile Pro Glu Thr Thr Thr Ser Pro Gln Pro Val Ile Thr Thr Gln Lys
    210                 215                 220

Pro Lys Pro Leu Trp Asn Phe Asn Cys Thr Ser Ile Gln Glu Arg Lys
225                 230                 235                 240

Asn Asp Gly Gly Asp Cys Gly Lys Pro Ala Cys Thr Thr Leu Leu Asn
                245                 250                 255

Cys Ala Asn Phe Leu Ser Cys Leu Cys Ser Thr Cys Ala Leu Cys Arg
            260                 265                 270

Lys Arg
```

<210> SEQ ID NO 31
<211> LENGTH: 273
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 31

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Asp Gln Thr Leu
            20                  25                  30

Val Asn Cys Gln Asn Ile Arg Leu Ala Ser Val Pro Ala Gly Ile Pro
        35                  40                  45
```

```
Thr Asp Lys Gln Arg Leu Trp Leu Asn Asn Asn Gln Ile Thr Lys Leu
    50                  55                  60

Glu Pro Gly Val Phe Asp Ser Leu Thr Gln Leu Thr Ile Leu Ala Leu
65                  70                  75                  80

Asn Asp Asn Gln Leu Gln Ala Leu Ser Glu Gly Leu Phe Asp His Leu
                85                  90                  95

Val Asn Leu Gln Gly Leu Gly Leu Gln Asn Asn Gln Leu Lys Ser Ile
            100                 105                 110

Pro Arg Gly Ala Phe Asp Asn Leu Lys Ser Leu Thr His Ile Tyr Leu
        115                 120                 125

Phe Asn Asn Pro Trp Asp Cys Ala Cys Ser Asp Ile Leu Tyr Leu Ser
    130                 135                 140

Arg Trp Ile Ser Gln His Pro Gly Val Val Arg Thr Ala Asp Ser Trp
145                 150                 155                 160

Thr Arg Val Asp Leu Asp Ser Ala Arg Cys Ser Gly Thr Asn Thr Pro
                165                 170                 175

Val Arg Ala Val Thr Glu Ala Ser Thr Ser Pro Ser Lys Cys Pro Gly
            180                 185                 190

Tyr Val Ala Thr Thr Thr Thr Pro Thr Thr Thr Thr Pro Glu Phe Ile
        195                 200                 205

Pro Glu Thr Thr Thr Ser Pro Gln Pro Val Ile Thr Thr Gln Lys Pro
    210                 215                 220

Lys Pro Leu Trp Asn Phe Asn Cys Thr Ser Ile Gln Glu Arg Lys Asn
225                 230                 235                 240

Asp Gly Gly Asp Cys Gly Lys Pro Ala Cys Thr Thr Leu Leu Asn Cys
                245                 250                 255

Ala Asn Phe Leu Ser Cys Leu Cys Ser Thr Cys Ala Leu Cys Arg Lys
            260                 265                 270

Arg
```

<210> SEQ ID NO 32
<211> LENGTH: 224
<212> TYPE: PRT
<213> ORGANISM: Artificial Sequence
<220> FEATURE:
<223> OTHER INFORMATION: Description of Artificial Sequence; note = synthetic construct

<400> SEQUENCE: 32

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Val
            20                  25                  30

Asp Cys Asn Ser Arg Arg His Ala Ser Val Pro Ala Gly Ile Pro Thr
        35                  40                  45

Asn Val Gln Ile Leu Asn Leu Tyr Asn Asn Gln Ile Thr Asn Leu Glu
    50                  55                  60

Pro Gly Val Phe Asp Ser Leu Thr Gln Leu Thr Thr Leu Tyr Leu Ser
65                  70                  75                  80

Asn Asn Lys Leu Thr Ala Leu Pro Ala Gly Leu Phe Asp Glu Leu Thr
                85                  90                  95

Gln Val Tyr Ser Leu Ser Leu His Thr Asn Gln Leu Lys Ser Ile Pro
            100                 105                 110

Arg Gly Ala Phe Asp Asn Leu Lys Ser Leu Thr Gln Ile Trp Leu Tyr
        115                 120                 125
```

```
Asn Asn Pro Trp Asp Cys Ala Cys Ser Asp Ile Leu Tyr Leu Ser Arg
    130                 135                 140

Trp Ile Ser Gln Asn Leu Ala Ala Val Arg Asp Thr Asn Tyr Lys Thr
145                 150                 155                 160

Asp Pro Asp Gln Pro Arg Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220


<210> SEQ ID NO 33
<211> LENGTH: 227
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 33

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Glu
            20                  25                  30

Val His Cys Gln Lys Lys Ser Leu Ala Ser Val Pro Ala Gly Ile Pro
        35                  40                  45

Thr Thr Thr Gln Val Leu Tyr Leu His Val Asn Gln Ile Thr Lys Leu
    50                  55                  60

Glu Pro Gly Val Phe Asp Arg Leu Val Asn Leu Gln Lys Leu Trp Leu
65                  70                  75                  80

Asn Ser Asn Gln Leu Thr Ser Leu Pro Ala Gly Val Glu Asp Lys Leu
                85                  90                  95

Thr Leu Leu Ala Gly Leu Ser Leu His Asp Asn Gln Leu Lys Ser Ile
            100                 105                 110

Pro Arg Gly Ala Phe Asp Asn Leu Lys Ser Leu Thr His Ile Tyr Leu
        115                 120                 125

Tyr Asn Asn Pro Trp Asp Cys Glu Cys Arg Asp Ile Met Tyr Leu Arg
    130                 135                 140

Asn Trp Val Ala Asp His Thr Ser Ile Val Met Arg Trp Asp Gly Lys
145                 150                 155                 160

Ala Val Asn Asp Pro Asp Ser Ala Lys Cys Ala Gly Thr Asn Thr Pro
                165                 170                 175

Val Arg Ala Val Thr Glu Ala Ser Thr Ser Pro Ser Lys Cys Pro Gly
            180                 185                 190

Tyr Val Ala Thr Thr Thr Thr Pro Thr Thr Thr Thr Pro Glu Phe Ile
        195                 200                 205

Pro Glu Thr Thr Thr Ser Pro Gln Pro Val Ile Thr Thr Gln Lys Pro
    210                 215                 220

Lys Pro Leu
225


<210> SEQ ID NO 34
<211> LENGTH: 273
<212> TYPE: PRT
<213> ORGANISM: Artificial Sequence
<220> FEATURE:
```

<223> OTHER INFORMATION: Description of Artificial Sequence; note =
synthetic construct

<400> SEQUENCE: 34

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Asp Gln Thr Leu
20 25 30

Val Asn Cys Gln Asn Ile Arg Leu Ala Ser Val Pro Ala Gly Ile Pro
35 40 45

Thr Asp Lys Gln Arg Leu Trp Leu Asn Asn Asn Gln Ile Thr Lys Leu
50 55 60

Glu Pro Gly Val Phe Asp His Leu Val Met Leu Gln Gln Leu Tyr Phe
65 70 75 80

Asn Ser Asn Lys Leu Thr Ala Ile Pro Thr Gly Val Phe Asp Lys Leu
85 90 95

Thr Gln Leu Thr Gln Leu Asp Leu Asn Asp Asn His Leu Lys Ser Ile
100 105 110

Pro Arg Gly Ala Phe Asp Asn Leu Lys Ser Leu Thr His Ile Tyr Leu
115 120 125

Tyr Asn Asn Pro Trp Asp Cys Glu Cys Arg Asp Ile Met Tyr Leu Arg
130 135 140

Asn Trp Val Ala Asp His Thr Ser Ile Val Met Arg Trp Asp Gly Lys
145 150 155 160

Ala Val Asn Asp Pro Asp Ser Ala Lys Cys Ala Gly Thr Asn Thr Pro
165 170 175

Val Arg Ala Val Thr Glu Ala Ser Thr Ser Pro Ser Lys Cys Pro Gly
180 185 190

Tyr Val Ala Thr Thr Thr Thr Pro Thr Thr Thr Thr Pro Glu Phe Ile
195 200 205

Pro Glu Thr Thr Thr Ser Pro Gln Pro Val Ile Thr Thr Gln Lys Pro
210 215 220

Lys Pro Leu Trp Asn Phe Asn Cys Thr Ser Ile Gln Glu Arg Lys Asn
225 230 235 240

Asp Gly Gly Asp Cys Gly Lys Pro Ala Cys Thr Thr Leu Leu Asn Cys
245 250 255

Ala Asn Phe Leu Ser Cys Leu Cys Ser Thr Cys Ala Leu Cys Arg Lys
260 265 270

Arg

<210> SEQ ID NO 35
<211> LENGTH: 275
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 35

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Ser Val Val Asn
20 25 30

Gly Leu Gln Arg Thr His Cys Gly Gly Ile Gly Leu Arg Ser Val Pro
35 40 45

Ser Gly Ile Ser Asp Asn Thr His Trp Leu Asp Leu Asp Arg Asn Arg
50 55 60

```
Ile Glu Arg Leu Pro Gln Gly Val Phe Asp Arg Leu Ala Asn Leu Arg
65                  70                  75                  80

Glu Leu His Leu Trp Gly Asn Gln Leu Val Ser Leu Pro Pro Gly Val
                85                  90                  95

Phe Asp Asn Leu Thr Gln Leu Ser Ile Leu Asn Met His Thr Asn Gln
            100                 105                 110

Leu Lys Ser Ile Pro Arg Gly Ala Phe Asp Asn Leu Lys Ser Leu Thr
        115                 120                 125

His Ile Phe Leu Tyr Asn Asn Pro Trp Asp Cys Ala Cys Ser Asp Ile
    130                 135                 140

Leu Tyr Leu Ser Arg Trp Ile Ser Arg Asn Leu Ala Ala Val Arg Asp
145                 150                 155                 160

Thr Asn Tyr Lys Thr Asp Pro Asp Gln Pro Arg Cys Ser Gly Thr Asn
                165                 170                 175

Thr Pro Val Arg Ala Val Thr Glu Ala Ser Thr Ser Pro Ser Lys Cys
            180                 185                 190

Pro Gly Tyr Val Ala Thr Thr Thr Thr Pro Thr Thr Thr Thr Pro Glu
        195                 200                 205

Phe Ile Pro Glu Thr Thr Thr Ser Pro Gln Pro Val Ile Thr Thr Gln
    210                 215                 220

Lys Pro Lys Pro Leu Trp Asn Phe Asn Cys Thr Ser Ile Gln Glu Arg
225                 230                 235                 240

Lys Asn Asp Gly Gly Asp Cys Gly Lys Pro Ala Cys Thr Thr Leu Leu
                245                 250                 255

Asn Cys Ala Asn Phe Leu Ser Cys Leu Cys Ser Thr Cys Ala Leu Cys
            260                 265                 270

Arg Lys Arg
        275


<210> SEQ ID NO 36
<211> LENGTH: 269
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 36

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Asp Gln Thr Thr
            20                  25                  30

Val Asp Cys Arg Asn Lys Arg Phe Ser Ser Val Pro Ala Gly Ile Pro
        35                  40                  45

Thr Asp Arg Gln Asn Leu Trp Leu Asn Asn Asn Gln Ile Thr Lys Leu
    50                  55                  60

Glu Pro Gly Val Phe Asp Ser Leu Thr Glu Leu Thr Tyr Leu Asn Leu
65                  70                  75                  80

Asn Thr Asn Gln Leu Thr Ala Leu Pro Glu Gly Val Phe Asp Arg Leu
                85                  90                  95

Val Asn Leu Gln Arg Leu His Leu Asp Gln Asn Gln Leu Val Ser Leu
            100                 105                 110

Pro Thr Gly Val Phe Asp Lys Leu Thr Gln Leu Thr Tyr Leu His Leu
        115                 120                 125

Asp Ala Asn Gln Leu Lys Ser Ile Pro Arg Gly Ala Phe Asp Asn Leu
    130                 135                 140
```

```
Lys Ser Leu Thr His Ile Tyr Leu Tyr Asn Asn Pro Trp Asp Cys Ala
145                 150                 155                 160

Cys Ser Asp Ile Leu Tyr Leu Ser Arg Trp Ile Ser Gln His Pro Gly
                165                 170                 175

Leu Val Phe Asp Asp Asp Leu Asn Leu Asp Pro Asp Gln Ala His Cys
            180                 185                 190

Ser Gly Thr Asn Thr Pro Val Arg Ala Val Thr Glu Ala Ser Thr Ser
        195                 200                 205

Pro Ser Lys Cys Pro Gly Tyr Val Ala Thr Thr Thr Thr Pro Thr Thr
    210                 215                 220

Thr Thr Pro Glu Phe Ile Pro Glu Thr Thr Thr Ser Pro Gln Pro Val
225                 230                 235                 240

Ile Thr Thr Gln Lys Pro Lys Pro Leu Trp Asn Phe Asn Cys Thr Ser
                245                 250                 255

Ile Gln Glu Arg Lys Asn Asp Gly Gly Asp Cys Gly Lys
            260                 265
```

<210> SEQ ID NO 37
<211> LENGTH: 287
<212> TYPE: PRT
<213> ORGANISM: Artificial Sequence
<220> FEATURE:
<223> OTHER INFORMATION: Description of Artificial Sequence; note = synthetic construct

<400> SEQUENCE: 37

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asn Cys Gln Glu Arg Ser Leu Ala Ser Val Pro Ala Gly Ile Pro
        35                  40                  45

Thr Thr Thr Gln Val Leu Tyr Leu Tyr Thr Asn Gln Ile Thr Lys Leu
    50                  55                  60

Glu Pro Gly Val Phe Asp Ser Leu Thr Gln Leu Thr Arg Leu Asp Leu
65                  70                  75                  80

Tyr Asn Asn Gln Leu Thr Val Leu Pro Ala Gly Val Cys Asp Ser Leu
                85                  90                  95

Val Asn Leu Lys Glu Leu Arg Leu Tyr Asn Asn Gln Leu Ser Ala Leu
            100                 105                 110

Pro Thr Gly Val Phe Asp Asn Leu Thr Gln Leu Ser Ile Leu Asn Met
        115                 120                 125

His Thr Asn Gln Leu Lys Ser Ile Pro Arg Gly Ala Phe Asp Asn Leu
    130                 135                 140

Lys Ser Leu Thr His Ile Tyr Leu Phe Asn Asn Pro Trp Asp Cys Glu
145                 150                 155                 160

Cys Ser Asp Ile Leu Tyr Leu Lys Asn Trp Ile Val Gln His Ala Ser
                165                 170                 175

Ile Val Asn Pro His Pro His Gly Gly Val Asp Asn Val Lys Cys Ser
            180                 185                 190

Gly Thr Asn Thr Pro Val Arg Ala Val Thr Glu Ala Ser Thr Ser Pro
        195                 200                 205

Ser Lys Cys Pro Gly Tyr Val Ala Thr Thr Thr Thr Pro Thr Thr Thr
    210                 215                 220

Thr Pro Glu Phe Ile Pro Glu Thr Thr Thr Ser Pro Gln Pro Val Ile
225                 230                 235                 240
```

```
Thr Thr Gln Lys Pro Lys Pro Leu Trp Asn Phe Asn Cys Thr Ser Ile
                245                 250                 255

Gln Glu Arg Lys Asn Asp Gly Gly Asp Cys Gly Lys Pro Ala Cys Thr
            260                 265                 270

Thr Leu Leu Asn Cys Ala Asn Phe Leu Ser Cys Leu Cys Ser Thr
        275                 280                 285


<210> SEQ ID NO 38
<211> LENGTH: 277
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 38

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Glu
            20                  25                  30

Val His Cys Ala Gly Lys Ser Leu Ala Ser Val Pro Ala Gly Ile Pro
        35                  40                  45

Thr Thr Thr Gln Tyr Leu Asn Leu His Val Asn Gln Ile Thr Lys Leu
    50                  55                  60

Glu Pro Gly Val Phe Asp Arg Leu Val Asn Leu Gln Lys Leu Tyr Leu
65                  70                  75                  80

Ser Gly Asn Gln Leu Gln Ala Leu Pro Ala Gly Val Phe Asp Lys Leu
                85                  90                  95

Ser Gln Leu Thr Phe Leu Ser Leu Asp Glu Asn Lys Leu Thr Ala Leu
            100                 105                 110

Pro Asn Gly Val Phe Asp Lys Leu Thr Gln Leu Thr Ile Leu Gly Leu
        115                 120                 125

His Thr Asn Gln Leu Lys Ser Val Pro Arg Gly Ala Phe Asp Asn Leu
    130                 135                 140

Lys Ser Leu Thr His Ile Trp Leu Phe Gly Asn Pro Trp Asp Cys Ala
145                 150                 155                 160

Cys Ser Asp Ile Leu Tyr Leu Ser Arg Trp Ile Gly Gln Asn Ser Gly
                165                 170                 175

Lys Val Thr Lys Glu Ser Val Asn Asn Pro Asp Ser Ala Val Cys Ser
            180                 185                 190

Gly Thr Asn Thr Pro Val Arg Ala Val Thr Glu Ala Ser Thr Ser Pro
        195                 200                 205

Ser Lys Cys Pro Gly Tyr Val Ala Thr Thr Thr Thr Pro Thr Thr Thr
    210                 215                 220

Thr Pro Glu Phe Ile Pro Glu Thr Thr Thr Ser Pro Gln Pro Val Ile
225                 230                 235                 240

Thr Thr Gln Lys Pro Lys Pro Leu Trp Asn Phe Asn Cys Thr Ser Ile
                245                 250                 255

Gln Glu Arg Lys Asn Asp Gly Gly Asp Cys Gly Lys Pro Ala Cys Thr
            260                 265                 270

Thr Leu Leu Asn Cys
        275


<210> SEQ ID NO 39
<211> LENGTH: 234
<212> TYPE: PRT
<213> ORGANISM: Artificial Sequence
```

<220> FEATURE:
<223> OTHER INFORMATION: Description of Artificial Sequence; note = synthetic construct

<400> SEQUENCE: 39

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Gly Lys Phe Ser
            20                  25                  30

Trp Ser Gly Glu Leu Gln Thr Thr Asp Cys Asp Gly Lys Gly Leu Ser
        35                  40                  45

Ser Val Pro Ser Gly Ile Pro Asp Asn Thr Gln Asn Leu Asp Leu Arg
    50                  55                  60

Lys Asn Gln Ile Asp Arg Leu Pro Glu Gly Val Phe Asp Lys Leu Thr
65                  70                  75                  80

Glu Leu Thr Ile Leu Asp Leu Arg Thr Asn Gln Leu Gln Ala Leu Pro
                85                  90                  95

Thr Leu Val Phe Asp Ser Leu Val Asn Leu Gln Lys Leu Trp Leu Asn
            100                 105                 110

Ser Asn Gln Leu Thr Ser Leu Pro Ala Gly Val Phe Asp Arg Leu Val
        115                 120                 125

Asn Leu Gln Lys Leu Trp Leu Asn Ser Asn Gln Leu Lys Ser Ile Pro
    130                 135                 140

Arg Gly Ala Phe Asp Asn Leu Lys Ser Leu Thr His Ile Trp Leu Phe
145                 150                 155                 160

Gly Asn Pro Trp Asp Cys Gln Cys Thr Asp Ile Leu Tyr Leu Ser Gly
                165                 170                 175

Trp Val Ala Gln His Ser Gly Ile Val Arg Glu Gln Trp Thr Gly Ser
            180                 185                 190

Ser Trp Thr Val Asn Pro Asp Ser Ala Lys Cys Ala Gly Thr Asn Thr
        195                 200                 205

Pro Val Arg Ala Val Thr Glu Ala Ser Thr Ser Pro Ser Lys Cys Pro
    210                 215                 220

Gly Tyr Val Ala Thr Thr Thr Thr Pro Thr
225                 230
```

<210> SEQ ID NO 40
<211> LENGTH: 304
<212> TYPE: PRT
<213> ORGANISM: Artificial Sequence
<220> FEATURE:
<223> OTHER INFORMATION: Description of Artificial Sequence; note = synthetic construct

<400> SEQUENCE: 40

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Gly Glu Gln Ser
            20                  25                  30

Trp Ala Pro Gly Leu Gln Ala Thr Asn Cys Tyr Asp Lys Gly Leu Ser
        35                  40                  45

Ser Val Pro Ala Gly Ile Pro Asp Asn Thr Gln Ala Leu Thr Val Gln
    50                  55                  60

Lys Asn Arg Ile Glu Ser Leu Pro Glu Arg Val Phe Asp Arg Leu Val
65                  70                  75                  80

Asn Leu Gln Lys Leu Trp Leu Asn Ser Asn Gln Leu Thr Ser Leu Pro
                85                  90                  95
```

```
Ala Gly Val Phe Asp Arg Leu Gly Asn Leu Gln Gln Leu Tyr Leu Gly
            100                 105                 110

Gly Asn Gln Leu Thr Ser Leu Pro Ala Gly Val Phe Asp Arg Leu Val
        115                 120                 125

Asn Leu Gln Ser Leu Val Leu His Thr Asn Gln Leu Lys Ser Ile Pro
    130                 135                 140

Arg Gly Ala Phe Asp Asn Leu Lys Ser Leu Thr His Ile Trp Leu Tyr
145                 150                 155                 160

Gly Asn Pro Trp Asp Cys Glu Cys Arg Asp Ile Met Tyr Leu Arg Asn
                165                 170                 175

Trp Val Ala Asp His Thr Ser Ile Val Met Arg Trp Asp Gly Lys Ala
            180                 185                 190

Val Asn Asp Pro Asp Ser Ala Lys Cys Ser Gly Thr Asn Thr Pro Val
        195                 200                 205

Arg Ala Val Thr Glu Ala Ser Thr Ser Pro Ser Lys Cys Pro Gly Tyr
    210                 215                 220

Val Ala Thr Thr Thr Thr Pro Thr Thr Thr Thr Pro Glu Phe Ile Pro
225                 230                 235                 240

Glu Thr Thr Thr Ser Pro Gln Pro Val Ile Thr Thr Gln Lys Pro Lys
                245                 250                 255

Pro Leu Trp Asn Phe Asn Cys Thr Ser Ile Gln Glu Arg Lys Asn Asp
            260                 265                 270

Gly Gly Asp Cys Gly Lys Pro Ala Cys Thr Thr Leu Leu Asn Cys Ala
        275                 280                 285

Asn Phe Leu Ser Cys Leu Cys Ser Thr Cys Ala Leu Cys Arg Lys Arg
    290                 295                 300
```

<210> SEQ ID NO 41
<211> LENGTH: 285
<212> TYPE: PRT
<213> ORGANISM: Artificial Sequence
<220> FEATURE:
<223> OTHER INFORMATION: Description of Artificial Sequence; note = synthetic construct

<400> SEQUENCE: 41

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Gln
            20                  25                  30

Val Asn Cys His Glu Arg Ser Leu Ala Ser Val Pro Ala Gly Ile Pro
        35                  40                  45

Thr Thr Thr Gln Val Leu Tyr Leu Tyr Thr Asn Gln Ile Thr Lys Leu
    50                  55                  60

Glu Pro Gly Val Phe Asp Ser Leu Thr Pro Leu Thr Glu Leu Asp Leu
65                  70                  75                  80

Gly Thr Asn Gln Leu Thr Val Leu Pro Thr Gly Val Phe Asp Arg Leu
                85                  90                  95

Val Asn Leu Gln Lys Leu Trp Leu Asn Ser Asn Gln Leu Thr Ser Leu
            100                 105                 110

Pro Ala Gly Val Phe Asp Asn Leu Ala Asn Leu Glu Lys Leu His Leu
        115                 120                 125

Tyr Asp Asn Gln Leu Thr Ser Leu Pro Ala Gly Val Phe Asp Lys Leu
    130                 135                 140

Pro Lys Leu Thr His Leu Val Leu His Thr Asn Gln Leu Lys Ser Ile
145                 150                 155                 160
```

```
Pro Arg Gly Ala Phe Asp Asn Leu Lys Ser Leu Thr His Ile Trp Lys
                165                 170                 175

Asn Pro Trp Asp Cys Ala Cys Ser Asp Ile Leu Tyr Leu Ser Arg Trp
            180                 185                 190

Ile Ser Gln Asn Pro Gly Val Pro Lys Ala Ala Asp Ser Trp Thr Arg
        195                 200                 205

Val Asp Pro Asp Ser Ala Arg Cys Ser Gly Thr Asn Thr Pro Val Arg
    210                 215                 220

Ala Val Thr Glu Ala Ser Thr Ser Pro Ser Lys Cys Pro Gly Tyr Val
225                 230                 235                 240

Ala Thr Thr Thr Thr Pro Thr Thr Thr Thr Pro Glu Phe Ile Pro Glu
                245                 250                 255

Thr Thr Thr Ser Pro Gln Pro Val Ile Thr Thr Gln Lys Pro Lys Pro
            260                 265                 270

Leu Trp Asn Phe Asn Cys Thr Ser Ile Gln Glu Arg Lys
        275                 280                 285


<210> SEQ ID NO 42
<211> LENGTH: 272
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 42

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Gln
            20                  25                  30

Val Asn Cys His Glu Arg Arg Leu Ala Ser Val Pro Ala Glu Ile Pro
        35                  40                  45

Thr Thr Thr Lys Ile Leu Arg Leu Tyr Ile Asn Gln Ile Thr Lys Leu
    50                  55                  60

Glu Pro Gly Val Phe Asp Ser Leu Val Asn Leu Gln Thr Leu Tyr Leu
65                  70                  75                  80

His Gln Asn Glu Leu Thr Thr Leu Pro Ala Gly Val Phe Asp His Leu
                85                  90                  95

Val Lys Leu Lys Glu Leu His Leu Tyr Arg Asn Gln Met Lys Ala Leu
            100                 105                 110

Pro Glu Gly Gly Phe Asp Arg Leu Val Asn Leu Gln Gln Leu Trp Leu
        115                 120                 125

Glu Ile Asn Gln Leu Thr Ser Leu Pro Ala Gly Val Phe Asp Lys Leu
    130                 135                 140

Thr Gln Leu Lys Glu Leu Gly Leu Asp Gln Asn Gln Leu Thr Ala Leu
145                 150                 155                 160

Pro Ala Gly Leu Phe Asp Glu Leu Thr Gln Val Tyr Ser Leu Ser Leu
                165                 170                 175

Asn Asp Asn Gln Leu Lys Ser Ile Pro His Gly Ala Phe Asp Arg Leu
            180                 185                 190

Ser Ser Leu Thr His Ala Tyr Leu Phe Gly Asn Pro Trp Asp Cys Glu
        195                 200                 205

Cys Arg Asp Ile Met Tyr Leu Arg Asn Trp Val Ala Asp His Thr Ser
    210                 215                 220

Ile Val Met Arg Trp Asp Gly Lys Ala Val Asn Asp Pro Asp Ser Ala
225                 230                 235                 240
```

```
Lys Cys Ser Gly Thr Asn Thr Pro Val Arg Ala Val Thr Glu Ala Ser
                245                 250                 255

Thr Ser Pro Ser Lys Cys Pro Gly Tyr Val Ala Thr Thr Thr Thr Pro
            260                 265                 270
```

<210> SEQ ID NO 43
<211> LENGTH: 273
<212> TYPE: PRT
<213> ORGANISM: Artificial Sequence
<220> FEATURE:
<223> OTHER INFORMATION: Description of Artificial Sequence; note = synthetic construct

<400> SEQUENCE: 43

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Asp Gln Thr Leu
            20                  25                  30

Val Asn Cys Gln Asn Ile Arg Leu Ala Ser Val Pro Ala Gly Ile Pro
        35                  40                  45

Thr Asp Lys Gln Arg Leu Trp Leu Asn Asn Asn Gln Ile Thr Lys Leu
    50                  55                  60

Glu Pro Gly Val Phe Asp His Leu Val Asn Leu Gln Gln Leu Tyr Phe
65                  70                  75                  80

Asn Ser Asn Lys Leu Thr Ala Ile Pro Thr Gly Val Phe Asp Lys Leu
                85                  90                  95

Thr Gln Leu Thr Gln Leu Asp Leu Asn Asp Asn His Leu Lys Ser Ile
            100                 105                 110

Pro Arg Gly Ala Phe Asp Asn Leu Lys Ser Leu Thr His Ile Tyr Leu
        115                 120                 125

Tyr Asn Asn Pro Trp Asp Cys Glu Cys Arg Asp Ile Met Tyr Leu Arg
    130                 135                 140

Asn Trp Val Ala Asp His Thr Ser Ile Val Met Arg Trp Asp Gly Lys
145                 150                 155                 160

Ala Val Asn Asp Pro Asp Ser Ala Lys Cys Ala Gly Thr Asn Thr Pro
                165                 170                 175

Val Arg Ala Val Thr Glu Ala Ser Thr Ser Pro Ser Lys Cys Pro Gly
            180                 185                 190

Tyr Val Ala Thr Thr Thr Thr Pro Thr Thr Thr Thr Pro Glu Phe Ile
        195                 200                 205

Pro Glu Thr Thr Thr Ser Pro Gln Pro Val Ile Thr Thr Gln Lys Pro
    210                 215                 220

Lys Pro Leu Trp Asn Phe Asn Cys Thr Ser Ile Gln Glu Arg Lys Asn
225                 230                 235                 240

Asp Gly Gly Asp Cys Gly Lys Pro Ala Cys Thr Thr Leu Leu Asn Cys
                245                 250                 255

Ala Asn Phe Leu Ser Cys Leu Cys Ser Thr Cys Ala Leu Cys Arg Lys
            260                 265                 270

Arg
```

<210> SEQ ID NO 44
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 44
ggcgccctgg tgcaaagtgc ggtagcatgt ccctcgcagt gttcgtgctc agcgacaact 60
gtgaactgtg atagcagaag cctcgcgtct gtgcctgcgg aaatccccac caccacgaag 120
atcctgcggc tgtacatcaa tcagataacg aagctcgagc caggggtgtt tgatcgcctg 180
gtgaatctgc agcatctgca tttgaataaa aacccactat cagctctccc cgctggggtg 240
tttaaccgtc tgactcaact gacgacactg gttctggaca ccaaccagct gaagagcatt 300
cccaggggcg cctttgacaa cctcaagagc ctcactcaca tctggctgtt cggcaacccc 360
tgggactgcg agtgttcgga catcctctat ctgaagaact ggattgtgca gcacgcaagc 420
atcgtgaatc cattgggcaa tgggggagtt gataacgtga agtgctctgg taccaatacc 480
cccgtccgt 489

<210> SEQ ID NO 45
<211> LENGTH: 185
<212> TYPE: PRT
<213> ORGANISM: Artificial Sequence
<220> FEATURE:
<223> OTHER INFORMATION: Description of Artificial Sequence; note = synthetic construct

<400> SEQUENCE: 45

Gly Ala Leu Val Gln Ser Ala Ala Ala Cys Pro Ser Gln Cys Ser Cys
1 5 10 15

Ser Arg Thr Thr Val Asp Cys Asn Ser Arg Ser Leu Ala Ser Val Pro
20 25 30

Ala Ala Ile Pro Ile Thr Thr Gln Arg Leu Trp Leu Ser Asn Asn Gln
35 40 45

Leu Thr Lys Leu Asp Pro Gly Val Phe Asp Ser Leu Thr Gln Leu Thr
50 55 60

Tyr Leu Asn Leu Ala Val Asn Gln Leu Thr Ala Leu Pro Val Gly Val
65 70 75 80

Phe Asp Arg Leu Val Asn Leu Gln Lys Leu Trp Leu Asn Ser Asn Gln
85 90 95

Leu Ser Ala Leu Pro Val Gly Val Phe Asp Lys Leu Thr Gln Leu Thr
100 105 110

Tyr Leu Gly Val Asn Gln Leu Lys Ser Ile Pro Arg Gly Val Phe Asp
115 120 125

Asn Leu Lys Ser Leu Thr His Ile Trp Leu Tyr Asp Asn Pro Trp Asp
130 135 140

Cys Glu Cys Ser Asp Ile Leu Tyr Leu Lys Asn Trp Ile Val Gln His
145 150 155 160

Ala Ser Ile Val Asn Leu Glu Gly His Gly Gly Val Asp Asn Val Lys
165 170 175

Cys Ser Gly Thr Asn Thr Pro Val Arg
180 185

<210> SEQ ID NO 46
<211> LENGTH: 187
<212> TYPE: PRT
<213> ORGANISM: Artificial Sequence
<220> FEATURE:
<223> OTHER INFORMATION: Description of Artificial Sequence; note = synthetic construct

<400> SEQUENCE: 46

Gly Ala Leu Val Gln Ser Ala Val Ala Cys Pro Ser Gln Cys Ser Cys
1 5 10 15

-continued

```
Ser Gly Thr Gln Val Asn Cys His Glu Arg Arg Leu Ala Ser Val Pro
            20                  25                  30

Ala Gly Ile Pro Thr Thr Thr Gln Ile Leu Arg Leu Tyr Arg Asn Gln
        35                  40                  45

Ile Thr Lys Leu Glu Leu Gly Val Phe Asp Ser Leu Arg Glu Leu Thr
    50                  55                  60

Leu Leu Asn Val Gly Asp Asn Gln Leu Thr Ala Leu Pro Glu Gly Val
65                  70                  75                  80

Phe Asp Arg Leu Val Asn Leu Gln Lys Leu Trp Leu Asn Ser Asn Gln
                85                  90                  95

Leu Thr Thr Val Pro Ala Gly Val Phe Asp Arg Leu Gly Asn Leu Gln
            100                 105                 110

Arg Phe Gly Leu His Asp Asn Gln Leu Lys Ser Ile Pro Arg Gly Ala
        115                 120                 125

Phe Asp Asn Leu Lys Ser Leu Thr His Ile Trp Leu Phe Gly Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Leu Glu Gly Tyr Gly Gly Val Asp Asn
                165                 170                 175

Val Lys Cys Ser Gly Thr Asn Thr Pro Val Arg
            180                 185


<210> SEQ ID NO 47
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 47

Gly Ala Leu Val Gln Ser Ala Val Ala Cys Pro Ser Gln Cys Ser Cys
 1               5                  10                  15

Ser Gly Thr Thr Val Asn Cys Asp Ser Arg Ser Leu Ala Ser Val Pro
            20                  25                  30

Gly Gly Ile Pro Thr Thr Thr Gln Val Leu Tyr Leu Tyr Asp Asn Gln
        35                  40                  45

Ile Thr Lys Phe Glu Pro Gly Val Phe Asp Ser Leu Thr Ala Leu Thr
    50                  55                  60

Leu Leu Asn Val Gly Asp Asn Gln Leu Thr Ala Leu Pro Glu Gly Val
65                  70                  75                  80

Phe Asp Arg Leu Val Asn Leu Gln Ser Leu Val Leu Asn Ile Asn Gln
                85                  90                  95

Leu Lys Ser Ile Pro Arg Gly Ala Phe Asp Asn Leu Lys Ser Leu Thr
            100                 105                 110

His Ile Tyr Leu Phe Asn Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

Gln Pro Tyr Gly Gly Val Asp Asn Val Lys Cys Ser Gly Thr Asn Thr
145                 150                 155                 160

Pro Val Arg


<210> SEQ ID NO 48
<211> LENGTH: 257
<212> TYPE: PRT
```

<213> ORGANISM: Artificial Sequence
<220> FEATURE:
<223> OTHER INFORMATION: Description of Artificial Sequence; note = synthetic construct

<400> SEQUENCE: 48

```
Gly Ala Leu Val Gln Ser Ala Val Ala Cys Pro Ser Gln Cys Ser Cys
 1               5                  10                  15

Ser Gly Thr His Val Asn Cys Glu Arg Lys Arg Leu Thr Ser Val Pro
            20                  25                  30

Ala Gly Ile Pro Thr Thr Thr Lys Ile Leu Arg Leu Tyr Ile Asn Gln
        35                  40                  45

Ile Thr Lys Leu Glu Pro Gly Val Phe Asp Ser Leu Thr Ala Leu Thr
    50                  55                  60

Phe Leu Asn Leu Gly Asn Asn Gln Leu Thr Ala Leu Pro Glu Gly Val
65                  70                  75                  80

Phe Asp His Leu Val Asn Leu Gln Lys Leu Trp Leu Asn Ser Asn Gln
                85                  90                  95

Leu Thr Ser Leu Pro Ala Gly Val Phe Asp Lys Leu Thr Gln Leu Lys
            100                 105                 110

Glu Leu Gly Leu Asp Gln Asn Gln Leu Lys Ser Ile Ser Ala Gly Met
        115                 120                 125

Phe Asp Arg Val Leu Gln Glu Leu His Leu Ser Ser Lys Gln Leu Thr
    130                 135                 140

Asp Leu Pro Glu Gly Gly Phe Glu Arg Leu Val Asn Leu Lys Glu Leu
145                 150                 155                 160

His Leu Tyr Arg Asn Gln Met Lys Ala Leu Pro Ala Gly Leu Phe Asp
                165                 170                 175

Glu Leu Thr Gln Leu Thr Leu Leu Glu Leu Gln Asn Asn Gln Leu Lys
            180                 185                 190

Ser Ile Pro Arg Gly Ala Phe Asp Asn Leu Lys Ser Leu Thr His Ile
        195                 200                 205

Tyr Leu Phe Asn Asn Pro Trp Asp Cys Glu Cys Ser Asp Ile Leu Tyr
    210                 215                 220

Leu Lys Asn Trp Ile Val Gln His Ala Ser Ile Val Asn Pro Gly Asn
225                 230                 235                 240

Tyr Gly Gly Val Asp Asn Val Lys Cys Ser Gly Thr Asn Thr Pro Val
                245                 250                 255

Arg
```

<210> SEQ ID NO 49
<211> LENGTH: 218
<212> TYPE: PRT
<213> ORGANISM: Artificial Sequence
<220> FEATURE:
<223> OTHER INFORMATION: Description of Artificial Sequence; note = synthetic construct

<400> SEQUENCE: 49

```
Gly Ala Leu Val Gln Ser Ala Val Ala Cys Pro Ser Gln Cys Ser Cys
 1               5                  10                  15

Gly Lys Phe Ser Trp Ser Gly Glu Leu Gln Thr Thr Asp Cys Asp Gly
            20                  25                  30

Lys Gly Leu Ser Ser Val Pro Ser Gly Ile Pro Asp Asn Thr Gln Asn
        35                  40                  45

Leu Asp Leu Arg Lys Asn Gln Ile Asp Arg Leu Pro Glu Gly Val Phe
    50                  55                  60
```

```
Asp Arg Leu Val Asn Leu Gln Lys Leu Trp Leu Asn Ser Asn Gln Leu
65                  70                  75                  80

Thr Ser Leu Pro Ala Gly Val Phe Asp Ser Leu Thr Gln Leu Thr Arg
                85                  90                  95

Leu Asp Leu Asp Asn Asn Gln Leu Thr Val Leu Pro Ala Gly Val Cys
            100                 105                 110

Asp Ser Leu Val Asn Leu Lys Glu Leu Arg Leu Tyr Asn Asn Gln Leu
        115                 120                 125

Thr Ala Leu Pro Ala Gly Val Phe Asp Lys Leu Thr Leu Leu Ala Gly
    130                 135                 140

Leu Ser Leu His Asp Asn Gln Leu Lys Ser Ile Pro Arg Ser Ala Phe
145                 150                 155                 160

Asp Asn Leu Lys Ser Leu Thr His Ile Tyr Leu Phe Asn Asn Pro Trp
                165                 170                 175

Asp Cys Glu Cys Ser Asp Ile Leu Tyr Leu Lys Asn Trp Ile Val Gln
            180                 185                 190

His Ala Ser Ile Val Asn Pro Gly Asn Tyr Gly Gly Val Asp Asn Val
        195                 200                 205

Lys Cys Ser Gly Thr Asn Thr Pro Val Arg
    210                 215


<210> SEQ ID NO 50
<211> LENGTH: 161
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 50

Gly Ala Leu Val Gln Ser Ala Val Ala Cys Pro Ser Gln Cys Ser Cys
 1               5                  10                  15

Ser Gly Thr Thr Val Asp Cys Arg Ser Leu Ala Ser Val Pro Ala Gly
            20                  25                  30

Ile Pro Thr Thr Thr Gln Val Leu Gly Leu Ser Ser Asn Gln Ile Thr
        35                  40                  45

Lys Leu Glu Pro Gly Val Phe Asp Arg Leu Val Asn Leu Gln Gln Leu
    50                  55                  60

Trp Leu Glu Ile Asn Gln Leu Thr Ser Leu Pro Ala Gly Val Phe Asp
65                  70                  75                  80

Lys Leu Thr Gln Leu Thr Tyr Leu Asn Leu Arg Asp Asn Gln Leu Lys
                85                  90                  95

Ser Ile Pro Arg Gly Ala Phe Asp Asn Leu Lys Ser Leu Thr His Ile
            100                 105                 110

Tyr Leu Phe Asn Asn Pro Trp Asp Cys Glu Cys Ser Asp Ile Leu Tyr
        115                 120                 125

Leu Lys Asn Trp Ile Val Gln His Ala Ser Ile Val Asn Pro Gly Asn
    130                 135                 140

Tyr Gly Gly Val Asp Asn Val Lys Cys Ser Gly Thr Asn Thr Pro Val
145                 150                 155                 160

Arg


<210> SEQ ID NO 51
<211> LENGTH: 163
<212> TYPE: PRT
<213> ORGANISM: Artificial Sequence
<220> FEATURE:
<223> OTHER INFORMATION: Description of Artificial Sequence; note =
```

synthetic construct

<400> SEQUENCE: 51

Gly Ala Leu Val Gln Ser Ala Val Ala Cys Pro Ser Gln Cys Ser Cys
1 5 10 15

Asp Gln Thr Thr Val Asp Cys Arg Asn Lys Arg Phe Ser Ser Val Pro
20 25 30

Ala Gly Ile Pro Thr Asp Ser Gln Ser Leu Trp Leu Asn Asp Asn Gln
35 40 45

Ile Thr Lys Leu Glu Pro Gly Leu Phe Asp Arg Met Glu Asn Leu Gln
50 55 60

His Leu Tyr Met Glu Asn Ile Lys Leu Ser Ala Val Pro Val Gly Gln
65 70 75 80

Phe Asp Lys Leu Thr Gln Leu Thr His Leu Gly Leu His Asn Asn Gln
85 90 95

Leu Lys Ser Ile Pro Arg Gly Ala Phe Asp Asn Leu Lys Ser Leu Thr
100 105 110

His Ile Trp Leu Phe Gly Asn Pro Trp Asp Cys Glu Cys Ser Asp Ile
115 120 125

Leu Tyr Leu Lys Asn Trp Ile Val Gln His Ala Ser Ile Val Asn Pro
130 135 140

Gly Asn Tyr Gly Gly Val Asp Asn Val Lys Cys Ser Gly Thr Asn Thr
145 150 155 160

Pro Val Arg

<210> SEQ ID NO 52
<211> LENGTH: 139
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 52

Gly Ala Leu Val Gln Ser Ala Val Ala Cys Pro Ser Gln Cys Ser Cys
1 5 10 15

Asp Gln Thr Thr Val Asp Cys Arg Asn Lys Arg Phe Ser Ser Val Pro
20 25 30

Ala Gly Ile Pro Thr Thr Thr Arg Val Leu Tyr Leu Asn Ser Asn Gln
35 40 45

Ile Thr Lys Leu Glu Pro Gly Val Phe Asp Arg Leu Gly Asn Leu Gln
50 55 60

Arg Val Asp Leu Ser Asn Asn Gln Leu Lys Ser Ile Pro Arg Gly Ala
65 70 75 80

Phe Asp Asn Leu Lys Ser Leu Thr His Ile Trp Leu Phe Gly Asn Pro
85 90 95

Trp Asp Cys Glu Cys Ser Asp Ile Leu Tyr Leu Lys Asn Trp Ile Val
100 105 110

Gln His Ala Ser Ile Val Asn Leu Trp Gly Tyr Gly Gly Val Asp Asn
115 120 125

Val Lys Cys Ser Gly Thr Asn Thr Pro Val Arg
130 135

<210> SEQ ID NO 53
<211> LENGTH: 495
<212> TYPE: DNA
<213> ORGANISM: Artificial Sequence
<220> FEATURE:

<223> OTHER INFORMATION: Description of Artificial Sequence; note = synthetic construct

<400> SEQUENCE: 53

```
ggcgccctgg tgcaaagtgc ggtagcatgt ccctcgcagt gttcgtgctc agggacagaa      60
gtgcactgtc agaaaaaaag cctcgcgtct gtgcctgcgg gaatccccac caccacgcga     120
gtactgcatt tgcacaccaa tcagatcacg aagctcgagc ccggggtgtt tgacagtctg     180
acccagctga cagttctgtc tctgcctaca aaccacctgc aggcccttcc cgatggagtg     240
tttgacaaac tgacccagct cactcttcta gaactgcaaa acaaccagct gaagagtatt     300
cccaggggcg cctttgacaa cctcaagagc ctcactcaca tctggctgtt cgacaaccc     360
tgggactgtg cctgctcaga catcctgtac ctcagtcgct ggatctctca gcacccaggg     420
gtcttgagga atgccggttc ctacaatatc aaccccgacc aggcacactg ctctggtacc     480
aatacccccg tccgt                                                     495
```

<210> SEQ ID NO 54
<211> LENGTH: 163
<212> TYPE: PRT
<213> ORGANISM: Artificial Sequence
<220> FEATURE:
<223> OTHER INFORMATION: Description of Artificial Sequence; note = synthetic construct

<400> SEQUENCE: 54

```
Gly Ala Leu Val Gln Ser Ala Val Ala Cys Pro Ser Gln Cys Ser Cys
  1               5                  10                  15

Asp Gln Thr Leu Val Asn Cys Gln Asn Ile Arg Leu Ala Ser Val Pro
             20                  25                  30

Ala Gly Ile Pro Thr Asp Lys Gln Arg Leu Trp Leu Asn Asn Asn Gln
         35                  40                  45

Ile Thr Lys Leu Glu Pro Gly Val Phe Asp Ser Leu Val Asn Leu Gln
     50                  55                  60

Lys Leu Tyr Leu Trp Gly Asn Gln Leu Gln Ala Leu Pro Ala Arg Val
 65                  70                  75                  80

Phe Asp Lys Leu Thr Gln Leu Ala His Leu Glu Leu Gln Asn Asn Gln
                 85                  90                  95

Leu Lys Ser Ile Pro Arg Gly Ala Phe Asp Asn Leu Lys Ser Leu Thr
            100                 105                 110

His Ile Trp Leu Phe Gly Asn Pro Trp Asp Cys Glu Cys Ser Asp Ile
        115                 120                 125

Leu Tyr Leu Lys Asn Trp Ile Val Gln His Ala Ser Ile Val Asn Leu
    130                 135                 140

Gln Gly His Gly Gly Val Asp Asn Val Lys Cys Ser Gly Thr Asn Thr
145                 150                 155                 160

Pro Val Arg
```

<210> SEQ ID NO 55
<211> LENGTH: 417
<212> TYPE: DNA
<213> ORGANISM: Artificial Sequence
<220> FEATURE:
<223> OTHER INFORMATION: Description of Artificial Sequence; note = synthetic construct

<400> SEQUENCE: 55

```
ggcgccctgg tgcaaagtgc ggtagcatgt ccctcgcagt gttcgtgctc aggggcagaa      60
gtgcgctgtg tgagcaaaag cctcgcgtct gtgcctgcag gaatccccat caccacgcag     120
```

tctctgtctt tgcactatac tcagatcacg aagctcgagc ccggggtgtt tgaccgcctg 180
gtgaatctgc agcagctgta tctgggctcg aaccagctga agagcattcc taggggcgcc 240
tttgacaacc tcaagagcct cactcacatc tatctgttca acaacccctg ggactgcgag 300
tgttcggaca tcctctatct gaagaactgg attgtgcagc atgcaagcat cgtgaatcta 360
cggggccatg gggagttga taacgtgaag tgctctggta ccaatacccc cgtccgt 417

<210> SEQ ID NO 56
<211> LENGTH: 183
<212> TYPE: PRT
<213> ORGANISM: Artificial Sequence
<220> FEATURE:
<223> OTHER INFORMATION: Description of Artificial Sequence; note = synthetic construct

<400> SEQUENCE: 56

```
Gly Ala Leu Val Gln Ser Ala Val Ala Cys Pro Ser Gln Cys Ser Cys
 1               5                  10                  15

Asp Gln Thr Thr Val Asn Cys His Asn Arg Arg Leu Thr Ser Val Pro
            20                  25                  30

Ala Gly Ile Pro Thr Asn Arg Gln Asn Leu Trp Leu His Asp Asn Gln
        35                  40                  45

Ile Thr Lys Leu Glu Pro Gly Val Phe Asp Ser Leu Val Asn Leu Gln
    50                  55                  60

Arg Leu His Leu Asp Gln Asn Gln Leu Gln Ala Leu Pro Ala Gly Leu
65                  70                  75                  80

Phe Asn Arg Leu Gly Asn Leu Gln Glu Leu Tyr Met Cys Cys Asn Lys
                85                  90                  95

Phe Thr Glu Leu Pro His Gly Ile Asp Lys Leu Thr Gln Leu Ser Leu
            100                 105                 110

Asn Gln Asn Gln Leu Lys Ser Ile Pro Asp Gly Ala Phe Ala Arg Leu
        115                 120                 125

Pro Ser Leu Thr His Val Trp Leu His Thr Asn Pro Trp Asp Cys Glu
    130                 135                 140

Cys Ser Asp Ile Leu Tyr Leu Lys Asn Trp Ile Val Gln His Ala Ser
145                 150                 155                 160

Ile Val Asn Pro His Pro Tyr Gly Gly Val Asp Asn Val Lys Cys Ser
                165                 170                 175

Gly Thr Asn Thr Pro Val Arg
            180
```

<210> SEQ ID NO 57
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 57
ggcgccctgg tgcaaagtgc ggtagcatgt ccctcgcagt gttcgtgctc agggacagaa 60
gtgaactgtg cagggaaaag cctcgcgtct gtgcctgcag gaatccccac cacaacgcga 120
gtgctgtatt tgaacagcaa tcagatcacg aagctcgagc ccggggtgtt tgacagtctg 180
acggcactaa cttatttggg tcttggtggc aaccagctgg cagctctacc cgagaatgtg 240
tttgaccgtc tgactcaact gacacgactg gatctttaca ataaccagtt gacagttctc 300
cccgccgggg tgtgtgacag cctggtgaat ctgaaggagc tgcgtttgta caacaaccag 360
ctgaagagca ttcccagggg cgcctttgac aacctcaaga gcctcactca catctatctg 420
ttcaacaacc cctgggactg cgagtgttcg gacatcctct atctgaagaa ctggattgtg 480
cagcacgcaa gcatcgtgaa tccacacccc tatgggggag ttgataacgt gaagtgctct 540
ggtaccaata cccccgtccg t 561

<210> SEQ ID NO 58
<211> LENGTH: 468
<212> TYPE: DNA
<213> ORGANISM: Artificial Sequence
<220> FEATURE:
<223> OTHER INFORMATION: Description of Artificial Sequence; note = synthetic construct

<400> SEQUENCE: 58
ggcgccctgg tgcaaagtgc ggtagcatgt ccctcgcagt gttcgtgcga tcagacaact 60
gtggactgcc ggaacaaacg cttctcgtct gtgcctgcgg gaatccccac cgacaggcag 120
aacctgtggt tgaataacaa tcagatcacg aagctcgagc ccggggtgtt tgaccgattg 180
actcaattga cgcatctgga tctggatagg aaccaactga agtctctgcc gcctgggatc 240
tttgacaaac tggagaagct gacgcgtctg gagctgtaca ataaccagct gacgaccgtt 300
cccgagggcg cctttaacag cctcatgaag ctgcaataca tttggctgca cagtaacccc 360
tgggactgtg cttgctcaga catcctctac ctcagcggct ggctgggcca gcacgcaggg 420
aaagagcagg gccaggctgt ctgctctggt accaataccc ccgtccgt 468

<210> SEQ ID NO 59
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 59
ggcgccctgg tgcaaagtgc ggtagcatgt ccctcgcagt gttcgtgcga tcagacactt 60
gtgaactgcc agaatacacg cctcgcatct gtgcctgcgg gaatccccac cacaacgcga 120
gtgctgtatt tgaacagcaa tcagatcacg aagctcgagc ccggggtgtt tgaccgcctg 180
ttgaatctgc aacagttgta tttgcatctg aaccgactgt cgtccatacc cgctggggtg 240
tttgacaaat tgcccaagct cacacatttg gttctgcaca ccaaccagct gaagagcatt 300
cccaggggcg cctttgacaa cctcaagagc ctcactcaca tctacctgca caacaacccc 360
tgggactgcg agtgttcgga catcctctat ctgaagaact ggattgtgca gcacgcaagc 420
atcgtgaatc catcgggcta tgggggagtt gataacgtga agtgctctgg taccaatacc 480
cccgtccgt 489

<210> SEQ ID NO 60
<211> LENGTH: 187
<212> TYPE: PRT
<213> ORGANISM: Artificial Sequence
<220> FEATURE:
<223> OTHER INFORMATION: Description of Artificial Sequence; note = synthetic construct

<400> SEQUENCE: 60

Gly Ala Leu Val Gln Ser Ala Val Ala Cys Pro Ser Gln Cys Ser Cys
1 5 10 15

Asp Gln Thr Thr Val Tyr Cys His Ser Arg Arg Leu Thr Ser Val Pro

```
            20                  25                  30

Ala Gly Ile Pro Thr Thr Thr Arg Gly Leu His Leu His Thr Asn Gln
        35                  40                  45

Ile Thr Lys Leu Glu Pro Gly Val Phe Asp Ser Leu Thr Gln Leu Thr
    50                  55                  60

Glu Pro Tyr Leu Ser Ala Asn Gln Leu Thr Thr Leu Pro Ala Gly Leu
65                  70                  75                  80

Phe Asp Arg Leu Val Lys Leu Lys Glu Leu Tyr Leu Trp Gly Asn Gln
                85                  90                  95

Leu Ser Ala Leu Pro Val Gly Val Phe Asp Lys Leu Thr Arg Leu Lys
            100                 105                 110

Gln Leu Gly Leu His Thr Asn Gln Leu Lys Ser Ile Pro Arg Gly Ala
        115                 120                 125

Phe Asp Asn Leu Lys Ser Leu Thr His Ile Trp Leu Phe Gly Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Pro Ser Gly His Gly Gly Val Asp Asn
                165                 170                 175

Val Lys Cys Ser Gly Thr Asn Thr Pro Val Arg
            180                 185


<210> SEQ ID NO 61
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 61

Gly Ala Leu Val Gln Ser Ala Val Ala Cys Pro Ser Gln Cys Ser Cys
 1               5                  10                  15

Asp Gln Thr Thr Val Asn Cys His Ser Arg Arg Leu Thr Ser Val Pro
            20                  25                  30

Ala Gly Ile Pro Thr Asn Arg Gln Asn Leu Trp Leu His Asp Asn Gln
        35                  40                  45

Ile Thr Lys Leu Glu Pro Gly Val Phe Asp Ser Leu Thr Gln Leu Thr
    50                  55                  60

Tyr Leu His Leu Ala Ala Asn Gln Leu Thr Ala Leu Pro Val Gly Val
65                  70                  75                  80

Phe Asp Lys Leu Pro Lys Leu Thr His Leu Val Leu His Thr Asn Gln
                85                  90                  95

Leu Lys Ser Val Pro Arg Gly Ala Phe Asp Asn Leu Lys Ser Leu Thr
            100                 105                 110

His Ile Trp Leu Phe Gly Asn Pro Trp Asp Cys Glu Cys Ser Asp Ile
        115                 120                 125

Leu Tyr Leu Lys Asn Trp Ile Val Gln His Ala Ser Ile Val Asn Leu
    130                 135                 140

Gln Gly His Gly Gly Val Asp Asn Val Lys Cys Ser Gly Thr Asn Thr
145                 150                 155                 160

Pro Val Arg


<210> SEQ ID NO 62
<211> LENGTH: 139
<212> TYPE: PRT
<213> ORGANISM: Artificial Sequence
```

<220> FEATURE:
<223> OTHER INFORMATION: Description of Artificial Sequence; note = synthetic construct

<400> SEQUENCE: 62

```
Gly Ala Leu Val Gln Ser Ala Val Ala Cys Pro Ser Gln Cys Ser Cys
 1               5                  10                  15

Asp Gln Thr Thr Val Tyr Cys His Ser Arg Arg Leu Thr Ser Val Pro
            20                  25                  30

Ala Gly Ile Pro Thr Asn Ala Gln Ile Leu Tyr Leu His Asp Asn Gln
        35                  40                  45

Ile Thr Lys Leu Glu Pro Gly Leu Phe Asp Lys Leu Thr Gln Leu Thr
    50                  55                  60

Arg Leu Glu Leu Gln Thr Asn Gln Leu Lys Ser Ile Pro Arg Gly Ala
65                  70                  75                  80

Phe Asp Asn Leu Lys Ser Leu Thr His Ile Trp Leu Leu Asn Asn Pro
                85                  90                  95

Trp Asp Cys Glu Cys Ser Asp Ile Leu Tyr Leu Lys Asn Trp Ile Val
            100                 105                 110

Gln His Ala Ser Ile Val Asn Leu Gln Gly His Gly Gly Val Asp Asn
        115                 120                 125

Val Lys Cys Ser Gly Thr Asn Thr Pro Val Arg
    130                 135
```

<210> SEQ ID NO 63
<211> LENGTH: 187
<212> TYPE: PRT
<213> ORGANISM: Artificial Sequence
<220> FEATURE:
<223> OTHER INFORMATION: Description of Artificial Sequence; note = synthetic construct

<400> SEQUENCE: 63

```
Gly Ala Leu Val Gln Ser Ala Val Ala Cys Pro Ser Gln Cys Ser Cys
 1               5                  10                  15

Asp Gln Thr Thr Val Tyr Cys His Ser Arg Arg Leu Thr Ser Val Pro
            20                  25                  30

Ala Gly Ile Pro Thr Asp Arg Gln Asn Leu Trp Leu Tyr Asp Asn Gln
        35                  40                  45

Ile Thr Lys Leu Glu Pro Gly Val Phe Asp Arg Leu Thr Gln Leu Thr
    50                  55                  60

Ile Leu Ser Leu Tyr Asp Asn Gln Leu Ser Ala Leu Pro Ala Gly Val
65                  70                  75                  80

Phe Asp Arg Leu Val Asn Leu Gln Gln Leu Tyr Leu Gly Gly Asn Gln
                85                  90                  95

Leu Gly Ala Leu Pro Val Gly Val Phe Asp Asn Leu Thr Gln Leu Ser
            100                 105                 110

Ile Leu Asn Met His Thr Asn Gln Leu Lys Ser Ile Pro Arg Gly Ala
        115                 120                 125

Phe Asp Asn Leu Lys Ser Leu Thr His Ile Trp Leu Leu Asn Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Pro Ser Gly His Gly Gly Val Asp Asn
                165                 170                 175

Val Lys Cys Ser Gly Thr Asn Thr Pro Val Arg
            180                 185
```

<210> SEQ ID NO 64
<211> LENGTH: 163
<212> TYPE: PRT
<213> ORGANISM: Artificial Sequence
<220> FEATURE:
<223> OTHER INFORMATION: Description of Artificial Sequence; note = synthetic construct

<400> SEQUENCE: 64

```
Gly Ala Leu Val Gln Ser Ala Val Ala Cys Pro Ser Gln Cys Ser Cys
 1               5                  10                  15

Asp Gln Thr Thr Val Lys Cys His Ser Arg Arg Leu Thr Ser Val Pro
            20                  25                  30

Ala Gly Ile Pro Thr Thr Thr Arg Val Leu Tyr Leu Asn Asp Asn Gln
        35                  40                  45

Ile Thr Lys Leu Glu Pro Gly Val Phe Asp Arg Leu Val Asn Leu Gln
    50                  55                  60

Gln Leu Tyr Leu Gly Ala Asn Gln Leu Ser Ala Leu Pro Asp Gly Val
65                  70                  75                  80

Phe Asn Lys Leu Thr Gln Leu Thr His Leu Ser Leu Tyr Asn Asn Gln
                85                  90                  95

Leu Lys Asn Ile Pro Arg Gly Ala Phe Asp Asn Leu Lys Ser Leu Thr
            100                 105                 110

Tyr Ile Tyr Leu Phe Asn Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

Ser Gly His Gly Gly Val Asp Asn Val Lys Cys Ser Gly Thr Asn Thr
145                 150                 155                 160

Pro Val Arg
```

<210> SEQ ID NO 65
<211> LENGTH: 161
<212> TYPE: PRT
<213> ORGANISM: Artificial Sequence
<220> FEATURE:
<223> OTHER INFORMATION: Description of Artificial Sequence; note = synthetic construct

<400> SEQUENCE: 65

```
Gly Ala Leu Val Gln Ser Ala Val Ala Cys Pro Ser Gln Cys Ser Cys
 1               5                  10                  15

Asp Gln Thr Thr Val Tyr Cys His Ser Arg Arg Leu Thr Ser Val Pro
            20                  25                  30

Ala Gly Ile Pro Thr Thr Thr Gln Val Leu Tyr Lys Asn Gln Ile Thr
        35                  40                  45

Lys Leu Glu Pro Gly Val Phe Asp Arg Leu Gly Asn Leu Gln Gln Leu
    50                  55                  60

Tyr Leu Gly Gly Asn Gln Leu Ser Ala Leu Pro Thr Gly Val Phe Asp
65                  70                  75                  80

Lys Leu Thr Gln Leu Thr Leu Leu Glu Leu Gln Asn Asn Gln Leu Thr
                85                  90                  95

Ser Ile Pro Arg Gly Ala Phe Asp Asn Leu Lys Ser Leu Thr His Ile
            100                 105                 110

Tyr Leu Phe Asn Asn Pro Trp Asp Cys Glu Cys Ser Asp Ile Leu Tyr
        115                 120                 125

Leu Lys Asn Trp Ile Val Gln His Ala Ser Ile Val Asn Pro Leu Gly
    130                 135                 140
```

Asn Gly Gly Val Asp Asn Val Lys Cys Ser Gly Thr Asn Thr Pro Val
145 150 155 160

Arg

<210> SEQ ID NO 66
<211> LENGTH: 417
<212> TYPE: DNA
<213> ORGANISM: Artificial Sequence
<220> FEATURE:
<223> OTHER INFORMATION: Description of Artificial Sequence; note = synthetic construct

<400> SEQUENCE: 66
ggcgccctgg tgcaaagtgc ggtagcatgt ccctcgcagt gttcgtgctc agggacagaa 60
gtgcactgtc agaaaaaaag cctcgcgtct gtgcctgcag gaatccccac caccacgcaa 120
gtgctgtatt tgcacgtcaa tcagatcacg aagctcaagc ccggggtgtt tgaccgcctg 180
gtgaatctgc aacgcctgta tctgaatcag aaccagctga agagcattcc caggggcgcc 240
tttgacaacc tcaagagcct cactcagatc tggctgttca acaacccctg ggactgcgag 300
tgttcggaca tcctctatct gaagaactgg attgtgcagc acgcaagcat cgtgaatcca 360
tcgggccatg ggggagttga taacgtgaag tgctctggta ccaatacccc cgtccgt 417

<210> SEQ ID NO 67
<211> LENGTH: 630
<212> TYPE: DNA
<213> ORGANISM: Artificial Sequence
<220> FEATURE:
<223> OTHER INFORMATION: Description of Artificial Sequence; note = synthetic construct

<400> SEQUENCE: 67
ggcgccctgg tgcaaagtgc ggtagcatgt ccctcgcagt gttcgtgcga tcagacaact 60
gtgaaatgcc atagcagacg cctcacgtct gtgcctgcgg gaatccccac aaacaggcag 120
aacctgtggt tgcacgacaa tcagatcacg aagctcgagc ccggggtgtt tgaccgcctg 180
gggaatctgc agcagattaa tctgagcaac aaccagctgc aggcgctacc cgctgggctg 240
tttgacagcc tgacgcaact gacttatctg aaccttgctg ttaaccagct gcaggctctt 300
cccgctgggt tgtttgaccg cctggggaat ctagaggttc tgggtttgtg ctgcaacaag 360
ctcacagagc tgcccagtgg cgtgtttgac aaacttaccc ggctgaagtg gttgggtctg 420
gaccagaatc aactgaagag catccctgac ggcgcgttcg ctcgtctccc gagcctcact 480
cacatctggc tgtacggcaa cccctgggac tgcgagtgtt cggacatcct ctatctgaag 540
aactggattg tgcagcacgc aagcatcgtg aatccaggca acgggggagt tgataacgtc 600
aagtgctctg gtaccaatac ccccgtccgt 630

<210> SEQ ID NO 68
<211> LENGTH: 187
<212> TYPE: PRT
<213> ORGANISM: Artificial Sequence
<220> FEATURE:
<223> OTHER INFORMATION: Description of Artificial Sequence; note = synthetic construct

<400> SEQUENCE: 68

Gly Ala Leu Val Gln Ser Ala Val Ala Cys Pro Ser Gln Cys Ser Cys
1 5 10 15

Ser Gly Thr Thr Val Asp Cys Arg Ser Lys Arg His Ala Ser Val Pro
20 25 30

```
Ala Gly Ile Pro Thr Asn Ala Gln Ile Leu Tyr Leu His Asp Asn Gln
        35                  40                  45

Ile Thr Lys Leu Glu Pro Gly Val Phe Asn Ser Leu Ala Asn Leu Arg
    50                  55                  60

Glu Leu His Leu Trp Gly Asn Gln Leu Val Ser Leu Pro Pro Gly Val
65                  70                  75                  80

Phe Asp Arg Leu Val Asn Leu Gln Thr Leu Asp Leu His Asn Asn Gln
                85                  90                  95

Leu Ser Ala Leu Pro Val Gly Val Phe Asp Asn Leu Thr Gln Leu Ser
            100                 105                 110

Ile Leu Asn Met His Thr Asn Gln Leu Lys Ser Ile Pro Arg Gly Ala
        115                 120                 125

Phe Asp Asn Leu Lys Ser Leu Thr His Ile Trp Leu Ser Asn Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Pro Ser Gly Tyr Gly Gly Val Asp Asn
                165                 170                 175

Val Lys Cys Ser Gly Thr Asn Thr Pro Val Arg
            180                 185


<210> SEQ ID NO 69
<211> LENGTH: 187
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 69

Gly Ala Leu Val Gln Ser Ala Val Ala Cys Pro Ser Gln Cys Ser Cys
 1              5                   10                  15

Ser Gly Thr Thr Val Asp Cys Arg Ser Lys Arg His Ala Ser Val Pro
            20                  25                  30

Ala Gly Ile Pro Thr Asn Ala Gln Ile Leu Tyr Leu His Asp Asn Gln
        35                  40                  45

Ile Thr Lys Leu Glu Pro Gly Val Phe Asp Ser Leu Thr Pro Leu Thr
    50                  55                  60

Phe Leu Asn Leu Gly Asn Asn Gln Leu Thr Ala Leu Pro Glu Gly Val
65                  70                  75                  80

Leu Asp Phe Leu Thr Gln Leu Thr Ser Leu Thr Leu His Thr Asn Gln
                85                  90                  95

Leu Gln Ala Leu Pro Ala Gly Leu Phe Asp Arg Leu Val Asn Leu Gln
            100                 105                 110

Lys Leu Tyr Leu His Glu Asn Gln Leu Lys Ser Ile Pro Arg Gly Ala
        115                 120                 125

Phe Asp Asn Leu Lys Ser Leu Thr His Ile Trp Leu Ser Asn Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Leu Glu Gly His Gly Gly Val Asp Asn
                165                 170                 175

Val Lys Cys Ser Gly Thr Asn Thr Pro Val Arg
            180                 185


<210> SEQ ID NO 70
```

-continued

<211> LENGTH: 163
<212> TYPE: PRT
<213> ORGANISM: Artificial Sequence
<220> FEATURE:
<223> OTHER INFORMATION: Description of Artificial Sequence; note = synthetic construct

<400> SEQUENCE: 70

```
Gly Ala Leu Val Gln Ser Ala Val Ala Cys Pro Ser Gln Cys Ser Cys
 1               5                  10                  15

Ser Gly Thr Thr Val Asp Cys Arg Ser Lys Arg His Ala Ser Val Pro
            20                  25                  30

Ala Gly Ile Pro Thr Asn Ala Gln Ile Leu Tyr Leu His Asp Asn Gln
        35                  40                  45

Ile Thr Lys Leu Glu Pro Gly Val Phe Asp Ser Leu Thr Gln Leu Thr
    50                  55                  60

Glu Leu Tyr Leu Ser Ala Asn Gln Leu Gln Ala Leu Pro Glu Gly Val
65                  70                  75                  80

Phe Asp Arg Leu Val Asn Leu Gln Arg Leu Trp Leu Asn Asn Asn Gln
                85                  90                  95

Leu Lys Ser Ile Pro Arg Gly Ala Phe Asp Asn Leu Lys Ser Leu Thr
            100                 105                 110

His Ile Trp Leu Phe Gly Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

His Pro His Gly Gly Val Asp Asn Val Lys Cys Ser Gly Thr Asn Thr
145                 150                 155                 160

Pro Val Arg
```

<210> SEQ ID NO 71
<211> LENGTH: 139
<212> TYPE: PRT
<213> ORGANISM: Artificial Sequence
<220> FEATURE:
<223> OTHER INFORMATION: Description of Artificial Sequence; note = synthetic construct

<400> SEQUENCE: 71

```
Gly Ala Leu Val Gln Ser Ala Val Ala Cys Pro Ser Gln Cys Ser Cys
 1               5                  10                  15

Ser Gly Thr Thr Val Asp Cys Arg Ser Lys Arg His Ala Ser Val Pro
            20                  25                  30

Ala Gly Ile Pro Thr Thr Thr His Phe Leu Tyr Leu His Ser Asn Gln
        35                  40                  45

Ile Thr Lys Leu Glu Pro Gly Val Phe Asp Ser Leu Gly Asn Leu Gln
    50                  55                  60

Lys Leu Trp Leu His Arg Asn Gln Leu Lys Asn Ile Pro Arg Gly Ala
65                  70                  75                  80

Phe Asp Asn Leu Lys Ser Leu Thr Tyr Ile Tyr Leu Phe Asn Asn Pro
                85                  90                  95

Trp Asp Cys Glu Cys Ser Asp Ile Leu Tyr Leu Lys Asn Trp Ile Val
            100                 105                 110

Gln His Ala Ser Ile Val Asn Pro His Pro Tyr Gly Gly Val Asp Asn
        115                 120                 125

Val Lys Cys Ser Gly Thr Asn Thr Pro Val Arg
    130                 135
```

<210> SEQ ID NO 72
<211> LENGTH: 139
<212> TYPE: PRT
<213> ORGANISM: Artificial Sequence
<220> FEATURE:
<223> OTHER INFORMATION: Description of Artificial Sequence; note = synthetic construct

<400> SEQUENCE: 72

```
Gly Ala Leu Val Gln Ser Ala Val Ala Cys Pro Ser Gln Cys Ser Cys
 1               5                  10                  15

Ser Gly Thr Ser Val Asp Cys Asn Ser Arg Arg His Ala Ser Val Pro
            20                  25                  30

Ala Gly Ile Pro Thr Thr Thr Arg Val Leu Tyr Leu Asn Asp Asn Gln
        35                  40                  45

Ile Thr Lys Leu Glu Pro Gly Val Phe Asp Ser Leu Val Asn Leu Gln
    50                  55                  60

Gln Leu Ala Leu Asn Asn Asn Gln Leu Lys Gly Val Pro Arg Gly Ala
65                  70                  75                  80

Phe Asp Asn Leu Lys Ser Leu Thr His Ile Trp Leu Leu Asn Asn Pro
                85                  90                  95

Trp Asp Cys Glu Cys Ser Asp Ile Leu Tyr Leu Lys Asn Trp Ile Val
            100                 105                 110

Gln His Ala Ser Ile Val Asn Leu Trp Asn Asn Gly Gly Val Asp Asn
        115                 120                 125

Val Lys Cys Ser Gly Thr Asn Thr Pro Val Arg
    130                 135
```

<210> SEQ ID NO 73
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 73

```
ggcgccctgg tgcaaagtgc ggtagcatgt ccctcgcagt gttcgtgctc agggacatct      60

gtggattgcc ggagcagaag acacgcgtct gtgcctgcgg gaatccccac caatgcgcag     120

attctgtatt tacacgacaa tcagatcacg aagctcgagc ccggggtgtt tgacagtctg     180

acccagttga ctattttgga tcttaatagc aaccagctgc aggctcttcc cgctgggttg     240

tttgaccgcc tggtgaatct gcagcagctg tggttagaaa tcaaccagct gtcggctcta     300

cctgttgggg tgtttgacaa cctgacccag cttagcatac tgaatatgca caccaaccag     360

ctgaagagcg ttcccagggg cgcctttgac aacctcaaga gcctcactca catctggctg     420

ttgaacaacc cctgggactg cgagtgttcg gacatcctct atctgaagaa ctggattgta     480

cagcacgcaa gcatcgtgaa tctacagggc catgggggag ttgataacgt gaagtgctct     540

ggtaccaata cccccgtccg t                                               561
```

<210> SEQ ID NO 74
<211> LENGTH: 417
<212> TYPE: DNA
<213> ORGANISM: Artificial Sequence
<220> FEATURE:
<223> OTHER INFORMATION: Description of Artificial Sequence; note = synthetic construct

<400> SEQUENCE: 74

```
ggcgccctgg tgcaaagtgc ggtagcatgt ccctcgcagt gttcgtgcga tcagacaact      60
```

-continued

```
gtgaaatgcc atagcagacg cctcacgtct gtgcctgcgg gaatccccac aaacaggcag    120

aacctgtggt tgtacgacaa tcagatcacg aagctcgagc ccggggtgtt tgacaaactg    180

acccagctca cacatttggt tctgcacacc aaccagctga agagcattcc caggggcgcc    240

tttgacaacc tcaagagcct cactcacatc tggctgtacg gcaacccctg ggactgcgcc    300

tgcacggaca ttatgtatct cagcacgtgg atcggtcaga attcgggtaa agtaactaag    360

gaaagtgtaa acaacccaga tagcgccgtg tgctctggta ccaatacccc cgtccgt       417
```

<210> SEQ ID NO 75
<211> LENGTH: 162
<212> TYPE: PRT
<213> ORGANISM: Artificial Sequence
<220> FEATURE:
<223> OTHER INFORMATION: Description of Artificial Sequence; note = synthetic construct

<400> SEQUENCE: 75

```
Gly Ala Leu Val Gln Ser Ala Val Ala Cys Pro Ser Gln Cys Ser Cys
 1               5                  10                  15

Ser Gly Thr Glu Val Arg Cys Val Ser Lys Ser Leu Ala Ser Val Pro
            20                  25                  30

Ala Gly Ile Pro Ile Thr Thr Gln Ser Leu Ser Leu His Tyr Thr Gln
        35                  40                  45

Ile Thr Lys Leu Glu Pro Gly Val Phe Asp Ser Leu Val Asn Leu Gln
    50                  55                  60

Gln Leu Trp Leu Glu Ile Asn Gln Leu Thr Ser Leu Pro Ala Gly Leu
65                  70                  75                  80

Phe Asp Arg Leu Gly Asn Leu Gln Gln Ile Asn Leu Ser Asn Asn Gln
                85                  90                  95

Leu Lys Ser Ile Pro Arg Gly Ala Phe Asp Asn Leu Lys Ser Leu Thr
            100                 105                 110

His Val Trp Leu His Thr Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

Gly Ser Gly Gly Val Asp Asn Val Lys Cys Ser Gly Thr Asn Thr Pro
145                 150                 155                 160

Val Arg
```

<210> SEQ ID NO 76
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 76

```
ggcgccctgg tgcaaagtgc ggtagcatgt ccctcgcagt gttcgtgctc agggacagaa     60

gtgcactgtg cagggaaaag cctcgcgtct gtgcctgcgg gaatccccac caccacgcag    120

tatctgaatt tgcacgtcaa tcagatcacg aagctcgagc ccggggtgtt tgacagtctg    180

acgccactga ctattctggc tctgaatgac aaccagctgc aggccctttc cgagggattg    240

tttgaccgcc tgggaaatct acagaagctg tggctgcaca gaaaccagct gaagagcatt    300

cccaggggca cctttgataa cctcaagagc ctcactcaca tctatctgtt caacaacccc    360

tgggactgcg aatgttcgga catcctctat ctgaagaact ggattgtgca gcacgcaagc    420
```

```
atcgtgaatc cagggaacta tgggggagtt gataacgtga agtgctctgg taccaatacc    480

cccgtccgt                                                            489


<210> SEQ ID NO 77
<211> LENGTH: 187
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 77

Gly Ala Leu Val Gln Ser Ala Val Ala Cys Pro Ser Gln Cys Ser Cys
 1               5                  10                  15

Ser Gly Thr Glu Val His Cys Gln Lys Lys Ser Leu Ala Ser Val Pro
            20                  25                  30

Ala Gly Ile Pro Thr Thr Thr Gln Val Leu Tyr Leu His Val Asn Gln
        35                  40                  45

Ile Thr Lys Leu Glu Pro Gly Val Phe Asp Arg Leu Val Asn Leu Gln
    50                  55                  60

Gln Leu Trp Leu Asn Arg Asn Gln Met Lys Ala Leu Pro Ala Gly Val
65                  70                  75                  80

Phe Asp Ser Leu Thr Glu Leu Thr Ile Leu Ala Leu Asp Ser Asn Gln
                85                  90                  95

Leu Gln Ala Leu Pro Val Gly Val Phe Asp Arg Leu Gly Asn Leu Gln
            100                 105                 110

Gln Ile Asn Leu Ser Asn Asn Gln Leu Lys Ser Ile Pro Arg Gly Ala
        115                 120                 125

Phe Asp Asn Leu Lys Ser Leu Thr His Ile Tyr Leu Phe Asn Asn Pro
    130                 135                 140

Trp Asp Cys Glu Cys Ser Asp Ile Leu Tyr Leu Lys Asn Trp Ile Val
145                 150                 155                 160

Gln His Ala Ser Ile Val Asn Pro Leu Gly Asn Gly Gly Val Asp Asn
                165                 170                 175

Val Lys Cys Ser Gly Thr Asn Thr Pro Val Arg
            180                 185


<210> SEQ ID NO 78
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 78

Gly Ala Leu Val Gln Ser Ala Val Ala Cys Pro Ser Gln Cys Ser Cys
 1               5                  10                  15

Ser Gly Thr Glu Val His Cys Ala Gly Lys Ser Leu Ala Ser Val Pro
            20                  25                  30

Ala Gly Ile Pro Thr Thr Thr Gln Tyr Leu Asn Leu His Val Asn Gln
        35                  40                  45

Ile Thr Lys Leu Glu Pro Gly Val Phe Asp Ser Leu Thr Pro Leu Thr
    50                  55                  60

Ile Leu Ala Leu Asn Asp Asn Gln Leu Gln Ala Leu Ser Glu Gly Leu
65                  70                  75                  80

Phe Asp Arg Leu Gly Asn Leu Gln Lys Leu Trp Leu His Arg Asn Gln
                85                  90                  95
```

Leu Lys Ser Ile Pro Arg Gly Thr Phe Asp Asn Leu Lys Ser Leu Thr
100 105 110

His Ile Tyr Leu Phe Asn Asn Pro Trp Asp Cys Glu Cys Ser Asp Ile
115 120 125

Leu Tyr Leu Lys Asn Trp Ile Val Gln His Ala Ser Ile Val Asn Pro
130 135 140

Gly Asn Tyr Gly Gly Val Asp Asn Val Lys Cys Ser Gly Thr Asn Thr
145 150 155 160

Pro Val Arg

<210> SEQ ID NO 79
<211> LENGTH: 1325
<212> TYPE: DNA
<213> ORGANISM: Artificial Sequence
<220> FEATURE:
<223> OTHER INFORMATION: Description of Artificial Sequence; note = synthetic construct

<400> SEQUENCE: 79
tttgggttga ggatgcaatg cacttgcaat gtgcgccgat ccgatcagaa taactgggcg 60
tctgtatgtt ttatttaagt aaaacaatta attcgcctca tttaatttct ggactaacca 120
gggcacgaac ccgttcgctt ctgtctttgg ctcaaattca acagcagcaa tgaagacgca 180
gcctttcacg cgtcgcacac cccagcgtat acttcgagcg gccaatcggc tttttggcaa 240
attttggcac gcgcgtgaat cccgtcggtg cgagacgcgt ttgcgatggt acttaacgcg 300
ccctgtccgt ttttgtctct cgcccttcag cctgcaggag ccaaccatca tgtggatcaa 360
gtggatcgcc acgctggtcg cctttggcgc cctggtgcaa agtgcggtag catgtccctc 420
gcagtgttcg tgcgatcaga cacctgtata ctgccatagc agacgcctca cgtctgtgcc 480
tgcgggaatc cccaccgaca ggcagaacct gtggttgaat aacaatcaga tcacgaagct 540
cgagcccggg gtgtttaacg gtctggcgaa tttgagggag cttcatctgt gggggaacca 600
gctggtgtct cttccccctg ggtgtttgga ccgtctgacc cagctcactc atctgggtct 660
gcacaataac cagctgaaga gcattccaag ggcgcctttt gacagcctca cgaagctgca 720
atacatttat ctgtacagta accccctggga ctgcgcctgt tcagacatcc tgtacctcag 780
ccgctggatc tctcagcacc cagggctcgt gttcggctat ttgaatttgg accccgactc 840
agcacgctgc tctggtacca atacccccgt ccgtgcggtc accgaggcca gcactagccc 900
ctcgaaatgc ccaggctacg ttgctacgac cacgacgccg acgacgacca cgcccgaatt 960
catccctgag accaccacct cgccgcagcc cgtgatcaca acccagaaac ccaagcctct 1020
gtggaatttc aactgcacct caattcagga gaggaagaac gacggtggcg actgcggaaa 1080
gcccgcctgc acaactctcc tgaactgcgc gaatttcctc agctgcctct gctcgacctg 1140
cgccctctgc aggaaacgtt gatcggcgtg caaaggtcgg ggatggcggt gggaaggcgg 1200
gcgcggtggg gtggggggtg tagtggagaa ggtggaggag gaggagtgag gagaaggaag 1260
accaggaaga gggggagagt aataagcaga gacgatttga aaggttgaca aatttctcgc 1320
gcaaa 1325

<210> SEQ ID NO 80
<211> LENGTH: 1343
<212> TYPE: DNA
<213> ORGANISM: Artificial Sequence
<220> FEATURE:
<223> OTHER INFORMATION: Description of Artificial Sequence; note = synthetic construct

<400> SEQUENCE: 80
ttttatttaa gttaaacaat taattcccct catttaattt ctggactaac cagggcacga 60
acccgttcgc ttctgtcttt ggctcaaatt caacagcagc aatgaagacg cagcctttca 120
cgcgtcgcac accccagcgt atacttcgag cggccaatcg gctttttggc aaattttggc 180
acgcgcgtga atcccgtcgg tgcgagacgc gtttgcgatg gtacttaacg cgccctgtcc 240
gtttttgtct ctcgcccttc agcctgcagg agccaaccat catgtggatc aagtggatcg 300
ccacgctggt cgcctttggc gccctggtgc aaagtgcggt agcatgtccc tcgcagtgtt 360
cttgctcagg gacaactgtg aactgtgata gcagaagcct cgcgtctgtg cctggaggaa 420
tccccaccac cacgcaagtg ctgtatttgt acgacaatca gatcacgaag ctcgagcccg 480
gcgtgtttga cagtctgacg gcactgactg aactgaacct tgctgttaac cagctgacgg 540
ctcttcccgt tggggtgttt gacagcctga cccaactgac gattctggct cttgagagaa 600
accagctgcc ggctctccct gccggggtgt ttcacaaact gacccagctc actcaactgg 660
gtctgaacga caaccagctg aagagcattc ccaggggcgc ctttgacaac ctcaagagcc 720
tcactcagat ctatctgttc aacaacccct gggactgcga gtgttcggac atcctctatc 780
tgaagaactg gattgtacag cacgcaagca tcgtgaatct acagggccat gggggagttg 840
ataacgtgaa gtgctctggt accaataccc ccgtccgtgc ggtcaccgag gccagcacta 900
gcccctcgaa atgcccaggc tacgttgcta cgaccacgac gccgacgacg accacgcccg 960
aattcatccc tgagaccacc acctcgccgc agcccgtgat cacaacccag aaacccaagc 1020
ctctgtggaa tttcaactgc acctcaattc aggagaggaa gaacgacggt ggcgactgcg 1080
gaaagcccgc ctgcacaact ctcctgaact gcgcgaattt cctcagctgc ctctgctcga 1140
cctgcgccct ctgcaggaaa cgttgatcgg cgtgcaaagg tcggggatgg cggtgggaag 1200
gcgggcgcgg tggggtgggg ggtgtagtgg agaaggtgga ggaggaggag tgaggagaag 1260
gaagaccagg aagaggggga gagtaataag cagagacgat ttgaaaggtt gacaaatttc 1320
tcgcgcaaac tccaccacct tcg 1343

<210> SEQ ID NO 81
<211> LENGTH: 163
<212> TYPE: PRT
<213> ORGANISM: Artificial Sequence
<220> FEATURE:
<223> OTHER INFORMATION: Description of Artificial Sequence; note = synthetic construct

<400> SEQUENCE: 81

Gly Ala Leu Val Gln Ser Ala Val Ala Cys Pro Ser Gln Cys Ser Cys
1 5 10 15

Ser Gly Thr Gln Val Asn Cys His Glu Arg Arg Leu Ala Ser Val Pro
20 25 30

Ala Gly Ile Pro Thr Thr Thr Gln Val Leu Tyr Leu Tyr Thr Asn Lys
35 40 45

Ile Thr Lys Leu Glu Pro Gly Val Phe Asp Ser Leu Thr Gln Leu Thr
50 55 60

Arg Leu Asp Leu Tyr Asn Asn Gln Leu Thr Val Leu Pro Ala Gly Val
65 70 75 80

Phe Asp Ser Leu Val Asn Leu Gln Gln Leu Tyr Leu Gly Gly Asn Gln
85 90 95

Leu Thr Thr Val Pro Arg Gly Ala Phe Asp Asn Leu Lys Ser Leu Thr
100 105 110

```
His Ile Trp Leu Tyr Asn Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

Ser Gly His Gly Gly Val Asp Asn Val Lys Cys Ser Gly Thr Asn Thr
145                 150                 155                 160

Pro Val Arg


<210> SEQ ID NO 82
<211> LENGTH: 268
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 82

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Asp Gln Thr Pro
            20                  25                  30

Val Tyr Cys His Ser Arg Arg Leu Thr Ser Val Pro Ala Gly Ile Pro
        35                  40                  45

Thr Asp Arg Gln Asn Leu Trp Leu Asn Asn Asn Gln Ile Thr Lys Leu
    50                  55                  60

Glu Pro Gly Val Phe Asn Gly Leu Ala Asn Leu Arg Glu Leu His Leu
65                  70                  75                  80

Trp Gly Asn Gln Leu Val Ser Leu Pro Pro Gly Val Phe Asp Arg Leu
                85                  90                  95

Thr Gln Leu Thr His Leu Gly Leu His Asn Asn Gln Leu Lys Ser Ile
            100                 105                 110

Pro Arg Gly Ala Phe Asp Ser Leu Thr Lys Leu Gln Tyr Ile Tyr Lys
        115                 120                 125

Asn Pro Trp Asp Cys Ala Cys Ser Asp Ile Leu Tyr Leu Ser Arg Trp
    130                 135                 140

Ile Ser Gln His Pro Gly Leu Val Phe Gly Tyr Leu Asn Leu Asp Pro
145                 150                 155                 160

Asp Ser Ala Arg Cys Ser Gly Thr Asn Thr Pro Val Arg Ala Val Thr
                165                 170                 175

Glu Ala Ser Thr Ser Pro Ser Lys Cys Pro Gly Tyr Val Ala Thr Thr
            180                 185                 190

Thr Thr Pro Thr Thr Thr Thr Pro Glu Phe Ile Pro Glu Thr Thr Thr
        195                 200                 205

Ser Pro Gln Pro Val Ile Thr Thr Gln Lys Pro Lys Pro Leu Trp Asn
    210                 215                 220

Phe Asn Cys Thr Ser Ile Gln Glu Arg Lys Asn Asp Gly Gly Asp Cys
225                 230                 235                 240

Gly Lys Pro Ala Cys Thr Thr Leu Leu Asn Cys Ala Asn Phe Leu Ser
                245                 250                 255

Cys Leu Cys Ser Thr Cys Ala Leu Cys Arg Lys Arg
            260                 265


<210> SEQ ID NO 83
<211> LENGTH: 270
<212> TYPE: PRT
<213> ORGANISM: Artificial Sequence
<220> FEATURE:
```

<223> OTHER INFORMATION: Description of Artificial Sequence; note =
synthetic construct

<400> SEQUENCE: 83

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asp Cys Arg Ser Lys Arg His Ala Ser Val Pro Ala Gly Ile Pro
        35                  40                  45

Thr Asn Ala Gln Ile Leu Tyr Leu His Asp Asn Gln Ile Thr Lys Leu
    50                  55                  60

Glu Pro Gly Val Phe Asp His Leu Val Asn Leu Gln Gly Leu Gly Leu
65                  70                  75                  80

Gln Asn Asn Gln Leu Thr Ser Leu Pro Asn Gly Val Phe Asn Lys Leu
                85                  90                  95

Thr Gln Leu Thr His Leu Ser Leu Tyr Asn Asn Gln Leu Lys Ser Ile
            100                 105                 110

Pro Arg Gly Ala Phe Asp Asn Leu Lys Ser Leu Thr Gln Ile Trp Leu
        115                 120                 125

Tyr Asn Asn Pro Trp Asp Cys Ala Cys Ser Asp Ile Leu Tyr Leu Ser
    130                 135                 140

Arg Trp Ile Ser Gln His Pro Gly Leu Val Phe Gly Tyr Leu Asn Leu
145                 150                 155                 160

Asp Pro Asp Ser Ala Arg Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln Glu Arg Lys Asn Gly Gly Gly
225                 230                 235                 240

Asp Cys Gly Lys Pro Ala Cys Thr Thr Leu Leu Asn Cys Ala Asn Phe
                245                 250                 255

Leu Ser Cys Leu Cys Ser Thr Cys Ala Leu Cys Arg Lys Arg
            260                 265                 270
```

<210> SEQ ID NO 84
<211> LENGTH: 167
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 84

```
Gly Ala Leu Val Gln Ser Ala Val Ala Cys Pro Ser Gln Cys Ser Cys
 1               5                  10                  15

Asp Gln Thr Thr Val Asp Cys Arg Asn Lys Arg Phe Ser Ser Val Pro
            20                  25                  30

Ala Gly Ile Pro Thr Asp Arg Gln Asn Leu Trp Leu Asn Asn Asn Gln
        35                  40                  45

Ile Thr Lys Leu Glu Pro Gly Val Phe Asp Ser Leu Ala Gln Leu Thr
    50                  55                  60

Arg Leu Gly Leu Ser His Asn Gln Phe Thr Ala Leu Pro Ala Arg Val
```

-continued

```
65                  70                  75                  80

Phe Asp Arg Met Gly Asn Leu Gln Gln Ile Asn Leu Ser Asn Asn Gln
                85                  90                  95

Leu Lys Ser Ile Pro Arg Gly Ala Phe Asp Asn Leu Lys Ser Leu Thr
            100                 105                 110

His Ile Trp Leu Tyr Gly Asn Pro Trp Asp Cys Ala Cys Ser Asp Ile
        115                 120                 125

Leu Tyr Leu Ser Arg Trp Ile Ser Gln His Pro Gly Val Val Arg Thr
    130                 135                 140

Ala Asp Asp Asp Trp Ser Arg Val Val Pro Asp Ser Ala Arg Cys Ser
145                 150                 155                 160

Gly Thr Asn Thr Pro Val Arg
                165


<210> SEQ ID NO 85
<211> LENGTH: 167
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 85

Gly Ala Leu Val Gln Ser Ala Val Ala Cys Pro Ser Gln Cys Ser Cys
 1               5                  10                  15

Asp Gln Thr Thr Val Asp Cys Arg Asn Lys Arg Phe Ser Ser Val Pro
            20                  25                  30

Ala Gly Ile Pro Thr Asp Arg Gln Asn Leu Trp Leu Asn Asn Asn Gln
        35                  40                  45

Ile Thr Lys Leu Glu Pro Gly Val Phe Asp Ser Leu Ala Gln Leu Thr
    50                  55                  60

Arg Leu Gly Leu Ser His Asn Gln Phe Thr Ala Leu Pro Ala Arg Val
65                  70                  75                  80

Phe Asp Arg Met Gly Asn Leu Gln Gln Ile Asn Leu Ser Asn Asn Gln
                85                  90                  95

Leu Lys Ser Ile Pro Arg Gly Ala Phe Asp Asn Leu Lys Ser Leu Thr
            100                 105                 110

His Ile Trp Leu Tyr Gly Asn Pro Trp Asp Cys Ala Cys Ser Asp Ile
        115                 120                 125

Leu Tyr Leu Ser Arg Trp Ile Ser Gln His Pro Gly Val Val Arg Thr
    130                 135                 140

Ala Asp Asp Asp Trp Ser Arg Val Val Pro Asp Ser Ala Arg Cys Ser
145                 150                 155                 160

Gly Thr Asn Thr Pro Val Arg
                165


<210> SEQ ID NO 86
<211> LENGTH: 274
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 86

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Glu
            20                  25                  30
```

```
Val Ser Cys Asp Arg Lys Arg Phe Ala Ser Val Pro Ala Glu Ile Pro
        35                  40                  45

Ile Thr Thr Gln Arg Leu Trp Leu Ser Asn Asn Gln Leu Thr Lys Leu
    50                  55                  60

Asp Pro Gly Val Phe Asp Ser Leu Ala Ala Leu Thr Phe Leu Asn Val
65                  70                  75                  80

Gly Asp Asn Gln Leu Thr Ala Leu Pro Glu Gly Val Phe Asp His Leu
                85                  90                  95

Val Asn Leu Lys Glu Leu Asn Leu Asn Ile Asn Gln Leu Lys Ser Val
            100                 105                 110

Pro Arg Gly Ala Phe Asp Asn Leu Lys Ser Leu Thr His Ile Trp Leu
        115                 120                 125

Phe Asp Asn Pro Trp Asp Cys Ala Cys Ser Asp Ile Leu Tyr Leu Ser
    130                 135                 140

His Trp Ile Ser Gln His Pro Gly Ile Val Arg Thr Glu Asp Asp Gly
145                 150                 155                 160

Trp Asn Arg Val Val Pro Asp Ser Ala Arg Cys Ser Gly Thr Asn Thr
                165                 170                 175

Pro Val Arg Ala Val Thr Glu Ala Ser Thr Ser Pro Ser Lys Cys Pro
            180                 185                 190

Gly Tyr Val Ala Thr Thr Thr Thr Pro Thr Thr Thr Thr Pro Glu Phe
        195                 200                 205

Ile Pro Glu Thr Thr Thr Ser Pro Gln Pro Val Ile Thr Thr Gln Lys
    210                 215                 220

Pro Lys Pro Leu Trp Asn Phe Asn Cys Thr Ser Ile Gln Glu Arg Lys
225                 230                 235                 240

Asn Asp Gly Gly Asp Cys Gly Lys Pro Ala Cys Thr Thr Leu Leu Asn
                245                 250                 255

Cys Ala Asn Phe Leu Ser Cys Leu Cys Ser Thr Cys Ala Leu Cys Arg
            260                 265                 270

Lys Arg


<210> SEQ ID NO 87
<211> LENGTH: 166
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 87

Gly Ala Leu Val Gln Ser Ala Val Ala Cys Pro Ser Gln Cys Ser Cys
 1               5                  10                  15

Ser Gly Thr Thr Val Asp Cys Ser Gly Lys Ser Leu Ala Ser Val Pro
            20                  25                  30

Ala Gly Ile Pro Ile Thr Thr Gln Ser Leu Ser Leu His Tyr Thr Gln
        35                  40                  45

Ile Thr Lys Leu Glu Pro Gly Val Phe Asp Ser Leu Val Asn Leu Gln
    50                  55                  60

Gln Leu Tyr Leu Gly Gly Asn Gln Leu Ser Ala Leu Pro Asp Gly Val
65                  70                  75                  80

Phe Asp Lys Leu Thr Gln Leu Thr His Ile Val Leu Ser Thr Asn Gln
                85                  90                  95

Leu Arg Ser Val Pro Arg Gly Ala Phe Asp Asn Leu Lys Ser Leu Thr
            100                 105                 110
```

```
His Ile Trp Leu Phe Asp Asn Pro Trp Asp Cys Ala Cys Ser Asp Ile
        115                 120                 125

Leu Tyr Leu Ser Arg Trp Ile Ser Gln His Pro Gly Val Val Arg Lys
    130                 135                 140

Asn Glu Ala Gly Tyr Pro Val Asp Pro Asp Ser Ala Arg Cys Ser Gly
145                 150                 155                 160

Thr Asn Thr Pro Val Arg
                165


<210> SEQ ID NO 88
<211> LENGTH: 321
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 88

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Asp Gln Thr Thr
            20                  25                  30

Val Tyr Cys His Ser Arg Arg Leu Thr Ser Val Pro Ala Gly Ile Pro
        35                  40                  45

Thr Asp Arg Gln Asn Leu Trp Leu Tyr Asn Asn Gln Ile Thr Lys Leu
    50                  55                  60

Glu Pro Gly Val Phe Asp Ser Leu Ala Ala Leu Thr Phe Leu Asn Val
65                  70                  75                  80

Gly Asp Asn Gln Leu Thr Ala Leu Pro Ala Gly Leu Phe Asp Glu Leu
                85                  90                  95

Thr Gln Val Tyr Ser Leu Ser Leu Asn Asp Asn Gln Leu Ser Ala Leu
            100                 105                 110

Pro Ala Gly Val Phe Asp Arg Leu Ile Asn Leu Lys Glu Leu Tyr Phe
        115                 120                 125

Ser Asn Asn Gln Leu Thr Ser Leu Pro Ala Gly Leu Phe Asp Lys Leu
    130                 135                 140

Ile Gln Leu Thr Asn Leu Asp Leu Arg Tyr Asn Gln Leu Lys Ser Ile
145                 150                 155                 160

Pro Arg Gly Ala Phe Asp Asn Leu Lys Ser Leu Thr His Ile Trp Leu
                165                 170                 175

Tyr Asn Asn Pro Trp Asp Cys Ala Cys Ser Asp Ile Leu Tyr Leu Ser
            180                 185                 190

Arg Trp Ile Ser Gln His Pro Gly Val Val Arg Lys Asn Glu Ala Gly
        195                 200                 205

Tyr Pro Val Asp Pro Asp Ser Ala Arg Cys Ser Gly Thr Asn Thr Pro
    210                 215                 220

Val Arg Ala Val Thr Glu Ala Ser Thr Ser Pro Ser Lys Cys Pro Gly
225                 230                 235                 240

Tyr Val Ala Thr Thr Thr Thr Pro Thr Thr Thr Thr Pro Glu Phe Ile
                245                 250                 255

Pro Glu Thr Thr Thr Ser Pro Gln Pro Val Ile Thr Thr Gln Lys Pro
            260                 265                 270

Lys Pro Leu Trp Asn Phe Asn Cys Thr Ser Ile Gln Glu Arg Lys Asn
        275                 280                 285

Asp Gly Gly Asp Cys Gly Lys Pro Ala Cys Thr Thr Leu Leu Asn Cys
    290                 295                 300
```

Ala Asn Phe Leu Ser Cys Leu Cys Ser Thr Cys Ala Leu Cys Arg Lys
305 310 315 320

Arg

<210> SEQ ID NO 89
<211> LENGTH: 296
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 89

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Ser Gly Thr Thr
20 25 30

Val Asn Cys Asp Ser Arg Ser Leu Ala Ser Val Pro Gly Gly Ile Pro
35 40 45

Thr Thr Thr Gln Val Leu Tyr Leu Tyr Asp Asn Gln Ile Thr Lys Leu
50 55 60

Glu Pro Gly Val Phe Asp Ser Leu Ala Ala Leu Thr Phe Leu Asn Leu
65 70 75 80

Gly Asn Asn Gln Leu Thr Ala Leu Pro Glu Gly Val Phe Asp Arg Leu
85 90 95

Val Asn Leu Gln Lys Leu Tyr Leu Trp Gly Asn Gln Leu Ser Ala Leu
100 105 110

Pro Val Gly Val Phe Asp Lys Leu Thr Gln Leu Thr Tyr Leu Gly Val
115 120 125

Asn Gln Leu Lys Ser Ile Pro Arg Gly Ala Phe Asp Asn Leu Lys Ser
130 135 140

Leu Thr His Ile Trp Leu Phe Asp Asn Pro Trp Asp Cys Ala Cys Ser
145 150 155 160

Asp Ile Leu Tyr Leu Ser Arg Trp Ile Ser Gln His Pro Gly Ile Val
165 170 175

Arg Thr Ala Asp Asp Gly Trp Asn Arg Val Asp Pro Asp Ser Ala Arg
180 185 190

Cys Ser Gly Thr Asn Thr Pro Val Arg Ala Val Thr Glu Ala Ser Thr
195 200 205

Ser Pro Ser Lys Cys Pro Gly Tyr Val Ala Thr Thr Thr Thr Pro Thr
210 215 220

Thr Thr Thr Pro Glu Phe Ile Pro Glu Thr Thr Thr Ser Pro Gln Pro
225 230 235 240

Val Ile Thr Thr Gln Lys Pro Lys Pro Leu Trp Asn Phe Asn Cys Thr
245 250 255

Ser Ile Gln Glu Arg Lys Asn Asp Gly Gly Asp Cys Gly Lys Pro Ala
260 265 270

Cys Thr Thr Leu Leu Asn Cys Ala Asn Phe Leu Ser Cys Leu Cys Ser
275 280 285

Thr Cys Ala Leu Cys Arg Lys Arg
290 295

<210> SEQ ID NO 90
<211> LENGTH: 263
<212> TYPE: PRT
<213> ORGANISM: Artificial Sequence
<220> FEATURE:
<223> OTHER INFORMATION: Description of Artificial Sequence; note = synthetic construct

<400> SEQUENCE: 90

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Pro Gly Thr Asp
20 25 30

Val Asn Cys His Glu Arg Arg Leu Ala Ser Val Pro Ala Glu Ile Pro
35 40 45

Thr Thr Thr Lys Ile Leu Trp Leu His Asp Asn Gln Ile Thr Lys Leu
50 55 60

Glu Pro Gly Val Phe Asp His Leu Val Asn Leu Lys Glu Leu Trp Leu
65 70 75 80

Asn Ser Asn Gln Leu Gln Ala Leu Pro Ala Gly Val Phe Asp Lys Leu
85 90 95

Thr Gln Leu Ala His Leu Glu Leu Gln Asn Asn Gln Leu Lys Asn Ile
100 105 110

Pro Arg Gly Ala Phe Asp Asn Leu Lys Ser Leu Thr Tyr Ile Trp Leu
115 120 125

His Asn Asn Pro Trp Asp Cys Ala Cys Ser Asp Ile Leu Tyr Leu Ser
130 135 140

Gly Trp Leu Gly Gln His Ala Gly Lys Glu Gln Gly Gln Ala Val Cys
145 150 155 160

Ser Gly Thr Asn Thr Pro Val Arg Ala Val Thr Glu Ala Ser Thr Ser
165 170 175

Pro Ser Lys Cys Pro Gly Tyr Val Ala Thr Thr Thr Thr Pro Thr Thr
180 185 190

Thr Thr Pro Glu Phe Ile Pro Glu Thr Thr Thr Ser Pro Gln Pro Val
195 200 205

Ile Thr Thr Gln Lys Pro Lys Pro Leu Trp Asn Phe Asn Cys Thr Ser
210 215 220

Ile Gln Glu Arg Lys Asn Asp Gly Gly Asp Cys Gly Lys Pro Ala Cys
225 230 235 240

Thr Thr Leu Leu Asn Cys Ala Asn Phe Leu Ser Cys Leu Cys Ser Thr
245 250 255

Cys Ala Leu Cys Arg Lys Arg
260

<210> SEQ ID NO 91
<211> LENGTH: 170
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 91

Met Trp Ile Lys Trp Ile Ala Thr Leu Val Ala Phe Gly Pro Leu Val
1 5 10 15

Gln Ser Ala Val Ala Cys Pro Ser Gln Cys Ser Cys Ser Gly Thr Glu
20 25 30

Val Arg Cys Glu Ser Arg Ser Leu Ala Ser Val Pro Ala Gly Ile Pro
35 40 45

Thr Thr Thr Arg Arg Leu His Leu His Arg Asn Gln Leu Thr Lys Leu
50 55 60

Glu Pro Gly Val Phe Asp Ser Leu Ala Ala Leu Thr Ile Leu Asp Leu
65 70 75 80

```
Arg Thr Asn Gln Leu Gln Ala Leu Pro Ala Gly Leu Phe Asp Glu Leu
                85                  90                  95

Thr Gln Val Tyr Ser Leu Ser Leu Asn Asp Asn Gln Leu Lys Ser Ile
            100                 105                 110

Pro Arg Gly Ala Phe Asp Asn Leu Lys Ser Leu Thr Tyr Ile Trp Leu
        115                 120                 125

Asp Arg Asn Pro Trp Asp Cys Ala Cys Ser Asp Ile Leu Tyr Leu Ser
    130                 135                 140

Gly Trp Leu Gly Gln His Ala Gly Lys Glu Gln Gly Gln Ala Val Cys
145                 150                 155                 160

Ser Gly Thr Asn Thr Pro Val Arg Ala Val
                165                 170


<210> SEQ ID NO 92
<211> LENGTH: 156
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 92

Gly Ala Leu Val Gln Ser Ala Val Ala Cys Pro Ser Gln Cys Ser Cys
 1               5                  10                  15

Ser Gly Thr Thr Val Asp Cys Ser Gly Lys Ser Leu Ala Ser Val Pro
            20                  25                  30

Ala Ala Ile Pro Ile Thr Thr Gln Arg Leu Trp Leu Ser Asn Asn Gln
        35                  40                  45

Leu Thr Lys Leu Asp Pro Gly Val Phe Asp Ser Leu Val Asn Leu Gln
    50                  55                  60

Gln Leu Tyr Leu Gly Gly Asn Gln Leu Ser Ala Leu Pro Asp Gly Val
65                  70                  75                  80

Phe Asp Lys Leu Thr Gln Leu Thr Asn Leu Tyr Leu His Asn Asn Gln
                85                  90                  95

Leu Lys Ser Val Pro Arg Gly Ala Phe Asp Asn Leu Lys Ser Leu Thr
            100                 105                 110

His Ile Trp Leu Tyr Asn Asn Pro Trp Asp Cys Ala Cys Ser Asp Ile
        115                 120                 125

Leu Tyr Leu Ser Gly Trp Leu Gly Gln His Ala Gly Lys Glu Gln Gly
    130                 135                 140

Gln Ala Val Cys Ser Gly Thr Asn Thr Pro Val Arg
145                 150                 155


<210> SEQ ID NO 93
<211> LENGTH: 156
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 93

Gly Ala Leu Val Gln Ser Ala Val Ala Cys Pro Ser Gln Cys Ser Cys
 1               5                  10                  15

Ser Gly Thr Thr Val Asp Cys Ser Gly Lys Ser Leu Ala Ser Val Pro
            20                  25                  30

Ala Ala Ile Pro Ile Thr Thr Gln Arg Leu Trp Leu Ser Asn Asn Gln
        35                  40                  45
```

```
Leu Thr Lys Leu Asp Pro Gly Val Phe Asp Ser Leu Val Asn Leu Gln
    50                  55                  60

Gln Leu Tyr Leu Gly Gly Asn Gln Leu Ser Ala Leu Pro Asp Gly Val
65                  70                  75                  80

Phe Asp Lys Leu Thr Gln Leu Thr Asn Leu Tyr Leu His Asn Asn Gln
                85                  90                  95

Leu Lys Ser Val Pro Arg Gly Ala Phe Asp Asn Leu Lys Ser Leu Thr
            100                 105                 110

His Ile Trp Leu Tyr Asn Asn Pro Trp Asp Cys Ala Cys Ser Asp Ile
        115                 120                 125

Leu Tyr Leu Ser Gly Trp Leu Gly Gln His Ala Gly Lys Glu Gln Gly
    130                 135                 140

Gln Ala Val Cys Ser Gly Thr Asn Thr Pro Val Arg
145                 150                 155


<210> SEQ ID NO 94
<211> LENGTH: 162
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 94

Gly Ala Leu Val Gln Ser Ala Val Ala Cys Pro Ser Gln Cys Ser Cys
 1               5                  10                  15

Tyr Val Gly Pro Val Asn Arg Leu His Tyr Phe Asp Cys Tyr Thr Lys
            20                  25                  30

Glu Leu Ser Ser Val Pro Ala Ala Ile Pro Val Asn Thr Gln Ile Leu
        35                  40                  45

Gln Leu Gln Asn Asn Arg Ile Gln Ser Leu Pro Val Gly Val Phe Asp
    50                  55                  60

Arg Leu Val Asn Leu Gln Lys Leu Tyr Leu Gly Glu Asn Gln Leu Ser
65                  70                  75                  80

Ala Leu Pro Ala Gly Val Phe Asp Arg Leu Val Asn Leu Gln Thr Leu
                85                  90                  95

Asp Leu His Asn Asn Gln Leu Lys Ser Ile Pro Arg Gly Ala Phe Asp
            100                 105                 110

Asn Leu Met Ser Leu Thr Asn Ile Trp Leu Ser Ser Asn Pro Trp Asp
        115                 120                 125

Cys Ala Cys Ser Asp Ile Leu Tyr Leu Ser Gly Trp Leu Gly Gln His
    130                 135                 140

Ala Gly Lys Glu Gln Gly Gln Ala Val Cys Ser Gly Thr Asn Thr Pro
145                 150                 155                 160

Val Arg


<210> SEQ ID NO 95
<211> LENGTH: 261
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 95

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30
```

```
Val Asp Cys Arg Ser Lys Arg His Ala Ser Val Pro Ala Gly Ile Pro
        35                  40                  45

Thr Thr Thr Gln Val Leu Tyr Lys Asn Gln Ile Thr Lys Leu Glu Thr
    50                  55                  60

Gly Val Phe Asp Gly Leu Thr Gln Leu Thr Tyr Leu Asn Leu Gly Gly
65                  70                  75                  80

Asn Gln Leu Thr Ala Leu Pro Val Gly Val Phe Asp Lys Leu Thr Lys
                85                  90                  95

Leu Thr His Leu Tyr Leu Gly Tyr Asn Gln Leu Lys Ser Ile Pro Arg
            100                 105                 110

Gly Ala Phe Asp Asn Leu Lys Ser Leu Thr His Ile Trp Leu Tyr Asn
        115                 120                 125

Asn Pro Trp Asp Cys Ala Cys Ser Asp Ile Leu Tyr Leu Ser Gly Trp
    130                 135                 140

Leu Gly Gln His Ala Gly Lys Glu Gln Gly Gln Ala Val Cys Ser Gly
145                 150                 155                 160

Thr Asn Thr Pro Val Arg Ala Val Thr Glu Ala Ser Thr Ser Pro Ser
                165                 170                 175

Lys Cys Pro Gly Tyr Val Ala Thr Thr Thr Thr Pro Thr Thr Thr Thr
            180                 185                 190

Pro Glu Phe Ile Pro Glu Thr Thr Thr Ser Pro Gln Pro Val Ile Thr
        195                 200                 205

Thr Gln Lys Pro Lys Pro Leu Trp Asn Phe Asn Cys Thr Ser Ile Gln
    210                 215                 220

Glu Arg Lys Asn Asp Gly Gly Asp Cys Gly Lys Pro Ala Cys Thr Thr
225                 230                 235                 240

Leu Leu Asn Cys Ala Asn Phe Leu Ser Cys Leu Cys Ser Thr Cys Ala
                245                 250                 255

Leu Cys Arg Lys Arg
            260


<210> SEQ ID NO 96
<211> LENGTH: 311
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 96

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Glu
            20                  25                  30

Val His Cys Gln Lys Lys Ser Leu Ala Ser Val Pro Ala Gly Ile Pro
        35                  40                  45

Thr Thr Thr Gln Val Leu Tyr Leu His Val Asn Gln Ile Thr Lys Leu
    50                  55                  60

Glu Pro Gly Val Phe Asp Ser Leu Val Asn Leu Gln Lys Leu Trp Leu
65                  70                  75                  80

Asn Ser Asn Gln Leu Thr Val Leu Pro Ala Gly Val Phe Asp Ser Leu
                85                  90                  95

Val Lys Leu Lys Glu Leu Cys Leu Asp His Asn Gln Leu Gln Ala Ile
            100                 105                 110

Pro Pro Thr Leu Phe Asp Arg Leu Thr Gln Leu Thr His Leu Asp Leu
        115                 120                 125
```

Asp Arg Asn Gln Leu Lys Ser Leu Pro Pro Gly Ile Phe Asp Lys Leu
    130                 135                 140

Glu Lys Leu Thr Arg Leu Glu Leu Tyr Asn Asn Gln Leu Lys Ser Ile
145                 150                 155                 160

Pro Arg Gly Ala Phe Asn Ser Leu Lys Ser Leu Thr His Ile Trp Leu
                165                 170                 175

Tyr Asn Asn Pro Trp Asp Cys Ala Cys Ser Asp Ile Leu Tyr Leu Ser
            180                 185                 190

Gly Trp Leu Gly Gln His Ala Gly Lys Glu Gln Gly Gln Ala Val Cys
        195                 200                 205

Ser Gly Thr Asn Thr Pro Val Arg Ala Val Thr Glu Ala Ser Thr Ser
    210                 215                 220

Pro Ser Lys Cys Pro Gly Tyr Val Ala Thr Thr Thr Thr Pro Thr Thr
225                 230                 235                 240

Thr Thr Pro Glu Phe Ile Pro Glu Thr Thr Thr Ser Pro Gln Pro Val
                245                 250                 255

Ile Thr Thr Gln Lys Pro Lys Pro Leu Trp Asn Phe Asn Cys Thr Ser
            260                 265                 270

Ile Gln Glu Arg Lys Asn Asp Gly Gly Asp Cys Gly Lys Pro Ala Cys
        275                 280                 285

Thr Thr Leu Leu Asn Cys Ala Asn Phe Leu Ser Cys Leu Cys Ser Thr
    290                 295                 300

Cys Ala Leu Cys Arg Lys Arg
305                 310

<210> SEQ ID NO 97
<211> LENGTH: 311
<212> TYPE: PRT
<213> ORGANISM: Artificial Sequence
<220> FEATURE:
<223> OTHER INFORMATION: Description of Artificial Sequence; note = synthetic construct

<400> SEQUENCE: 97

Met Trp Ile Lys Trp Ile Ala Thr Leu Val Ala Phe Ala Ala Leu Val
 1               5                  10                  15

Gln Ser Ala Val Ala Cys Pro Ser Gln Cys Ser Cys Ser Gly Thr Glu
            20                  25                  30

Val Arg Cys Gln Ser Arg Ser Leu Ala Ser Val Pro Ala Gly Ile Pro
        35                  40                  45

Thr Ala Thr Gln Val Leu Tyr Leu Tyr Thr Asn Lys Ile Thr Lys Leu
    50                  55                  60

Glu Pro Gly Val Phe Asp Ser Leu Thr Gln Leu Thr Arg Leu Asp Leu
65                  70                  75                  80

Tyr Asn Asn Gln Leu Thr Val Leu Pro Ala Gly Val Phe Asp Ser Leu
                85                  90                  95

Ala Asn Leu Glu Lys Leu His Leu Tyr Asp Asn Gln Leu Thr Ser Leu
            100                 105                 110

Pro Ala Gly Val Phe Asp Arg Leu Thr Gln Leu Thr Arg Leu Asp Leu
        115                 120                 125

Tyr Asn Asn Gln Leu Thr Val Leu Pro Ala Gly Val Phe Asp Arg Leu
    130                 135                 140

Val Asn Leu Gln Lys Leu Tyr Leu Tyr Glu Asn Gln Leu Lys Ser Ile
145                 150                 155                 160

Pro Arg Ser Ala Phe Asp Asn Leu Lys Ser Leu Thr His Ile Trp Leu
                165                 170                 175

```
His Ser Asn Pro Trp Asp Cys Ala Cys Ser Asp Ile Leu Tyr Leu Ser
            180                 185                 190

Gly Trp Leu Gly Gln His Ala Gly Lys Glu Gln Gly Gln Ala Val Cys
        195                 200                 205

Ser Gly Thr Asn Thr Pro Val Arg Ala Val Thr Glu Ala Ser Thr Ser
    210                 215                 220

Pro Ser Lys Cys Pro Gly Tyr Val Ala Thr Thr Thr Thr Pro Thr Thr
225                 230                 235                 240

Thr Thr Pro Glu Phe Ile Pro Glu Thr Thr Thr Ser Pro Gln Pro Val
                245                 250                 255

Ile Thr Thr Gln Lys Pro Lys Pro Leu Trp Asn Phe Asn Cys Thr Ser
            260                 265                 270

Ile Gln Glu Arg Lys Asn Asp Gly Gly Asp Cys Gly Lys Pro Ala Cys
        275                 280                 285

Thr Thr Leu Leu Asn Cys Ala Asn Phe Leu Ser Cys Leu Cys Ser Thr
    290                 295                 300

Cys Ala Leu Cys Arg Lys Arg
305                 310


<210> SEQ ID NO 98
<211> LENGTH: 265
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 98

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Glu
            20                  25                  30

Val His Cys Gln Lys Lys Ser Leu Ala Ser Val Pro Ala Gly Ile Pro
        35                  40                  45

Thr Thr Thr Gln Val Leu Tyr Leu His Val Asn Gln Ile Thr Lys Leu
    50                  55                  60

Glu Pro Gly Val Phe Asp Arg Leu Val Asn Leu Lys Glu Leu His Leu
65                  70                  75                  80

Trp Gly Asn Gln Leu Leu Ala Leu Ser Val Gly Val Phe Asn Lys Leu
                85                  90                  95

Thr Gln Leu Thr His Leu Ser Leu Tyr Asn Asn Gln Leu Lys Ser Ile
            100                 105                 110

Pro Arg Gly Ala Phe Asp Asn Leu Lys Ser Leu Thr His Ile Trp Leu
        115                 120                 125

Tyr Gly Asn Pro Trp Asp Cys Ala Cys Ser Asp Ile Leu Tyr Leu Ser
    130                 135                 140

His Trp Ala Asn Gly His Ala Asp Ile Val Gln Arg Met Ser Leu Thr
145                 150                 155                 160

Thr Cys Ser Gly Thr Asn Thr Pro Val Arg Ala Val Thr Glu Ala Ser
                165                 170                 175

Thr Ser Pro Ser Lys Cys Pro Gly Tyr Val Ala Thr Thr Thr Thr Pro
            180                 185                 190

Thr Thr Thr Thr Pro Glu Phe Ile Pro Glu Thr Thr Thr Ser Pro Gln
        195                 200                 205

Pro Val Ile Thr Thr Gln Lys Pro Lys Pro Leu Trp Asn Phe Asn Cys
    210                 215                 220
```

```
Thr Ser Ile Gln Glu Arg Lys Asn Asp Gly Gly Asp Cys Gly Lys Pro
225                 230                 235                 240

Ala Cys Thr Thr Leu Leu Asn Cys Ala Asn Phe Leu Ser Cys Leu Cys
                245                 250                 255

Ser Thr Cys Ala Leu Cys Arg Lys Arg
            260                 265


<210> SEQ ID NO 99
<211> LENGTH: 289
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 99

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asn Cys Asp Ser Arg Ser Leu Ala Ser Val Pro Gly Gly Ile Pro
        35                  40                  45

Thr Thr Thr Gln Val Leu Tyr Leu Tyr Asp Asn Gln Ile Thr Lys Phe
    50                  55                  60

Glu Pro Gly Val Phe Asp Ser Leu Thr Ala Leu Thr Val Leu Asn Leu
65                  70                  75                  80

Ala Ile Asn Gln Leu Thr Ala Leu Pro Val Trp Leu Leu His Arg Leu
                85                  90                  95

Glu Asn Leu Lys Gln Leu Tyr Leu Gly Ser Asn Gln Leu Gly Ala Leu
            100                 105                 110

Pro Val Gly Val Phe Asp Lys Leu Thr Gln Leu Lys Gln Leu Ser Leu
        115                 120                 125

Leu Gln Asn Gln Leu Lys Ser Ile Pro Arg Gly Val Phe Asp Asn Leu
    130                 135                 140

Lys Ser Leu Thr His Ile Tyr Leu Phe Asn Asn Pro Trp Asp Cys Ala
145                 150                 155                 160

Cys Ser Asp Ile Leu Tyr Leu Ser His Trp Ala Asn Gly His Ala Asp
                165                 170                 175

Ile Val Gln Arg Met Ser Leu Thr Thr Cys Ser Gly Thr Asn Thr Pro
            180                 185                 190

Val Arg Ala Val Thr Glu Ala Ser Thr Ser Pro Ser Lys Cys Pro Gly
        195                 200                 205

Tyr Val Ala Thr Thr Thr Thr Pro Thr Thr Thr Thr Pro Glu Phe Ile
    210                 215                 220

Pro Glu Thr Thr Thr Ser Pro Gln Pro Val Ile Thr Thr Gln Lys Pro
225                 230                 235                 240

Lys Pro Leu Trp Asn Phe Asn Cys Thr Ser Ile Gln Glu Arg Lys Asn
                245                 250                 255

Asp Gly Gly Asp Cys Gly Lys Pro Ala Cys Thr Thr Leu Leu Asn Cys
            260                 265                 270

Ala Asn Phe Leu Ser Cys Leu Cys Ser Thr Cys Ala Leu Cys Arg Lys
        275                 280                 285

Arg


<210> SEQ ID NO 100
<211> LENGTH: 295
```

<212> TYPE: PRT
<213> ORGANISM: Artificial Sequence
<220> FEATURE:
<223> OTHER INFORMATION: Description of Artificial Sequence; note = synthetic construct

<400> SEQUENCE: 100

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Gln
            20                  25                  30

Val Asn Cys His Glu Arg Ser Leu Ala Ser Val Pro Ala Glu Ile Pro
        35                  40                  45

Thr Asn Arg Gln Ile Leu Phe Leu Ser Ser Asn Gln Ile Lys Lys Leu
    50                  55                  60

Glu Pro Gly Val Phe Asp Ser Leu Val Lys Leu Lys Glu Leu Tyr Leu
65                  70                  75                  80

Asp His Asn Gln Leu Gln Ala Ile Pro Pro Ala Leu Phe Tyr Ser Leu
                85                  90                  95

Thr Glu Leu Thr Arg Leu Glu Leu Glu Asp Asn Gln Leu Lys Ser Leu
            100                 105                 110

Pro Pro Gly Ile Phe Asp Arg Leu Gly Lys Leu Met Tyr Leu His Leu
        115                 120                 125

His Glu Asn Gln Leu Lys Ser Ile Pro Arg Gly Ala Phe Asp Asn Leu
    130                 135                 140

Lys Ser Leu Thr His Ile Tyr Leu Tyr Asn Asn Pro Trp Asp Cys Gln
145                 150                 155                 160

Cys Thr Asp Ile Leu Tyr Leu Ser Gly Trp Val Ala Gln His Ser Gly
                165                 170                 175

Ile Val Gly Glu Gly Trp Trp Thr Val Lys Pro Asp Asn Val Lys Cys
            180                 185                 190

Ala Gly Thr Asn Thr Pro Val Arg Ala Val Thr Glu Ala Ser Thr Ser
        195                 200                 205

Pro Ser Lys Cys Pro Gly Tyr Val Ala Thr Thr Thr Thr Pro Thr Thr
    210                 215                 220

Thr Thr Pro Glu Phe Ile Pro Glu Thr Thr Thr Ser Pro Gln Pro Val
225                 230                 235                 240

Ile Thr Thr Gln Lys Pro Lys Pro Leu Trp Asn Phe Asn Cys Thr Ser
                245                 250                 255

Ile Gln Glu Arg Lys Asn Asp Gly Gly Asp Cys Gly Lys Pro Ala Cys
            260                 265                 270

Thr Thr Leu Leu Asn Cys Ala Asn Phe Leu Ser Cys Leu Cys Ser Thr
        275                 280                 285

Cys Ala Leu Cys Arg Lys Arg
    290                 295
```

<210> SEQ ID NO 101
<211> LENGTH: 164
<212> TYPE: PRT
<213> ORGANISM: Artificial Sequence
<220> FEATURE:
<223> OTHER INFORMATION: Description of Artificial Sequence; note = synthetic construct

<400> SEQUENCE: 101

```
Gly Ala Leu Val Gln Ser Ala Val Ala Cys Pro Ser Gln Cys Ser Cys
 1               5                  10                  15

Ser Gly Thr Gln Val Asn Cys His Glu Arg Ser Leu Ala Ser Val Pro
```

```
            20                  25                  30

Ala Gly Ile Pro Thr Thr Thr Gln Val Leu Tyr Leu Tyr Thr Asn Gln
        35                  40                  45

Ile Thr Lys Leu Glu Pro Gly Val Phe Asp Arg Leu Thr Ala Leu Glu
    50                  55                  60

Glu Leu Tyr Leu Asp His Asn Gln Leu Gln Ala Leu Pro Ala Arg Val
65                  70                  75                  80

Phe Asp Lys Leu Thr Gln Leu Ile Tyr Leu Val Leu Asp Thr Asn Gln
                85                  90                  95

Leu Lys Ser Ile Pro Arg Gly Ala Phe Asp Asn Leu Lys Ser Leu Thr
            100                 105                 110

His Val Trp Leu His Thr Asn Pro Trp Asp Cys Gln Cys Thr Asp Ile
        115                 120                 125

Leu Tyr Leu Ser Gly Trp Val Ala Gln His Ser Gly Ile Val Gly Glu
    130                 135                 140

Gly Trp Trp Thr Val Lys Pro Asp Asn Val Lys Cys Ser Gly Thr Asn
145                 150                 155                 160

Thr Pro Val Arg


<210> SEQ ID NO 102
<211> LENGTH: 269
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 102

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asp Cys Arg Ser Lys Arg His Ala Ser Val Pro Ala Gly Ile Pro
        35                  40                  45

Thr Thr Thr Gln Val Leu Tyr Leu Tyr Thr Asn Lys Ile Thr Lys Leu
    50                  55                  60

Glu Pro Gly Val Phe Asp Ser Leu Ala Asn Leu Arg Glu Leu His Leu
65                  70                  75                  80

Gly Gly Ser Gln Leu Ser Ala Leu Pro Asp Gly Val Phe Asn Arg Leu
                85                  90                  95

Thr Gln Leu Thr Thr Leu Glu Leu Gln Ile Asn Gln Leu Lys Ser Val
            100                 105                 110

Pro Thr Gly Ala Phe Asn Asn Leu Lys Ser Leu Thr His Ile Tyr Leu
        115                 120                 125

Phe Asn Asn Pro Trp Asp Cys Glu Cys Ser Asp Ile Leu Tyr Leu Lys
    130                 135                 140

Asn Trp Ile Val Gln His Ala Ser Ile Val Asn Pro Gly Ser Gly Gly
145                 150                 155                 160

Val Asp Asn Val Lys Cys Ser Gly Thr Asn Thr Pro Val Arg Ala Val
                165                 170                 175

Thr Glu Ala Ser Thr Ser Pro Ser Lys Cys Pro Gly Tyr Val Ala Thr
            180                 185                 190

Thr Thr Thr Pro Thr Thr Thr Thr Pro Glu Phe Ile Pro Glu Thr Thr
        195                 200                 205

Thr Ser Pro Gln Pro Val Ile Thr Thr Gln Lys Pro Lys Pro Leu Trp
    210                 215                 220
```

```
Asn Phe Asn Cys Thr Ser Ile Gln Glu Arg Lys Asn Asp Gly Gly Asp
225                 230                 235                 240

Cys Gly Lys Pro Ala Cys Thr Thr Leu Leu Asn Cys Ala Asn Phe Leu
                245                 250                 255

Ser Cys Leu Cys Ser Thr Cys Ala Leu Cys Arg Lys Arg
            260                 265
```

<210> SEQ ID NO 103
<211> LENGTH: 246
<212> TYPE: PRT
<213> ORGANISM: Artificial Sequence
<220> FEATURE:
<223> OTHER INFORMATION: Description of Artificial Sequence; note = synthetic construct

<400> SEQUENCE: 103

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asp Cys Asn Ser Arg Arg His Ala Ser Val Pro Ala Gly Ile Pro
        35                  40                  45

Thr Asn Val Gln Ile Leu Asn Leu Tyr Asn Asn Gln Ile Thr Asn Leu
    50                  55                  60

Glu Pro Gly Val Phe Asp Arg Leu Gly Lys Leu Gln His Leu Asp Leu
65                  70                  75                  80

Ser Lys Asn Gln Leu Lys Ser Ile Pro Arg Gly Ala Phe Asp Asn Leu
                85                  90                  95

Lys Ser Leu Thr His Ile Tyr Leu Phe Asn Asn Pro Trp Asp Cys Glu
            100                 105                 110

Cys Ser Asp Ile Leu Tyr Leu Lys Asn Trp Ile Val Gln His Ala Ser
        115                 120                 125

Ile Val Asn Leu Arg Gly His Gly Gly Val Asp Asn Val Lys Cys Ser
    130                 135                 140

Gly Thr Asn Thr Pro Val Arg Ala Val Thr Glu Ala Ser Thr Ser Pro
145                 150                 155                 160

Ser Lys Cys Pro Gly Tyr Val Ala Thr Thr Thr Thr Pro Thr Thr Thr
                165                 170                 175

Thr Pro Glu Phe Ile Pro Glu Thr Thr Thr Ser Pro Gln Pro Val Ile
            180                 185                 190

Thr Thr Gln Lys Pro Lys Pro Leu Trp Asn Phe Asn Cys Thr Ser Ile
        195                 200                 205

Gln Glu Arg Lys Asn Asp Gly Gly Asp Cys Gly Lys Pro Ala Cys Thr
    210                 215                 220

Thr Leu Leu Asn Cys Ala Asn Phe Leu Ser Cys Leu Cys Ser Thr Cys
225                 230                 235                 240

Ala Leu Cys Arg Lys Arg
                245
```

<210> SEQ ID NO 104
<211> LENGTH: 270
<212> TYPE: PRT
<213> ORGANISM: Artificial Sequence
<220> FEATURE:
<223> OTHER INFORMATION: Description of Artificial Sequence; note = synthetic construct

<400> SEQUENCE: 104

-continued

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asp Cys Arg Ser Lys Arg His Ala Ser Val Pro Ala Ala Ile Pro
        35                  40                  45

Ile Thr Thr Gln Arg Leu Trp Leu Ser Asn Asn Gln Ile Thr Lys Leu
    50                  55                  60

Glu Pro Gly Val Phe Asp Ser Leu Thr Gln Leu Thr Tyr Leu Asn Leu
65                  70                  75                  80

Gly Gly Asn Gln Leu Thr Ala Leu Pro Val Gly Val Phe Asp Arg Leu
                85                  90                  95

Val Asn Leu Gln Glu Leu Thr Leu Tyr Asn Asn Gln Leu Lys Ser Ile
            100                 105                 110

Pro Arg Gly Ala Ser Asp Asn Leu Lys Ser Leu Thr His Ile Tyr Leu
        115                 120                 125

Phe Asn Asn Pro Trp Asp Cys Glu Cys Ser Asp Ile Leu Tyr Leu Lys
    130                 135                 140

Asn Trp Ile Val Gln His Ala Ser Ile Met Asn Leu Glu Gly His Gly
145                 150                 155                 160

Gly Val Asp Asn Val Lys Cys Ser Gly Thr Asp Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln Glu Arg Lys Asn Asp Gly Gly
225                 230                 235                 240

Asp Cys Gly Lys Pro Ala Cys Thr Thr Leu Leu Asn Cys Ala Asn Phe
                245                 250                 255

Leu Gly Cys Leu Cys Ser Thr Cys Ala Leu Cys Arg Lys Arg
            260                 265                 270
```

<210> SEQ ID NO 105
<211> LENGTH: 162
<212> TYPE: PRT
<213> ORGANISM: Artificial Sequence
<220> FEATURE:
<223> OTHER INFORMATION: Description of Artificial Sequence; note = synthetic construct

<400> SEQUENCE: 105

```
Gly Ala Leu Val Gln Ser Ala Val Ala Cys Pro Ser Gln Cys Ser Cys
 1               5                  10                  15

Asp Gln Thr Thr Val Lys Cys His Ser Arg Arg Leu Thr Ser Val Pro
            20                  25                  30

Ala Gly Ile Pro Thr Asn Arg Gln Asn Leu Trp Leu His Asp Asn Gln
        35                  40                  45

Ile Thr Lys Leu Glu Pro Gly Val Phe Asp Arg Leu Thr Glu Leu Thr
    50                  55                  60

Ile Leu Asp Leu Arg Thr Asn Gln Leu Gln Ala Leu Pro Thr Leu Val
65                  70                  75                  80

Phe Asp Asn Leu Thr Gln Leu Ser Ile Leu Asn Met His Thr Asn Gln
                85                  90                  95
```

Leu Lys Ser Ile Pro Arg Gly Ala Phe Asp Asn Leu Lys Ser Leu Thr
100 105 110

His Ile Tyr Leu Phe Asn Asn Pro Trp Asp Cys Glu Cys Ser Asp Ile
115 120 125

Leu Tyr Leu Lys Asn Trp Ile Val Gln His Ala Ser Ile Val Asn Pro
130 135 140

Gly Ser Gly Gly Val Asp Asn Val Lys Cys Ala Gly Thr Asn Thr Pro
145 150 155 160

Val Arg

<210> SEQ ID NO 106
<211> LENGTH: 162
<212> TYPE: PRT
<213> ORGANISM: Artificial Sequence
<220> FEATURE:
<223> OTHER INFORMATION: Description of Artificial Sequence; note = synthetic construct

<400> SEQUENCE: 106

Gly Ala Leu Val Gln Ser Ala Val Ala Cys Pro Ser Gln Cys Ser Cys
1 5 10 15

Asp Gln Thr Thr Val Lys Cys His Ser Arg Arg Leu Thr Ser Val Pro
20 25 30

Ala Gly Ile Pro Thr Asn Arg Gln Asn Leu Trp Leu His Asp Asn Gln
35 40 45

Ile Thr Lys Leu Glu Pro Gly Val Phe Asp Arg Leu Thr Glu Leu Thr
50 55 60

Ile Leu Asp Leu Arg Thr Asn Gln Leu Gln Ala Leu Pro Thr Leu Val
65 70 75 80

Phe Asp Asn Leu Thr Gln Leu Ser Ile Leu Asn Met His Thr Asn Gln
85 90 95

Leu Lys Ser Ile Pro Arg Gly Ala Phe Asp Asn Leu Lys Ser Leu Thr
100 105 110

His Ile Tyr Leu Phe Asn Asn Pro Trp Asp Cys Glu Cys Ser Asp Ile
115 120 125

Leu Tyr Leu Lys Asn Trp Ile Val Gln His Ala Ser Ile Val Asn Pro
130 135 140

Gly Ser Gly Gly Val Asp Asn Val Lys Cys Ala Gly Thr Asn Thr Pro
145 150 155 160

Val Arg

<210> SEQ ID NO 107
<211> LENGTH: 298
<212> TYPE: PRT
<213> ORGANISM: Artificial Sequence
<220> FEATURE:
<223> OTHER INFORMATION: Description of Artificial Sequence; note = synthetic construct

<400> SEQUENCE: 107

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Gly Glu Gln Ser
20 25 30

Trp Ala Pro Gly Leu Gln Ala Thr Asn Cys Tyr Asp Lys Gly Leu Ser
35 40 45

Ser Val Pro Ala Gly Ile Pro Asp Asn Thr Gln Ala Leu Thr Val Gln
50 55 60

```
Lys Asn Arg Ile Glu Ser Leu Pro Glu Arg Val Phe Asp Arg Leu Val
65                  70                  75                  80

Asn Leu Gln Gln Leu Tyr Leu His Leu Asn Arg Leu Ser Ser Ile Pro
                85                  90                  95

Ala Gly Met Phe Asp Lys Leu Ser Gln Leu Thr Phe Leu Ser Leu Asp
            100                 105                 110

Glu Asn Lys Leu Thr Ala Leu Pro Asn Gly Val Phe Asp Lys Leu Thr
        115                 120                 125

Gln Leu Thr Ile Leu Gly Leu Arg Asp Asn Gln Leu Lys Ser Thr Pro
    130                 135                 140

Arg Gly Ala Phe Asp Asn Leu Lys Ser Leu Thr His Ile Trp Lys Asn
145                 150                 155                 160

Pro Trp Asp Cys Glu Cys Ser Asp Ile Leu Tyr Leu Lys Asn Trp Ile
                165                 170                 175

Val Gln His Ala Ser Ile Val Asn Pro Gly Ser Gly Gly Val Asp Asn
            180                 185                 190

Val Lys Cys Ser Gly Thr Asn Thr Pro Val Arg Ala Val Thr Glu Ala
        195                 200                 205

Ser Thr Ser Pro Ser Lys Cys Pro Gly Tyr Val Ala Thr Thr Thr Thr
    210                 215                 220

Pro Thr Thr Thr Thr Pro Glu Phe Ile Pro Glu Thr Thr Thr Ser Pro
225                 230                 235                 240

Gln Pro Val Ile Thr Thr Gln Lys Pro Lys Pro Leu Trp Asn Phe Asn
                245                 250                 255

Cys Thr Ser Ile Gln Glu Arg Lys Asn Asp Gly Gly Asp Cys Gly Lys
            260                 265                 270

Pro Ala Cys Thr Thr Leu Leu Asn Cys Ala Asn Phe Leu Ser Cys Leu
        275                 280                 285

Cys Ser Thr Cys Ala Leu Cys Arg Lys Arg
    290                 295


<210> SEQ ID NO 108
<211> LENGTH: 280
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 108

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Gly Lys Phe Ser
            20                  25                  30

Trp Ser Gly Glu Leu Gln Thr Thr Asp Cys Asp Gly Lys Gly Leu Ser
        35                  40                  45

Ser Val Pro Ser Gly Ile Pro Asp Asn Thr Gln Ala Leu Thr Val Gln
    50                  55                  60

Lys Asn Arg Ile Glu Ser Leu Pro Glu Gly Val Phe Asp Arg Leu Val
65                  70                  75                  80

Asn Leu Gln Arg Leu Trp Leu Asn Asn Asn Gln Leu Thr Ser Leu Pro
                85                  90                  95

Ala Gly Val Phe Asp Lys Leu Thr Gln Leu Thr Gln Leu Gly Leu Trp
            100                 105                 110

Asp Asn Gln Leu Lys Ser Ile Pro Arg Gly Ala Phe Asp Asn Leu Lys
        115                 120                 125
```

```
Ser Leu Thr His Ile Trp Leu Tyr Gly Asn Pro Trp Asp Cys Ala Cys
    130                 135                 140

Ser Asp Ile Leu Tyr Leu Ser Arg Trp Ile Ser Gln Tyr Pro Gly Val
145                 150                 155                 160

Leu Arg Ala Ala Asp Ser Trp Tyr Ile Val Asp Pro Asp Ser Ala Arg
                165                 170                 175

Cys Ser Gly Thr Asn Thr Pro Val Arg Ala Val Thr Glu Ala Ser Thr
            180                 185                 190

Ser Pro Ser Lys Cys Pro Gly Tyr Val Ala Thr Thr Thr Thr Pro Thr
        195                 200                 205

Thr Thr Thr Pro Glu Phe Ile Pro Glu Thr Thr Thr Ser Pro Gln Pro
    210                 215                 220

Val Ile Thr Thr Gln Lys Pro Lys Pro Leu Trp Asn Phe Asn Cys Thr
225                 230                 235                 240

Ser Ile Gln Glu Arg Lys Asn Asp Gly Gly Asp Cys Gly Lys Pro Ala
                245                 250                 255

Cys Thr Thr Leu Leu Asn Cys Ala Asn Phe Leu Ser Cys Leu Cys Ser
            260                 265                 270

Thr Cys Ala Leu Cys Arg Lys Arg
        275                 280
```

<210> SEQ ID NO 109
<211> LENGTH: 322
<212> TYPE: PRT
<213> ORGANISM: Artificial Sequence
<220> FEATURE:
<223> OTHER INFORMATION: Description of Artificial Sequence; note = synthetic construct

<400> SEQUENCE: 109

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Arg Val Trp Ser
            20                  25                  30

Gly Leu Gln Arg Ala Lys Cys His Ser Lys Gly Leu Ile Ser Val Pro
        35                  40                  45

Ser Gly Ile Ser Glu Asn Thr Gln Ala Ser Ser Val Glu Asn Asn Arg
    50                  55                  60

Ile Glu Ser Leu Pro Glu Gly Val Phe Asp Arg Leu Val Asn Leu Gln
65                  70                  75                  80

Arg Leu Trp Leu Asn Asn Asn Gln Leu Thr Ser Leu Pro Ala Gly Val
                85                  90                  95

Phe Asp Arg Leu Thr Gln Leu Thr Arg Leu Asp Leu Tyr Asn Asn Gln
            100                 105                 110

Leu Thr Val Leu Pro Ala Gly Val Phe Asp Ser Leu Val Asn Leu Gln
        115                 120                 125

Gly Leu Trp Leu Tyr Asn Asn Lys Leu Thr Ala Leu Thr Asn Gly Val
    130                 135                 140

Phe Asp Lys Leu Thr Arg Leu Lys Trp Leu Gly Leu Asp Gln Asn Gln
145                 150                 155                 160

Leu Lys Ser Ile Pro Arg Gly Ala Phe Asp Asn Leu Lys Ser Leu Thr
                165                 170                 175

Tyr Ile Tyr Leu Phe Asn Asn Pro Trp Asp Cys Glu Cys Ser Asp Ile
            180                 185                 190

Leu Tyr Leu Lys Asn Trp Ile Val Gln His Ala Ser Ile Val Asn Pro
        195                 200                 205
```

```
Ser Gly His Gly Gly Val Asp Asn Val Lys Cys Ser Gly Thr Asn Thr
    210                 215                 220

Pro Val Arg Ala Val Thr Gly Ala Ser Thr Ser Pro Ser Lys Cys Pro
225                 230                 235                 240

Gly Tyr Val Ala Thr Thr Thr Thr Pro Thr Thr Thr Thr Pro Glu Phe
                245                 250                 255

Ile Pro Glu Thr Thr Thr Ser Pro Gln Pro Val Ile Thr Thr Gln Lys
            260                 265                 270

Pro Lys Pro Leu Trp Asn Phe Asn Cys Thr Ser Ile Gln Glu Arg Lys
        275                 280                 285

Asn Asp Gly Gly Asp Cys Gly Lys Pro Ala Cys Thr Thr Leu Leu Asn
    290                 295                 300

Cys Ala Asn Phe Leu Ser Cys Leu Cys Ser Thr Cys Ala Leu Cys Arg
305                 310                 315                 320

Lys Arg


<210> SEQ ID NO 110
<211> LENGTH: 212
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 110

Gly Ala Leu Val Gln Ser Ala Val Ala Cys Pro Ser Gln Cys Ser Cys
 1               5                  10                  15

Ser Gly Thr Thr Val Asn Arg Asp Ser Arg Ser Leu Ala Ser Val Pro
            20                  25                  30

Ala Gly Ile Pro Thr Thr Thr Gln Ser Leu Gly Phe Tyr Asn Asn Gln
        35                  40                  45

Ile Thr Lys Leu Glu Pro Gly Val Phe Asp Arg Leu Val Asn Leu Gln
    50                  55                  60

Lys Leu Tyr Leu Trp Gly Asn Gln Leu Ser Ala Leu Pro Val Gly Val
65                  70                  75                  80

Phe Asp Lys Leu Thr Gln Leu Val Thr Leu Asp Leu Asn Gly Asn Gln
                85                  90                  95

Leu Ser Ser Val Pro Ala Asp Val Phe His Gln Leu Val Lys Leu Glu
            100                 105                 110

Lys Leu Trp Leu Lys Asn Asn Lys Leu Thr Ala Leu Pro Pro Gly Val
        115                 120                 125

Phe Asp His Leu Val Asn Leu Gln Gln Leu Ser Leu His Thr Asn Gln
    130                 135                 140

Leu Lys Ser Ile Pro His Gly Ala Phe Asp Arg Leu Ser Ser Leu Thr
145                 150                 155                 160

His Ala Tyr Lys Asn Pro Trp Asp Cys Glu Cys Arg Asp Ile Met Tyr
                165                 170                 175

Leu Arg Asn Trp Val Ala Asp His Thr Ser Ile Val Met Arg Trp Asp
            180                 185                 190

Gly Lys Ala Val Asn Asp Pro Asp Ser Ala Lys Cys Ala Gly Thr Asn
        195                 200                 205

Thr Pro Val Arg
    210


<210> SEQ ID NO 111
<211> LENGTH: 321
<212> TYPE: PRT
```

<213> ORGANISM: Artificial Sequence
<220> FEATURE:
<223> OTHER INFORMATION: Description of Artificial Sequence; note = synthetic construct

<400> SEQUENCE: 111

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Ser Gly Thr Glu
20 25 30

Val His Cys Asp Ser Arg Ser Leu Ala Ser Val Pro Ala Arg Ile Pro
35 40 45

Thr Thr Thr Gln Arg Leu Trp Leu Asn Asn Asn Gln Ile Thr Lys Leu
50 55 60

Glu Pro Gly Val Phe Asp Arg Leu Gly Asn Leu Gln Lys Leu Trp Leu
65 70 75 80

Asn Ser Asn Gln Leu Thr Ser Leu Pro Ala Gly Val Phe Asp Lys Leu
85 90 95

Ile Gln Leu Val Thr Leu Asp Leu Asn Gly Asn Gln Leu Ser Ser Val
100 105 110

Pro Ala Asp Val Phe His Gln Leu Val Lys Leu Glu Lys Leu Trp Leu
115 120 125

Lys Asn Asn Lys Leu Thr Thr Leu Pro Ala Gly Leu Phe Asp Glu Leu
130 135 140

Thr Gln Val Tyr Ser Leu Ser Leu Asn Asp Asn Gln Leu Lys Ser Ile
145 150 155 160

Pro His Gly Ala Phe Asp Arg Leu Ser Ser Leu Thr His Ala Tyr Leu
165 170 175

Phe Gly Asn Pro Trp Asp Cys Glu Cys Arg Asp Ile Met Tyr Leu Arg
180 185 190

Asn Trp Val Ala Asp His Thr Ser Ile Val Met Arg Trp Asp Gly Lys
195 200 205

Ala Val Asn Asp Pro Asp Ser Ala Lys Cys Ala Gly Thr Asn Thr Pro
210 215 220

Val Arg Ala Val Thr Glu Ala Ser Thr Ser Pro Ser Lys Cys Pro Gly
225 230 235 240

Tyr Val Ala Thr Thr Thr Thr Pro Thr Thr Thr Thr Pro Glu Phe Ile
245 250 255

Pro Glu Thr Thr Thr Ser Pro Gln Pro Val Ile Thr Thr Gln Lys Pro
260 265 270

Lys Pro Leu Trp Asn Phe Asn Cys Thr Ser Ile Gln Glu Arg Lys Asn
275 280 285

Asp Gly Gly Asp Cys Gly Lys Pro Ala Cys Thr Thr Leu Leu Asn Cys
290 295 300

Ala Asn Phe Leu Ser Cys Leu Cys Ser Thr Cys Ala Leu Cys Arg Lys
305 310 315 320

Arg

<210> SEQ ID NO 112
<211> LENGTH: 321
<212> TYPE: PRT
<213> ORGANISM: Artificial Sequence
<220> FEATURE:
<223> OTHER INFORMATION: Description of Artificial Sequence; note = synthetic construct

<400> SEQUENCE: 112

-continued

```
Met Trp Ile Lys Trp Ile Ala Thr Leu Val Ala Phe Gly Ala Leu Val
 1               5                  10                  15

Gln Ser Ala Val Ala Cys Pro Ser Gln Cys Pro Cys Ser Gly Thr Glu
            20                  25                  30

Val His Cys Gln Lys Lys Ser Leu Ala Ser Val Pro Ala Gly Ile Pro
        35                  40                  45

Thr Thr Thr Gln Val Leu Tyr Leu His Val Asn Gln Ile Thr Lys Leu
    50                  55                  60

Glu Pro Gly Val Phe Asp Arg Leu Val Asn Leu Gln Glu Leu Thr Leu
65                  70                  75                  80

Tyr Asn Asn Gln Leu Thr Ala Leu Pro Asn Gly Ile Phe Asp Lys Leu
                85                  90                  95

Thr Gln Leu Val Thr Leu Asp Leu Asn Gly Asn Gln Leu Ser Ser Val
            100                 105                 110

Pro Ala Asp Val Phe His Gln Leu Val Lys Leu Glu Lys Leu Trp Leu
        115                 120                 125

Lys Asn Asn Lys Leu Thr Ala Leu Pro Ala Gly Leu Phe Asp Asn Leu
    130                 135                 140

Thr Gln Leu Lys Gln Leu Ser Leu His Thr Asn Gln Leu Lys Ser Ile
145                 150                 155                 160

Pro Arg Gly Ala Phe Asp Asn Leu Lys Ser Leu Thr His Ile Phe Leu
                165                 170                 175

Tyr Asn Asn Pro Trp Asp Cys Glu Cys Arg Asp Ile Met Tyr Leu Arg
            180                 185                 190

Asn Trp Val Ala Asp His Thr Ser Ile Val Met Arg Trp Asp Gly Lys
        195                 200                 205

Ala Val Asn Asp Pro Asp Ser Ala Lys Cys Ala Gly Thr Asn Thr Pro
    210                 215                 220

Val Arg Ala Val Thr Glu Ala Ser Thr Ser Pro Ser Lys Cys Pro Gly
225                 230                 235                 240

Tyr Val Ala Thr Thr Thr Thr Pro Thr Thr Thr Thr Pro Glu Phe Ile
                245                 250                 255

Pro Glu Thr Thr Thr Ser Pro Gln Pro Val Ile Thr Thr Gln Lys Pro
            260                 265                 270

Lys Pro Leu Trp Asn Phe Asn Cys Thr Ser Ile Gln Glu Arg Lys Asn
        275                 280                 285

Asp Gly Gly Asp Cys Gly Lys Pro Ala Cys Thr Thr Leu Leu Asn Cys
    290                 295                 300

Ala Asn Phe Leu Ser Cys Leu Cys Ser Thr Cys Ala Leu Cys Arg Lys
305                 310                 315                 320

Arg
```

<210> SEQ ID NO 113
<211> LENGTH: 166
<212> TYPE: PRT
<213> ORGANISM: Artificial Sequence
<220> FEATURE:
<223> OTHER INFORMATION: Description of Artificial Sequence; note = synthetic construct

<400> SEQUENCE: 113

```
Gly Ala Leu Val Gln Ser Ala Val Ala Cys Pro Ser Gln Cys Ser Cys
 1               5                  10                  15

Asp Gln Thr Leu Val Asn Cys Gln Asn Ile Arg Leu Ala Ser Val Pro
            20                  25                  30

Ala Gly Ile Pro Thr Asp Lys Gln Arg Leu Trp Leu Asn Asn Asn Gln
```

```
        35                  40                  45

Ile Thr Lys Leu Glu Pro Gly Val Phe Asp His Leu Val Asn Leu Gln
    50                  55                  60

Gln Leu Tyr Phe Asn Ser Asn Lys Leu Thr Ala Ile Pro Thr Gly Val
65                  70                  75                  80

Phe Asp Lys Leu Thr Gln Leu Thr Gln Leu Asp Leu Asn Asp Asn His
                85                  90                  95

Leu Lys Ser Ile Pro Arg Gly Ala Phe Asp Asn Leu Lys Ser Leu Thr
            100                 105                 110

His Ile Tyr Leu Tyr Asn Asn Pro Trp Asp Cys Glu Cys Arg Asp Ile
        115                 120                 125

Met Tyr Leu Arg Asn Trp Val Ala Asp His Thr Ser Ile Val Met Arg
    130                 135                 140

Trp Asp Gly Lys Ala Val Asn Asp Pro Asp Ser Ala Lys Cys Ala Gly
145                 150                 155                 160

Thr Asn Thr Pro Val Arg
                165


<210> SEQ ID NO 114
<211> LENGTH: 166
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 114

Gly Ala Leu Val Gln Ser Ala Val Ala Cys Pro Ser Gln Cys Ser Cys
 1               5                  10                  15

Asp Gln Thr Leu Val Asn Cys Gln Asn Ile Arg Leu Ala Ser Val Pro
            20                  25                  30

Ala Gly Ile Pro Thr Asp Lys Gln Arg Leu Trp Leu Asn Asn Asn Gln
        35                  40                  45

Ile Thr Lys Leu Glu Pro Gly Val Phe Asp His Leu Val Asn Leu Gln
    50                  55                  60

Gln Leu Tyr Phe Asn Ser Asn Lys Leu Thr Ala Ile Pro Thr Gly Val
65                  70                  75                  80

Phe Asp Lys Leu Thr Gln Pro Thr Gln Leu Asp Leu Asn Asp Asn His
                85                  90                  95

Leu Lys Ser Ile Pro Arg Gly Ala Phe Asp Asn Leu Lys Ser Leu Thr
            100                 105                 110

His Ile Tyr Leu Tyr Asn Asn Pro Trp Asp Cys Glu Cys Arg Asp Ile
        115                 120                 125

Met Tyr Leu Arg Asn Trp Val Ala Asp His Thr Ser Ile Val Met Arg
    130                 135                 140

Trp Asp Gly Lys Ala Val Asn Asp Pro Asp Ser Ala Lys Cys Ala Gly
145                 150                 155                 160

Thr Asn Thr Pro Val Arg
                165


<210> SEQ ID NO 115
<211> LENGTH: 253
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 115
```

Met Trp Ile Lys Trp Ile Ala Thr Leu Val Ala Phe Gly Ala Leu Val
1 5 10 15

Gln Ser Ala Val Ala Cys Pro Ser Gln Cys Ser Cys Ser Gly Thr Thr
20 25 30

Val Asp Cys Arg Ser Arg Arg His Ala Ser Val Pro Ala Gly Ile Pro
35 40 45

Thr Thr Thr Gln Tyr Leu Tyr Leu Leu Val Asn Gln Ile Thr Lys Leu
50 55 60

Glu Pro Gly Val Phe Asp Leu Leu Val Asn Leu Gln His Leu His Leu
65 70 75 80

Asn Ser Asn Lys Leu Thr Ala Ile Pro Ala Gly Val Phe Asp Asn Leu
85 90 95

Thr Gln Leu Asn His Leu Phe Leu Asn Asn Asn Gln Leu Lys Ser Ile
100 105 110

Pro Arg Gly Ala Phe Asp Asn Phe Lys Ser Leu Thr His Ile Trp Leu
115 120 125

Tyr Gly Asn Pro Trp Asp Cys Glu Cys Arg Asp Ile Met Tyr Leu Arg
130 135 140

Asn Trp Val Ala Asp His Thr Ser Ile Val Met Arg Trp Asp Gly Lys
145 150 155 160

Ala Val Asn Asp Pro Asp Ser Ala Lys Cys Ala Gly Thr Asn Thr Pro
165 170 175

Val Arg Ala Val Thr Glu Ala Ser Thr Ser Pro Ser Lys Cys Pro Gly
180 185 190

Tyr Val Ala Thr Thr Thr Thr Pro Thr Thr Thr Thr Pro Glu Phe Ile
195 200 205

Pro Glu Thr Thr Thr Ser Pro Gln Pro Val Ile Thr Thr Gln Lys Pro
210 215 220

Lys Pro Leu Trp Asn Phe Asn Cys Thr Ser Ile Gln Glu Arg Lys Asn
225 230 235 240

Asp Gly Gly Asp Trp Thr Cys Ala Leu Cys Arg Lys Arg
245 250

<210> SEQ ID NO 116
<211> LENGTH: 294
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 116

Met Trp Ile Lys Trp Ile Ala Thr Leu Val Ala Phe Gly Ala Leu Val
1 5 10 15

Gln Ser Ala Val Ala Cys Pro Ser Gln Cys Pro Cys Ser Gly Thr Glu
20 25 30

Val Arg Cys Gln Ser Arg Ser Leu Ala Ser Val Pro Ala Gly Ile Pro
35 40 45

Thr Thr Thr Arg Arg Leu His Leu His Arg Asn Gln Leu Thr Lys Leu
50 55 60

Glu Pro Gly Val Ser Asp Ser Leu Val Asn Leu Gln Ile Leu Val Leu
65 70 75 80

Tyr Gln Asn Gln Leu Thr Thr Leu Pro Ala Gly Val Phe Asp Arg Leu
85 90 95

Val Asn Leu Gln Ile Leu Val Leu Tyr Gln Asn Gln Leu Thr Thr Leu
100 105 110

```
Pro Ala Gly Val Phe Asp Arg Leu Val Lys Leu Thr Thr Leu Glu Leu
        115                 120                 125

Gln Ile Asn Gln Leu Lys Ser Ile Pro Arg Gly Ala Phe Asp Asn Leu
    130                 135                 140

Lys Ser Leu Thr His Ile Trp Leu Phe Asn Asn Pro Trp Asp Cys Glu
145                 150                 155                 160

Cys Ser Asp Ile Leu Tyr Leu Lys Asn Trp Ile Val Gln His Ala Ser
                165                 170                 175

Ile Val Asn Leu Arg Gly His Gly Gly Val Asp Asn Val Lys Cys Ser
            180                 185                 190

Gly Thr Asn Thr Pro Val Arg Ala Val Thr Glu Ala Ser Thr Ser Pro
        195                 200                 205

Ser Lys Cys Pro Gly Tyr Val Ala Thr Thr Thr Thr Pro Thr Thr Thr
    210                 215                 220

Thr Pro Glu Phe Ile Pro Glu Thr Thr Thr Ser Pro Gln Pro Val Ile
225                 230                 235                 240

Thr Thr Gln Lys Pro Lys Pro Leu Trp Asn Phe Asn Cys Thr Ser Ile
                245                 250                 255

Gln Glu Arg Lys Asn Asp Gly Gly Asp Cys Gly Lys Pro Ala Cys Thr
            260                 265                 270

Thr Leu Leu Asn Cys Ala Asn Phe Leu Ser Cys Leu Cys Ser Thr Cys
        275                 280                 285

Ala Leu Cys Arg Lys Arg
    290


<210> SEQ ID NO 117
<211> LENGTH: 292
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 117

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Thr
            20                  25                  30

Val Asn Cys Asp Ser Arg Ser Leu Ala Ser Val Pro Gly Gly Ile Pro
        35                  40                  45

Thr Thr Thr Gln Val Leu Tyr Leu Tyr Asp Asn Gln Ile Thr Lys Leu
    50                  55                  60

Glu Pro Gly Val Phe Asp Ser Leu Thr Ala Leu Thr Glu Leu Asn Leu
65                  70                  75                  80

Ala Val Asn Gln Leu Thr Ala Leu Pro Val Gly Val Phe Asp Ser Leu
                85                  90                  95

Thr Gln Leu Thr Ile Leu Ala Leu Glu Arg Asn Gln Leu Pro Ala Leu
            100                 105                 110

Pro Ala Gly Val Phe His Lys Leu Thr Gln Leu Thr Gln Leu Gln Asp
        115                 120                 125

Asn Gln Leu Lys Ser Ile Pro Arg Gly Ala Phe Asp Asn Leu Lys Ser
    130                 135                 140

Leu Thr Gln Ile Tyr Leu Phe Asn Asn Pro Trp Asp Cys Glu Cys Ser
145                 150                 155                 160

Asp Ile Leu Tyr Leu Lys Asn Trp Ile Val Gln His Ala Ser Ile Val
                165                 170                 175
```

```
Asn Leu Gln Gly His Gly Gly Val Asp Asn Val Lys Cys Ser Gly Thr
            180                 185                 190

Asn Thr Pro Val Arg Ala Val Thr Glu Ala Ser Thr Ser Pro Ser Lys
        195                 200                 205

Cys Pro Gly Tyr Val Ala Thr Thr Thr Thr Pro Thr Thr Thr Thr Pro
    210                 215                 220

Glu Phe Ile Pro Glu Thr Thr Thr Ser Pro Gln Pro Val Ile Thr Thr
225                 230                 235                 240

Gln Lys Pro Lys Pro Leu Trp Asn Phe Asn Cys Thr Ser Ile Gln Glu
                245                 250                 255

Arg Lys Asn Asp Gly Gly Asp Cys Gly Lys Pro Ala Cys Thr Thr Leu
            260                 265                 270

Leu Asn Cys Ala Asn Phe Leu Ser Cys Leu Cys Ser Thr Cys Ala Leu
        275                 280                 285

Cys Arg Lys Arg
    290


<210> SEQ ID NO 118
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 118

Gly Ala Leu Val Gln Ser Ala Val Ala Cys Pro Ser Gln Cys Ser Cys
 1               5                  10                  15

Ser Gly Thr Gln Val Asn Cys His Glu Arg Ser Leu Ala Ser Val Pro
            20                  25                  30

Ala Gly Ile Pro Thr Thr Thr Gln Val Leu Tyr Leu Tyr Thr Asn Gln
        35                  40                  45

Ile Thr Lys Leu Glu Pro Gly Val Phe Asp Ser Leu Thr Gln Leu Thr
    50                  55                  60

Tyr Leu Asn Leu Ala Val Asn Gln Leu Thr Ala Leu Pro Ala Gly Val
65                  70                  75                  80

Phe Asp Lys Leu Pro Lys Leu Thr His Leu Val Leu His Thr Asn Gln
                85                  90                  95

Leu Lys Ser Ile Pro Arg Gly Ala Phe Asp Asn Leu Lys Ser Leu Thr
            100                 105                 110

His Ile Trp Leu Leu Asn Asn Pro Trp Asp Cys Glu Cys Ser Asp Ile
        115                 120                 125

Leu Tyr Leu Lys Asn Trp Ile Val Gln His Ala Ser Ile Val Asn Leu
    130                 135                 140

Gln Gly His Gly Gly Val Asp Asn Val Lys Cys Ser Gly Thr Asn Thr
145                 150                 155                 160

Pro Val Arg


<210> SEQ ID NO 119
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 119

Gly Ala Leu Val Gln Ser Ala Val Ala Cys Pro Ser Gln Cys Ser Cys
```

-continued

```
1               5                   10                  15

Ser Gly Thr Gln Val Asn Cys His Glu Arg Ser Leu Ala Ser Val Pro
            20                  25                  30

Ala Gly Ile Pro Thr Thr Thr Gln Val Leu Tyr Leu Tyr Thr Asn Gln
        35                  40                  45

Ile Thr Lys Leu Glu Pro Gly Val Phe Asp Ser Leu Ala Asn Leu Arg
    50                  55                  60

Glu Leu His Leu Trp Gly Asn Gln Leu Val Ser Leu Pro Pro Gly Val
65                  70                  75                  80

Phe Asp Lys Leu Thr Gln Leu Thr Gln Leu Gly Leu Trp Asp Asn Gln
                85                  90                  95

Leu Lys Ser Ile Pro Arg Gly Ala Phe Asp Asn Leu Lys Ser Leu Thr
            100                 105                 110

His Ile Trp Leu Phe Gly Asn Pro Trp Asp Cys Glu Cys Ser Asp Ile
        115                 120                 125

Leu Tyr Leu Lys Asn Trp Ile Val Gln His Ala Ser Ile Val Asn Pro
    130                 135                 140

Ser Gly Tyr Gly Gly Val Asp Asn Val Lys Cys Ser Gly Thr Asn Thr
145                 150                 155                 160

Pro Val Arg
```

<210> SEQ ID NO 120
<211> LENGTH: 1742
<212> TYPE: DNA
<213> ORGANISM: Artificial Sequence
<220> FEATURE:
<223> OTHER INFORMATION: Description of Artificial Sequence; note = synthetic construct

<400> SEQUENCE: 120

```
ctcggctctg cagctctcaa cagctccagc tacagccacc actgtcccct ctctcgctct     60

ctcgctcccc aacactctca cgctctccgc tactcgggtg agcctgcaat acttctgctc    120

ggagcctatc cgtgccattt cgaaagatgt tgcttacttg ttaaatgccc gtttgaatct    180

tgcttcgtga gaaatgttcg cattgtgtgt ggcggtgcgc tcgtcaaatt gtctttgtgg    240

tcgttgctgc tgaattctga tggggatgga tccacacagg tttggcagcg cgtgccggcg    300

ccttcacact tgatggctct gcaccgagtg ttaattatgt tcagtcgatc gaatgtgaag    360

acaaaacgtt gctcgtttga tgaacgtttt ggtcgaggac gcaatgcact tgcaatgtgc    420

cccgatccga tcagaataac tgggcgtctg tatgtttttg tcgaaagtta aacaatgaat    480

tcacctaatt taatttctgg actaacttgg gcgtgaaccc gttcgcttcg acctttggct    540

caaattcaac agcagcaatg aagacgcagc ctttcacgcg tcgcacaact cagcgtataa    600

cttcgggcgg ccaatcgcat ttttttgtaa attttggcaa attttggcac gcgcatgaat    660

cacttcggtg cgagatgcgt ttgcgatggt acttaacgcg ccctgtccgt tttgtctct     720

cgcccttcag cctgcaggag ccaaccatca tgtggatcaa gtggatcgcc acgctggtcg    780

tctttggcgc cctggtgcaa agtgcggtag catgtccctc gcagtgttcg ttcgatcaga    840

cacttgtgaa ctgccagaat atacgcctcg catctgtgcc tgcgggaatc cccaccacca    900

cgcaaactct gtggggggac agtaatcaga tcacgaagct cgagcccggg gtgtttgacc    960

gcctggtgaa tctgcagaag ctgcgtttgt acaacaacca gctgcaggct ctacccactt   1020

tggtgtttga ccgcctggtg aatctgcagc ggctgtggtt gaacaacaac cagctgacct   1080

ctctccccgc tggtgtgttt gaccgtctga ctcaactgac acgactggat cttgacaata   1140
```

accagttgac agttctcccg ccgggggtgt ttgacaaact aacccagcta aagcagttga 1200
gtctgctgca gaatcaactg aagagcattc ccaggggtgc cttagacaac ctcaagagcc 1260
tcactcacat ctggctgttt gacaacccct gggactgcgc ctgctcagac atcctgtacc 1320
tcagccgctg gatctctcag aaccctggag ttccgaaggc ggcagatagt tggaccagag 1380
tggatctcga ctcagcgcgc tgctctggta ccaataccc cgtccgtgcg gtcaccgagg 1440
ccagcactag cccctcgaaa tgcccaggct acgttgctac gaccacgacg ccgacgacga 1500
ccacgcccga attcatccct gagaccacca cctcgccgca gcccgtgatc acaacccaga 1560
aacccaagcc tctgtggaat ttcaactgca cctcaattca ggagaggaag aacgacggtg 1620
gcgactgcgg aaagcccgcc tgcacaactc tcctgaactg cgcgaatttc ctcagctgcc 1680
tctgctcgac ctgcgccctc tgcaggaaac gttgatcggc gtgcaaaggt cggggatggc 1740
gg 1742

<210> SEQ ID NO 121
<211> LENGTH: 1729
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 121
ctcggctctg cagctctcaa cagctccggc tacagccacc actgtcccct ctctcgctct 60
ctcgctcccc aacactctca cgctctccgc tactcgggtg agcctgcaat acttctgctc 120
ggagcctatc cgtgccattt cgaaagatgt tgctttcctg ttaaatgccc gtttgaatct 180
tgcttcgtga gaaatgttcg cattgtgtgt ggtggtgcgc tcttcaaatt gtctttgtgg 240
tcgttgctgc tgaattctga tgggaatgta tccacacagg tttggcagcg cgtgccggcg 300
ccttcacact tgatggctct gcaccgagtg ttaattatgc tcagtcgatc gaatgtgaag 360
acaaaacgtt gctcgtttga ttaacgtttg ggttgaggat gcaatgcact tgcaatgtgc 420
gccgatccga tcagaataac tgggcgtctg tatgttttat ttaagttaaa caattaattc 480
gcctcattta atttctggac taaccagggc acgaacccgt tcgcttctgt ctttggctca 540
aattcaacag cagcaatgaa gacgcagcct ttcacgcgtc gcacaaccca gcgtataact 600
tcgagcggcc aatcggcttt ttggcaaatt ttggcacgcg cgtgaatccc gtcggtgcga 660
gacgcgtttg cgatggtact taacgcgccc tgtccgtttt tgtctctcgc ccttcagcct 720
gcaggagcca accatcatgt ggatcaagtg gatcgccacg ctggtcgcct ttggcgccct 780
ggtgcaaagt gcggtagcat gtccctcgca gtgtccgtgc tcagggacag aagtgcactg 840
tcagaaaaaa agcctcgcgt ctgtgcctgc aggaatcccc accaccacgc aagtgctgta 900
tttgcacgtc aatcagatca cgaagctcga gcccggggtg tttgaccgcc tggtgaatct 960
gcaagagctg actctgtaca acaaccagct gacagctcta cccaatggaa ttttcgacaa 1020
actcacccag ctcgtaacac tggatctgaa tggaaaccaa ctgtcatccg ttcccgcaga 1080
cgtgttccat cagcttgtga aattagagaa gctgtggctc aaaaacaaca aactgacggc 1140
tcttcccgct gggttgttcg acaacctgac ccagctaaag cagttgagtc tgcacaccaa 1200
ccagctgaag agcattccca ggggcgcctt tgacaacctc aagagcctaa ctcacatctt 1260
tctgtacaac aacccatggg attgcgagtg cagggacatt atgtacctca ggaactgggt 1320
cgcagaccac acttctattg taatgcgctg ggatgggaag gccgttaacg accccgactc 1380
tgccaagtgc gctggtacca atacccccgt ccgtgcggtc accgaggcca gcactagccc 1440

```
ctcgaaatgc ccaggctacg ttgctacgac cacgacgccg acgacgacca cgcccgaatt   1500

catccctgag accaccacct cgccgcagcc cgtgatcaca acccagaaac ccaagcctct   1560

gtggaatttc aactgcacct caattcagga gaggaagaac gacggtggcg actgcggaaa   1620

gcccgcctgc acaactctcc tgaactgcgc gaatttcctc agctgcctct gctcgacctg   1680

cgccctctgc aggaaacgtt gatcggcgtg caaaggtcgg ggatggcgg              1729


<210> SEQ ID NO 122
<211> LENGTH: 167
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 122

Gly Ala Leu Val Gln Ser Ala Val Ala Cys Pro Ser Gln Cys Ser Cys
 1               5                  10                  15

Ser Gly Thr Gln Val Asn Cys His Glu Arg Arg Leu Ala Ser Val Pro
            20                  25                  30

Ala Gly Ile Pro Thr Thr Thr Gln Val Leu Tyr Leu Tyr Thr Asn Lys
        35                  40                  45

Ile Thr Lys Leu Glu Pro Gly Val Phe Asp Ser Leu Thr Ala Leu Thr
    50                  55                  60

Tyr Leu Asn Leu Gly Gly Asn Gln Leu Thr Ala Leu Pro Val Gly Val
65                  70                  75                  80

Phe Asp Lys Leu Thr Lys Leu Thr His Leu Ala Leu His Ile Asn Gln
                85                  90                  95

Leu Lys Ser Val Pro Arg Gly Ala Phe Asp Asn Leu Lys Ser Leu Thr
            100                 105                 110

His Ile Trp Leu Tyr Asn Asn Pro Trp Asp Cys Ala Cys Ser Asp Ile
        115                 120                 125

Leu Tyr Leu Ser Arg Trp Ile Ser Gln His Pro Gly Val Val Arg Thr
    130                 135                 140

Ala Asp Asp Gly Trp Asn Arg Val Val Pro Asp Ser Ala Arg Cys Ser
145                 150                 155                 160

Gly Thr Asn Thr Pro Val Arg
                165


<210> SEQ ID NO 123
<211> LENGTH: 298
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 123

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr Gln
            20                  25                  30

Val Asn Cys His Glu Arg Arg Leu Ala Ser Val Pro Ala Gly Ile Pro
        35                  40                  45

Thr Thr Thr Gln Val Leu Tyr Leu Tyr Thr Asn Lys Ile Thr Lys Leu
    50                  55                  60

Glu Pro Gly Val Phe Asp Ser Leu Ala Ala Leu Thr Glu Leu Tyr Leu
65                  70                  75                  80
```

```
His Tyr Asn Gln Leu Thr Thr Leu Pro Tyr Gly Val Phe Asp Ser Leu
                85                  90                  95

Thr Gln Leu Thr Tyr Leu Asn Leu Ala Val Asn Gln Leu Thr Ser Val
            100                 105                 110

Pro Ala Gly Val Phe Asp Glu Leu Thr Gln Val Tyr Ser Leu Ser Leu
        115                 120                 125

Asn Asp Asn Gln Leu Lys Ser Ile Pro Arg Gly Ala Phe Asp Asn Leu
    130                 135                 140

Lys Ser Leu Thr His Ile Phe Leu Tyr Asn Asn Pro Trp Asp Cys Ala
145                 150                 155                 160

Cys Ser Asp Ile Leu Tyr Leu Ser Arg Trp Ile Ser Gln His Pro Gly
                165                 170                 175

Val Val Arg Ser Ala Asp Asp Asp Trp Ser Arg Val Val Pro Asp Ser
            180                 185                 190

Ala Arg Cys Ser Gly Thr Asn Thr Pro Val Arg Ala Val Thr Glu Ala
        195                 200                 205

Ser Thr Ser Pro Ser Lys Cys Pro Gly Tyr Val Ala Thr Thr Thr Thr
    210                 215                 220

Pro Thr Thr Thr Thr Pro Glu Phe Ile Pro Glu Thr Thr Thr Ser Pro
225                 230                 235                 240

Gln Pro Val Ile Thr Thr Gln Lys Pro Lys Pro Leu Trp Asn Phe Asn
                245                 250                 255

Cys Thr Ser Ile Gln Glu Arg Lys Asn Asp Gly Gly Asp Cys Gly Lys
            260                 265                 270

Pro Ala Cys Thr Thr Leu Leu Asn Cys Ala Asn Phe Leu Ser Cys Leu
        275                 280                 285

Cys Ser Thr Cys Ala Leu Cys Arg Lys Arg
    290                 295


<210> SEQ ID NO 124
<211> LENGTH: 191
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 124

Gly Ala Leu Val Gln Ser Ala Val Ala Cys Pro Ser Gln Cys Ser Cys
 1               5                  10                  15

Ser Gly Thr Gln Val Asn Cys His Glu Arg Ser Leu Ala Ser Val Pro
            20                  25                  30

Ala Gly Ile Pro Thr Thr Thr Gln Val Leu Tyr Leu Tyr Thr Asn Gln
        35                  40                  45

Ile Thr Lys Leu Glu Pro Gly Val Phe Asp Ser Leu Thr Ala Leu Thr
    50                  55                  60

Tyr Leu Gly Leu Gly Gly Asn Gln Leu Ala Ala Leu Pro Val Gly Leu
65                  70                  75                  80

Phe Asp Arg Leu Gly Asn Leu Gln Arg Leu His Leu Asp Gln Asn Gln
                85                  90                  95

Leu Gln Ala Leu Pro Thr Gly Val Phe Asn Lys Leu Thr Gln Leu Thr
            100                 105                 110

His Leu Ser Leu His Thr Asn Gln Leu Lys Ser Ile Pro Arg Gly Ala
        115                 120                 125

Phe Asp Asn Leu Lys Ser Leu Thr His Ile Trp Leu Phe Gly Asn Pro
    130                 135                 140
```

Trp Asp Cys Ala Cys Ser Asp Ile Leu Tyr Leu Ser Arg Trp Ile Ser
145 150 155 160

Gln His Pro Gly Ile Val Arg Ser Ala Asp Asp Gly Trp Asn Arg Val
165 170 175

Asn Pro Asp Ser Ala Arg Cys Ser Gly Thr Asn Thr Pro Val Arg
180 185 190

<210> SEQ ID NO 125
<211> LENGTH: 167
<212> TYPE: PRT
<213> ORGANISM: Artificial Sequence
<220> FEATURE:
<223> OTHER INFORMATION: Description of Artificial Sequence; note = synthetic construct

<400> SEQUENCE: 125

Gly Ala Leu Val Gln Ser Ala Val Ala Cys Pro Ser Gln Cys Ser Cys
1 5 10 15

Ser Gly Thr Glu Val His Cys Ala Gly Lys Ser Leu Ala Ser Val Pro
20 25 30

Ala Gly Ile Pro Ile Thr Thr Gln Arg Leu Trp Leu Ser Asn Asn Gln
35 40 45

Leu Thr Lys Leu Asp Pro Gly Val Phe Asp Ser Leu Val Asn Leu Gln
50 55 60

Lys Leu Trp Leu Asn Ser Asn Gln Leu Thr Ser Leu Pro Ala Gly Val
65 70 75 80

Phe Asn Arg Leu Thr Gln Leu Thr Thr Leu Glu Leu Gln Ile Asn Gln
85 90 95

Leu Lys Ser Ile Pro Arg Gly Ala Phe Asp Asn Leu Lys Ser Leu Thr
100 105 110

His Ile Trp Leu Tyr Asn Asn Pro Trp Asp Cys Ala Cys Ser Asp Ile
115 120 125

Leu Tyr Leu Ser Arg Trp Ile Ser Gln His Pro Gly Ile Val Arg Ser
130 135 140

Ala Asp Asp Gly Trp Asn Arg Val Asn Pro Asp Ser Ala Arg Cys Ser
145 150 155 160

Gly Thr Asn Thr Pro Val Arg
165

<210> SEQ ID NO 126
<211> LENGTH: 1712
<212> TYPE: DNA
<213> ORGANISM: Artificial Sequence
<220> FEATURE:
<223> OTHER INFORMATION: Description of Artificial Sequence; note = synthetic construct

<400> SEQUENCE: 126
ctcggctctg cagctctcaa cagctccagc tacagccacc actgtcccct ctctcgctct 60
ctcgctcccc aacactctca cgctctccgc tactcgggtg agcctgcaat acttctgctc 120
ggagcctctc cgtgcgattt cgaaagatgt tgcttactcg ttaaatgccc gtttgaatct 180
tgcttcgtga gaaatgttcg cattgtgtgt ggcggtgcgc tcgtcaaact gtctttgtgg 240
tcgttgctgc tgaattctga tggggatgga tccacacagg tttggcagcg cgtgccggcg 300
ccttcacact cgatggctct gcaccgagtg ttaattgtgt tcagtcgatc gaatatgaag 360
acaaatcgtt gctcgtttga tgaacgcttt ggtcgaggac gcaatgcact tgcaatgtgc 420
accgattcga tcagaataac tgggcgtctg tatgttttcg tcgaaagtta aacaatgaat 480

```
tcacctaatt taatttctgg actaacttgg gcgtgaaccc gttcgcttcg acctttggct    540
caaattcaac agcagcaatg aagacgcagc ctttcacgcg tcgcacaact cagcgtataa    600
cttcgagcgg ccaatcgcat ttgtttgtaa attttggcaa attttggcac gcgcatgaat    660
cacttcggtg cgagatgcgt ttgcgatggt acttaacgcg ccctgtccgt tttgtctctt    720
cgcccttcag cctgcaggag ccaaccatca tgtggatcaa gtggatcgcc acgctggtcg    780
cctttgccgc cctggtgcaa agtgcggtag catgtccctc gcagtgttcg tgctcaggga    840
cagaagtgcg ctgtcagagc agaagcctcg cgtctgtgcc tgcgggaatc cccaccgcca    900
cgcaagtgct gtatttgtac accaataaga tcacgaagct cgagcccggc gtgtttgaca    960
gtctgactca actgacacga ctggatcttt acaataacca gttgacagtt ctccccgccg   1020
gggtgtttga cagcctggca aatctggaga agctgcattt gtacgacaac cagctaacgt   1080
ctctccccgc tggtgtgttt gaccgtctga ctcaactgac acgactggat ctttacaata   1140
accagttgac agttctcccc gctggcgtat ttgaccgcct agtgaatctg cagaagctgt   1200
atttgtatga gaaccaactg aagagcattc ccaggagcgc ctttgacaac ctcaagagcc   1260
tcactcacat ttggctgcac agtaacccct gggactgtgc ttgctcagac atcctctacc   1320
tcagcggctg gctgggccag cacgcaggga aagagcaggg ccaggctgtc tgctctggta   1380
ccaatacccc cgtccgtgcg gtcaccgagg ccagcactag cccctcgaaa tgcccaggct   1440
acgttgctac gaccacgacg ccgacgacga ccacgcccga attcatccct gagaccacca   1500
cctcgccgca gcccgtgatc acaacccaga aacccaagcc tctgtggaat ttcaactgca   1560
cctcaattca ggagaggaag aacgacggtg gcgactgcgg aaagcccgcc tgcacaactc   1620
tcctgaactg cgcgaatttc ctcagctgcc tctgctcgac ctgcgccctc tgcaggaaac   1680
gttgatcggc gtgcaaaggt cggggatggc gg                                 1712
```

```
<210> SEQ ID NO 127
<211> LENGTH: 1648
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 127
```

```
ctcggctctg cagctctcaa cagctccagc tacagccacc actgtcccct ctctcgctct     60
ctcgctcccc aacactctca cgctctccgc tactcgggtg agcctgcaat acttctgctc    120
ggagcctatc cgtgccattt cgaaagatgt tgctttcctg ttaaatgccc gtttgaatct    180
tgcttcgtga gaaatgttcg cattgtgtgt ggtggtgcgc tcttcaaatt gtctttgtgg    240
tcgctgctgc tgaattctga tgggaatgta tccacacagg tttggcagcg cgtgccggcg    300
ccttcacact tgatggctct gcaccgagtg ttaattatgc tcagtcgatc gaatgtgaag    360
acaaaacgtt gctcgtttga ttaacgtttg ggttgaggat gcaatgcact tgcaatgtgc    420
gccgatccga tcagaataac tgggcgtctg tatgttttat ttaagttaaa caattaattc    480
gcctcattta atttctggac taaccagggc acgaacccgt tcgcttctgt ctttggctca    540
aattcaacag cagcaatgaa gacgcagcct ttcacgcgtc gcacaaccca gcgtataact    600
tcgagcggcc aatcggcttt ttggcaaatt ttggcacgcg cgtgaatccc gtcggtgcga    660
gacgtgtttg cgatggtact taacccgccc tgtccgtttt tgtctctcgc ccttcagcct    720
gcagaagcca accatcatgt ggatcaagtg gatcgccacg ctggtcgcct ttggcgccct    780
```

ggtgcaaagt gcggtagcat gtccctcgca gtgtccgtgt tcagggacag aagtgcgctg 840
tcagagcaga agcctcgcgt ctgtgcctgc gggaatcccc accaccacgc gaaggttgca 900
tttgcacaga aatcaactca cgaagctcga gcccggggtg tctgacagtc tggtgaatct 960
gcagatcctg gttttgtatc agaatcagct aacaactctg cccgccgggg tatttgaccg 1020
tctggtgaat ctgcagatcc tggttttgta tcagaatcag ctaacaactc tgcccgccgg 1080
ggtatttgac cgtctggtga aactgacgac actggagctg cagatcaacc agctgaagag 1140
cattcccagg ggcgcctttg acaacctcaa gagcctcact cacatctggc tgttcaacaa 1200
cccctgggac tgcgagtgtt cggacatcct ctatctgaag aactggattg tgcagcatgc 1260
aagcatcgtg aatctacggg gccatggggg agttgataat gtgaagtgct ctggtaccaa 1320
tacccccgtc cgtgcggtca ccgaggccag cactagcccc tcgaaatgcc caggctacgt 1380
tgctacgacc acgacgccga cgacgaccac gcccgaattc atccctgaga ccaccacctc 1440
gccgcagccc gtgatcacaa cccagaaacc caagcctctg tggaatttca actgcacctc 1500
aattcaggag aggaagaacg acggtggcga ctgcggaaag cccgcctgca caactctcct 1560
gaactgcgcg aatttcctca gctgcctctg ctcgacctgc gccctctgca ggaaacgttg 1620
atcggcgtgc aaaggtcggg gatggcgg 1648

<210> SEQ ID NO 128
<211> LENGTH: 1313
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 128
tttggctcaa attcaacagc agcaatgaag acgcagcctt tcacgcgtcg cacaccccag 60
cgtatacttc gagcggccaa tcggcttttt ggcaaatttt ggcacgcgcg tgaatcccgt 120
cggtgcgaga cgcgtttgcg atggtactta acgcgccctg tccgtttttg tctctcgccc 180
ttcagcctgc aggagccaac catcatgtgg atcaagtgga tcgccacgct ggtcgccttt 240
ggcgccctgg tgcaaagtgc ggtagcatgt ccctcgcagt gttcgtgctc agggacagaa 300
gtgcactgtc agaaaaaaag cctcgcgtct gtgcctgcag gaatccccac caccacgcaa 360
gtgctgtatt tgcacgtcaa tcagatcacg aagctcgagc ccggggtgtt tgacagtctg 420
gtgaatctgc agaagctgtg gttgaacagc aaccagttga cagttcttcc cgccggggtg 480
tttgacagcc tggtgaaact gaaggagctg tgtctggacc ataaccaact gcaggcaata 540
ccgcccactc tgtttgaccg attgactcaa ttgacgcatc tggatctgga taggaaccaa 600
ctgaagtctc tgccgcctgg gatctttgac aaactggaga agctgacgcg tctggagctg 660
tacaataacc agctgaagag tattcccagg ggcgccttta acagcctcaa gagcctcact 720
cacatctggc tgtacaacaa cccctgggac tgtgcttgct cagacatcct ctacctcagc 780
ggctggctgg gccagcacgc agggaaagag cagggccagg ctgtctgctc tggtaccaat 840
acccccgtcc gtgcggtcac cgaggccagc actagcccct cgaaatgccc aggctacgtt 900
gctacgacca cgacgccgac gacgaccacg cccgaattca tccctgagac caccacctcg 960
ccgcagcccg tgatcacaac ccagaaaccc aagcctctgt ggaatttcaa ctgcacctca 1020
attcaggaga ggaagaacga cggtggcgac tgcggaaagc ccgcctgcac aactctcctg 1080
aactgcgcga atttcctcag ctgcctctgc tcgacctgcg ccctctgcag gaaacgttga 1140
tcggcgtgca aaggtcgggg atggcggtgg gaaggcgggc gcggtggggt ggggggtgta 1200
gtggagaagg tggaggagga ggagtgagga gaaggaagac caggaagagg gggagagtaa 1260
taagcagaga cgatttgaaa ggttgacaaa tttctcgcgc aaactccacc acc 1313

<210> SEQ ID NO 129
<211> LENGTH: 204
<212> TYPE: PRT
<213> ORGANISM: Artificial Sequence
<220> FEATURE:
<223> OTHER INFORMATION: Description of Artificial Sequence; note = synthetic construct

<400> SEQUENCE: 129

Gly Ala Leu Val Gln Ser Ala Val Ala Cys Pro Ser Gln Cys Ser Cys
1 5 10 15

Ser Gly Thr Asp Val Gln Cys Asp Arg Arg Ser Leu Val Ser Val Pro
20 25 30

Ala Gly Ile Pro Thr Thr Thr Arg Asp Leu Tyr Leu His Asp Asn Gln
35 40 45

Ile Thr Lys Leu Glu Pro Gly Val Phe Asp Ser Leu Ala Asn Leu Glu
50 55 60

Lys Leu His Leu Tyr Asp Asn Gln Leu Thr Ser Leu Pro Ala Gly Val
65 70 75 80

Phe Asn Arg Leu Val Asn Leu Gln Lys Leu His Leu Tyr Gln Asn Gln
85 90 95

Met Ser Ala Leu Pro Asn Gly Val Phe Asp Gln Leu Thr Glu Leu Thr
100 105 110

Arg Leu Asp Met Glu Ala Asn Gln Leu Lys Ser Leu Pro Pro Lys Ile
115 120 125

Phe Asp Lys Leu Gly Lys Leu Met His Leu Gln Leu His Ala Asn Gln
130 135 140

Leu Thr Thr Val Pro Glu Gly Ala Phe Asn Ser Leu Met Lys Leu Gln
145 150 155 160

Tyr Ile Trp Leu His Ser Asn Pro Trp Asp Cys Ala Cys Ser Asp Ile
165 170 175

Leu Tyr Leu Ser Gly Trp Leu Gly Gln His Ala Gly Lys Glu Gln Gly
180 185 190

Gln Ala Val Cys Ser Gly Thr Asn Thr Pro Val Arg
195 200

<210> SEQ ID NO 130
<211> LENGTH: 180
<212> TYPE: PRT
<213> ORGANISM: Artificial Sequence
<220> FEATURE:
<223> OTHER INFORMATION: Description of Artificial Sequence; note = synthetic construct

<400> SEQUENCE: 130

Gly Ala Leu Val Gln Ser Ala Val Ala Cys Pro Ser Gln Cys Ser Cys
1 5 10 15

Asp Gln Thr Thr Val Tyr Cys His Ser Arg Arg Leu Thr Ser Val Pro
20 25 30

Ala Gly Ile Pro Thr Asp Arg Gln Asn Leu Trp Leu Tyr Asn Asn Gln
35 40 45

Ile Thr Lys Leu Glu Pro Gly Val Phe Asp Arg Leu Val Asn Leu Gln
50 55 60

Lys Leu Tyr Leu Trp Gly Asn Gln Leu Ser Ala Leu Pro Val Gly Val
65 70 75 80

```
Cys Asp Ser Leu Val Asn Leu Lys Glu Leu Arg Leu Tyr Asn Asn Gln
                85                  90                  95

Leu Thr Ala Leu Pro Glu Gly Val Phe Asp His Leu Val Asn Leu Gln
            100                 105                 110

Gln Leu Ala Leu Asn Asn Asn Gln Leu Lys Ser Ile Pro Arg Gly Ala
        115                 120                 125

Phe Asp Asn Leu Lys Ser Leu Thr His Ile Trp Leu Tyr Asn Asn Pro
    130                 135                 140

Trp Asp Cys Ala Cys Ser Asp Ile Leu Tyr Leu Ser Gly Trp Leu Gly
145                 150                 155                 160

Gln His Ala Gly Lys Glu Gln Gly Gln Ala Val Cys Ser Gly Thr Asn
                165                 170                 175

Thr Pro Val Arg
            180


<210> SEQ ID NO 131
<211> LENGTH: 180
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 131

Gly Ala Leu Val Gln Ser Ala Val Ala Cys Pro Ser Gln Cys Ser Cys
 1               5                  10                  15

Ser Gly Ala Glu Val Arg Cys Val Ser Lys Ser Leu Ala Ser Val Pro
            20                  25                  30

Ala Gly Ile Pro Ile Thr Thr Gln Ser Leu Ser Leu His Tyr Thr Gln
        35                  40                  45

Ile Thr Lys Leu Glu Pro Gly Val Phe Asp His Leu Val Asn Leu Gln
    50                  55                  60

Gln Leu Trp Leu Glu Ile Asn Gln Leu Thr Ser Leu Pro Ala Gly Val
65                  70                  75                  80

Phe Asp Lys Leu Thr Glu Leu Thr Tyr Leu Asn Leu Asn Thr Asn Gln
                85                  90                  95

Leu Thr Ala Leu Pro Ala Gly Val Phe Asp Lys Leu Thr Leu Leu Ala
            100                 105                 110

Gly Leu Ser Leu His Asp Asn Gln Leu Lys Ser Ile Pro Arg Gly Ala
        115                 120                 125

Phe Asp Asn Leu Lys Ser Leu Thr Gln Ile Trp Leu Tyr Asn Asn Pro
    130                 135                 140

Trp Asp Cys Ala Cys Ser Asp Ile Leu Tyr Leu Ser Gly Trp Leu Gly
145                 150                 155                 160

Gln His Ala Gly Lys Glu Gln Gly Gln Ala Val Cys Ser Gly Thr Asn
                165                 170                 175

Thr Pro Val Arg
            180


<210> SEQ ID NO 132
<211> LENGTH: 156
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 132
```

-continued

```
Gly Ala Leu Val Gln Ser Ala Val Ala Cys Pro Ser Gln Cys Ser Cys
 1               5                  10                  15

Ser Gly Ala Glu Val Arg Cys Val Ser Lys Ser Leu Ala Ser Val Pro
            20                  25                  30

Ala Gly Ile Pro Ile Thr Thr Gln Tyr Leu Asn Leu His Val Asn Gln
        35                  40                  45

Ile Thr Lys Leu Glu Pro Gly Val Phe Asp Ser Leu Thr Gln Leu Thr
    50                  55                  60

Thr Leu Tyr Leu Ser Asn Asn Gln Leu Thr Ala Leu Pro Ala Gly Val
65                  70                  75                  80

Phe Glu Lys Leu Thr Gln Leu Ile His Leu Ala Leu Arg Asn Asn Gln
                85                  90                  95

Leu Lys Ile Val Pro Arg Gly Ala Phe Asp Asn Leu Lys Ser Leu Thr
            100                 105                 110

His Ile Trp Leu Leu Asn Asn Pro Trp Asp Cys Ala Cys Ser Asp Ile
        115                 120                 125

Leu Tyr Leu Ser Gly Trp Leu Gly Gln His Ala Gly Lys Glu Gln Gly
    130                 135                 140

Gln Ala Val Cys Ser Gly Thr Asn Thr Pro Val Arg
145                 150                 155
```

<210> SEQ ID NO 133
<211> LENGTH: 1462
<212> TYPE: DNA
<213> ORGANISM: Artificial Sequence
<220> FEATURE:
<223> OTHER INFORMATION: Description of Artificial Sequence; note = synthetic construct

<400> SEQUENCE: 133

```
aatgtgcgcc gatccgatca gaataactgg gcgtctgtat gttttattta agttaaacaa     60

ttaattcgcc tcatttaatt tctggactaa ccagggcacg aacccgttcg cttctgtctt    120

tggctcaaat tcaacagcag caatgaagac gcagcctttc acgcgtcgca caacccagcg    180

tatacttcga gcggccaatc ggctttttgg caaattttgg cacgcgcgtg aatcccgtcg    240

gtgcgagacg cgtttgcgat ggtacttaac gcgccctgtc cgtttttgtc tctcgccctt    300

cagcctgcag gagccaacca tcatgtggat caagtggatc gccacgctgg tcgcctttgg    360

cgccctggtg caaagtgcgg tagcatgtcc ctcgcagtgt tcctgctcag ggacaactgt    420

ggattgccgg agcaaacgcc acgcatctgt gcctgcggga atccccacca ccacgcaagt    480

gctgtatttg tacaccaata agatcacgaa gctcgagccc ggggtgtttg acagtctggc    540

gaatctgagg gaactgcatc tgggggggag ccagctgtcg gctctacccg atggggtgtt    600

taaccgtctg actcaactga cgacactgga gctgcagatc aaccagctga agagcgttcc    660

cacgggcgcg tttaacaacc tcaagagcct cacccacatc tatctgttca acaacccctg    720

ggactgcgag tgttcggaca tcctctatct gaagaactgg attgtacagc acgcaagcat    780

cgtgaatcca ggcagcgggg gagttgataa cgtgaagtgc tctggtacca atacccccgt    840

ccgtgcggtc accgaggcca gcactagccc ctcgaaatgc ccaggctacg ttgctacgac    900

cacgacgccg acgacgacca cgcccgaatt catccctgag accaccacct cgccgcagcc    960

cgtgatcaca acccagaaac ccaagcctct gtggaatttc aactgcacct caattcagga   1020

gaggaagaac gacggtggcg actgcggaaa gcccgcctgc acaactctcc tgaactgcgc   1080

gaatttcctc agctgcctct gctcgacctg cgccctctgc aggaaacgtt gatcggcgtg   1140

caaaggtcgg ggatggcggt gggaaggcgg gcgcggtggg gtggggggtg tagtggagaa   1200
```

```
ggtggaggag gaggagtgag gagaaggaag accaggaaga gggggagagt aataagcaga   1260

gacgatttga aaggttgaca aatttctcgc gcaaactcca ccaccttcgc gtccgaacga   1320

ccatgaggat accgcgacga cgacgatgat aatgaacaac ccagcaagga atcaacgacc   1380

actcttgtcg aatcgcttcg tcagcggctg ttgccgacac acacgcacgc acgcgcacac   1440

gcacgcgcgc atttgaaaac aa                                            1462


<210> SEQ ID NO 134
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 134

Gly Ala Leu Val Gln Ser Ala Val Ala Cys Pro Ser Gln Cys Ser Cys
 1               5                  10                  15

Asp Gln Thr Thr Val Asp Cys Arg Asn Lys Arg Phe Ser Ser Val Pro
            20                  25                  30

Ala Gly Ile Pro Thr Asp Arg Gln Asn Leu Trp Leu Asn Asn Asn Gln
        35                  40                  45

Ile Thr Lys Leu Glu Pro Gly Val Phe Asp Arg Leu Thr Gln Leu Thr
    50                  55                  60

Arg Leu Asp Leu Tyr Asn Asn Gln Leu Thr Val Leu Pro Thr Gly Val
65                  70                  75                  80

Phe Asp Lys Leu Thr Gln Leu Thr Leu Leu Glu Leu Gln Asn Asn Gln
                85                  90                  95

Leu Lys Gly Val Pro Arg Gly Ala Phe Asp Asn Leu Lys Ser Leu Thr
            100                 105                 110

His Ile Trp Leu Phe Gly Asn Pro Trp Asp Cys Ala Cys Thr Asp Ile
        115                 120                 125

Met Tyr Leu Ser Thr Trp Ile Gly Gln Asn Ser Gly Lys Val Thr Lys
    130                 135                 140

Asp Arg Val Asn Asn Pro Asp Ser Ala Val Cys Ser Gly Thr Asn Thr
145                 150                 155                 160

Pro Val Arg


<210> SEQ ID NO 135
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 135

Gly Ala Leu Val Gln Ser Ala Val Ala Cys Pro Ser Gln Cys Ser Cys
 1               5                  10                  15

Ser Gly Thr Asp Val Gln Cys Asp Arg Arg Ser Leu Val Ser Val Pro
            20                  25                  30

Ala Gly Ile Pro Thr Thr Thr Gln Val Leu Tyr Leu Tyr Thr Asn Gln
        35                  40                  45

Ile Thr Lys Leu Glu Pro Gly Val Phe Asp Arg Leu Val Asn Leu Gln
    50                  55                  60

Lys Leu Trp Leu Asn Ser Asn Gln Leu Ser Ala Leu Pro Val Gly Val
65                  70                  75                  80
```

```
Phe Asp Lys Leu Thr Gln Leu Thr Arg Leu Glu Leu Gln Thr Asn Gln
                85                  90                  95

Leu Lys Ser Ile Pro Arg Gly Ala Phe Asp Asn Leu Lys Ser Leu Thr
            100                 105                 110

His Ile Tyr Leu Tyr Asn Asn Pro Trp Asp Cys Ala Cys Thr Tyr Ile
        115                 120                 125

Leu Tyr Leu Ser Thr Trp Ile Gly Gln Asn Ser Gly Lys Val Thr Lys
    130                 135                 140

Glu Ser Val Asn Asn Pro Asp Ser Ala Val Cys Ser Gly Thr Asn Thr
145                 150                 155                 160

Pro Val Arg


<210> SEQ ID NO 136
<211> LENGTH: 187
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 136

Gly Ala Leu Val Gln Ser Ala Val Ala Cys Pro Ser Gln Cys Ser Cys
 1               5                  10                  15

Ser Gly Thr Asp Val Gln Cys Asp Arg Arg Ser Leu Val Ser Val Pro
            20                  25                  30

Gly Gly Ile Pro Thr Thr Thr Gln Val Leu Tyr Leu His Thr Asn Gln
        35                  40                  45

Ile Thr Lys Leu Glu Pro Gly Val Phe Asp Ser Leu Thr Gln Leu Thr
    50                  55                  60

Glu Leu His Leu Ser His Asn Gln Leu Thr Thr Leu Pro Glu Gly Val
65                  70                  75                  80

Phe Asp Ser Leu Val Asn Leu Gln Arg Leu His Leu Asp Gln Asn Gln
                85                  90                  95

Leu Val Ser Leu Pro Ala Gly Val Phe Asp Lys Leu Thr Gln Leu Thr
            100                 105                 110

Arg Leu Glu Leu Gln Thr Asn Gln Leu Lys Ser Ile Pro Arg Gly Ala
        115                 120                 125

Phe Asp Asn Leu Lys Ser Leu Thr His Ile Tyr Leu Tyr Asn Asn Pro
    130                 135                 140

Trp Asp Cys Ala Cys Thr Tyr Ile Leu Tyr Leu Ser Thr Trp Ile Gly
145                 150                 155                 160

Gln Asn Ser Gly Lys Val Thr Lys Glu Ser Val Asn Asn Pro Asp Ser
                165                 170                 175

Ala Val Cys Ser Gly Thr Asn Thr Pro Val Arg
            180                 185


<210> SEQ ID NO 137
<211> LENGTH: 163
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 137

Gly Ala Leu Val Gln Ser Ala Val Ala Cys Pro Ser Gln Cys Ser Cys
 1               5                  10                  15

Ser Gly Thr Gln Val Asn Cys His Glu Arg Ser Leu Ala Ser Val Pro
            20                  25                  30
```

```
Ala Ala Ile Pro Ile Thr Thr Gln Arg Leu Trp Leu Ser Asn Asn Gln
        35                  40                  45

Leu Thr Lys Leu Asp Pro Gly Val Phe Asp Ser Leu Val Asn Leu Gln
    50                  55                  60

Arg Leu His Leu Asp Gln Asn Gln Leu Val Ser Leu Pro Ala Gly Val
65                  70                  75                  80

Phe Asp Lys Leu Thr Gln Leu Thr Arg Leu Ala Leu Ser Thr Asn Gln
                85                  90                  95

Leu Lys Ser Val Pro Arg Gly Ala Phe Asp Asn Leu Lys Ser Leu Thr
            100                 105                 110

His Ile Phe Leu Tyr Asn Asn Pro Trp Asp Cys Ala Cys Thr Tyr Ile
        115                 120                 125

Leu Tyr Leu Ser Thr Trp Ile Gly Gln Asn Ser Gly Lys Val Thr Lys
    130                 135                 140

Glu Ser Val Asn Asn Pro Asp Ser Ala Val Cys Ser Gly Thr Asn Thr
145                 150                 155                 160

Pro Val Arg


<210> SEQ ID NO 138
<211> LENGTH: 321
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 138

Met Trp Ile Lys Trp Ile Ala Thr Leu Val Val Phe Gly Ala Leu Val
 1               5                  10                  15

Gln Ser Ala Val Ala Cys Pro Ser Gln Cys Ser Phe Asp Gln Thr Leu
            20                  25                  30

Val Asn Cys Gln Asn Ile Arg Leu Ala Ser Val Pro Ala Gly Ile Pro
        35                  40                  45

Thr Thr Thr Gln Thr Leu Trp Gly Asp Ser Asn Gln Ile Thr Lys Leu
    50                  55                  60

Glu Pro Gly Val Phe Asp Arg Leu Val Asn Leu Gln Lys Leu Arg Leu
65                  70                  75                  80

Tyr Asn Asn Gln Leu Gln Ala Leu Pro Thr Leu Val Phe Asp Arg Leu
                85                  90                  95

Val Asn Leu Gln Arg Leu Trp Leu Asn Asn Asn Gln Leu Thr Ser Leu
            100                 105                 110

Pro Ala Gly Val Phe Asp Arg Leu Thr Gln Leu Thr Arg Leu Asp Leu
        115                 120                 125

Asp Asn Asn Gln Leu Thr Val Leu Pro Pro Gly Val Phe Asp Lys Leu
    130                 135                 140

Thr Gln Leu Lys Gln Leu Ser Leu Leu Gln Asn Gln Leu Lys Ser Ile
145                 150                 155                 160

Pro Arg Gly Ala Leu Asp Asn Leu Lys Ser Leu Thr His Ile Trp Leu
                165                 170                 175

Phe Asp Asn Pro Trp Asp Cys Ala Cys Ser Asp Ile Leu Tyr Leu Ser
            180                 185                 190

Arg Trp Ile Ser Gln Asn Pro Gly Val Pro Lys Ala Ala Asp Ser Trp
        195                 200                 205

Thr Arg Val Asp Leu Asp Ser Ala Arg Cys Ser Gly Thr Asn Thr Pro
    210                 215                 220
```

```
Val Arg Ala Val Thr Glu Ala Ser Thr Ser Pro Ser Lys Cys Pro Gly
225                 230                 235                 240

Tyr Val Ala Thr Thr Thr Thr Pro Thr Thr Thr Thr Pro Glu Phe Ile
                245                 250                 255

Pro Glu Thr Thr Thr Ser Pro Gln Pro Val Ile Thr Thr Gln Lys Pro
            260                 265                 270

Lys Pro Leu Trp Asn Phe Asn Cys Thr Ser Ile Gln Glu Arg Lys Asn
        275                 280                 285

Asp Gly Gly Asp Cys Gly Lys Pro Ala Cys Thr Thr Leu Leu Asn Cys
    290                 295                 300

Ala Asn Phe Leu Ser Cys Leu Cys Ser Thr Cys Ala Leu Cys Arg Lys
305                 310                 315                 320

Arg


<210> SEQ ID NO 139
<211> LENGTH: 166
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 139

Gly Ala Leu Val Gln Ser Ala Val Ala Cys Pro Ser Gln Cys Ser Cys
 1               5                  10                  15

Asp Gln Thr Thr Val Asn Cys His Asn Arg Arg Leu Thr Ser Val Pro
            20                  25                  30

Ala Gly Ile Pro Thr Asn Arg Gln Asn Leu Trp Leu His Asp Asn Gln
        35                  40                  45

Ile Thr Lys Leu Glu Pro Gly Val Phe Asp Ser Leu Thr Gln Leu Thr
    50                  55                  60

Tyr Leu Ser Leu Gly Tyr Asn Gln Leu Lys Ser Val Pro Arg Gly Val
65                  70                  75                  80

Phe Asp Lys Leu Thr Arg Leu Lys Arg Leu Gly Leu Asp Gln Asn Gln
                85                  90                  95

Leu Lys Ser Ile Pro Arg Gly Ala Phe Asp Asn Leu Lys Ser Leu Thr
            100                 105                 110

His Ile Arg Leu Phe Gly Asn Pro Trp Asp Cys Ala Cys Ser Asp Ile
        115                 120                 125

Leu Tyr Leu Ser Arg Trp Ile Ser Gln His Pro Gly Val Pro Lys Ala
    130                 135                 140

Ala Asp Ser Trp Thr Arg Val Asp Leu Asp Ser Ala Arg Cys Ser Gly
145                 150                 155                 160

Thr Asn Thr Pro Val Arg
                165


<210> SEQ ID NO 140
<211> LENGTH: 321
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 140

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Asp Gln Thr Thr
            20                  25                  30
```

```
Val Asp Cys Arg Asn Lys Arg Phe Ser Ser Val Pro Ala Gly Ile Pro
        35                  40                  45

Thr Asp Arg Gln Asn Leu Trp Leu Asn Asn Asn Gln Ile Thr Lys Leu
    50                  55                  60

Glu Pro Gly Val Phe Asp Arg Leu Ala Gln Leu Thr Gly Leu Asp Leu
65                  70                  75                  80

Ser His Asn Gln Phe Thr Ala Leu Pro Ala Gln Val Phe Asp Arg Leu
                85                  90                  95

Val Asn Leu Gln Lys Leu Trp Leu Asn Ser Asn Lys Leu Thr Ala Ile
            100                 105                 110

Pro Ala Gly Val Phe Asp Lys Leu Thr Glu Leu Thr Tyr Leu Asn Leu
        115                 120                 125

Asn Thr Asn Gln Leu Thr Ala Leu Pro Glu Gly Val Phe Asp Lys Leu
    130                 135                 140

Pro Lys Leu Thr His Leu Val Leu His Thr Asn Gln Leu Thr Ser Ile
145                 150                 155                 160

Pro Arg Gly Ala Phe Asp Asn Leu Lys Ser Leu Thr His Ile Trp Leu
                165                 170                 175

Phe Asp Asn Pro Trp Asp Cys Ala Cys Ser Asp Ile Leu Tyr Leu Ser
            180                 185                 190

Arg Trp Ile Ser Gln His Pro Gly Val Val Arg Lys Asp Glu Ala Gly
        195                 200                 205

Tyr Pro Val Asp Pro Asp Ser Ala Arg Cys Ser Gly Thr Asn Thr Pro
    210                 215                 220

Val Arg Ala Val Thr Glu Ala Ser Thr Ser Pro Ser Lys Cys Pro Gly
225                 230                 235                 240

Tyr Val Ala Thr Thr Thr Thr Pro Thr Thr Thr Thr Pro Glu Phe Ile
                245                 250                 255

Pro Glu Thr Thr Thr Ser Pro Gln Pro Val Ile Thr Thr Gln Lys Pro
            260                 265                 270

Lys Pro Leu Trp Asn Phe Asn Cys Thr Ser Ile Gln Glu Arg Lys Asn
        275                 280                 285

Asp Gly Gly Asp Cys Gly Lys Pro Ala Cys Thr Thr Leu Leu Asn Cys
    290                 295                 300

Ala Asn Phe Leu Ser Cys Leu Cys Ser Thr Cys Ala Leu Cys Arg Lys
305                 310                 315                 320

Arg


<210> SEQ ID NO 141
<211> LENGTH: 190
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 141

Gly Ala Leu Val Gln Ser Ala Val Ala Cys Pro Ser Gln Cys Ser Cys
 1               5                  10                  15

Asp Gln Thr Thr Val Asp Cys Arg Asn Lys Arg Phe Ser Ser Val Pro
            20                  25                  30

Ala Gly Ile Pro Thr Asp Arg Gln Asn Leu Trp Leu Asn Asn Asn Gln
        35                  40                  45

Ile Thr Lys Leu Glu Pro Gly Val Phe Asp Ser Leu Ala Gln Leu Thr
    50                  55                  60
```

Gly Leu Asp Leu Ser His Asn Gln Phe Thr Ala Leu Pro Ala Gln Val
65 70 75 80

Phe Asp Arg Leu Val Lys Leu Lys Glu Leu Ser Leu Asn Ser Asn Lys
85 90 95

Leu Thr Ala Ile Pro Ala Gly Val Phe Asp Lys Leu Thr Gln Leu Lys
100 105 110

Gln Leu Ser Leu Leu Gln Asn Gln Leu Lys Ser Ile Pro Arg Gly Ala
115 120 125

Phe Asp Asn Leu Lys Ser Leu Thr His Ile Trp Leu Tyr Asn Asn Pro
130 135 140

Trp Asp Cys Ala Cys Ser Asp Ile Leu Tyr Leu Ser Arg Trp Ile Ser
145 150 155 160

Gln His Pro Gly Val Val Arg Lys Asp Glu Ala Gly Tyr Pro Val Asp
165 170 175

Pro Asp Ser Ala Arg Cys Ser Gly Thr Asn Thr Pro Val Arg
180 185 190

<210> SEQ ID NO 142
<211> LENGTH: 236
<212> TYPE: PRT
<213> ORGANISM: Artificial Sequence
<220> FEATURE:
<223> OTHER INFORMATION: Description of Artificial Sequence; note = synthetic construct

<400> SEQUENCE: 142

Gly Ala Leu Val Gln Ser Ala Val Ala Cys Pro Ser Gln Cys Ser Cys
1 5 10 15

Ser Gly Thr His Val Asn Cys Glu Arg Lys Arg Leu Thr Ser Val Pro
20 25 30

Ala Gly Ile Pro Thr Asn Ala Gln Ile Leu Tyr Leu His Asp Asn Gln
35 40 45

Ile Thr Lys Leu Glu Pro Gly Val Phe Asp Arg Leu Val Asn Leu Gln
50 55 60

Gln Leu Tyr Leu Ser Gly Asn Gln Leu Gln Ala Leu Pro Ala Gly Leu
65 70 75 80

Phe Asp Arg Leu Gly Asn Leu Gln Gln Leu Tyr Leu His Leu Asn Arg
85 90 95

Leu Ser Ser Ile Pro Ala Gly Val Phe Asp Lys Leu Thr Glu Leu Thr
100 105 110

Leu Met Asp Leu Gly Lys Asn Gln Leu Arg Ala Phe Pro Glu Gly Ala
115 120 125

Phe Asp Arg Leu Val Asn Leu Gln Glu Leu Tyr Leu Asn Lys Asn Pro
130 135 140

Leu Leu Ala Leu Pro Ala Gly Val Phe Asp Lys Leu Thr Gln Leu Thr
145 150 155 160

Gln Leu Gly Asn Asn Gln Leu Lys Ser Ile Pro Arg Gly Ala Phe Asp
165 170 175

Asn Leu Lys Ser Leu Thr His Ile Trp Leu Tyr Gly Asn Pro Trp Asp
180 185 190

Cys Ala Cys Ser Asp Ile Leu Tyr Leu Ser Arg Trp Ile Ser Gln His
195 200 205

Pro Gly Val Val Arg Lys Asp Glu Ala Gly Tyr Pro Val Asp Pro Asp
210 215 220

Ser Ala Arg Cys Ser Gly Thr Asn Thr Pro Val Arg
225 230 235

<210> SEQ ID NO 143
<211> LENGTH: 166
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 143

```
Gly Ala Leu Val Gln Ser Ala Val Ala Cys Pro Ser Gln Cys Ser Cys
 1               5                  10                  15

Asp Gln Thr Thr Val Lys Cys His Ser Arg Arg Leu Thr Ser Val Pro
            20                  25                  30

Ala Gly Ile Pro Thr Asn Val Gln Ile Leu Asn Leu Tyr Asn Asn Gln
        35                  40                  45

Ile Thr Lys Leu Glu Pro Gly Val Phe Asp Arg Leu Val Asn Leu Gln
    50                  55                  60

Gln Leu Tyr Ile Ser Trp Asn Gln Leu Gln Ala Leu Pro Thr Gly Val
65                  70                  75                  80

Phe Asn Lys Leu Thr Gln Leu Thr His Leu Ser Leu Tyr Asn Asn Gln
                85                  90                  95

Leu Lys Ser Ile Pro Arg Gly Ala Phe Asp Asn Leu Lys Ser Leu Thr
            100                 105                 110

His Ile Trp Leu Ser Ser Asn Pro Trp Asp Cys Ala Cys Ser Asp Ile
        115                 120                 125

Leu Tyr Leu Ser Arg Trp Ile Ser Gln His Pro Gly Val Val Arg Lys
    130                 135                 140

Asp Glu Ala Gly Tyr Pro Val Asp Pro Asp Ser Ala Arg Cys Ser Gly
145                 150                 155                 160

Thr Asn Thr Pro Val Arg
                165
```

<210> SEQ ID NO 144
<211> LENGTH: 187
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 144

```
Gly Ala Leu Val Gln Ser Ala Val Ala Cys Pro Ser Gln Cys Ser Cys
 1               5                  10                  15

Pro Gly Thr Asp Val Asn Cys His Glu Arg Arg Leu Ala Ser Val Pro
            20                  25                  30

Ala Glu Ile Pro Thr Thr Thr Lys Ile Leu Arg Leu Tyr Ile Asn Gln
        35                  40                  45

Ile Thr Lys Leu Glu Pro Gly Val Phe Asp Ser Leu Thr Ala Leu Thr
    50                  55                  60

Ser Leu Glu Leu Gly Gly Asn Gln Leu Thr Ala Leu Pro Glu Gly Val
65                  70                  75                  80

Phe Asp Arg Leu Val Asn Leu Gln Lys Leu Tyr Phe Ser Asp Asn Gln
                85                  90                  95

Leu Gln Ala Leu Pro Ala Gly Val Phe Asp Lys Leu Thr Gln Leu Thr
            100                 105                 110

His Leu Gly Leu His Thr Asn Gln Leu Lys Gly Ile Pro Arg Gly Ala
        115                 120                 125

Phe Asp Asn Leu Lys Ser Leu Thr His Ile Trp Leu Leu Asn Asn Pro
```

```
    130                 135                 140

Trp Asp Cys Ala Cys Ser Asp Ile Leu Tyr Leu Ser Arg Trp Ile Ser
145                 150                 155                 160

Gln His Pro Gly Leu Val Phe Gly Tyr Leu Asn Leu Asp Pro Asp Ser
                165                 170                 175

Ala Arg Cys Ser Gly Thr Asn Thr Pro Val Arg
            180                 185
```

```
<210> SEQ ID NO 145
<211> LENGTH: 654
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 145

ggcgccctgg tgcaaagtgc ggtagcatgt ccctcgcagt gttcgtgtgg caagttcagt     60

tggtctggtg aacttcaaac aacggactgt gacggcaaag gactgagttc agttccctct    120

gggatccccg acaacaccca gaatctggat ttgcgaaaaa atcagataga tagactaccc    180

gagggggtgt ttgaccgcct ggtgaatctg cagaagctgt ggttgaacag caaccagctg    240

acctctctcc ccgctggggt gtttgacagt ctgactcaac tgacacgact ggatcttgac    300

aataaccagt tgacagttct ccccgccggg gtgtgtgaca gcctggtgaa tctgaaggag    360

ctgcgtttgt acaacaacca gctgacagct ctacccgctg ggtgtttga caaattgacc    420

ctgctcgctg gtctgagtct gcacgacaac caactgaaga gtattcccag gagcgccttt    480

gacaacctca agagcctcac tcacatctat ctgttcaaca acccctggga ctgcgaatgt    540

tcggacatcc tctatctgaa gaactggatt gtgcagcacg caagcatcgt gaatccaggg    600

aactatgggg gagttgataa cgtgaagtgc tctggtacca atacccccgt ccgt          654
```

```
<210> SEQ ID NO 146
<211> LENGTH: 212
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 146

Gly Ala Leu Val Gln Ser Ala Val Ala Cys Pro Ser Gln Cys Ser Cys
 1               5                  10                  15

Ser Gly Thr Gln Val Asn Cys His Glu Arg Ser Leu Ala Ser Val Pro
            20                  25                  30

Ala Gly Ile Pro Thr Thr Thr Gln Val Leu Tyr Leu Tyr Thr Asn Gln
        35                  40                  45

Ile Thr Lys Leu Glu Pro Gly Val Phe Asp Ser Leu Thr Gln Leu Thr
    50                  55                  60

Arg Leu Asp Leu Tyr Asn Asn Gln Leu Thr Val Leu Pro Ala Gly Val
65                  70                  75                  80

Phe Asp Ser Leu Thr Gln Leu Thr Tyr Leu Asn Leu Ala Val Asn Gln
                85                  90                  95

Leu Thr Ala Leu Pro Val Gly Val Phe Asp Arg Val Thr Gln Leu Thr
            100                 105                 110

Ile Leu Ala Leu Asn Asp Asn Gln Leu Gln Ala Leu Pro Ala Gly Val
        115                 120                 125

Phe Asp Lys Leu Pro Lys Leu Thr His Leu Val Leu His Thr Asn Gln
```

```
    130                 135                 140

Leu Lys Ser Ile Pro Arg Gly Ala Phe Asp Asn Leu Lys Ser Leu Thr
145                 150                 155                 160

His Ile Trp Leu Phe Gly Asn Pro Trp Asp Cys Ala Cys Ser Asp Ile
                165                 170                 175

Leu Tyr Leu Ser Arg Trp Ile Gly Gln Asn Gly Gly Lys Leu Val Asn
            180                 185                 190

Ser Ala Gly Asn Phe Asp Gly Asn Ser Ala Val Cys Ser Gly Thr Asn
        195                 200                 205

Thr Pro Val Arg
    210


<210> SEQ ID NO 147
<211> LENGTH: 164
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 147

Gly Ala Leu Val Gln Ser Ala Val Ala Cys Pro Ser Gln Cys Ser Cys
 1               5                  10                  15

Thr Gly Ala Ser Val Glu Cys Gln Ser Arg Arg His Thr Ser Val Pro
            20                  25                  30

Ala Gly Ile Pro Thr Asn Val Gln Ile Phe Glu Leu Tyr Asp Asn Gln
        35                  40                  45

Ile Thr Lys Leu Glu Pro Gly Val Phe Asp Ser Leu Ala Asn Leu Arg
    50                  55                  60

Glu Leu His Leu Trp Gly Asn Gln Leu Ser Ala Leu Pro Val Gly Val
65                  70                  75                  80

Phe Asp Lys Leu Pro Lys Leu Thr His Leu Val Leu His Thr Asn Gln
                85                  90                  95

Leu Lys Ser Val Pro Arg Gly Ala Phe Asp Asn Leu Lys Ser Leu Thr
            100                 105                 110

Asn Ile Trp Leu Ser Ser Asn Pro Trp Asp Cys Ala Cys Ser Asp Ile
        115                 120                 125

Leu Tyr Leu Ser Arg Trp Ile Gly Gln Asn Gly Gly Lys Leu Val Asn
    130                 135                 140

Ser Ala Gly Asn Phe Asp Gly Asn Ser Ala Val Cys Ser Gly Thr Asn
145                 150                 155                 160

Thr Pro Val Arg


<210> SEQ ID NO 148
<211> LENGTH: 162
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 148

Gly Ala Leu Val Gln Ser Ala Val Ala Cys Pro Ser Gln Cys Ser Cys
 1               5                  10                  15

Ser Gly Thr Glu Val His Cys Gln Lys Lys Ser Leu Ala Ser Val Pro
            20                  25                  30

Ala Gly Ile Pro Thr Thr Thr Gln Val Leu Tyr Leu His Val Asn Gln
        35                  40                  45
```

```
Ile Thr Lys Leu Glu Pro Gly Val Phe Asp Arg Leu Val Asn Leu Gln
    50                  55                  60

Lys Leu Tyr Leu Trp Gly Asn Gln Leu Ser Ala Leu Pro Val Gly Val
65                  70                  75                  80

Phe Asp Lys Leu Thr Gln Leu Thr Tyr Leu Gly Val Asn Gln Leu Lys
                85                  90                  95

Ser Val Pro Arg Gly Ala Phe Asp Asn Leu Lys Ser Leu Thr His Ile
            100                 105                 110

Trp Leu Phe Gly Asn Pro Trp Asp Cys Ala Cys Ser Asp Ile Leu Tyr
        115                 120                 125

Leu Ser Arg Trp Ile Gly Gln Asn Gly Gly Lys Leu Val Asn Ser Ala
    130                 135                 140

Gly Asn Phe Asp Gly Asn Ser Ala Val Cys Ser Gly Thr Asn Thr Pro
145                 150                 155                 160

Val Arg


<210> SEQ ID NO 149
<211> LENGTH: 134
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 149

Gly Ala Leu Val Gln Ser Ala Val Ala Cys Pro Ser Gln Cys Ser Cys
 1               5                  10                  15

Ser Gly Thr Glu Val Asn Cys His Glu Arg Arg Leu Ala Ser Val Pro
            20                  25                  30

Ala Gly Ile Pro Thr Thr Thr Gln Val Leu Gly Leu Ser Ser Asn Gln
        35                  40                  45

Ile Thr Lys Leu Glu Pro Gly Val Phe Asp Ser Leu Thr Gln Leu Thr
    50                  55                  60

Tyr Leu Asp Leu Asn Asn Asn Gln Leu Lys Ser Ile Pro Arg Gly Ala
65                  70                  75                  80

Phe Asp Asn Leu Lys Ser Leu Thr His Ile Trp Leu Tyr Gly Asn Pro
                85                  90                  95

Trp Asp Cys Ala Cys Ser Asp Ile Leu Tyr Leu Ser His Trp Ala Asn
            100                 105                 110

Gly His Ala Asp Ile Val Gln Arg Met Ser Leu Thr Thr Cys Ser Gly
        115                 120                 125

Thr Asn Thr Pro Val Arg
    130


<210> SEQ ID NO 150
<211> LENGTH: 310
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 150

Gly Ala Leu Val Gln Ser Ala Val Ala Cys Pro Ser Gln Cys Ser Cys
 1               5                  10                  15

Ser Gly Thr Glu Val His Cys Gln Lys Lys Ser Leu Ala Ser Val Pro
            20                  25                  30

Ala Gly Ile Pro Thr Thr Thr Gln Val Leu Tyr Leu His Val Asn Gln
        35                  40                  45
```

```
Ile Thr Lys Leu Glu Pro Gly Val Phe Asp Arg Leu Thr Gln Leu Thr
    50                  55                  60

Arg Leu Asp Leu Tyr Asn Asn Gln Leu Thr Val Leu Pro Ala Gly Val
65                  70                  75                  80

Phe Asp Ser Leu Val Asn Leu Gln Ile Leu Val Leu Tyr Gln Asn Gln
                85                  90                  95

Leu Thr Thr Leu Pro Ala Gly Val Phe Asp Arg Leu Val Lys Leu Lys
            100                 105                 110

Glu Leu Tyr Leu Asp His Asn Gln Leu Gln Ala Ile Leu Pro Ala Leu
        115                 120                 125

Phe His Ser Leu Thr Glu Leu Thr Arg Leu Glu Leu Glu Asp Asn Gln
    130                 135                 140

Leu Lys Ser Leu Pro Ala Arg Ile Phe Asp Arg Leu Gly Lys Leu Met
145                 150                 155                 160

Tyr Leu His Leu His Glu Lys Gln Leu Met Thr Val Pro Ala Gly Val
                165                 170                 175

Phe Asp Ser Leu Val Asn Leu Lys Glu Leu Arg Leu Tyr Asn Asn Gln
            180                 185                 190

Leu Ala Ala Pro Pro Glu Asn Val Phe Asp Arg Leu Val Asn Leu Gln
        195                 200                 205

Lys Leu Trp Leu Asn Ser Asn Gln Leu Thr Ser Leu Pro Thr Gly Val
    210                 215                 220

Phe Asp Asn Leu Thr Gln Leu Ser Ile Leu Asn Met His Thr Asn Gln
225                 230                 235                 240

Leu Lys Ser Ile Pro Arg Gly Ala Phe Asp Asn Leu Lys Ser Leu Thr
                245                 250                 255

His Ile Phe Leu Tyr Asn Asn Pro Trp Asp Cys Glu Cys Arg Asp Ile
            260                 265                 270

Met Tyr Leu Arg Asn Trp Val Ala Asp Asn Thr Ser Ile Val Met Arg
        275                 280                 285

Trp Asp Gly Lys Ala Val Asn Asp Pro Asp Ser Ala Lys Cys Ala Gly
    290                 295                 300

Thr Asn Thr Pro Val Arg
305                 310


<210> SEQ ID NO 151
<211> LENGTH: 190
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 151

Gly Ala Leu Val Gln Ser Ala Val Ala Cys Pro Ser Gln Cys Ser Cys
 1               5                  10                  15

Ser Gly Thr Glu Val Asn Cys Ala Gly Lys Ser Leu Ala Ser Val Pro
            20                  25                  30

Ala Gly Ile Pro Thr Thr Thr Arg Val Leu Tyr Leu Asn Ser Asn Gln
        35                  40                  45

Ile Thr Lys Leu Glu Pro Gly Val Phe Asp Arg Leu Thr Gln Leu Thr
    50                  55                  60

Arg Leu Asp Leu Asp Asn Asn Gln Leu Thr Val Leu Pro Ala Gly Val
65                  70                  75                  80

Phe Asp Ser Leu Val Asn Leu Gln Thr Leu Tyr Leu His Gln Asn Glu
                85                  90                  95
```

```
Leu Thr Thr Leu Pro Ala Gly Val Phe Asp Lys Leu Thr Gln Leu Thr
            100                 105                 110

Arg Leu Ala Leu Ser Thr Asn Gln Leu Lys Ser Ile Pro Arg Gly Ala
        115                 120                 125

Phe Asp Asn Leu Lys Ser Leu Thr His Ile Phe Leu Tyr Asn Asn Pro
    130                 135                 140

Trp Asp Cys Glu Cys Arg Asp Ile Met Tyr Leu Arg Asn Trp Val Ala
145                 150                 155                 160

Asp Thr Pro Ser Ile Val Met Arg Trp Asp Gly Lys Ala Val Asn Asp
                165                 170                 175

Pro Asp Ser Ala Lys Cys Ala Gly Thr Asn Thr Pro Val Arg
            180                 185                 190


<210> SEQ ID NO 152
<211> LENGTH: 166
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 152

Gly Ala Leu Val Gln Ser Ala Val Ala Cys Pro Ser Gln Cys Ser Cys
 1               5                  10                  15

Ser Gly Thr Glu Val His Cys Gln Arg Lys Ser Leu Ala Ser Val Pro
            20                  25                  30

Ala Gly Ile Pro Thr Thr Thr Arg Val Leu Tyr Leu His Val Asn Gln
        35                  40                  45

Ile Thr Lys Leu Glu Thr Gly Val Phe Asp Arg Leu Val Asn Leu Gln
    50                  55                  60

Lys Leu Trp Leu Asn Ser Asn Gln Leu Thr Ser Leu Pro Ala Gly Val
65                  70                  75                  80

Phe Asp Arg Leu Thr Gln Leu Thr Arg Leu Asp Leu Tyr Asn Asn Gln
                85                  90                  95

Leu Lys Ser Ile Pro His Gly Ala Phe Asp Arg Leu Ser Ser Leu Thr
            100                 105                 110

His Ala Tyr Leu Phe Gly Asn Pro Trp Asp Cys Glu Cys Arg Asp Ile
        115                 120                 125

Met Tyr Leu Arg Asn Trp Val Ala Asp His Thr Ser Ile Val Met Arg
    130                 135                 140

Trp Asp Gly Lys Ala Val Asn Asp Pro Asp Ser Ala Lys Cys Ala Gly
145                 150                 155                 160

Thr Asn Thr Pro Val Arg
                165


<210> SEQ ID NO 153
<211> LENGTH: 213
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 153

Gly Ala Leu Val Gln Ser Ala Val Ala Cys Pro Ser Gln Cys Ser Cys
 1               5                  10                  15

Asp Gln Thr Thr Val Asp Cys Arg Asn Lys Arg Phe Ser Ser Val Pro
            20                  25                  30
```

```
Ala Gly Ile Pro Thr Asp Arg Gln Asn Leu Trp Leu Asn Asn Asn Gln
        35                  40                  45

Ile Thr Lys Leu Glu Pro Gly Val Phe Asp Ser Leu Thr Ala Leu Thr
    50                  55                  60

Glu Leu Lys Leu Gly Gly Asn Gln Leu Pro Ala Ile Pro Gln Gly Val
65                  70                  75                  80

Phe Asp Lys Leu Thr Gln Leu Thr Val Leu Asn Leu Arg His Asn Gln
                85                  90                  95

Leu Gln Phe Val Pro Val Gly Val Phe Glu Arg Leu Val Ser Leu Arg
            100                 105                 110

Glu Leu Phe Leu Gly Asp Asn Lys Phe Thr Glu Leu Pro Ala Gly Val
        115                 120                 125

Gly Lys Leu Pro Thr Leu Thr His Leu Gly Leu Asp Leu Asn Gln Leu
    130                 135                 140

Lys Ser Ile Pro His Gly Ala Phe Asp Arg Leu Ser Ser Leu Thr His
145                 150                 155                 160

Ala Tyr Leu Phe Gly Asn Pro Trp Asp Cys Glu Cys Arg Asp Ile Met
                165                 170                 175

Tyr Leu Arg Asn Trp Val Ala Asp His Thr Ser Ile Val Met Arg Trp
            180                 185                 190

Asp Gly Lys Ala Val Asn Asp Pro Asp Ser Ala Lys Cys Ala Gly Thr
        195                 200                 205

Asn Thr Pro Val Arg
    210


<210> SEQ ID NO 154
<211> LENGTH: 142
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 154

Gly Ala Leu Val Gln Ser Ala Val Ala Cys Pro Ser Gln Cys Ser Cys
 1               5                  10                  15

Ser Gly Thr His Val Asn Cys Glu Arg Lys Arg Leu Ala Ser Val Pro
            20                  25                  30

Ala Gly Ile Pro Thr Asn Arg Gln Asn Leu Trp Leu His Asp Asn Gln
        35                  40                  45

Ile Thr Lys Leu Glu Pro Gly Val Phe Asp His Leu Val Asn Leu Gln
    50                  55                  60

Gly Leu Thr Leu Tyr Asn Asn Gln Leu Lys Ser Val Pro Arg Gly Ala
65                  70                  75                  80

Phe Asp Asn Leu Lys Ser Leu Thr Asn Ile Trp Leu Ser Ser Asn Pro
                85                  90                  95

Trp Asp Cys Glu Cys Arg Asp Ile Met Tyr Leu Arg Asn Trp Val Ala
            100                 105                 110

Asp His Thr Ser Ile Val Met Arg Trp Asp Gly Lys Ala Val Asn Asp
        115                 120                 125

Pro Asp Ser Ala Lys Cys Ala Gly Thr Asn Thr Pro Val Arg
    130                 135                 140


<210> SEQ ID NO 155
<211> LENGTH: 214
<212> TYPE: PRT
<213> ORGANISM: Artificial Sequence
<220> FEATURE:
```

<223> OTHER INFORMATION: Description of Artificial Sequence; note = synthetic construct

<400> SEQUENCE: 155

```
Gly Ala Leu Val Gln Ser Ala Val Ala Cys Pro Ser Gln Cys Ser Cys
 1               5                  10                  15

Pro Gly Thr Asp Val Asn Cys His Glu Arg Arg Leu Ala Ser Val Pro
            20                  25                  30

Ala Glu Ile Pro Thr Thr Thr Gln Ile Leu Arg Leu Tyr Arg Asn Gln
        35                  40                  45

Ile Thr Lys Leu Glu Leu Gly Val Phe Asp Ser Leu Met Glu Leu Thr
    50                  55                  60

Tyr Leu Thr Leu Arg Asn Asn Gln Leu Thr Ala Leu Pro Ala Arg Val
65                  70                  75                  80

Phe Asn Lys Leu Thr Arg Leu Thr Val Leu Asp Leu Ser Gly Asn Gln
                85                  90                  95

Leu Gln Ala Leu Pro Glu Gly Val Phe Asp Ser Leu Val Asn Leu Gln
            100                 105                 110

Arg Leu His Leu Asp Gln Asn Gln Leu Val Ser Leu Pro Ala Gly Val
        115                 120                 125

Leu Asp Lys Leu Thr Gln Leu Thr His Leu Glu Leu Gln Asn Asn Gln
    130                 135                 140

Leu Lys Ser Ile Pro Arg Gly Ala Phe Asp Asn Leu Lys Ser Leu Thr
145                 150                 155                 160

His Ile Phe Leu Tyr Asn Asn Pro Trp Asp Cys Glu Cys Arg Asp Ile
                165                 170                 175

Met Tyr Leu Arg Asn Trp Val Ala Asp His Thr Ser Ile Val Met Arg
            180                 185                 190

Trp Asp Gly Lys Ala Val Asn Asp Pro Asp Ser Ala Lys Cys Ala Gly
        195                 200                 205

Thr Asn Thr Pro Val Arg
    210
```

<210> SEQ ID NO 156
<211> LENGTH: 818
<212> TYPE: DNA
<213> ORGANISM: Artificial Sequence
<220> FEATURE:
<223> OTHER INFORMATION: Description of Artificial Sequence; note = synthetic construct

<400> SEQUENCE: 156

```
atgtggatca agtggatcgc cacgctggtc gcctttggcg ccctggtgca aagtgcggta      60

gcatgtccct cgcagtgttc gtgcgatcag acattgtaac tgccagaata tacgcctcgc     120

atctgtgcct gcgggaatcc ccaccgacaa gcagaggctg tggttgaaca acaatcagat     180

cacgaagctt gagcccgggg tgtttgacca tctggtgaat ctgcagcagc tctattttaa     240

cagcaacaag ctaacagcta tacccactgg ggtgtttgac aaactcaccc agctcactca     300

actggatttg aatgacaacc atctgaagag cattcccagg ggcgcctttg acaacctcaa     360

gagcctaact cacatctatc tgtacaacaa cccatgggat tgcgagtgca gggacattat     420

gtacctcagg aactgggtcg cagaccacac ttctattgta atgcgctggg atgggaaggc     480

cgttaacgac cccgactctg ccaagtgcgt ggtaccaata cccccgtccg tgcggtcacc     540

gaggccagca ctagcccctc gaaatgccca ggctacgttg ctacgaccac gacgccgacg     600

acgaccacgc ccgaattcat ccctgagacc accacctcgc cgcagcccgt gatcacaacc     660
```

```
cagaaaccca agcctctgtg aatttcaact gcacctcaat tcaggagagg aagaacgacg    720

gtggcgactg cggaaagccc gcctgcacaa ctctcctgaa ctgcgcgaat ttcctcagct    780

gcctctgctc gacctgcgcc ctctgcagga aacgttga                            818


<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 157

Cys Pro Ser Gln Cys Ser Cys
 1               5


<210> SEQ ID NO 158
<211> LENGTH: 19
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 158

Thr Asn Thr Pro Val Arg Ala Val Thr Glu Ala Ser Thr Ser Pro Ser
 1               5                   10                  15

Lys Cys Pro


<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 159

ctcggctctg cagctctca                                                  19


<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 160

tggcgccctg gtgcaaagt                                                  19


<210> SEQ ID NO 161
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 161

gaacactgcg agggacatg                                                  19


<210> SEQ ID NO 162
<211> LENGTH: 26
<212> TYPE: DNA
<213> ORGANISM: Artificial Sequence
```

<220> FEATURE:
<223> OTHER INFORMATION: Description of Artificial Sequence; note =
synthetic construct

<400> SEQUENCE: 162
aaaagatctt gtccctcgca gtgttc 26

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 163
acggacgggg gtattggta 19

<210> SEQ ID NO 164
<211> LENGTH: 19
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 164
atccctgaga ccaccacct 19

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 165
cacgccgatc aacgtttcct 20

<210> SEQ ID NO 166
<211> LENGTH: 26
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 166
aaagtcgaca cgccgatcaa cgtttc 26

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 167
ccgccatccc cgacctttg 19

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence; note = synthetic construct

<400> SEQUENCE: 168
ccggttggac actagtgttg 20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence; note = synthetic construct

<400> SEQUENCE: 169
gtgccattgg gatcagtggt 20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence; note = synthetic construct

<400> SEQUENCE: 170
gaacatcggc atcaatgggt 20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence; note = synthetic construct

<400> SEQUENCE: 171
gaggccttat cgatggtggt 20

<210> SEQ ID NO 172
<211> LENGTH: 1320
<212> TYPE: DNA
<213> ORGANISM: Artificial Sequence
<220> FEATURE:
<223> OTHER INFORMATION: Description of Artificial Sequence; note = synthetic construct

<400> SEQUENCE: 172
cttcgagcgg ccaatcggct ttttggcaaa ttttggcacg cgcgtgaatc ccgtcggtgc 60
gagacgcgtt tgcgatggta cttaacgcgc cctgtccgtt tttgtctctc gcccttcagc 120
ctgcaggagc caaccatcat gtggatcaag tggatcgcca cgctggtcgc ctttggcgcc 180
ctggtgcaaa gtgcggtagc atgtccctcg cagtgttcgt gtggggaaca gtcgtgggct 240
ccaggtctcc aagcaacgaa ctgttacgac aaaggactga gttcagttcc cgctgggatc 300
cctgacaaca cacaggcctt gaccgtgcag aaaaatcgca tagagagtct ccctgagagg 360
gtgtttgacc gcctggtcaa tctgcaacag ttgtatttgc atctgaaccg actgtcgtcc 420
atacccgccg ggatgtttga caaactttcc caactgactt ttctgtcttt ggatgaaaat 480
aaactaactg ctctccccaa cggggtgttt gacaaactca cccagctgac gatactgggt 540
ctgcgagaca accagttgaa gagcactcca aggggcgcct ttgacaacct caagagccta 600
actcacatct ggctgtacag taacccctgg gactgcgagt gttcggacat cctctatctg 660
aagaactgga ttgtacagca cgcaagcatc gtgaatccag gcagcggggg agttgataac 720

```
gtgaagtgct ctggtaccaa tacccccgtc cgtgcggtca ccgaggccag cactagcccc    780

tcgaaatgcc caggctacgt tgctacgacc acgacgccga cgacgaccac gcccgaattc    840

atccctgaga ccaccacctc gccgcagccc gtgatcacaa cccagaaacc caagcctctg    900

tggaatttca actgcacctc aattcaggag aggaagaacg acggtggcga ctgcggaaag    960

cccgcctgca caactctcct gaactgcgcg aatttcctca gctgcctctg ctcgacctgc   1020

gccctctgca ggaaacgttg atcggcgtgc aaaggtcggg gatggcggtg ggaaggcggg   1080

cgcggtgggg tggggggtgt agtggagaag gtggaggagg aggagtgagg agaaggaaga   1140

ccaggaagag ggggagagta ataagcagag acgatttgaa aggttgacaa atttctcgcg   1200

caaactccac caccttcgcg tccgaacgac catgaggata ccgcgacgac gacgatgata   1260

atgaacaacc cagcaggaat caacgaccac tcttgtcgaa tcgcttcgtc agcggctgtt   1320
```

<210> SEQ ID NO 173
<211> LENGTH: 1447
<212> TYPE: DNA
<213> ORGANISM: Artificial Sequence
<220> FEATURE:
<223> OTHER INFORMATION: Description of Artificial Sequence; note = synthetic construct

<400> SEQUENCE: 173

```
ctccgctact cggcctgcaa tacttctgct cggagcctat ccgtgccatt tcgaaagatg     60

ttgctttcct gttaaatgcc cgtttgaatc ttgcttcgtg agaaatgttc gcattgtgtg    120

tggtggtgcg ctcttcaaat tgtctttgtg gtcgttgctg ctgaattctg atgggaatgt    180

atccacacag gtttggcagc gcgtgccggc gccttcacac ttgatggctc tgcaccgagt    240

gttaattatg ctcagtcgat cgaatgtgaa gacaaaacgt tgctcgtttg attaacgttt    300

gggttgagga tgcaatgcac ttgcaatgtg cgccgatccg atcagaataa ctgggcgtct    360

gtatgtttta tttaagttaa acaattaatt cgcctcattt aatttctgga ctaaccaggg    420

cacgaacccg ttcgcttctg tctttggctc aaattcaaca gcagcaatga agacgcagcc    480

tttcacgcgt cgcacaaccc agcgtataac ttcgaacggc caatcggctt tttggcaaat    540

tttggcacgc gcgtgaatcc cgtcggtgcg agacgcgttt gcgatggtac ttaacgcgcc    600

ctgtccgttt ttgtctctcg cccttcagcc tgcaggagcc aaccatcatg tggatcaagt    660

ggatcgccac gctggtcgcc tttggcgccc tggtgcaaag tgcggtagca tgtccctcgc    720

agtgttcgtg cccagggaca gatgttaact gtcatgagag acgcttggcg tctgtgcctg    780

cggaaatccc caccaccacg aagatcctgt ggttgcacga caatcagatc acgaagctcg    840

agcccggggt gtttgaccat ctggtgaatc tgaaggagct gtggttgaac agcaaccagc    900

tgcaggcgct acccgccggg gtgtttgaca aactgaccca gctcgctcat ctagaactgc    960

aaaacaacca gctgaagaac attcccaggg gcgcctttga taacctgaag agcctcactt   1020

acatctggct gcacaacaac ccctgggact gtgcttgctc agacatcctc tacctcagcg   1080

gctggctggg ccagcacgca gggaaagagc agggccaggc tgtctgctct ggtaccaata   1140

cccccgtccg tgcggtcacc gaggccagca ctagcccctc gaaatgccca ggctacgttg   1200

ctacgaccac gacgccgacg acgaccacgc ccgaattcat ccctgagacc accacctcgc   1260

cgcagcccgt gatcacaacc cagaaaccca agcctctgtg gaatttcaac tgcacctcaa   1320

ttcaggagag gaagaacgac ggtggcgact gcgggaagcc cgcctgcaca actctcctga   1380

actgcgcgaa tttcctcagc tgcctctgct cgacctgcgc cctctgcagg aaacgttgat   1440

cggcgtg                                                             1447
```

<210> SEQ ID NO 174
<211> LENGTH: 853
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 174
ctccgctact cggcctgcag gagccaacca tcatgtggat caagtggatc gccacgctgg 60
tcgcctttgg cgccctggtg caaagtgcgg tagcatgtcc ctcgcagtgt tcctgctcag 120
ggacaactgt ggattgccgg agcaaacgcc acgcatctgt gcctgcggga atccccacca 180
atgcgcagat tctgtattta cacgacaatc agatcacgaa gctcgagccc ggggtgtttg 240
accatctggt gaatctgcag ggctgggtc tgcagaacaa ccagctgacc tctctcccca 300
acggggtgtt taataaacta acccagctca ctcatctgag tctgtacaat aaccagctga 360
agagcattcc caggggcgcc tttgacaacc tcaagagcct cactcagatc tggctgtaca 420
acaacccctg ggactgcgcc tgttcagaca tcttgtacct cagccgctgg atctctcagc 480
acccagggct cgtgttcggc tatttgaatt tggaccccga ctcagcgcgc tgctctggta 540
ccaatacccc cgtccgtgcg gtcaccgagg ccagcactag cccctcgaaa tgcccaggct 600
acgttgctac gaccacgacg ccgacgacga ccacgcccga attcatccct gagaccacca 660
cctcaccgca gcccgtgatc acaacccaga aacccaagcc tctgtggaat ttcaactgca 720
cctcaattca ggagaggaag aacggcggtg gcgactgcgg aaagcccgcc tgcacaactc 780
tcctgaactg cgcgaatttc ctcagctgcc tctgctcgac ctgcgccctc tgcaggaaac 840
gttgatcggc gtg 853

<210> SEQ ID NO 175
<211> LENGTH: 1417
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 175
ctccgctact cggcctgcaa tacttctgct cggagcctat ccgtgccatt tcgaaagatg 60
ttgctttcct gttaaatgcc cgtttgaatc ttgcttcgtg agaaatgttc gcattgtgtg 120
tggtggtgcg ctcttcaaat tgtctttgtg gccgttgctg ctgaattctg atgggaatgt 180
atccacacag gtttggcagc gcgtgccggc gccttcacac ttgatggctc tgcaccgagt 240
gttaattatg ctcagtcgat cgaatgtgaa gacaaaacgt tgctcgtttg attaactttt 300
gggttgagga tgcaatgcac ttgcaatgtg cgccgatccg atcagaataa ctgggcgtct 360
gtatgtttta tttaagttaa acaattaatt cgcctcattt aatttctgga ctaaccaggg 420
cacgaacccg ttcgcttctg tctttggctc aaattcaaca gcagcaatgg agacgcagcc 480
tttcacgcgt cgcacaaccc agcgtataac ttcgagcggc caatcggctt tttggcaaat 540
tttggcacgc gcgtgaatcc cgtcggtgcg agacgcgttt gcgatggtac ttaacgcgcc 600
ctgtccgttt ttgtctctcg cccttcagcc tgcaggagcc aaccatcatg tggatcaagt 660
ggatcgccac gctggtcgcc tttggcgccc tggtgcaaag tgcggtagca tgtccctcgc 720
agtgttcgtg ctcagggaca actgtggatt gccggagcag aagacacgcg tctgtgcctg 780
cgggaatccc caccaccacg cagtatctgt atttgctcgt caatcaaatc acgaagctcg 840
agcccggggt gtttgacctc ctggtgaatc tgcagcatct gcatttgaac agcaacaagc 900
taacagctat acccgctggg gtgtttgaca acctgaccca gctcaatcat ctgtttctga 960
acaacaacca gctgaagagc attcccaggg gcgcctttga caacttcaag agcctcactc 1020
acatctggct gtacggcaac ccatgggatt gcgagtgcag ggacattatg tacctcagga 1080
actgggtcgc agaccacact tctattgtaa tgcgctggga tgggaaggcc gttaacgacc 1140
ccgactctgc caagtgcgct ggtaccaata cccccgtccg tgcggtcacc gaggccagca 1200
ctagcccctc gaaatgccca ggctacgttg ctacgaccac gacgccgacg acgaccacgc 1260
ccgaattcat ccctgagacc accacctcgc cgcagcccgt gatcacaacc cagaaaccca 1320
agcctctgtg gaatttcaac tgcacctcaa ttcaggagag gaagaacgac ggtggcgact 1380
ggacctgcgc cctctgcagg aaacgttgat cggcgtg 1417

<210> SEQ ID NO 176
<211> LENGTH: 1006
<212> TYPE: DNA
<213> ORGANISM: Artificial Sequence
<220> FEATURE:
<223> OTHER INFORMATION: Description of Artificial Sequence; note = synthetic construct

<400> SEQUENCE: 176
ctccgctact cggcctgcag gagccaacca tcatgtggat caagtggatc gccacgctgg 60
tcgcctttgg cgccctggtg caaagtgcgg tagcatgtcc ctcgcagtgt tcgtgcgatc 120
agacaactgt atactgccat agcagacgcc tcacgtctgt gcctgcggga atccccaccg 180
acaggcagaa cctgtggttg tacaacaatc agatcacgaa gctcgagccc ggcgtgtttg 240
acagtctggc ggcactgact tttctgaacg ttggtgacaa ccagctgacg gctcttcccg 300
ctgggttgtt tgacgaactg acccaggttt attctctgag tctgaacgac aaccaactct 360
cggctctgcc cgccggggtg tttgaccgcc tcataaatct gaaggagctg tatttttcta 420
ataaccagct gacatctctc cccgctgggc tgtttgacaa actcatccag ctgactaatc 480
tggatctgag gtataaccag ctgaagagca ttcccagggg cgcctttgac aacctcaaga 540
gcctaactca catctggctg tacaacaacc cctgggactg tgcctgctca gacatcctgt 600
acctcagccg ctggatctct cagcaccctg gagtcgtgag gaagaatgaa gcaggctacc 660
ctgtggaccc cgactcagcg cgctgctctg gtaccaatac cccgtccgt gcggtcaccg 720 aggccagcac tagcccctcg aaatgcccag gctacgttgc tacgaccacg acgccgacga 780
cgaccacgcc cgaattcatc cctgagacca ccacctcgcc gcagcccgtg atcacaaccc 840
agaaacccaa gcctctgtgg aatttcaact gcacctcaat tcaggagagg aagaacgacg 900
gtggcgactg cggaaagccc gcctgcacaa ctctcctgaa ctgcgcgaat ttcctcagct 960
gcctctgctc gacctgcgcc ctctgcagga aacgttgatc ggcgtg 1006

<210> SEQ ID NO 177
<211> LENGTH: 883
<212> TYPE: DNA
<213> ORGANISM: Artificial Sequence
<220> FEATURE:
<223> OTHER INFORMATION: Description of Artificial Sequence; note = synthetic construct

<400> SEQUENCE: 177
ctccgctact cggcctgcag gagccaacca tcatgtggat caagtggatc gccacgctgg 60
tcgcctttgg cgccctggtg caaagtgcgg tagcatgtcc ctcgcagtgt tcgtgtggca 120
agttcagttg gtctggtgaa cttcaaacaa cggactgtga cggcaaagga ctgagttcag 180
ttccctctgg gatccccgac aacacacagg ccctgaccgt gcagaaaaat cgcatagaga 240
gtctccccga gggggtgttt gaccgcctgg tgaatctgca gcggctgtgg ttgaacaaca 300
accagctgac ctctctcccc gctggagtgt ttgacaaact gacccagctc actcaactgg 360
gtctgtggga caaccagctg aagagcattc ccaggggcgc ctttgacaac ctcaagagcc 420
tcactcacat ctggctgtac ggcaacccct gggactgcgc ctgttcagac atcctgtacc 480
tcagccgctg gatctctcag taccctggag tcttgagggc ggctgattca tggtatattg 540
ttgaccccga ctcagcgcgc tgctctggta ccaatacccc cgtccgtgcg gtcaccgagg 600
ccagcactag cccctcgaaa tgcccaggct acgttgctac gaccacgacg ccgacgacga 660
ccacgcccga attcatccct gagaccacca cctcgccgca gcccgtgatc acaacccaga 720
aacccaagcc tctgtggaat ttcaactgca cctcaattca ggagaggaag aacgacggtg 780
gcgactgcgg aaagcccgcc tgcacaactc tcctgaactg cgcgaatttc ctcagctgcc 840
tctgctcgac ctgcgccctc tgcaggaaac gttgatcggc gtg 883

<210> SEQ ID NO 178
<211> LENGTH: 838
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 178
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacagaagt gcactgtcag aaaaaaagcc tcgcgtctgt gcctgcagga atccccacca 180
ccacgcaagt gctgtatttg cacgtcaatc agatcacgaa gctcgagccc ggggtgtttg 240
accgcctggt gaatctgaaa gagctgcatc tgtggggaaa ccagctgttg gctctatccg 300
ttggggtgtt taataaacta acccagctca ctcatctgag tctgtacaat aaccagctga 360
agagcattcc caggggcgcc tttgacaacc tcaagagcct cactcacatc tggctgtacg 420
gcaacccctg ggactgcgcc tgctcagaca tcctatacct gagccactgg gcaaatgggc 480
acgcagacat agtgcagaga atgtcactta ctacgtgctc tggtaccaat acccccgtcc 540
gtgcggtcac cgaggccagc actagcccct cgaaatgccc aggctacgtt gctacgacca 600
cgacgccgac gacgaccacg cccgaattca tccctgagac caccacctcg ccgcagcccg 660
tgatcacaac ccagaaaccc aagcctctgt ggaatttcaa ctgcacctca attcaggaga 720
ggaagaacga cggtggcgac tgcggaaagc ccgcctgcac aactctcctg aactgcgcga 780
atttcctcag ctgcctctgc tcgacctgcg ccctctgcag gaaacgttga tcggcgtg 838

<210> SEQ ID NO 179
<211> LENGTH: 1009
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 179
ctccgctact cggcctgcag gagccaacca tcatgtggat caagtggatc gccacgctgg 60
tcgcctttgg cgccctggtg caaagtgcgg tagcatgtcc ctcgcagtgt tcgtgtcgcg 120
tgtggtctgg actccaaaga gcaaagtgcc acagcaaagg actgatctca gttccctctg 180
ggatctctga aaacacccag gcctcgagtg tggagaacaa tcgcatagag agtctccccg 240
agggggtgtt tgaccgcctg gtgaatctgc agcggctgtg gttgaacaac aaccagctga 300
cctctctccc cgctggggtg tttgaccgtc tgactcaact gacacgactg gatctttaca 360
ataaccagtt gacagttctc cccgccgggg tgtttgacag cctggtgaat ctgcaggggc 420
tctggctgta caacaacaaa ctgacagctc taaccaatgg ggtgtttgac aaacttaccc 480
ggctgaagtg gttgggtctg gaccagaatc aactgaagag cattcccagg ggcgcctttg 540
ataacctgaa gagcctcact tacatctatc tgttcaacaa cccctgggac tgcgagtgtt 600
cggacatcct ctatctgaag aactggattg tacagcacgc aagcatcgtg aatccatcgg 660
gccatggggg agttgataac gtgaagtgct ctggtaccaa taccccccgtc cgtgcggtca 720 ccggggccag cactagcccc tcgaaatgcc caggctacgt tgctacgacc acgacgccga 780
cgacgaccac gcccgaattc atccctgaga ccaccacctc gccgcagccc gtgatcacaa 840
cccagaaacc caagcctctg tggaatttca actgcacctc aattcaggag aggaagaacg 900
acggtggcga ctgcggaaag cccgcctgca caactctcct gaactgcgcg aatttcctca 960
gctgcctctg ctcgacctgc gccctctgca ggaaacgttg atcggcgtg 1009

<210> SEQ ID NO 180
<211> LENGTH: 853
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 180
ctccgctact cggcctgcag gagccaacca tcatgtggat caagtggatc gccacgctgg 60
tcgcctttgg cgccctggtg caaagtgcgg tagcatgtcc ctcgcagtgt tcctgctcag 120
ggacaactgt ggattgccgg agcaaacgcc acgcatctgt gcctgcggca atccctatca 180
ccacgcaaag gctgtggttg agcaacaatc agatcacgaa gctcgagccc ggggtgtttg 240
acagtctgac gcaactgact tatctgaacc ttggcggcaa ccagctgacg gctcttcccg 300
ttggggtgtt tgaccgcctg gtgaatctgc aggagctgac tctgtacaac aaccagctga 360
agagcattcc caggggcgcc tctgacaacc tcaagagcct cactcacatc tatctgttca 420
acaacccctg ggactgcgag tgttcggaca tcctctatct gaagaactgg attgtgcagc 480
acgcaagcat catgaatcta gagggccatg ggggagttga taacgtgaag tgctctggta 540
ccgatacccc cgtccgtgcg gtcaccgagg ccagcactag cccctcgaaa tgcccaggct 600
acgttgctac gaccacgacg ccgacgacga ccacgcccga attcatccct gagaccacca 660
cctcgccgca gcccgtgatc acaacccaga aacccaagcc tctgtggaat ttcaactgca 720
cctcaattca ggagaggaag aacgacggtg gcgactgcgg aaagcccgcc tgcacaactc 780
tcctgaactg cgcgaatttc ctcggctgcc tctgctcgac ctgcgccctc tgcaggaaac 840
gttgatcggc gtg 853

<210> SEQ ID NO 181
<211> LENGTH: 1006
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 181
ctccgctact cggcctgcag gagccaacca tcatgtggat caagtggatc gccacgctgg 60
tcgcctttgg cgccctggtg caaagtgcgg tagcatgtcc ctcgcagtgt tcgtgcgatc 120
agacaactgt ggactgccgg aacaaacgct tctcgtctgt gcctgcggga atccccaccg 180
acaggcagaa cctgtggttg aataacaatc agatcacgaa gctcgagccc ggggtgtttg 240
accgtctggc tcagctgaca ggactagatt taagccacaa ccagttcaca gctctccccg 300
ctcaggtgtt tgaccgcttg gtgaatctgc agaagctgtg gttgaacagc aacaagctaa 360
cagctatacc cgctggggtg tttgacaaac tgacagagct tacttatttg aacctcaata 420
ccaaccagct aacggctcta ccggaggggg tgtttgacaa attgcccaag ctcacacatt 480
tggttctgca caccaaccag ttgacgagca ttcccagggg cgcctttgac aacctcaaga 540
gcctcactca catctggctg ttcgacaacc cctgggactg tgcctgctca gacatcctgt 600
acctcagccg ctggatctct cagcacccag ggtggtgag gaaggatgaa gcaggctacc 660
ctgtggaccc cgactcagcg cgctgctctg gtaccaatac ccccgtccgt gcggtcaccg 720
aggccagcac tagcccctcg aaatgcccag gctacgttgc tacgaccacg acgccgacga 780
cgaccacgcc cgaattcatc cctgagacca ccacctcgcc gcagcccgtg atcacaaccc 840
agaaacccaa gcctctgtgg aatttcaact gcacctcaat tcaggagagg aagaacgacg 900
gtggcgactg cggaaagccc gcctgcacaa ctctcctgaa ctgcgcgaat ttcctcagct 960
gcctctgctc gacctgcgcc ctctgcagga aacgttgatc ggcgtg 1006

<210> SEQ ID NO 182
<211> LENGTH: 612
<212> TYPE: DNA
<213> ORGANISM: Artificial Sequence
<220> FEATURE:
<223> OTHER INFORMATION: Description of Artificial Sequence; note = synthetic construct

<400> SEQUENCE: 182
ggcgccctgg tgcaaagtgc ggtagcatgt ccctcgcagt gttcgtgctc agggacagat 60
gttcaatgtg acaggagaag cctcgtgtct gtgcctgcgg gaatccccac caccacgcga 120
gatctgtatt tgcacgacaa tcagatcacg aagctcgagc ccggggtgtt tgacagtctg 180
gcaaatctgg agaagctgca tttgtacgac aaccagctaa cgtctctccc tgctggggta 240
tttaaccgtc tggttaattt gcagaagctg catttgtatc agaaccaaat gtcagctctc 300
ccgaatgggg tgtttgacca attgactgaa ctgacgcgac tggatatgga agctaaccaa 360
ctgaagtccc tgccaccaaa gatctttgac aaactgggga agctgatgca tctgcagctg 420
cacgccaacc agctgacgac cgttcccgag ggcgccttta acagcctcat gaagctgcaa 480
tacatttggc tgcacagtaa cccctgggac tgtgcttgct cagacatcct ctacctcagc 540
ggctggctgg gccagcacgc agggaaagag cagggccagg ctgtctgctc tggtaccaat 600
acccccgtcc gt 612

<210> SEQ ID NO 183
<211> LENGTH: 1294
<212> TYPE: DNA
<213> ORGANISM: Artificial Sequence
<220> FEATURE:
<223> OTHER INFORMATION: Description of Artificial Sequence; note = synthetic construct

<400> SEQUENCE: 183

```
ctccgctact cggcctgcag gagccaacca tcatgtggat caagtggatc gccacgctgg     60
tcgcctttgg cgccctggtg caaagtgcgg tagcatgtcc ctcgcagtgt tcgtgctcag    120
ggacagaagt gcactgtcag aaaaaaagcc tcgcgtctgt gcctgcagga atccccacca    180
ccacgcaagt gctgtatttg cacgtcaatc agatcacgaa gctcgagccc ggggtgtttg    240
accgtctgac tcaactgaca cgactggatc tttacaataa ccagttgaca gttctccccg    300
ccggggtgtt tgacagcctg gtgaatctgc agatcctggt tttgtatcag aatcagctaa    360
caactctgcc cgccggggta tttgaccgtc tggtgaaatt gaaggagctg tatctggacc    420
ataaccaatt gcaggcgata ctgcccgctc tgtttcacag tttgactgaa ctcacgcgac    480
ttgaactgga agataaccaa ctgaagtctc tgcccgccag gatctttgac agactgggga    540
agctgatgta tttgcacctg cacgagaagc agctgatgac tgttcccgcc ggggtgtttg    600
acagcctggt gaatctgaag gagctgcgtt tgtacaacaa ccagctggca gctccacccg    660
agaatgtgtt tgaccgcctg gtgaatctgc agaagctgtg gttgaacagc aaccagctga    720
cctctctccc caccggggtg tttgacaacc tgacccagct tagcatactg aatatgcaca    780
ccaaccagct gaagagcatt cccaggggcg cctttgacaa cctcaagagc ctaactcaca    840
tctttctgta caacaaccca tgggattgcg agtgcaggga cattatgtac ctcaggaact    900
gggtcgcaga caacacttct attgtaatgc gctgggatgg gaaggccgtt aacgaccccg    960
actctgccaa gtgcgctggt accaataccc ccgtccgtgc ggtcaccgag gccagcacta   1020
gcccctcgaa atgcccaggc tacgttgcta cgaccacgac gccgacgacg accacgcccg   1080
aattcatccc tgagaccacc acctcgccgc agcccgtgat cacaacccag aaacccaagc   1140
ctctgtggaa tttcaactgc acctcaattc aggagaggaa gaacgacggt ggcgactgcg   1200
gaaagcccgc ctgcacaact ctcctgaact gcgcgaattt cctcagctgc ctctgctcga   1260
cctgcgccct ctgcaggaaa cgttgatcgg cgtg                              1294
```

<210> SEQ ID NO 184
<211> LENGTH: 770
<212> TYPE: DNA
<213> ORGANISM: Artificial Sequence
<220> FEATURE:
<223> OTHER INFORMATION: Description of Artificial Sequence; note = synthetic construct

<400> SEQUENCE: 184

```
ggcgccctgg tgcaaagtgc ggtagcatgt ccctcgcagt gttcgtgctc agggacacat     60
gtgaactgtg aacggaaacg cctcacgtct gtgcctgcgg gaatccccac caccacgaag    120
atcctgcggc tgtacatcaa tcagatcacg aagctcgagc caggggtgtt tgatagtctg    180
acggcactga cttttctgaa ccttggtaac aaccagctga cggctctacc cgagggggtg    240
tttgaccacc tggtgaatct gcagaagctg tggttgaaca gcaaccagct gacctctctc    300
cccgctgggg tgtttgacaa actcacccag ctgaaggagt tgggtctgga ccagaatcaa    360
ctgaagagca tttccgctgg gatgtttgac cgcttcttca ggagctgcat ttgtccagca    420
aacagctaac agacctaccc gagggagggt ttgaacgcct ggtgaatctg aaggagctgc    480
atttgtacag gaaccagatg aaagctctac ccgctgggtt gtttgacgaa ctgacccagc    540
tcactcttct agaactgcaa aacaaccagc tgaagagcat tcccaggggc gcctttgaca    600
acctcaagag cctcactcac atctatctgt tcaacaaccc ctgggactgc gagtgttcgg    660
acatcctcta tctgaagaac tggattgtgc agcacgcaag catcgtgaat ccagggaact    720
```

atgggggagt tgataacgtg aagtgctctg gtaccaatac ccccgtccgt 770

<210> SEQ ID NO 185
<211> LENGTH: 714
<212> TYPE: DNA
<213> ORGANISM: Artificial Sequence
<220> FEATURE:
<223> OTHER INFORMATION: Description of Artificial Sequence; note = synthetic construct

<400> SEQUENCE: 185
ggcgccctgg tgcaaagtgc ggtagcatgt ccctcgcagt gttcgtgctc agggacacat 60
gtgaactgtg aacggaaacg cctcacgtct gtgcctgcgg gaatccccac caatgcgcag 120
attctgtatt tacacgacaa tcagatcacg aagctcgagc ccggagtgtt tgaccgcctg 180
gtgaatctgc agcagctcta tttgagtggg aatcagctgc aggctctacc cgctgggttg 240
tttgaccgcc tggggaatct gcaacagttg tatttgcatc tgaaccgact gtcgtccata 300
cccgctgggg tgtttgacaa actgacagag ctcacactaa tggatcttgg caaaaaccag 360
ctgcgggcct ttcccgaggg agcgtttgac cgcctggtca atctgcagga gctgtatttg 420
aataaaaacc cactattggc tctacccgct ggagtgtttg acaaactgac ccagctcact 480
caactgggtt tgtacaacaa ccagctgaag agcattccca ggggcgcctt tgacaacctc 540
aagagcctca ctcacatctg gctgtacggc aacccctggg actgtgcctg ctcagacatc 600
ctgtacctca gccgctggat ctctcagcac ccaggggtgg tgaggaagga tgaagcaggc 660
taccctgtgg accccgactc agcgcgctgc tctggtacca atacccccgt ccgt 714

<210> SEQ ID NO 186
<211> LENGTH: 1377
<212> TYPE: DNA
<213> ORGANISM: Artificial Sequence
<220> FEATURE:
<223> OTHER INFORMATION: Description of Artificial Sequence; note = synthetic construct

<400> SEQUENCE: 186
tcatttaatt tctggactaa ccagggcacg aacccgttcg cttctgtctt tggctcaaat 60
tcaacagcag caatgaagac gcagcctttc acgcgtcgca caccccagcg tatacttcga 120
gcggccaatc ggctttttgg caaattttgg cacgcgcgtg aatcccgtcg gtgcgagacg 180
cgtttgcgat ggtacttaac gcgccctgtc cgtttttgtc tctcgccctt cagcctgcag 240
gagccaacca tcatgtggat caagtggatc gccacgctgg tcgcctttgg cgccctggtg 300
caaagtgcgg tagcatgtcc ctcgcagtgt tcttgctcag ggacaactgt gaactgtgat 360
agcagaagcc tcgcgtctgt gcctggagga atccccacca ccacgcaagt gctgtatttg 420
tacgacaatc agatcacgaa gctcgagccc ggcgtgtttg acagtctggc ggcactgact 480
tttctgaacc ttggtaacaa ccagctgacg gctctacccg agggggtgtt tgaccgcttg 540
gtgaatctgc agaagctgta tctgtgggga aaccagctgt cggctctacc cgttggggtg 600
tttgacaaac tgactcagct cacttatctg ggtctgtacg tcaatcaact gaagagcatt 660
cccaggggcg cctttgacaa cctcaagagc ctcactcaca tctggctgtt cgacaacccc 720
tgggactgtg cctgttcaga catcctctac ctcagccgct ggatctctca gcacccagga 780
atcgtgagga cggcagatga tggttggaac agagtggacc ccgactcagc gcgctgctct 840
ggtaccaata cccccgtccg tgcggtcacc gaggccagca ctagcccctc gaaatgccca 900
ggctacgttg ctacgaccac gacgccgacg acgaccacgc ccgaattcat ccctgagacc 960

-continued accacctcgc cgcagcccgt gatcacaacc cagaaaccca agcctctgtg gaatttcaac 1020
tgcacctcaa ttcaggagag gaagaacgac ggtggcgact gcggaaagcc cgcctgcaca 1080
actctcctga actgcgcgaa tttcctcagc tgcctctgct cgacctgcgc cctctgcagg 1140
aaacgttgat cggcgtgcaa aggtcgggga tggcggtggg aaggcgggcg cggtggggtg 1200
gggggtgtag tggagaaggt ggaggaggag gagtgaggag aaggaagacc aggaagaggg 1260
ggagagtaat aagcagagac gatttgaaag gttgacaaat ttctcgcgca aactccacca 1320
ccttcgcgtc cgaacgacca tgaggatacc gcgacgacga cgatgataat gaacaac 1377

<210> SEQ ID NO 187
<211> LENGTH: 1244
<212> TYPE: DNA
<213> ORGANISM: Artificial Sequence
<220> FEATURE:
<223> OTHER INFORMATION: Description of Artificial Sequence; note = synthetic construct

<400> SEQUENCE: 187
gtcgcacacc ccagcgtata cttcgagcgg ccaatcggct ttttggcaaa ttttggcacg 60
cgcgtgaatc ccgtcggtgc gagacgcgtt tgcgatggta cttaacgcgc cctgtccgtt 120
tttgtctctc gcccttcagc ctgcaggagc caaccatcat gtggatcaag tggatcgcca 180
cgctggtcgc ctttggcgcc ctggtgcaaa gtgcggtagc atgtccctcg cagtgttcgt 240
gctcagggac acaagtgaac tgccatgaga gaagactcgc gtctgtgcct gcgggaatcc 300
ccaccaccac gcaagtgctg tatttgtaca ccaataagat cacgaagctc gagcccggcg 360
tgtttgacag tctggcggca ctgactgaac tctaccttca ctacaaccag ctgacgactc 420
ttccctacgg ggtgtttgac agtctgacgc aactgactta tctgaacctt gctgttaacc 480
agctgacatc tgtccctgct ggagtgtttg acgaactgac ccaggtttat tctctgagtc 540
tgaacgacaa ccagctgaag agcattccca ggggcgcctt tgacaacctc aagagcctca 600
ctcacatctt tctgtacaac aacccatggg actgcgcctg ttcagacatc ttgtacctca 660
gccgctggat ctctcagcac ccaggagtcg tgaggtcggc agatgatgat tggagcagag 720
tggtccccga ctcagcgcgc tgctctggta ccaatacccc cgtccgtgcg gtcaccgagg 780
ccagcactag cccctcgaaa tgcccaggct acgttgctac gaccacgacg ccgacgacga 840
ccacgcccga attcatccct gagaccacca cctcgccgca gcccgtgatc acaacccaga 900
aacccaagcc tctgtggaat ttcaactgca cctcaattca ggagaggaag aacgacggtg 960
gcgactgcgg aaagcccgcc tgcacaactc tcctgaactg cgcgaatttc ctcagctgcc 1020
tctgctcgac ctgcgccctc tgcaggaaac gttgatcggc gtgcaaaggt cggggatggc 1080
ggtgggaagg cgggcgcggt ggggtggggg gtgtagtgga gaaggtggag gaggaggagt 1140
gaggagaagg aagaccagga agagggggag agtaataagc agagacgatt tgaaaggttg 1200
acaaatttct cgcgcaaact ccaccacctt cgcgtccgaa cgac 1244

<210> SEQ ID NO 188
<211> LENGTH: 1352
<212> TYPE: DNA
<213> ORGANISM: Artificial Sequence
<220> FEATURE:
<223> OTHER INFORMATION: Description of Artificial Sequence; note = synthetic construct

<400> SEQUENCE: 188
aagacaaacg tgctcgttga taacgttggg ttgaggatgc aatgccctgc aatgtgcgcg 60

```
atccgatcag aataactggc gtctgtatgt tttatttaag ttaaacaatt aattcgcctc    120
atttaatttc tggactaacc agggcacgaa cccgttcgct tctgtctttg gctcaaattc    180
aacagcagca atgaagacgc agcctttcac gcgtcgcaca acccagcgta tacttcgagc    240
ggccaatcgg ctttttggca aattttggca cgcgcgtgaa tcccgtcggt gcgagacgcg    300
tttgcgatgg tacttaacgc gccctgtccg tttttgtctc tcgcccttca gcctgcagga    360
gccaaccatc atgtggatca agtggatcgc cacgctggtc gcctttggcg ccctggtgca    420
aagtgcggta gcatgtccct cgcagtgttc gtgctcaggg acagaagtga gctgtgacag    480
gaaacgcttc gcgtctgtgc ctgcggaaat ccctatcacc acgcaaaggc tgtggttgag    540
caacaatcag ttaactaagc tcgaccccgg agtgtttgac agcctggcgg cactgacttt    600
tctgaacgtt ggtgacaacc agctgacggc tctacccgag gggtgtttg accacctggt    660
gaatctgaag gagctgaatt tgaacatcaa ccagctgaag agcgttccca ggggcgcctt    720
tgacaacctc aagagcctca ctcacatctg gctgttcgac aacccctggg actgtgcctg    780
ttcagacatc ctgtacctca gccactggat ctctcagcac ccaggaatcg tgaggacgga    840
agatgatggt tggaacagag tggtccccga ctcagcgcgc tgctctggta ccaatacccc    900
cgtccgtgcg gtcaccgagg ccagcactag cccctcgaaa tgcccaggct acgttgctac    960
gaccacgacg ccgacgacga ccacgcccga attcatccct gagaccacca cctcgccgca   1020
gcccgtgatc acaacccaga aacccaagcc tctgtggaat ttcaactgca cctcaattca   1080
ggagaggaag aacgacggtg gcgactgcgg aaagcccgcc tgcacaactc tcctgaactg   1140
cgcgaatttc ctcagctgcc tctgctcgac ctgcgccctc tgcaggaaac gttgatcggc   1200
gtgcaaaggt cggggatggc ggtgggaagg cgggcgcggt ggggtggggg gtgtagtgga   1260
gaaggtggag gaggaggagt gaggagaagg aagaccagga agagggggag agtaataagc   1320
agagacgatt tgaaaggttg acaaatttct cc                                 1352
```

<210> SEQ ID NO 189
<211> LENGTH: 1501
<212> TYPE: DNA
<213> ORGANISM: Artificial Sequence
<220> FEATURE:
<223> OTHER INFORMATION: Description of Artificial Sequence; note = synthetic construct

<400> SEQUENCE: 189

```
agtgtaatta tgctcagtcg atcgaatgtg aagacaaaac gttgctcgtt tgattaacgt     60
ttgggttgag gatgcaatgc acttgcaatg tgcgccgatc cgatcagaat aactgggcgt    120
ctgtatgttt tatttaagtt aaacaattaa ttcgcctcat ttaatttctg gactaaccag    180
ggcacgaacc cgttcgcttc tgtctttggc tcaaattcaa cagcagcaat gaagacgcag    240
cctttcacgc gtcgcacaac ccagcgtata cttcgagcgg ccaatcggct ttttggcaaa    300
ttttggcacg cgcgtgaatc ccgtcggtgc gagacgcgtt tgcgatggta cttaacgcgc    360
cctgtccgtt tttgtctctc gcccttcagc ctgcaggagc caaccatcat gtggatcaag    420
tggatcgcca cgctggtcgc ctttggcgcc ctggtgcaaa gtgcggtagc atgtccctcg    480
cagtgttcgt gctcagggac aactgtggat tgcaacagca gaagacatgc gtctgtgcct    540
gcgggaatcc ccaccaatgt gcagattttg aatttgtaca acaatcagat cacgaatctc    600
gagcccggcg tgtttgaccg cctggggaag ctgcagcatt tagatctgtc aaagaaccag    660
ctgaagagca ttcccagggg cgcctttgac aacctcaaga gcctcactca catctatctg    720
ttcaacaacc cctgggactg cgagtgttcg gacatcctct atctgaagaa ctggattgtg    780
```

cagcatgcaa gcatcgtgaa tctacggggc catgggggag ttgataacgt gaagtgctct 840
ggtaccaata cccccgtccg tgcggtcacc gaggccagca ctagcccctc gaaatgccca 900
ggctacgttg ctacgaccac gacgccgacg acgaccacgc ccgaattcat ccctgagacc 960
accacctcgc cgcagcccgt gatcacaacc cagaaaccca agcctctgtg gaatttcaac 1020
tgcacctcaa ttcaggagag gaagaacgac ggtggcgact gcggaaagcc cgcctgcaca 1080
actctcctga actgcgcgaa tttcctcagc tgcctctgct cgacctgcgc cctctgcagg 1140
aaacgttgat cggcgtgcaa aggtcgggga tggcggtggg aaggcgggcg cggtggggtg 1200
gggggtgtag tggagaaggt ggaggaggag gagtgaggag aaggaagacc aggaagaggg 1260
ggagagtaat aagcagagac gatttgaaag gttgacaaat ttctcgcgca aactccacca 1320
ccttcgcgtc cgaacgacca tgaggatacc gcgacgacga cgatgataat gaacaaccca 1380
gcaaggaatc aacgaccact cttgtcgaat cgcttcgtca gcggctgttg ccgacacaca 1440
cgcacgcacg cgcacacgca cgcgcgcatt tgaaaacaaa tagagtcgat ttagtttgtt 1500
t 1501

<210> SEQ ID NO 190
<211> LENGTH: 417
<212> TYPE: DNA
<213> ORGANISM: Artificial Sequence
<220> FEATURE:
<223> OTHER INFORMATION: Description of Artificial Sequence; note = synthetic construct

<400> SEQUENCE: 190
ggcgccctgg tgcaaagtgc ggtagcatgt ccctcgcagt gttcgtgcga tcagacaact 60
gtgaaatgcc atagcagacg cctcacgtct gtgcctgcgg gaatccccac aaacaggcag 120
aacctgtggt tgcacgacaa tcagatcacg aagctcgagc ccggggtgtt taataaacta 180
acccagctca ctcatctgag tctgtacaat aaccagctga agagcattcc caggggcgct 240
tttgacaacc tcaagagcct cactcacatc tatctgttca acaacccctg ggactgcgaa 300
tgttcggaca tcctctatct gaagaactgg attgtgcagc acgcaagcat cgtgaatcca 360
gggaactatg gggagttga taacgtgaag tgctctggta ccaatacccc cgtccgt 417

<210> SEQ ID NO 191
<211> LENGTH: 576
<212> TYPE: DNA
<213> ORGANISM: Artificial Sequence
<220> FEATURE:
<223> OTHER INFORMATION: Description of Artificial Sequence; note = synthetic construct

<400> SEQUENCE: 191
ggcgccctgg tgcaaagtgc ggtagcatgt ccctcgcagt gttcgtgctc agggacagaa 60
gtgcactgtc agaaaaaaag cctcgcgtct gtgcctgcag gaatccccac caccacgcaa 120
gtgctgtatt tgcacgtcaa tcagatcacg aagctcgagc ccggggtgtt tgacagcctg 180
gtgaatctgc agcgcctgca tctggatcaa aaccagctgg tgtctctccc cgctggtgtg 240
tttgaccgtc tgactcaact gacacgactg gatcttgaca ataaccagtt gacagttctc 300
cccgccgggg tgattagccg cctggtgaat ctgcattggt tggctctgca cgacaatcag 360
ctgaagagca ttcccagggg cgcctttgac aacctcaaga gcctcactca catctggctg 420
ttcggcaacc cctgggactg tcaatgcacg gacatcctct acttgagtgg ctgggtcgct 480
cagcactcgg gcatcgtgcg agagcagtgg actgggtcgt cgtggaccgt gaacccagac 540
agcgccaagt gctctggtac caataccccc gtccgt 576

<210> SEQ ID NO 192
<211> LENGTH: 420
<212> TYPE: DNA
<213> ORGANISM: Artificial Sequence
<220> FEATURE:
<223> OTHER INFORMATION: Description of Artificial Sequence; note = synthetic construct

<400> SEQUENCE: 192
ggcgccctgg tgcaaagtgc ggtagcatgt ccctcgcagt gttcgtgctc agggacagat 60
gtgaactgtg atagcagaag cctcgcgtct gtgcctggag gaatccccac caccacgcaa 120
gtgctgtatt tgtacgacaa tcagatcacg aagctcgagc ccggcgtgtt tgacagtctg 180
gcggcactga cttttctgaa ccttggtaac aaccagctga cggctctacc cgagggggtg 240
tttgacaaac tcacacagct cactcacatc tggctgtcca acaaccccctg ggactgcgcc 300 tgctcggaca tcctgtatct cagtcgctgg atcggtcaaa acgggggaa gttggttaac 360 tctgcaggaa actttgacgg caacagtgct gtgtgctctg gtaccaatac cccgtccgt 420

<210> SEQ ID NO 193
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 193
ggcgccctgg tgcaaagtgc ggtagcatgt ccctcgcagt gttcgtgctc agggacagaa 60
gtgcactgtc agaaaaaaag cctcgcgtct gtgcctgcgg gaatccccac caacgcactg 120
aatctatggt tgaacgacaa tcagataacg aacctcgagc ccggagtgtt tgacagcctg 180
acgcaactga cttatctgga cctggctcct aaccagctga cggctcttcc cgtgggagtg 240
tttgaccgcc tggtgaatct gcagcggctg tggttgaaca acaaccagct gacctctctc 300
cccgctgggg tgtttgaccg cttggttaat ctgcagacgc tggatttgca caacaaccag 360
ctgaagagca ttcctagggg cgcctttgac aacctcaaga gcctcactca catctggctg 420
tccagcaacc cctgggactg cgagtgttcg gacatcctct atctgaagaa ctggattgtg 480
cagcacgcaa gcatcgtgaa tccatcgggc aatgggggag ttgataacgt gaagtgctct 540
ggtaccaata cccccgtccg t 561

<210> SEQ ID NO 194
<211> LENGTH: 414
<212> TYPE: DNA
<213> ORGANISM: Artificial Sequence
<220> FEATURE:
<223> OTHER INFORMATION: Description of Artificial Sequence; note = synthetic construct

<400> SEQUENCE: 194
ggcgccctgg tgcaaagtgc ggtagcatgt ccctcgcagt gttcgtgttc agggacagaa 60
gtgcgctgtg agagcagaag cctcgcgtct gtgcctgcgg gaatccccac caccacgcga 120
tggctgcatt tgcacagaaa tcaactcacg aagctcgagc ccggggtgtt tgacaaactg 180
accaaactca ctcatctgta tctgggatat aaccagctga agagcattcc caggggcgcc 240
tttgacaacc tcaagagcct cactcacatc tggctgtaca acaaccccctg ggactgcgag 300 tgttcggaca tcctctatct gaagaactgg attgtgcagc acgcaagcat cgtgaatcca 360
ggcaacgggg gagttgataa cttgaagtgc tctggtacca atacccccgt ccgt 414

<210> SEQ ID NO 195
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 195
ggcgccctgg tgcaaagtgc ggtagcatgt ccctcgcagt gttcgtgctc aggggcagaa 60
gtgcgctgtg tgagcaaaag cctcgcgtct gtgcctgcag gaatccccat caccacgcag 120
tctctgtctt tgcactatac tcagatcacg aagctcgagc ccggggtgtt tgaccgtctg 180
gctcagctga caggactaga tttaagccac aaccagttca cagctctccc cgctcaggta 240
tttgaccgcc tggtgaatct gcagctgttg catttaaaca acaacccgct gaagaggttt 300
cccgggggcg cgtttgacaa acttacccgg ctgaagcggt tggttctgca caccaaccag 360
ctgaagagca ttcccagggg cgcctttgac aacctcaaga gcctcactca catctggctg 420
tccaacaacc cctgggactg cgagtgttcg gacatcctct atctgaagaa ctggattgtg 480
cagcacgcaa gcatcgtgaa tccacacccc catgggggag ttgataacgt gaagtgctct 540
ggtaccaata cccccgtccg t 561

<210> SEQ ID NO 196
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 196
ggcgccctgg tgcaaagtgc ggtagcatgt ccctcgcagt gttcgtgcga tcagacaact 60
gtatactgcc atagcagacg cctcacgtct gtgcctgcgg gaatccccac cgacaggcag 120
aacctgtggt tgtacgacaa tcagatcacg aagctcgagc ctggggtgtt tgacctcctg 180
gtgaatctgc agcatctgca tttgaacagc aacaagctaa cagctatacc cgccggggtg 240
ttcgacaaac tgacccagct cactcatctg ggtctgcacg tcaaccagct gaagagcatt 300
cccaggggcg cctttgacaa cctcaagagc ctcactcaca tctatctgtt caacaacccc 360
tgggactgcg agtgttcgga cattctctat ctgaagaact ggattgtgca gcacgcaagc 420
atcgtgaatc cacaccccca tgggggagtt gataacgtga agtgctctgg taccaatacc 480
cccgtccgt 489

<210> SEQ ID NO 197
<211> LENGTH: 633
<212> TYPE: DNA
<213> ORGANISM: Artificial Sequence
<220> FEATURE:
<223> OTHER INFORMATION: Description of Artificial Sequence; note = synthetic construct

<400> SEQUENCE: 197
ggcgccctgg tgcaaagtgc ggtagcatgt ccctcgcagt gttcgtgcac aggggcatct 60
gtggaatgcc agagcagaag acacacgtct gtgcctgcgg gaatccccat caatgtgcag 120
atttttgaat tgtacgacaa tcagatcacg aagcttgagc ccggggtgtt tgaccgcctg 180
gtgaatctgc agcagctgta tctgggctcg aaccagctgg gggctctacc cgttggggtg 240
tttgacagtc tgacgcaact gacttatctg gacctggctc ctaaccagct gcaggctctt 300
cccgaggggg tgtttgaccg cttggtgaat ctgcagcagc tgtatctggg ctcgaaccag 360
ctgggggctc tccccacttg ggtgtttgac aaactgaccc agctcactta tctggatctg 420
aacaacaacc agctgaagag cattcccagg ggcgcctttg acaacctcaa gagcctcact 480
cacatctggc tgtccaacaa cccctgggac tgcgagtgtt cggacatcct ctatctaaag 540
aactggattg tgcagcatgc aagcatcgtg aatccagacg gccatggggg agttgataac 600
gtgaagtgct ctggtaccaa taccccgtc cgt 633

<210> SEQ ID NO 198
<211> LENGTH: 561
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 198
ggcgccctgg tgcaaagtgc ggtagcatgt ccctcgcagt gttcgtgcga tcagacaact 60
gtatactgcc atagcagacg cctcacgtct gtgcctgcgg gaatccccac cgacaggcag 120
aacctgtggt tgaataacaa tcagatcacg aagctcgagc ccggggtgtt tgaccgcctg 180
gtgaatctgc agaagctcta tttgagtggg aatcagctgc aggctcttcc tgagggggtg 240
tttgaccgcc tcataaatct gaaggagctg tatttttcta ataaccagct gacatctctc 300
cccgccaggg tgtttgacaa actcacccag ctcactcaac tggatttgaa tgacaaccag 360
ctgaagagca ttcccagggg cgcctttgac aacctcaaga gcctcactca catctttctg 420
tacaacaacc cctgggactg cgagtgttcg gacatcctct atctgaagaa ctggattgtg 480
cagcacgcaa gcatcgtgaa tccacacccc catgggggag ttgataacgt gaagtgctct 540
ggtaccaata cccccgtccg t 561

<210> SEQ ID NO 199
<211> LENGTH: 501
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 199
ggcgccctgg tgcaaagtgc ggtagcatgt ccctcgcagt gttcgtgctc agggacacaa 60
gtgaactgcc atgagagaag actcgcgtct gtgcctgcgg gaatccccac caccacgcaa 120
gtgttgtatt tgtacaccaa taagatcacg aagctcgagc ccggcgtgtt tgacagtctg 180
acggcactga cttttctgaa ccttggtaac aaccagctga cggctctacc caccggggtg 240
tttgacaacc tgacccagct tagcatactg aatatgcaca ccaaccagct gaagagtatt 300
cccaggggcg cctttgacaa cctcaagagc ctcactcaca tctggctgtt gaacaacccc 360
tgggactgtg cctgctcaga catcctgtac ctcagccgct ggatctctca gcacccagga 420
gtcgtgagga cggcagatga tgattggagc agagtggtcc ccgactcagc gcgctgctct 480
ggtaccaata cccccgtccg t 501

<210> SEQ ID NO 200
<211> LENGTH: 498

<212> TYPE: DNA
<213> ORGANISM: Artificial Sequence
<220> FEATURE:
<223> OTHER INFORMATION: Description of Artificial Sequence; note =
synthetic construct

<400> SEQUENCE: 200
ggcgccctgg tgcaaagtgc ggtagcatgt ccctcgcagt gttcgtgcga tcagacaact 60
gtgaactgcc ataacagacg tctcacgtct gtgcctgcgg gaatccccac aaacaggcag 120
aacctgtggt tgcacgacaa tcagatcacg aagctcgagc ccggggtgtt tgacagtctg 180
acccagctca cttatctgtc tctgggatat aaccagctga agagcgttcc caggggcgtg 240
tttgacaaac ttacccggct gaagcggttg ggtctggacc agaatcaact gaagagcatt 300
cccaggggcg cctttgacaa cctcaagagc ctcactcaca tccggctgtt cggcaacccc 360
tgggactgtg cctgctcaga catcctgtac ctcagccgct ggatctctca gcacccagga 420
gttccgaagg cggcagatag ttggaccaga gtggatctcg actcagcgcg ctgctctggt 480
accaataccc ccgtccgt 498

<210> SEQ ID NO 201
<211> LENGTH: 489
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 201
ggcgccctgg tgcaaagtgc ggtagcatgt ccctcgcagt gttcgtgctc agggacagat 60
gttcaatgtg acaggagaag cctcgtgtct gtgcctgcgg gaatccccac caccacgcaa 120
gtgctgtatt tgtacaccaa tcagatcacg aagctcgagc ccggcgtgtt tgaccgcctg 180
gtgaatctgc agaagctgtg gttgaacagc aaccagctgt cggctctacc cgttggggtg 240
tttgacaaac tgacccagct cactcgtcta gaactgcaaa ccaaccagct gaagagcatt 300
cccaggggcg cctttgacaa cctcaagagc ctcactcaca tctatctgta caacaacccc 360
tgggactgcg cctgcacgta catcttgtat ctcagcacgt ggatcggtca gaattcgggt 420
aaagtaacta aggaaagtgt aaacaaccca gatagcgccg tgtgctctgg taccaatacc 480
cccgtccgt 489

<210> SEQ ID NO 202
<211> LENGTH: 558
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 202
ggcgccctgg tgcaaagtgc ggtagcatgt ccctcgcagt gttcgtgcga tcagacaact 60
gtgaactgcc ataacagacg tctcacgtct gtgcctgcgg gaatccccac aaacaggcag 120
aacctgtggt tgcacgacaa tcagatcacg aagctcgagc ccggggtgtt tgacagcctg 180
gtgaatctgc agcgcctgca tctggatcaa aaccagctgc aggctcttcc cgctgggttg 240
tttaaccgcc tggggaatct gcaggagctg tacatgtgct gcaacaagtt cacagagctt 300
ccccatggca ttgacaaact cactcagttg aggcggttga gtcttaacca gaatcaactg 360
aagagcatcc ctgacggcgc gttcgctcgt ctcccgagcc tcacccacgt gtggctccac 420
accaacccct gggactgcga gtgttcggac atcctctatc tgaagaactg gattgtgcag 480
cacgcaagca tcgtgaatcc acacccctat gggggagttg ataacgtgaa gtgctctggt 540
accaataccc ccgtccgt 558

<210> SEQ ID NO 203
<211> LENGTH: 540
<212> TYPE: DNA
<213> ORGANISM: Artificial Sequence
<220> FEATURE:
<223> OTHER INFORMATION: Description of Artificial Sequence; note = synthetic construct

<400> SEQUENCE: 203
ggcgccctgg tgcaaagtgc ggtagcatgt ccctcgcagt gttcgtgctc aggggcagaa 60
gtgcgctgtg tgagcaaaag cctcgcgtct gtgcctgcag gaatccccat caccacgcag 120
tctctgtctt tgcactatac tcagatcacg aagctcgagc ccggggtgtt tgaccacctg 180
gtgaatctgc agcagctgtg gttagaaatc aaccagctga cgtctctccc cgctggggtg 240
tttgacaaac tgacagagct tacttatttg aacctcaata ccaaccagct aacggctctg 300
cccgctgggg tgtttgacaa attgaccctg ctcgctggtc tgagtctgca cgacaaccag 360
ctgaagagca ttcccagggg cgcctttgac aacctcaaga gcctcactca gatctggctg 420
tacaacaacc cctgggactg tgcttgctca gacatcctct acctcagcgg ctggctgggc 480
cagcacgcag ggaaagagca gggccaggct gtctgctctg gtaccaatac ccccgtccgt 540

<210> SEQ ID NO 204
<211> LENGTH: 639
<212> TYPE: DNA
<213> ORGANISM: Artificial Sequence
<220> FEATURE:
<223> OTHER INFORMATION: Description of Artificial Sequence; note = synthetic construct

<400> SEQUENCE: 204
ggcgccctgg tgcaaagtgc ggtagcatgt ccctcgcagt gttcgtgcga tcagacaact 60
gtggactgcc ggaacaaacg cttctcgtct gtgcctgcgg gaatccccac cgacaggcag 120
aacctgtggt tgaataacaa tcagatcacg aagctcgagc ccggggtgtt tgacagtctg 180
acggcactga ctgaactgaa acttggtggc aaccagctgc cggctatccc tcagggggtg 240
tttgataaac tcacccagct cactgttctg aatctgcgtc acaaccaact gcaattcgtt 300
cctgttggcg tgtttgagcg gctggtgagt ctacgggagc ttttcctcgg tgataacaaa 360
tttacggagt tgcccgcagg cgtagggaag ttgccgacac tgactcactt aggtctggac 420
ctaaaccagc tgaagagcat cccgcatgga gcgttcgacc gtctcagctc cctcacccac 480
gcctatttat ttggcaaccc atgggattgc gagtgcaggg acattatgta cctcaggaac 540
tgggtcgcag accacacttc tattgtaatg cgctgggatg ggaaggccgt taacgacccc 600
gactctgcca agtgcgctgg taccaatacc cccgtccgt 639

<210> SEQ ID NO 205
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 205
ggcgccctgg tgcaaagtgc ggtagcatgt ccctcgcagt gttcgtgccc agggacagat 60

```
gttaactgtc atgagagacg cttggcgtct gtgcctgcgg aaatccccac caccacgaag    120

atcctgcggc tgtacatcaa tcagatcacg aagctcgagc caggggtgtt tgatagtctg    180

acggcactga cttctctgga acttggtggc aaccagctga cggctcttcc tgagggggtg    240

tttgaccgcc tggtgaatct gcagaagctg tatttcagtg acaaccagct gcaggctcta    300

cccgccgggg tgtttgacaa actgacccag ctcactcatc tgggtctgca cactaaccag    360

ctgaagggca ttcccagggg cgcctttgac aacctcaaga gcctcactca catctggctg    420

ttgaacaacc cctgggactg tgcctgttca gacatcttgt acctcagccg ctggatctct    480

cagcacccag ggctcgtgtt cggctatttg aatttggacc ccgactcagc gcgctgctct    540

ggtaccaata cccccgtccg t                                              561
```

<210> SEQ ID NO 206
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 206

```
ggcgccctgg tgcaaagtgc ggtagcatgt ccctcgcagt gttcgtgctc agggacagat     60

gttcaatgtg acaggagaag cctcgtgtct gtgcctggag gaatccccac caccacgcaa    120

gtgctgtatt tgcacaccaa tcagatcacg aagctcgagc ccggggtgtt tgacagtctg    180

acgcaactga ctgaactcca ccttagtcac aaccagctga cgactcttcc cgagggggtg    240

tttgacagcc tggtgaatct gcagcgcctg catctggatc aaaaccagct ggtgtctcta    300

cccgctgggg tgtttgacaa actgacccag ctcactcgcc tagaactgca aaccaaccag    360

ctgaagagca ttcccagggg cgcctttgac aacctcaaga gcctcactca catctatctg    420

tacaacaacc cctgggactg cgcctgcacg tacatcttgt atctcagcac gtggatcggt    480

cagaattcgg gtaaagtaac taaggaaagt gtaaacaacc cagatagcgc cgtgtgctct    540

ggtaccaata cccccgtccg t                                              561
```

<210> SEQ ID NO 207
<211> LENGTH: 573
<212> TYPE: DNA
<213> ORGANISM: Artificial Sequence
<220> FEATURE:
<223> OTHER INFORMATION: Description of Artificial Sequence; note = synthetic construct

<400> SEQUENCE: 207

```
ggcgccctgg tgcaaagtgc ggtagcatgt ccctcgcagt gttcgtgctc agggacacaa     60

gtgaactgcc atgagagaag cctcgcgtct gtgcctgcgg gaatccccac caccacgcaa    120

gtgctgtatt tgtacaccaa tcagatcacg aagctcgagc ccggcgtgtt tgacagtctg    180

acggcactaa cttatttggg tcttggtggc aaccagctgg cagctcttcc cgttgggttg    240

tttgaccgcc tggggaatct gcagcgcctg catctggatc aaaaccagct acaggctcta    300

cccacagggg tgtttaataa actaacccag ctcactcatc tgagtctgca cactaaccag    360

ctgaagagca ttcccagggg cgcctttgac aacctcaaga gcctcactca catctggctg    420

ttcggcaacc cctgggactg tgcctgttca gacatcctgt acctcagccg ctggatctct    480

cagcacccag gaatcgtgag atcagcagat gatggttgga acagagtgaa ccccgactca    540

gcgcgctgct ctggtaccaa tacccccgtc cgt                                 573
```

<210> SEQ ID NO 208
<211> LENGTH: 636
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 208
ggcgccctgg tgcaaagtgc ggtagcatgt ccctcgcagt gttcgtgctc agggacacaa 60
gtgaactgcc atgagagaag cctcgcgtct gtgcctgcgg gaatccccac caccacgcaa 120
gtgctgtatt tgtacaccaa tcagatcacg aagctcgagc ccggcgtgtt tgacagtctg 180
actcaactga cacgactgga tctttacaat aaccagttga cagttctccc cgccggggtg 240
tttgacagcc tgacgcaact gacttatctg aaccttgctg ttaaccagct gacggctctt 300
cccgttgggg tgtttgacag agtcacccag ctgactattc tggctctgaa tgacaaccag 360
ctgcaggcgc tacccgccgg ggtgtttgac aaattgccca agctcacaca tttggttctg 420
cacaccaacc agctgaagag cattcccagg ggcgcctttg acaacctcaa gagcctcact 480
cacatctggc tgttcggcaa cccctgggac tgtgcctgct cggacatcct gtatctcagt 540
cgctggatcg gtcaaaacgg ggggaagttg gttaactctg caggaaactt tgacggcaac 600
agtgctgtgt gctctggtac caataccccc gtccgt 636

<210> SEQ ID NO 209
<211> LENGTH: 486
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 209
ggcgccctgg tgcaaagtgc ggtagcatgt ccctcgcagt gttcgtgctc agggacagaa 60
gtgcgctgtg tgagcaaaag cctcgcgtct gtgcctgcag gaatccccat caccacgcag 120
tctctgtctt tgcactatac tcagatcacg aagctcgagc ccggggtgtt tgacagtctg 180
gtgaatctgc agcagctgtg gttagaaatc aaccagctga catctctccc cgctgggttg 240
tttgaccgcc tggggaatct gcagcagatt aatctgagca acaaccagct gaagagcatt 300
cccaggggcg cctttgacaa cctcaagagc ctcacccacg tgtggctcca caccaacccc 360
tgggactgcg agtgttcgga catcctctat ctgaagaact ggattgtaca gcacgcaagc 420
atcgtgaatc caggcagcgg gggagttgat aacgtgaagt gctctggtac caataccccc 480
gtccgt 486

<210> SEQ ID NO 210
<211> LENGTH: 642
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 210
ggcgccctgg tgcaaagtgc ggtagcatgt ccctcgcagt gttcgtgccc agggacagat 60
gttaactgtc atgagagacg cttggcgtct gtgcctgcgg aaatccccac caccacgcag 120
atcctgcggc tgtacagaaa tcagatcacg aagctcgagc tcggggtgtt tgacagtctg 180

-continued atggaactga cttatctcac ccttcgtaac aaccagctga cagctctacc cgctagggtg 240
tttaacaaac tgacccggct gactgttttg gatctaagtg gcaaccagct gcaggctctt 300
cccgaggggg tgtttgacag cctggtgaat ctgcagcgcc tgcatctgga tcaaaaccag 360
ctggtgtctc tccccgctgg ggtgcttgac aaactgaccc agctcactca tctagaactt 420
caaaacaacc agctgaagag cattcccagg ggcgcctttg acaacctcaa gagcctaact 480
cacatctttc tgtacaacaa cccatgggat tgcgagtgca gggacattat gtacctcagg 540
aactgggtcg cagaccacac ttctattgta atgcgctggg atgggaaggc cgttaacgac 600
cccgactctg ccaagtgcgc tggtaccaat acccccgtcc gt 642

<210> SEQ ID NO 211
<211> LENGTH: 498
<212> TYPE: DNA
<213> ORGANISM: Artificial Sequence
<220> FEATURE:
<223> OTHER INFORMATION: Description of Artificial Sequence; note = synthetic construct

<400> SEQUENCE: 211
ggcgccctgg tgcaaagtgc ggtagcatgt ccctcgcagt gttcgtgctc aggaacagaa 60
gtgcactgtc agagaaaaag cctcgcgtct gtgcctgcag gaatccccac cacaacgcga 120
gtgctgtatt tgcacgtcaa tcagatcacg aagctcgaga ccggggtgtt tgaccgcctg 180
gtgaatctgc agaagctgtg gttgaacagc aaccagctga cctctctccc cgctggtgtg 240
tttgaccgtc tgactcaact gacacgactg gatctttaca ataaccagtt gaagagcatc 300
ccgcatggag cgttcgaccg tctcagctcc ctcacccacg cctatttatt tggcaaccca 360
tgggattgcg agtgcaggga cattatgtac ctcaggaact gggtcgcaga ccacacttct 420
attgtaatgc gctgggatgg gaaggccgtt aacgaccccg actctgccaa gtgcgctggt 480
accaataccc ccgtccgt 498

<210> SEQ ID NO 212
<211> LENGTH: 492
<212> TYPE: DNA
<213> ORGANISM: Artificial Sequence
<220> FEATURE:
<223> OTHER INFORMATION: Description of Artificial Sequence; note = synthetic construct

<400> SEQUENCE: 212
ggcgccctgg tgcaaagtgc ggtagcatgt ccctcgcagt gttcgtgcac aggggcatct 60
gtggaatgcc agagcagaag acacacgtct gtgcctgcgg gaatccccac caatgtgcag 120
atttttgaat tgtacgacaa tcagatcacg aagcttgagc ccggggtgtt tgacagtctg 180
gcgaatttga gggagcttca tctgtggggg aaccagctgt cggctctacc cgttggggtg 240
tttgacaaat tgcccaagct cacacatttg gttctgcaca ccaaccagct gaagagcgtt 300
cccaggggcg cgtttgacaa cctcaagagc ctcactaaca tctggctgtc cagcaacccc 360
tgggactgcg cctgctcgga catcctgtat ctcagtcgct ggatcggtca aaacgggggg 420
aagttagtta actctgcagg aaactttgac ggcaacagtg ctgtgtgctc tggtaccaat 480
acccccgtcc gt 492

<210> SEQ ID NO 213
<211> LENGTH: 561
<212> TYPE: DNA
<213> ORGANISM: Artificial Sequence
<220> FEATURE:

<223> OTHER INFORMATION: Description of Artificial Sequence; note = synthetic construct

<400> SEQUENCE: 213

```
ggcgccctgg tgcaaagtgc ggtagcatgt ccctcgcagt gttcgtgctc agggacacaa     60
gtgaactgcc atgagagaag actcgcgtct gtgcctgcgg gaatccccac caccacgcag    120
atcctgcggc tgtacagaaa tcagatcacg aagctcgagc tcggggtgtt tgacagtctg    180
agggaactga ctcttctgaa cgttggtgac aaccagctga cggctctacc cgagggggtg    240
tttgaccgcc tggtgaatct gcagaagctg tggttgaaca gcaaccagct gacaactgtt    300
cccgccgggg tgtttgaccg cctggggaat ctgcagcggt tcggtctgca cgacaaccag    360
ctgaagagca ttcccagggg cgccttcgac aacctcaaga gcctcactca catctggctg    420
ttcggcaacc cctgggactg cgagtgttcg gacatcctct atctgaagaa ctggattgtg    480
cagcacgcaa gcatcgtgaa tctagagggc tatgggggag ttgataacgt gaagtgctcc    540
ggtaccaata cccccgtccg t                                              561
```

<210> SEQ ID NO 214
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 214

```
ggcgccctgg tgcaaagtgc ggtagcatgt ccctcgcagt gttcgtgcga tcagacactt     60
gtgaactgcc agaatatacg cctcgcatct gtgcctgcgg gaatccccac cgacaagcag    120
aggctgtggt tgaacaacaa tcagatcacg aagcttgagc ccggggtgtt tgacagtctg    180
gtgaatctgc agaagctgta tctgtgggga aaccagctgc aggcactacc cgccagggtg    240
tttgacaaac tcacccagct cgctcatcta gaactgcaaa acaaccagct gaagagcatt    300
cccaggggcg cctttgacaa cctcaagagc ctcactcaca tctggctgtt cggcaacccc    360
tgggactgcg agtgttcgga catcctctat ctgaagaact ggattgtaca gcacgcaagc    420
atcgtgaatc tacagggcca tgggggagtt gataacgtga agtgctctgg taccaatacc    480
cccgtccgt                                                            489
```

<210> SEQ ID NO 215
<211> LENGTH: 492
<212> TYPE: DNA
<213> ORGANISM: Artificial Sequence
<220> FEATURE:
<223> OTHER INFORMATION: Description of Artificial Sequence; note = synthetic construct

<400> SEQUENCE: 215

```
ggcgccctgg tgcaaagtgc ggtagcatgt ccctcgcagt gttcgtgctc agggacagaa     60
gtgcactgtc agaaaaaaag cctcgcgtct gtgcctgcag gaatccccac caccacgcaa    120
gtgctgtatt tgcacgtcaa tcagatcacg aagctcgagc ccggggtgtt tgaccgcttg    180
gtgaatctgc agaagctgta tctgtgggga aaccagctgt cggctctacc cgttggggtg    240
tttgacaaac tgacccagct cacttatctg ggtctgtacg tcaatcaact gaagagcgtt    300
cccaggggcg cctttgacaa cctcaagagc ctcactcaca tctggctgtt cggcaacccc    360
tgggactgcg cctgctcgga catcctgtat ctcagtcgct ggatcggtca aaacgggggg    420
aagttggtta actctgcagg aaactttgac ggcaacagtg ctgtgtgctc tggtaccaat    480
```

acccccgtcc gt 492

<210> SEQ ID NO 216
<211> LENGTH: 468
<212> TYPE: DNA
<213> ORGANISM: Artificial Sequence
<220> FEATURE:
<223> OTHER INFORMATION: Description of Artificial Sequence; note = synthetic construct

<400> SEQUENCE: 216
ggcgccctgg tgcaaagtgc ggtagcatgt ccctcgcagt gttcgtgctc aggggcagaa 60
gtgcgctgtg tgagcaaaag cctcgcgtct gtgcctgcag gaatccccat caccacgcag 120
tatctgaatt tgcacgtcaa tcagatcacg aagctcgagc ccggggtgtt tgacagtctg 180
acgcaactga ctactctgta tctctcaaac aaccagctga cggctctccc tgctggagtg 240
tttgagaaac tgacccagct cattcatttg gctctgcgca acaaccagct gaagattgtt 300
cccaggggcg cctttgacaa cctcaagagc ctcactcaca tctggctgtt gaacaacccc 360
tgggactgtg cttgctcaga catcctctac ctcagcggct ggctgggcca gcacgcaggg 420
aaagagcagg gccaggctgt ctgctctggt accaataccc ccgtccgt 468

<210> SEQ ID NO 217
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 217
ggcgccctgg tgcaaagtgc ggtagcatgt ccctcgcagt gttcgtgcga tcagacaact 60
gtggactgcc ggaacaaacg cttctcgtct gtgcctgcgg gaatccccac cgacagtcag 120
agcctgtggt tgaacgacaa tcagatcacg aagctcgagc ccggactgtt tgaccgcatg 180
gagaatctgc agcatctgta tatggagaat atcaaactgt cggctgtacc cgttgggcag 240
tttgataaac tgacccagct cactcatctg ggtctgcaca ataaccagct gaagagcatt 300
cccaggggcg cctttgacaa cctcaagagc ctcactcaca tctggctgtt cggcaacccc 360
tgggactgcg aatgttcgga catcctctat ctgaagaact ggattgtgca gcacgcaagc 420
atcgtgaatc cagggaacta tgggggagtt gataacgtga agtgctctgg taccaatacc 480
cccgtccgt 489

<210> SEQ ID NO 218
<211> LENGTH: 417
<212> TYPE: DNA
<213> ORGANISM: Artificial Sequence
<220> FEATURE:
<223> OTHER INFORMATION: Description of Artificial Sequence; note = synthetic construct

<400> SEQUENCE: 218
ggcgccctgg tgcaaagtgc ggtagcatgt ccctcgcagt gttcgtgcga tcagacaact 60
gtggactgcc ggaacaaacg cttctcgtct gtgcctgcag gaatccccac cacaacgcga 120
gtgctgtatt tgaacagcaa tcagatcacg aagctcgagc ccggggtgtt tgaccgcctc 180
gggaatctgc agcgggttga tctgagtaac aaccaactga agagcattcc caggggcgcc 240
tttgacaacc tcaagagcct cactcacatc tggctgttcg gcaacccctg ggactgcgag 300
tgttcggaca tcctctatct gaagaactgg attgtgcagc acgcaagcat cgtgaatcta 360
tggggctatg ggggagttga taacgtgaag tgctctggta ccaatacccc cgtccgt 417

<210> SEQ ID NO 219
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 219
ggcgccctgg tgcaaagtgc ggtagcatgt ccctcgcagt gttcgtgcga tcagacaact 60
gtatactgcc atagcagacg cctcacgtct gtgcctgcgg gaatccccac caccacgcga 120
gggctgcatt tgcacaccaa tcagatcacg aagctcgagc ccggggtgtt tgacagtctg 180
acgcaactga ctgaaccgta ccttagtgcc aaccagctca cgactctacc cgccgggtta 240
tttgatcgcc tggtgaaact gaaggagctg tatctgtggg gaaaccagct gtcggctcta 300
cccgttgggg tgtttgacaa actcacccgg ctgaagcagt tgggtctgca caccaaccag 360
ctgaagagca ttcccagggg cgcctttgac aacctcaaga gcctcactca catctggctg 420
ttcggcaacc cctgggactg cgagtgttcg gacatcctct atctgaagaa ctggattgtg 480
cagcacgcaa gcatcgtgaa tccatcgggc catgggggag ttgataacgt gaagtgctct 540
ggtaccaata cccccgtccg t 561

<210> SEQ ID NO 220
<211> LENGTH: 642
<212> TYPE: DNA
<213> ORGANISM: Artificial Sequence
<220> FEATURE:
<223> OTHER INFORMATION: Description of Artificial Sequence; note = synthetic construct

<400> SEQUENCE: 220
ggcgccctgg tgcaaagtgc ggtagcatgt ccctcgcagt gttcgtgctc agggacaact 60
gtgaaccgtg atagcagaag cctcgcgtct gtgcctgcgg ggatcccaac cactacgcag 120
agcttggggt tttacaacaa tcagataacg aagctcgagc ccggggtgtt tgaccgcttg 180
gtgaatctgc agaagttgta tctgtgggga aaccagctgt cggctctacc cgttggggtg 240
tttgacaaac tcacccagct cgtaacactg gatctgaatg gaaaccaact gtcatccgtt 300
cccgcagacg tgttccatca gcttgtgaaa ttagagaagc tgtggctcaa aaacaacaaa 360
ctgacagcct taccccctgg ggtgtttgac cacctggtga atctgcagca gctgagtctg 420
cacaccaacc agttgaagag catcccgcat ggagcgttcg accgtctcag ctccctcacc 480
cacgcctatt tatatagcaa cccatgggat tgcgagtgca gggacattat gtacctcagg 540
aactgggtcg cagaccacac ttctattgta atgcgctggg atgggaaggc cgttaacgac 600
cccgactctg ccaagtgcgc tggtaccaat acccccgtcc gt 642

<210> SEQ ID NO 221
<211> LENGTH: 417
<212> TYPE: DNA
<213> ORGANISM: Artificial Sequence
<220> FEATURE:
<223> OTHER INFORMATION: Description of Artificial Sequence; note = synthetic construct

<400> SEQUENCE: 221
ggcgccctgg tgcaaagtgc ggtagcatgt ccctcgcagt gttcgtgctc agggacaact 60

```
gtggattgtc ggagcaaacg ccacgcatct gtgcctgcgg gaatccccac cactacgcac    120

tttctgtatt tacacagcaa tcagatcacg aagctcgagc ccggggtgtt tgacagtctg    180

ggaaatctac agaagctgtg gctgcacaga aaccagctga agaacattcc caggggcgcc    240

tttgataacc tgaagagcct cacttacatc tatctgttca acaacccctg ggactgcgag    300

tgttcggaca tcctctatct gaagaactgg attgtgcagc acgcaagcat cgtgaatcca    360

cacccctatg gggagttga taacgtgaag tgctctggta ccaatacccc cgtccgt       417
```

<210> SEQ ID NO 222
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 222

```
ggcgccctgg tgcaaagtgc ggtagcatgt ccctcgcagt gttcgtgctc agggacaact     60

gtgaactgtg atagcagaag cctcgcgtct gtgcctggag gaatccccac caccacgcaa    120

gtgctgtatt tgtacgacaa tcagatcacg aagttcgagc ccggcgtgtt tgacagtctg    180

acggcactga ctcttctgaa cgttggtgac aaccagctga cggctctacc cgagggggtg    240

tttgaccggc tggtgaatct gcagtcattg gttctgaaca tcaaccagtt gaagagcatt    300

cccaggggcg cctttgataa cctcaagagc ctcactcaca tctatctgtt caacaacccc    360

tgggactgcg agtgttcgga catcctctat ctgaagaact ggattgtgca gcacgcaagc    420

atcgtgaatc cacaacccta tggggagtt gataacgtga agtgctctgg taccaatacc     480

cccgtccgt                                                            489
```

<210> SEQ ID NO 223
<211> LENGTH: 490
<212> TYPE: DNA
<213> ORGANISM: Artificial Sequence
<220> FEATURE:
<223> OTHER INFORMATION: Description of Artificial Sequence; note = synthetic construct

<400> SEQUENCE: 223

```
ggcgccctgg tgcaaagtgc ggtagcatgt ccctcgcagt gttcgtgctc agggacaact     60

gtcgactgct atagcagaag cctcgcgtct gtgcctgcgg gaatccccac caccacgcaa    120

gtgctgggtt tgtccagcaa tcagatcacg aagctcgagc ccggggtgtt tgaccgcctg    180

gtgaatctgc agcagctgtg gttagaaatc aaccagctga catctctccc cgcaggggtg    240

tttgacaaac tgacccagct cacttatctg aatctgcgag acaaccagct gaagagcatt    300

cccaggggcg cctttgacaa cctcaagagc ctcactcaca tctatctgtt caacaacccc    360

tgggactgcg agtgttcgga catcctctat ctgaagaact ggattgtgca gcacgcaagc    420

atcgtgaatc cagggaacta tggggagtt gataacgtga agtgctctgg taccaatacc     480

cccgtccgta                                                           490
```

<210> SEQ ID NO 224
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 224
ggcgccctgg tgcaaagtgc ggtagcatgt ccctcgcagt gttcgtgctc agggacagaa 60
gtgcactgtc agaaaaaaag cctcgcgtct gtgcctgcag gaatccccac caccacgcaa 120
gtgctgtatt tgcacgtcaa tcagatcacg aagctcgagc ccggggtgtt tgaccgcctg 180
gtgaatctgc agcagctgtg gttgaacagg aaccagatga aagctctacc cgctggggtg 240
tttgacagtc taaccgagct gactattctg gctcttgata gcaaccagct gcaggctctt 300
cctgttgggg tgtttgaccg cctggggaat ctgcagcaga ttaatctgag caacaaccag 360
ctgaagagca ttcccagggg cgcctttgac aacctcaaga gcctcactca catctatctg 420
ttcaacaacc cctgggactg cgagtgttcg gacatcctct atctgaagaa ctggattgtg 480
cagcacgcaa gcatcgtgaa tccattgggc aatgggggag ttgataacgt gaagtgctct 540
ggtaccaata cccccgtccg t 561

<210> SEQ ID NO 225
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 225
ggcgccctgg tgcaaagtgc ggtagcatgt ccctcgcagt gttcgtgcga tcagacaact 60
gtggactgcc ggaacaaacg cttctcgtct gtgcctgcgg gaatccccac cgacaggcag 120
aacctgtggt tgaataacaa tcagatcacg aagctcgagc ccggggtgtt tgaccgcctg 180
actcaactga cacgactgga tctttacaat aaccagttga cagttctccc cactggagtg 240
tttgacaaac tgacccagct cactcttcta gaactgcaaa acaaccagct gaagggcgtt 300
cccaggggcg cctttgacaa cctcaagagc ctcactcaca tctggctgtt cggcaacccc 360
tgggactgcg cctgcacgga cattatgtat ctcagcacgt ggatcggtca gaattcgggt 420
aaagtcacta aggatagagt aaacaaccca gatagcgctg tgtgctctgg taccaatacc 480
cccgtccgt 489

<210> SEQ ID NO 226
<211> LENGTH: 501
<212> TYPE: DNA
<213> ORGANISM: Artificial Sequence
<220> FEATURE:
<223> OTHER INFORMATION: Description of Artificial Sequence; note = synthetic construct

<400> SEQUENCE: 226
ggcgccctgg tgcaaagtgc ggtagcatgt ccctcgcagt gttcgtgctc agggacacaa 60
gtgaactgcc atgagagaag actcgcgtct gtgcctgcgg gaatccccac caccacgcaa 120
gtgctgtatt tgtacaccaa taagatcacg aagctcgagc ccggcgtgtt tgacagtctg 180
acggcactga cttatctgaa ccttggcggc aaccagctga cggctcttcc cgttggggtg 240
tttgacaaac tgaccaaact cactcatctg gctctgcaca tcaatcaact gaagagcgtt 300
cccaggggcg cctttgacaa cctcaagagc ctcactcaca tctggctgta caacaacccc 360
tgggactgtg cctgttcaga catcctgtac ctcagccgct ggatctctca gcacccagga 420
gtcgtgagga cggcagatga tggttggaac agagtggtcc ccgactcagc gcgctgctct 480
ggtaccaata cccccgtccg t 501

<210> SEQ ID NO 227
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 227
ggcgccctgg tgcaaagtgc ggtagcatgt ccctcgcagt gttcgtgcga tcagacaact 60
gtgaactgcc atagcagacg cctcacgtct gtgcctgcgg gaatccccac aaacaggcag 120
aacctgtggt tgcacgacaa tcagatcacg aagctcgagc ccggggtgtt tgacagcctg 180
acgcaactga cttatctgca ccttgctgct aaccagctga cggctcttcc cgttggggtg 240
tttgacaaat tgcccaagct cacacatttg gttctgcaca ccaaccagct gaagagcgtt 300
cccaggggcg cctttgacaa cctcaagagc ctcactcaca tctggctgtt cggcaacccc 360
tgggactgcg agtgttcgga catcctctat ctgaagaact ggattgtaca gcacgcaagc 420
atcgtgaatc tacagggcca tgggggagtt gataacgtga agtgctctgg taccaatacc 480
cccgtccgt 489

<210> SEQ ID NO 228
<211> LENGTH: 426
<212> TYPE: DNA
<213> ORGANISM: Artificial Sequence
<220> FEATURE:
<223> OTHER INFORMATION: Description of Artificial Sequence; note = synthetic construct

<400> SEQUENCE: 228
ggcgccctgg tgcaaagtgc ggtagcatgt ccctcgcagt gttcgtgctc agggacacat 60
gtgaactgtg aacggaaacg cctcgcgtct gtgcctgcgg gaatccccac aaacaggcag 120
aacctgtggt tgcacgacaa tcagatcacg aagctcgagc ccggggtgtt tgaccatctg 180
gtgaatctgc aggggctgac tctgtacaac aaccagctga agagcgttcc taggggcgcc 240
tttgacaacc tcaagagcct cactaacatc tggctgtcca gcaacccatg ggattgcgag 300
tgcagggaca ttatgtacct caggaactgg gtcgcagacc acacttctat tgtaatgcgc 360
tgggatggga aggccgttaa cgaccccgac tctgccaagt gcgctggtac caataccccc 420
gtccgt 426

<210> SEQ ID NO 229
<211> LENGTH: 417
<212> TYPE: DNA
<213> ORGANISM: Artificial Sequence
<220> FEATURE:
<223> OTHER INFORMATION: Description of Artificial Sequence; note = synthetic construct

<400> SEQUENCE: 229
ggcgccctgg tgcaaagtgc ggtagcatgt ccctcgcagt gttcctgctc agggacaact 60
gtggattgcc ggagcaaacg ccacgcatct gtgcctgcgg gaatccccac caatgcgcag 120
attctgtatt tacacgacaa tcagatcacg aagctcgagc ccggggtgtt tgacaaactg 180
acccagctca cttatctggg tctgtacgtc aatcaactga agagcattcc caggggcgcc 240
tttgacaacc tcaagagcct cactcacatc tatctgttca acaacccctg ggactgcgag 300
tgttcggaca tcctctatct gaagaactgg attgtgcagc acgcaagcat cgtgaatcca 360
tcgggctatg gggagttga taacgtgaag tgctctggta ccaatacccc cgtccgt 417

<210> SEQ ID NO 230
<211> LENGTH: 540
<212> TYPE: DNA
<213> ORGANISM: Artificial Sequence
<220> FEATURE:
<223> OTHER INFORMATION: Description of Artificial Sequence; note = synthetic construct

<400> SEQUENCE: 230
ggcgccctgg tgcaaagtgc ggtagcatgt ccctcgcagt gttcgtgcga tcagacaact 60
gtatactgcc atagcagacg cctcacgtct gtgcctgcgg gaatccccac cgacaggcag 120
aacctgtggt tgtacaacaa tcagatcacg aagctcgagc ccggggtgtt tgaccgcttg 180
gtgaatctgc agaagctgta tctgtgggga aaccagctgt cggctctacc cgttggggtg 240
tgtgacagcc tggtgaatct gaaggagctg cgtttgtaca acaaccagct gacggctcta 300
cccgaggggg tgtttgacca cctggtgaat ctgcagcagt tggctctgaa caacaatcag 360
ctgaagagca ttcccagggg cgcctttgac aacctcaaga gcctcactca catctggctg 420
tacaacaacc cctgggactg tgcttgctca gacatcctct acctcagcgg ctggctgggc 480
cagcacgcag ggaaagagca gggccaggct gtctgctctg gtaccaatac ccccgtccgt 540

<210> SEQ ID NO 231
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 231
ggcgccctgg tgcaaagtgc ggtagcatgt ccctcgcagt gttcgtgctc agggacacaa 60
gtgaactgcc atgagagaag cctcgcgtct gtgcctgcgg gaatccccac caccacgcaa 120
gtgctgtatt tgtacaccaa tcagatcacg aagctcgagc ccggcgtgtt tgacagcctg 180
acgcaactga cttatctgaa ccttgctgtt aaccagctga cggctcttcc cgctggggtg 240
tttgacaaat tgcccaagct cacacatttg gttctgcaca ccaaccagct gaagagtatt 300
cccaggggcg cctttgacaa cctcaagagc ctcactcaca tctggctgtt gaacaacccc 360
tgggactgcg agtgttcgga catcctctat ctgaagaact ggattgtaca gcacgcaagc 420
atcgtgaatc tacagggcca tgggggagtt gataacgtga agtgctctgg taccaatacc 480
cccgtccgt 489

<210> SEQ ID NO 232
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 232
ggcgccctgg tgcaaagtgc ggtagcatgt ccctcgcagt gttcgtgctc agggacacaa 60
gtgaactgcc atgagagaag actcgcgtct gtgcctgcgg gaatccccac caccacgcaa 120
gtgctgtatt tgtacaccaa taagatcacg aagctcgagc ccggcgtgtt tgacagtctg 180
actcaactga cacgactgga tctttacaat aaccagttga cagttctccc cgccggggtg 240
tttgacagcc tggtgaatct gcagcagctg tatctgggag gtaaccagct gacgaccgtt 300
cctaggggcg cctttgacaa cctcaagagc ctcactcaca tctggctgta caacaacccc 360
tgggactgcg agtgttcgga catcctctat ctgaagaact ggattgtgca gcacgcaagc 420
atcgtgaatc catcgggcca tgggggagtt gataacgtga agtgctctgg taccaatacc 480
cccgtccgt 489

<210> SEQ ID NO 233
<211> LENGTH: 417
<212> TYPE: DNA
<213> ORGANISM: Artificial Sequence
<220> FEATURE:
<223> OTHER INFORMATION: Description of Artificial Sequence; note = synthetic construct

<400> SEQUENCE: 233
ggcgccctgg tgcaaagtgc ggtagcatgt ccctcgcagt gttcgtgcga tcagacaact 60
gtatactgcc atagcagacg cctcacgtct gtgcctgcgg gaatccccac caatgcgcag 120
attctgtatt tacacgacaa tcagatcacg aagctcgagc ccgggttgtt tgacaaactg 180
acccagctca ctcgtctaga actgcaaacc aaccagctga agagtattcc caggggcgcc 240
tttgacaacc tcaagagcct cactcacatc tggctgttga acaacccctg ggactgcgag 300
tgttcggaca tcctctatct gaagaactgg attgtacagc acgcaagcat cgtgaatcta 360
cagggccatg gggagttga taacgtgaag tgctctggta ccaatacccc cgtccgt 417

<210> SEQ ID NO 234
<211> LENGTH: 498
<212> TYPE: DNA
<213> ORGANISM: Artificial Sequence
<220> FEATURE:
<223> OTHER INFORMATION: Description of Artificial Sequence; note = synthetic construct

<400> SEQUENCE: 234
ggcgccctgg tgcaaagtgc ggtagcatgt ccctcgcagt gttcgtgcga tcagacaact 60
gtgaaatgcc atagcagacg cctcacgtct gtgcctgcgg gaatccccac caatgtgcag 120
attttgaatt tgtacaacaa tcagataacg aagctcgagc ctggggtgtt tgaccgtctg 180
gtgaatctgc agcagctgta tatcagttgg aaccagctac aggctctacc cacaggggtg 240
tttaataaac taacccagct cactcatctg agtctgtaca ataaccagct gaagagcatt 300
cccaggggcg cctttgacaa cctcaagagc ctcactcaca tctggctgtc cagcaacccc 360
tgggactgtg cctgttcaga catcctgtac ctcagccgct ggatctctca gcacccaggg 420
gtggtgagga aggatgaagc aggctaccct gtggaccccg actcagcgcg ctgctctggt 480
accaataccc ccgtccgt 498

<210> SEQ ID NO 235
<211> LENGTH: 570
<212> TYPE: DNA
<213> ORGANISM: Artificial Sequence
<220> FEATURE:
<223> OTHER INFORMATION: Description of Artificial Sequence; note = synthetic construct

<400> SEQUENCE: 235
ggcgccctgg tgcaaagtgc ggtagcatgt ccctcgcagt gttcgtgctc agggacagaa 60
gtgaactgtg cagggaaaag cctcgcgtct gtgcctgcag gaatccccac cacaacgcga 120
gtgctgtatt tgaacagcaa tcagatcacg aagctcgagc ccggcgtgtt tgaccgcctg 180
actcaactga cacgactgga tcttgacaat aaccagttga cagttctccc cgccggggtg 240

```
tttgacagcc tggtgaatct gcagacgctg tatttgcatc agaacgagct gacaactctc    300

cccgcagggg tgtttgacaa actcacccag ctcactcgtc tggctctgag caccaaccag    360

ctgaagagca ttcccagggg cgcctttgac aacctcaaga gcctcactca catctttctg    420

tacaacaacc catgggattg cgagtgcagg gacattatgt acctcaggaa ctgggtcgca    480

gacacacctt ctattgtaat gcgctgggat gggaaggccg ttaacgaccc cgactctgcc    540

aagtgcgctg gtaccaatac ccccgtccgt                                     570
```

```
<210> SEQ ID NO 236
<211> LENGTH: 489
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 236

ggcgccctgg tgcaaagtgc ggtagcatgt ccctcgcagt gttcgtgcga tcagacaact     60

gtgaaatgcc atagcagacg cctcacgtct gtgcctgcgg gaatccccac caccacgcga    120

gtgctgtatt tgaacgacaa tcagatcacg aagctcgaac ccggggtgtt tgaccgcctg    180

gtgaatctgc agcagctgta tctgggggca aaccagctgt cggctctacc cgatggggtg    240

tttaataaac taacccagct cactcatctg agtctgtaca ataaccagct gaagaacatt    300

cccaggggcg cctttgataa cctgaagagc ctcacttaca tctatctgtt caacaacccc    360

tgggactgcg agtgttcgga catcctctat ctgaagaact ggattgtgca gcacgcaagc    420

atcgtgaatc catcgggcca tgggggagtt gataacgtga agtgctctgg taccaatacc    480

cccgtccgt                                                            489
```

```
<210> SEQ ID NO 237
<211> LENGTH: 417
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 237

ggcgccctgg tgcaaagtgc ggtagcatgt ccctcgcagt gttcgtgctc agggacatct     60

gtggattgca acagcagaag acacgcgtct gtgcctgcgg gaatccccac caccacgcga    120

gtgctgtatt tgaacgacaa tcagatcacg aagctcgagc ccggggtgtt tgacagtctg    180

gtgaatctgc agcagttggc tctgaacaac aaccagctga agggcgttcc caggggcgcc    240

tttgacaacc tcaagagcct cactcacatc tggctgttga acaacccctg ggactgcgag    300

tgttcggaca tcctctatct gaagaactgg attgtccagc acgcaagcat cgtgaattta    360

tggaacaatg gggagttga taacgtgaag tgctctggta ccaatacccc cgtccgt       417
```

```
<210> SEQ ID NO 238
<211> LENGTH: 489
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 238

ggcgccctgg tgcaaagtgc ggtagcatgt ccctcgcagt gttcgtgcga tcagacaact     60
```

-continued

```
gtatactgcc atagcagacg cctcacgtct gtgcctgcgg gaatccctac caccacgcaa    120

gtgctgtatt tgtacagcaa tcaaatcacg aagctcgagc ccggagtgtt tgaccgcctg    180

gggaatctgc agcagctgta tctgggaggt aaccagctgt cggctctccc cactggagtg    240

tttgacaaac tgacccagct cactcttcta gaactgcaaa acaaccagtt gacgagcatt    300

cccaggggcg cctttgacaa cctcaagagc ctcactcaca tctatctgtt caacaacccc    360

tgggactgcg agtgttcgga catcctctat ctgaagaact ggattgtgca gcacgcaagc    420

atcgtgaatc cattgggcaa tgggggagtt gataacgtga agtgctctgg taccaatacc    480

cccgtccgt                                                            489
```

<210> SEQ ID NO 239
<211> LENGTH: 402
<212> TYPE: DNA
<213> ORGANISM: Artificial Sequence
<220> FEATURE:
<223> OTHER INFORMATION: Description of Artificial Sequence; note = synthetic construct

<400> SEQUENCE: 239

```
ggcgccctgg tgcaaagtgc ggtagcatgt ccctcgcagt gttcgtgctc agggacagaa     60

gttaactgcc atgagagaag actcgcgtct gtgcctgcgg gaattcccac caccacgcaa    120

gtgctgggtt tgtccagcaa tcagatcacg aagctcgagc ccggggtgtt tgacagtctg    180

acccagctca cttatctgga tctgaacaac aaccagctga agagcattcc caggggcgcc    240

tttgacaacc tcaagagcct cactcacatc tggctgtacg gcaacccctg ggactgcgcc    300

tgctcagaca tcctatacct gagccactgg gcaaatgggc acgcagacat agtgcagaga    360

atgtcactta ctacgtgctc tggtaccaat acccccgtcc gt                       402
```

<210> SEQ ID NO 240
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 240

```
ggcgccctgg tgcaaagtgc ggtagcatgt ccctcgcagt gttcgtgctc agggacacaa     60

gtgaactgcc atgagagaag cctcgcgtct gtgcctgcgg gaatccccac caccacgcaa    120

gtgctgtatt tgtacaccaa tcagatcacg aagctcgagc ccggggtgtt tgacagcctg    180

gcgaatttga gggagcttca tctgtggggg aaccagctgg tgtctcttcc ccctggagtg    240

tttgacaaac tgacccagct cactcaactg ggtctgtggg acaaccagct gaagagcatt    300

cccaggggcg cctttgacaa cctcaagagc ctcactcaca tctggctgtt cggcaacccc    360

tgggactgcg agtgttcgga catcctctat ctgaagaact ggattgtgca gcacgcaagc    420

atcgtgaatc catcgggcta tgggggagtt gataacgtga agtgctctgg taccaatacc    480

cccgtccgt                                                            489
```

<210> SEQ ID NO 241
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 241
ggcgccctgg tgcaaagtgc ggcagcatgt ccctcgcagt gttcgtgctc aaggacaact 60
gtggactgca atagcagaag cctcgcgtct gtgcctgcgg caatccctat caccacgcaa 120
aggctgtggt tgagcaacaa tcagttaact aagctcgacc ccggagtgtt tgacagcctg 180
acgcaactga cttatctgaa ccttgctgtt aaccagctga cggctcttcc cgttggggtg 240
tttgaccgcc tggtgaatct gcagaagctg tggttgaaca gcaaccagct gtcggctcta 300
cccgttgggg tgtttgacaa actgacccag ctcacttatc tgggtctgta cgtcaatcaa 360
ctgaagagca ttcccagggg cgtttttgac aacctcaaga gcctcactca catctggctg 420
tacgacaacc cctgggactg cgagtgttcg gacatcctct atctgaagaa ctggattgtg 480
cagcacgcaa gcatcgtgaa tctagagggc catgggggag ttgataacgt gaagtgctct 540
ggtaccaata cccccgtccg t 561

<210> SEQ ID NO 242
<211> LENGTH: 570
<212> TYPE: DNA
<213> ORGANISM: Artificial Sequence
<220> FEATURE:
<223> OTHER INFORMATION: Description of Artificial Sequence; note = synthetic construct

<400> SEQUENCE: 242
ggcgccctgg tgcaaagtgc ggtagcatgt ccctcgcagt gttcgtgcga tcagacaact 60
gtggactgcc ggaacaaacg cttctcgtct gtgcctgcgg gaatccccac cgacaggcag 120
aacctgtggt tgaataacaa tcagatcacg aagctcgagc ccggggtgtt tgacagtctg 180
gctcagctga caggactaga tttaagccac aaccagttca cagctctccc cgctcaggtg 240
tttgaccgcc tggtgaagct gaaggagctg tctttaaaca gcaacaagct aacagctata 300
cccgctgggg tgtttgacaa actaacccag ctaaagcagt tgagtctgct gcagaatcaa 360
ctgaagagca ttcccagggg cgcctttgac aacctcaaga gcctcactca catctggctg 420
tacaacaacc cctgggactg tgcctgctca gacatcctgt acctcagccg ctggatctct 480
cagcacccag gggtggtgag gaaggatgaa gcaggctacc ctgtggaccc cgactcagcg 540
cgctgctctg gtaccaatac ccccgtccgt 570

<210> SEQ ID NO 243
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 243
ggcgccctgg tgcaaagtgc ggtagcatgt ccctcgcagt gttcgtgcga tcagacaact 60
gtatactgcc atagcagacg cctcacgtct gtgcctgcgg gaatccccac cgacaggcag 120
aacctgtggt tgtatgacaa tcagatcacg aagctcgagc ccggggtgtt tgacagactg 180
actcaactaa ctatcttgag tctgtacgac aaccaactct cggctctgcc cgccggggtg 240
tttgaccgcc tggtgaatct gcagcagctg tatctgggag gtaaccagct gggggctcta 300
cccgttgggg tgtttgacaa cctgacccag cttagcatac tgaatatgca caccaaccag 360
ctgaagagta ttcccagggg cgcctttgac aacctcaaga gcctcactca catctggctg 420
ttgaacaacc cctgggactg cgagtgttcg gacatcctct atctgaagaa ctggattgtg 480
cagcacgcaa gcatcgtgaa tccatcgggc catgggggag ttgataacgt gaagtgctcc 540
ggtaccaata cccccgtccg t 561

<210> SEQ ID NO 244
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 244
ggcgccctgg tgcaaagtgc ggtagcatgt ccctcgcagt gttcctgctc agggacaact 60
gtggattgcc ggagcaaacg ccacgcatct gtgcctgcgg gaatccccac caatgcgcag 120
attctgtatt tacacgacaa tcagatcacg aagctcgagc ccggggtgtt taacagtctg 180
gcgaatctga gggaactgca tctgtggggg aaccagctgg tgtctcttcc ccctggggtg 240
tttgaccgct tggttaatct gcagacgctg gatttgcaca acaaccagct gtcggctcta 300
cccgttgggg tgtttgacaa cctgacccag cttagcatac tgaatatgca caccaaccag 360
ctgaagagta ttcccagggg cgcctttgac aacctcaaga gcctcactca catctggctg 420
tccaacaacc cctgggactg cgagtgttcg gacatcctct atctgaagaa ctggattgtg 480
cagcacgcaa gcatcgtgaa tccatcgggc tatgggggag ttgataacgt gaagtgctct 540
ggtaccaata cccccgtccg t 561

<210> SEQ ID NO 245
<211> LENGTH: 561
<212> TYPE: DNA
<213> ORGANISM: Artificial Sequence
<220> FEATURE:
<223> OTHER INFORMATION: Description of Artificial Sequence; note = synthetic construct

<400> SEQUENCE: 245
ggcgccctgg tgcaaagtgc ggtagcatgt ccctcgcagt gttcgtgctc agggacaact 60
gtggattgcc ggagcaaacg ccacgcatct gtgcctgcgg gaatccccac caatgcgcag 120
attctgtatt tacacgacaa tcagatcacg aagctcgagc ccggggtgtt tgacagtctg 180
acgccactga cttttctgaa ccttggtaac aaccagctga cggctctacc cgagggggtg 240
ttagacttct tgactcaact gacttccttg actctgcaca ccaaccagct gcaggctctt 300
cccgctgggt tgtttgaccg cctggtgaat ctgcagaagc tgtatttgca tgagaaccag 360
ctgaagagca ttcccagggg cgcctttgac aacctcaaga gcctcactca catctggctg 420
tccaacaacc cctgggactg cgagtgttcg gacatcctct atctgaagaa ctggattgtg 480
cagcacgcaa gcatcgtgaa tctagagggc catgggggag ttgataacgt gaagtgctct 540
ggtaccaata cccccgtccg t 561

<210> SEQ ID NO 246
<211> LENGTH: 489
<212> TYPE: DNA
<213> ORGANISM: Artificial Sequence
<220> FEATURE:
<223> OTHER INFORMATION: Description of Artificial Sequence; note = synthetic construct

<400> SEQUENCE: 246
ggcgccctgg tgcaaagtgc ggtagcatgt ccctcgcagt gttcctgctc agggacaact 60
gtggattgcc ggagcaaacg ccacgcatct gtgcctgcgg gaatccccac caatgcgcag 120
attctgtatt tacacgacaa tcagatcacg aagctcgagc ccggggtgtt tgacagtctg 180
acgcaactga ctgaactgta ccttagtgcc aaccagctgc aggctcttcc cgagggggtg 240
tttgaccgcc tggtgaatct gcagcggctg tggttgaaca acaaccagct gaagagcatt 300
cccaggggcg cctttgacaa cctcaagagc ctcactcaca tctggctgtt cggcaacccc 360
tgggactgcg agtgttcgga cattctctat ctgaagaact ggattgtgca gcacgcaagc 420
atcgtgaatc cacaccccca tgggggagtt gataacgtga agtgctctgg taccaatacc 480
cccgtccgt 489

<210> SEQ ID NO 247
<211> LENGTH: 501
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 247
ggcgccctgg tgcaaagtgc ggtagcatgt ccctcgcagt gttcgtgctc agggacagaa 60
gtgcactgtg cagggaaaag cctcgcgtct gtgcctgcgg gaatccctat caccacgcaa 120
aggctgtggt tgagcaacaa tcagttaact aagctcgacc ccggagtgtt tgacagcctg 180
gtgaatctgc agaagctgtg gttgaacagc aaccagctga cctctctccc cgctggggtg 240
tttaaccgtc tgactcaact gacgacactg gagctgcaga tcaaccagct gaagagcatt 300
cccaggggcg cctttgataa cctcaagagc ctcactcaca tctggctgta caacaacccc 360
tgggactgcg cctgttcaga catcctgtac ctcagccgct ggatctctca gcacccagga 420
atcgtgagat cagcagatga tggttggaac agagtgaacc ccgactcagc gcgctgctct 480
ggtaccaata cccccgtccg t 501

<210> SEQ ID NO 248
<211> LENGTH: 489
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 248
ggcgccctgg tgcaaagtgc ggtagcatgt ccctcgcagt gttcgtgctc agggacacaa 60
gtgaactgcc atgagagaag cctcgcgtct gtgcctgcgg caatccctat caccacgcaa 120
aggctgtggt tgagcaacaa tcagttaact aagctcgacc ccggagtgtt tgacagcctg 180
gtgaatctgc agcgcctgca tctggatcaa aaccagctgg tgtctctccc cgcaggggtg 240
tttgacaaac tcacccagct cactcgtctg gctctgagca ccaaccagct gaagagcgtt 300
cccaggggcg cctttgacaa cctcaagagc ctcactcaca tctttctgta caacaacccc 360
tgggactgcg cctgcacgta catcttgtat ctcagcacgt ggatcggtca gaattcgggt 420
aaagtaacta aggaaagtgt aaacaaccca gatagcgccg tgtgctctgg taccaatacc 480
cccgtccgt 489

<210> SEQ ID NO 249
<211> LENGTH: 1006
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 249
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacagaagt gcactgtgat agcagaagcc tcgcgtctgt gcctgcgaga atccccacca 180
ccacgcaaag gctgtggttg aacaacaatc agatcacgaa gctcgagcct ggggtgtttg 240
atcgcctggg gaatctgcag aagctgtggt tgaacagcaa ccagctgacc tctctccccg 300
ctggggtgtt tgacaaactc atccagctcg taacactgga tctgaatgga aaccaactgt 360
catccgttcc cgcagacgtg ttccatcagc ttgtgaaatt agagaagctg tggctcaaaa 420
acaacaaact gacgactctt cccgctgggt tgtttgacga actgacccag gtttattctc 480
tgagtctgaa cgacaaccag ttgaagagca tcccgcatgg agcgttcgac cgtctcagct 540
ccctcaccca cgcctattta tttggcaacc catgggattg cgagtgcagg gacattatgt 600
acctcaggaa ctgggtcgca gaccacactt ctattgtaat gcgctgggat gggaaggccg 660
ttaacgaccc cgactctgcc aagtgcgctg gtaccaatac ccccgtccgt gcggtcaccg 720
aggccagcac tagtccctcg aaatgcccag gctacgttgc tacgaccacg acgccgacga 780
cgaccacgcc cgaattcatc cctgagacca ccacctcgcc gcagcccgtg atcacaaccc 840
agaaacccaa gcctctgtgg aatttcaact gcacctcaat tcaggagagg aagaacgacg 900
gtggcgactg cggaaagccc gcctgcacaa ctctcctgaa ctgcgcgaat ttcctcagct 960
gcctctgctc gacctgcgcc ctctgcagga aacgttgatc ggcgtg 1006

<210> SEQ ID NO 250
<211> LENGTH: 832
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 250
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacaactgt ggattgccgg agcaaacgcc acgcatctgt gcctgcggga atccctacca 180
ccacgcaagt gctgtatttg tacagcaatc aaatcacgaa gctcgagacc ggggtgtttg 240
acggtctgac gcaactgact tatctgaacc ttggcggcaa ccagctgacg gctcttcccg 300
ttggggtgtt tgacaaactg accaaactca ctcatctgta tctgggatat aaccagctga 360
agagcattcc caggggcgcc tttgataacc tcaagagcct cactcacatc tggctgtaca 420
acaacccctg ggactgtgct tgctcagaca tcctctacct cagcggctgg ctgggccagc 480
acgcagggaa agagcagggc caggctgtct gctctggtac caatacccccc gtccgtgcgg 540 tcaccgaggc cagcactagc ccctcgaaat gcccaggcta cgttgctacg accacgacgc 600
cgacgacgac cacgcccgaa ttcatccctg agaccaccac ctcgccgcag cccgtgatca 660
caacccagaa acccaagcct ctgtggaatt tcaactgcac ctcaattcag gagaggaaga 720
acgacggtgg cgactgcgga aagcccgcct gcacaactct cctgaactgc gcgaatttcc 780
tcagctgcct ctgctcgacc tgcgccctct gcaggaaacg ttgatcggcg tg 832

<210> SEQ ID NO 251
<211> LENGTH: 779
<212> TYPE: DNA

<213> ORGANISM: Artificial Sequence
<220> FEATURE:
<223> OTHER INFORMATION: Description of Artificial Sequence; note = synthetic construct

<400> SEQUENCE: 251
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacaactgt gaactgtgat agcagaagcc tcgcgtctgt gcctggagga atccccaccg 180
acaagcagag gctgtggttg aacaacaatc agatcacgaa gcttgagccc ggggtgtttg 240
acagtctggt gaatctgcag tggttcagtt tgtccagcaa ttggctgaga gcgttcgcag 300
gggcgcgttc acagactcaa gagcctcact cacatctggc tgtacggcaa cccctgggac 360
tgcgagtgtt cggacatcct ctatctgaag aactggattg tccagcacgc aagcatcgtg 420
aatttatgga acaatggggg agttgataac gtgaagtgcg ctggtaccaa tacccccgtc 480
cgtgcggtca ccgaggccag cactagtccc tcgaaatgcc caggctacgt tgctacgacc 540
acgacgccga cgacgaccac gcccgaattc atccctgaga ccaccacctc gccgcagccc 600
gtgatcacaa cccagaaacc caagcctctg tggaatttca actgcacctc aattcaggag 660
aggaagaacg acggtggcga ctgcggaaag cccgcctgca caactctcct gaactgcgcg 720
aatttcctca gctgcctctg ctcgacctgc gccctctgca ggaaacgttg atcggcgtg 779

<210> SEQ ID NO 252
<211> LENGTH: 928
<212> TYPE: DNA
<213> ORGANISM: Artificial Sequence
<220> FEATURE:
<223> OTHER INFORMATION: Description of Artificial Sequence; note = synthetic construct

<400> SEQUENCE: 252
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacacaagt gaactgccat gagagaagcc tcgcgtctgt gcctgcggaa atccccacaa 180
acaggcagat tctgttttta agcagcaatc agatcaagaa gctcgagcct ggggtgtttg 240
acagcctggt gaaactgaag gagctgtatc tggaccataa ccaactgcag gcgataccgc 300
ccgctctgtt ttacagtttg actgaactca cgcgactgga actggaagat aaccaactga 360
agtctctgcc gccaggcatc tttgacagac tggggaagct gatgtatttg cacctgcacg 420
agaaccagct gaagagcatt cccaggggcg cctttgacaa cctcaagagc ctaactcaca 480
tctatctgta caacaacccc tgggactgtc aatgcacgga catcctctac ttgagtggct 540
gggtcgctca gcactcgggc atcgtgggtg agggttggtg gaccgtgaaa ccagacaacg 600
tcaagtgcgc tggtaccaat acccccgtcc gtgcggtcac cgaggccagc actagcccct 660
cgaaatgccc aggctacgtt gctacgacca cgacgccgac gacgaccacg cccgaattca 720
tccctgagac caccacctcg ccgcagcccg tgatcacaac ccagaaaccc aagcctctgt 780
ggaatttcaa ctgcacctca attcaggaga ggaagaacga cggtggcgac tgcggaaagc 840
ccgcctgcac aactctcctg aactgcgcga atttcctcag ctgcctctgc tcgacctgcg 900
ccctctgcag gaaacgttga tcggcgtg 928

<210> SEQ ID NO 253
<211> LENGTH: 910
<212> TYPE: DNA

<213> ORGANISM: Artificial Sequence
<220> FEATURE:
<223> OTHER INFORMATION: Description of Artificial Sequence; note =
synthetic construct

<400> SEQUENCE: 253
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacaactgt gaactgtgat agcagaagcc tcgcgtctgt gcctggagga atccccacca 180
ccacgcaagt gctgtatttg tacgacaatc agatcacgaa gttcgagccc ggcgtgtttg 240
acagtctgac ggcactgact gttctgaatc tcgcaataaa ccagctgacg gctctacccg 300
tctggctgct tcaccgcctg gagaatctga agcagctgta tctgggctcg aaccagctgg 360
gggctctacc cgttggggtg tttgacaaac taacccagct aaagcagttg agtctgctgc 420
agaatcagct gaagagcatt cccaggggcg tttttgacaa cctcaagagc ctcactcaca 480
tctatctgtt caacaacccc tgggactgcg cctgctcaga catcctatac ctgagccact 540
gggcaaatgg gcacgcagac atagtgcaga gaatgtcact tactacgtgc tctggtacca 600
atacccccgt ccgtgcggtc accgaggcca gcactagccc ctcgaaatgc ccaggctacg 660
ttgctacgac cacgacgccg acgacgacca cgcccgaatt catccctgag accaccacct 720
cgccgcagcc cgtgatcaca acccagaaac ccaagcctct gtggaatttc aactgcacct 780
caattcagga gaggaagaac gacggtggcg actgcggaaa gcccgcctgc acaactctcc 840
tgaactgcgc gaatttcctc agctgcctct gctcgacctg cgccctctgc aggaaacgtt 900
gatcggcgtg 910

<210> SEQ ID NO 254
<211> LENGTH: 832
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 254
ctccgctact cggcctgcag gagccaacca tcatgtggat caagtggatc gccacgctgg 60
tcgcctttgg gcccctggtg caaagtgcgg tagcatgtcc ctcgcagtgt tcgtgttcag 120
ggacagaagt gcgctgtgag agcagaagcc tcgcgtctgt gcctgcggga atccccacca 180
ccacgcgaag gttgcatttg cacagaaatc aactcacgaa gctcgagccc ggggtgtttg 240
acagtctggc ggcactgact atcttggatc tacgtaccaa ccagctgcag gctcttcccg 300
ctgggttgtt tgacgaactg acccaggttt attctctgag tctgaacgac aaccagttga 360
agagcattcc caggggcgcc tttgataacc tcaagagcct cacttacatc tggctggaca 420
gaaacccctg ggactgtgct tgctcagaca tcctctacct cagcggctgg ctgggccagc 480
acgcagggaa agagcagggc caggctgtct gctctggtac caataccccc gtccgtgcgg 540
tcaccgaggc cagcactagc ccctcgaaat gcccaggcta cgttgctacg accacgacgc 600
cgacgacgac cacgcccgaa ttcatccctg agaccaccac ctcgccgcag cccgtgatca 660
caacccagaa acccaagcct ctgtggaatt tcaactgcac ctcaattcag gagaggaaga 720
acgacggtgg cgactgcgga aagcccgcct gcacaactct cctaaactgc gcgaatttcc 780
tcagctgcct ctgctcgacc tgcgccctct gcaggaaacg ttgatcggcg tg 832

<210> SEQ ID NO 255

<211> LENGTH: 862
<212> TYPE: DNA
<213> ORGANISM: Artificial Sequence
<220> FEATURE:
<223> OTHER INFORMATION: Description of Artificial Sequence; note = synthetic construct

<400> SEQUENCE: 255

```
ctccgctact cggcctgcag gagccaacca tcatgtggat caagtggatc gccacgctgg     60

tcgcctttgg cgccctggtg caaagtgcgg tagcatgtcc ctcgcagtgt tcgtgcgatc    120

agacacttgt gaactgccag aatatacgcc tcgcatctgt gcctgcggga atccccaccg    180

acaagcagag gctgtggttg aacaacaatc agatcacgaa gcttgagccc ggggtgtttg    240

accatctggt gaatctgcag cagctctatt ttaacagcaa caagctaaca gctataccca    300

ctggggtgtt tgacaaactc acccagctca ctcaactgga tttgaatgac aaccatctga    360

agagcattcc caggggcgcc tttgacaacc tcaagagcct aactcacatc tatctgtaca    420

acaacccatg ggattgcgag tgcagggaca ttatgtacct caggaactgg gtcgcagacc    480

acacttctat tgtaatgcgc tgggatggga aggccgttaa cgaccccgac tctgccaagt    540

gcgctggtac caataccccc gtccgtgcgg tcaccgaggc cagcactagc ccctcgaaat    600

gcccaggcta cgttgctacg accacgacgc cgacgacgac tacgcccgaa ttcatccctg    660

agaccaccac ctcgccgcag cccgtgatca caacccagaa acccaagcct ctgtggaatt    720

tcaactgcac ctcaattcag gagaggaaga acgacggtgg cgactgcgga aagcccgcct    780

gcacaactct cctgaactgc gcgaatttcc tcagctgcct ctgctcgacc tgcgccctct    840

gcaggaaacg ttgatcggcg tg                                             862
```

<210> SEQ ID NO 256
<211> LENGTH: 862
<212> TYPE: DNA
<213> ORGANISM: Artificial Sequence
<220> FEATURE:
<223> OTHER INFORMATION: Description of Artificial Sequence; note = synthetic construct

<400> SEQUENCE: 256

```
ctccgctact cggcctgcag gagccaacca tcatgtggat caagtggatc gccacgctgg     60

tcgcctttgg cgccctggtg caaagtgcgg tagcatgtcc ctcgcagtgt tcgtgctcag    120

ggacaactgt ggattgtagt gggaaaagcc tcgcatctgt gcctgcagga atccccatca    180

ccacgcagtc tctgtctttg cactatactc agatcacgaa gctcgagccc ggggtgtttg    240

acagtctggt gaatctgcag cagctgtatc tgggaggtaa ccagctgtcg gctctacccg    300

atggggtgtt tgacaaactg acccagctca ctcacatagt gctgagcacc aaccagctca    360

ggagcgttcc caggggcgcc ttcgacaacc tcaagagcct cactcacatc tggctgttcg    420

acaaccccctg ggactgtgcc tgctcagaca tcctgtacct cagccgctgg atctctcagc    480

accctggagt cgtgaggaag aatgaagcag gctaccctgt ggaccccgac tcagcgcgct    540

gctctggtac caataccccc gtccgtgcgg tcaccgaggc cagcactagc ccctcgaaat    600

gcccaggcta cgttgctacg accacgacgc cgacgacgac cacgcccgaa ttcatccctg    660

agaccaccac ctcgccgcag cccgtgatca caacccagaa acccaagcct ctgtggaatt    720

tcaactgcac ctcaattcag gagaggaaga acgacggtgg cgactgcgga aagcccgcct    780

gcacaactct cctgaactgc gcgaatttcc tcagctgcct ctgctcgacc tgcgccctct    840

gcaggaaacg ttgatcggcg tg                                             862
```

<210> SEQ ID NO 257
<211> LENGTH: 791
<212> TYPE: DNA
<213> ORGANISM: Artificial Sequence
<220> FEATURE:
<223> OTHER INFORMATION: Description of Artificial Sequence; note = synthetic construct

<400> SEQUENCE: 257
ctccgctact cggcctgcag gagccaacca tcatgtggat caagtggatc gccacgctgg 60
tcgcctttgg cgccctggtg caaaatgcgg tagcatgtcc ctcgcagtgt tcgtgctcag 120
ggacacaagt gaactgtgaa ggttaaacgc ctcgcgtctg tgcctgcggc aatccctatc 180
accacgcaga gcttggggtt ttacaacaat cagataacga agctcgagcc tggggtgttt 240
gacagtctga ccaaactcac tcatctggat ctgcacatca atcaactgaa gagcgtgccc 300
tggggcgcct ttgacaacct caagagcctc acccacgcct atttatttgg caacccatgg 360
gattgcgagt gcagggacat tatgtacctc aggaactggg tcgcagacca cacttctatt 420
gtaatgcgcg gggatgggaa ggccgttaac gaccccgact ctgccaagtg cgctggtacc 480 aataccccccg tccgtgcggt caccgaggcc aacactagcc cctcgaaatg cccaggctac 540
gttgctacga ccacgacgcc gacgacgacc acgcccgaat tcatccctga gaccaccacc 600
tcgccgcagc ccgtgatcac aacccagaaa cccaagcctc tgtggaattt caactgcacc 660
tcaattcagg agaggaagaa cgacggtggc gactgcggaa agcccgcctg cacaactctc 720
ctgaactgcg cgaatttcct cagctgcctc tactcgacct gcgccctctg caggaaacgt 780
tgatcggcgt g 791

<210> SEQ ID NO 258
<211> LENGTH: 856
<212> TYPE: DNA
<213> ORGANISM: Artificial Sequence
<220> FEATURE:
<223> OTHER INFORMATION: Description of Artificial Sequence; note = synthetic construct

<400> SEQUENCE: 258
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacacaagt gaactgccat gagagaagcc tcgcgtctgt gcctgcggga atccccacca 180
ccacgcaagt gctgtatttg tacaccaatc agatcacgaa gctcgagccc ggggtgtttg 240
acagactgac ggcactggag gagctgtatc tggaccataa ccaactgcag gcgctacccg 300
ccagggtgtt tgacaaactg acccagctca tttatctggt tctggacacc aaccagttga 360
agagcattcc caggggcgcc tttgacaacc tcaagagcct cacccacgtg tggctccaca 420
ccaacccctg ggactgtcaa tgcacggaca tcctctactt gagtggctgg gtcgctcagc 480
actcgggcat cgtgggtgag ggttggtgga ccgtgaaacc agacaacgtg aagtgctctg 540
gtaccaatac ccccgtccgt gcggtcaccg aggccagcac tagcccctcg aaatgcccag 600
gctacgttgc tacgaccacg acgccgacga cgaccacgcc cgaattcatc cctgagacca 660
ccacctcacc gcagcccgtg atcacaaccc agaaacccaa gcctctgtgg aatttcaact 720
gcacctcaat tcaggagagg aagaacgacg gtggcgactg cggaaagccc gcctgcacaa 780
ctctcctgaa ctgcgcgaat ttcctcagct gcctctgctc gacctgcgcc ctctgcagga 840
aacgttgatc ggcgtg 856

<210> SEQ ID NO 259
<211> LENGTH: 832
<212> TYPE: DNA
<213> ORGANISM: Artificial Sequence
<220> FEATURE:
<223> OTHER INFORMATION: Description of Artificial Sequence; note = synthetic construct

<400> SEQUENCE: 259
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacaactgt ggattgtagt gggaaaagcc tcgcatctgt gcctgcggca atccctatca 180
ccacgcaaag gctgtggttg agcaacaatc agttaactaa gctcgacccc ggagtgtttg 240
acagcctggt gaatctgcag cagctgtatc tgggaggtaa ccagctgtcg gctctacccg 300
atggggtgtt tgacaaactg acccagctca ctaatctgta tctgcacaac aaccagctga 360
aaagcgttcc caggggcgcc tttgacaacc tcaagagcct cactcacatc tggctgtaca 420
acaacccctg ggactgtgct tgctcagaca tcctctacct cagcggctgg ctgggccagc 480
acgcagggaa agagcagggc caggctgtct gctctggtac caataccccc gtccgtgcgg 540
tcaccgaggc cagcactagc ccctcgaaat gcccaggcta cgttgctacg accacgacgc 600
cgacgacgac cacgcccgaa ttcatccctg agaccaccac ctcgccgcag cccgtgatca 660
caacccagaa acccaagcct ctgtggaatt tcaactgcac ctcaattcag gagaggaaga 720
acgacggtgg cgactgcgga aagcccgcct gcacaactct cctgaactgc gcgaatttcc 780
tcagctgcct ctgctcgacc tgcgccctct gcaggaaacg ttgatcggcg tg 832

<210> SEQ ID NO 260
<211> LENGTH: 850
<212> TYPE: DNA
<213> ORGANISM: Artificial Sequence
<220> FEATURE:
<223> OTHER INFORMATION: Description of Artificial Sequence; note = synthetic construct

<400> SEQUENCE: 260
ctccgctact cggcctgcag gagccaacca tcatgtggat caagtggatc gccacgctgg 60
tcgcctttgg cgccctggtg caaagtgcgg tagcatgtcc ctcgcagtgt tcgtgctacg 120
tgggtcctgt gaataggctc cattattttg actgttacac taaagaactg agttcagttc 180
ctgctgcgat ccctgtcaat acccagatcc tgcaattgca aaacaatcgg atacagagtc 240
tcccagtggg ggtgtttgac cgcttggtga atctacagaa gctgtatctg gggaaaaacc 300
aactgtcggc tctccccgct ggggtgtttg accgcttggt taatctgcag acgctggatt 360
tgcacaacaa ccagctgaag agcattccta ggggcgcctt tgacaacctc atgagcctca 420
ctaacatctg gctgtccagc aacccctggg actgtgcttg ctcagacatc ctctacctca 480
gcggctggct gggccagcac gcagggaaag agcagggcca ggctgtctgc tctggtacca 540
atacccccgt ccgtgcggtc accgaggcca gcactagccc ctcgaaatgc ccaggctacg 600
ttgctacgac cacgacgccg acgacgacca cgcccgaatt catccctgag accaccacct 660
cgccgcagcc cgtgatcaca acccagaaac ccaagcctct gtggaatttc aactgcacct 720
caattcagga gaggaagaac gacggtggcg actgcggaaa gcccgcctgc acaactctcc 780
taaactgcgc gaatttcctc agctgcctct gctcgacctg cgccctctgc aggaaacgtt 840
gatcggcgtg 850

<210> SEQ ID NO 261
<211> LENGTH: 865
<212> TYPE: DNA
<213> ORGANISM: Artificial Sequence
<220> FEATURE:
<223> OTHER INFORMATION: Description of Artificial Sequence; note = synthetic construct

<400> SEQUENCE: 261
ctccgctact cggcctgcag gagccaacca tcatgtggat caagtggatc gccacgctgg 60
tcgcctttgg cgccctggtg caaagtgcgg tagcatgtcc ctcgcagtgt tcgtgcgatc 120
agacaactgt ggactgccgg aacaaacgct tctcgtctgt gcctgcggga atccccaccg 180
acaggcagaa cctgtggttg aataacaatc agatcacgaa gctcgagccc ggggtgtttg 240
acagtctggc tcagctgaca cgactgggtc taagccacaa ccagttcaca gctcttcccg 300
ctcgggtgtt tgaccgcatg gggaatctgc agcagattaa tctgagcaac aaccagctga 360
agagcattcc caggggcgcc tttgacaacc tcaagagcct cactcacatc tggctgtacg 420
gcaacccctg ggactgtgcc tgttcagaca tcctgtacct cagccgctgg atctctcagc 480
acccaggagt cgtgaggacg gcagatgatg attggagcag agtggtcccc gactcagcgc 540
gctgctctgg taccaatacc cccgtccgtg cggtcaccga ggccagcact agcccctcga 600
aatgcccagg ctacgttgct acgaccacga cgccgacgac gaccacgccc gaattcatcc 660
ctgagaccac cacctcgccg cagcccgtga tcacaaccca gaaacccaag cctctgtggg 720
atttcaactg cacctcaatt caggagagga agaacgacgg tggcgactgc ggaaagcccg 780
cctgcacaac tctcctgaac tgcgcgaatt tcctcagctg cctctgctca acctgcgccc 840
tctgcaggaa acgttgatcg gcgtg 865

<210> SEQ ID NO 262
<211> LENGTH: 832
<212> TYPE: DNA
<213> ORGANISM: Artificial Sequence
<220> FEATURE:
<223> OTHER INFORMATION: Description of Artificial Sequence; note = synthetic construct

<400> SEQUENCE: 262
ctccgctact cggcctgcag gagccaacca tcatgtggat caagtggatc gccacgctgg 60
tcgcctttgg cgccctggtg caaagtgcgg tagcatgtcc ctcgcagtgt tcgtgctcag 120
ggacaactgt ggattgtagt gggaaaagcc tcgcatctgt gcctgcggca atccctatca 180
ccacgcaaag gctgtggttg agcaacaatc agttaactaa gctcgacccc ggagtgtttg 240
acagcctggt gaatctgcag cagctgtatc tgggaggtaa ccagctgtcg gctctacccg 300
atggggtgtt tgacaaactg acccagctca ctaatctgta tctgcacaac aaccagctga 360
aaagcgttcc caggggcgcc tttgacaacc tcaagagcct cactcacatc tggctgtaca 420
acaacccctg ggactgtgct tgctcagaca tcctctacct cagcggctgg ctgggccagc 480
acgcagggaa agagcagggc caggctgtct gctctggtac caatacccc gtccgtgcgg 540 tcaccgaggc cagcactagc ccctcgaaat gcccaggcta cgttgctacg accacgacgc 600
cgacgacgac cacgcccgaa ttcatccctg agaccaccac ctcgccgcag cccgtgatca 660
caacccagaa acccaagcct ctgtggaatt tcaactgcac ctcaattcag gagaggaaga 720
acgacggtgg cgactgcgga aagcccgcct gcacaactct cctgaactgc gcgaatttcc 780
tcagctgcct ctgctcgacc tgcgccctct gcaggaaacg ttgatcggcg tg 832

<210> SEQ ID NO 263
<211> LENGTH: 865
<212> TYPE: DNA
<213> ORGANISM: Artificial Sequence
<220> FEATURE:
<223> OTHER INFORMATION: Description of Artificial Sequence; note = synthetic construct

<400> SEQUENCE: 263
ctccgctact cggcctgcag gagccaacca tcatgtggat caagtggatc gccacgctgg 60
tcgcctttgg cgccctggtg caaagtgcgg tagcatgtcc ctcgcagtgt tcgtgcgatc 120
agacaactgt ggactgccgg aacaaacgct tctcgtctgt gcctgcggga atccccaccg 180
acaggcagaa cctgtggttg aataacaatc agatcacgaa gctcgagccc ggggtgtttg 240
acagtctggc tcagctgaca cgactgggtc taagccacaa ccagttcaca gctcttcccg 300
ctcgggtgtt tgaccgcatg gggaatctgc agcagattaa tctgagcaac aaccagctga 360
agagcattcc caggggcgcc tttgacaacc tcaagagcct cactcacatc tggctgtacg 420
gcaacccctg ggactgtgcc tgttcagaca tcctgtacct cagccgctgg atctctcagc 480
acccaggagt cgtgaggacg gcagatgatg attggagcag agtggtcccc gactcagcgc 540
gctgctctgg taccaatacc cccgtccgtg cggtcaccga ggccagcact agcccctcga 600
aatgcccagg ctacgttgct acgaccacga cgccgacgac gaccacgccc gaattcatcc 660
ctgagaccac cacctcgccg cagcccgtga tcacaaccca gaaacccaag cctctgtgga 720
atttcaactg cacctcaatt caggagagga agaacgacgg tggcgactgc ggaaagcccg 780
cctgcacaac tctcctgaac tgcgcgaatt tcctcagctg cctctgctca acctgcgccc 840
tctgcaggaa acgttgatcg gcgtg 865

<210> SEQ ID NO 264
<211> LENGTH: 862
<212> TYPE: DNA
<213> ORGANISM: Artificial Sequence
<220> FEATURE:
<223> OTHER INFORMATION: Description of Artificial Sequence; note = synthetic construct

<400> SEQUENCE: 264
ctccgctact cggcctgcag gagccaacca tcatgtggat caagtggatc gccacgctgg 60
tcgcctttgg cgccctggtg caaagtgcgg tagcatgtcc ctcgcagtgt tcgtgcgatc 120
agacacttgt gaactgccag aatatacgcc tcgcatctgt gcctgcggga atccccaccg 180
acaagcagag gctgtggttg aacaacaatc agatcacgaa gcttgagccc ggggtgtttg 240
accatctggt gaatctgcag cagctctatt ttaacagcaa caagctaaca gctataccca 300
ctggggtgtt tgacaaactc acccagccca ctcaactgga tttgaatgac aaccatctga 360
agagcattcc caggggcgcc tttgacaacc tcaagagcct aactcacatc tatctgtaca 420
acaacccatg ggattgcgag tgcagggaca ttatgtacct caggaactgg gtcgcagacc 480
acacttctat tgtaatgcgc tgggatggga aggccgttaa cgaccccgac tctgccaagt 540
gcgctggtac caataccccc gtccgtgcgg tcaccgaggc cagcactagc ccctcgaaat 600
gcccaggcta cgttgctacg accacgacgc cgacgacgac tacgcccgaa ttcatccctg 660
agaccaccac ctcgccgcag cccgtgatca caacccagaa acccaagcct ctgtggaatt 720
tcaactgcac ctcaattcag gagatgaaga acgacggtgg cgactgcgga aagcccgcct 780
gcacaactct cctgaactgc gcgaatttcc tcagctgcct ctgctcgacc tgcgccctct 840
gcaggaaacg ttgatcggcg tg 862

<210> SEQ ID NO 265
<211> LENGTH: 850
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 265
ctccgctact cggcctgcag gagccaacca tcatgtggat caagtggatc gccacgctgg 60
tcgcctttgg cgccctggtg caaagtgcgg tagcatgtcc ctcgcagtgt tcgtgcgatc 120
agacaactgt gaaatgccat agcagacgcc tcacgtctgt gcctgcggga atccccacaa 180
acaggcagaa cctgtggttg cacgacaatc agatcacgaa gctcgagccc ggggtgtttg 240
acagactgac tgaactgact atcttggatc tacgtaccaa ccagctgcag gctctaccca 300
ctttggtgtt tgacaacctg acccagctta gcatactgaa tatgcacacc aaccagctga 360
agagcattcc caggggcgcc tttgacaacc tcaagagcct cactcacatc tatctgttca 420
acaacccctg ggactgcgag tgttcggaca tcctctatct gaagaactgg attgtacagc 480
acgcaagcat cgtgaatcca ggcagcgggg gagttgataa cgtgaagtgc gctggtacca 540
atacccccgt ccgtgcggtc accgaggcca gcactagccc ctcgaaatgc ccaggctacg 600
ttgctacgac cacgacgccg acgacgacca cgcccgaatt catccctgag accaccacct 660
cgccgcagcc cgtgatcaca acccagaaac ccaagcctct gtggaatttc aactgcacct 720
caattcagga gaggaagaac gacggtggcg actgcggaaa gcccgcctgc acaactctcc 780
tgaactgcgc gaatttcctc agctgcctct gctcaacctg cgccctctgc aggaaacgtt 840
gatcggcgtg 850

<210> SEQ ID NO 266
<211> LENGTH: 850
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 266
ctccgctact cggcctgcag gagccaacca tcatgtggat caagtggatc gccacgctgg 60
tcgcctttgg cgccctggtg caaagtgcgg tagcatgtcc ctcgcagtgt tcgtgcgatc 120
agacaactgt gaaatgccat agcagacgcc tcacgtctgt gcctgcggga atccccacaa 180
acaggcagaa cctgtggttg cacgacaatc agatcacgaa gctcgagccc ggggtgtttg 240
acagactgac tgaactgact atcttggatc tacgtaccaa ccagctgcag gctctaccca 300
ctttggtgtt tgacaacctg acccagctta gcatactgaa tatgcacacc aaccagctga 360
agagcattcc caggggcgcc tttgacaacc tcaagagcct cactcacatc tatctgttca 420
acaacccctg ggactgcgag tgttcggaca tcctctatct gaagaactgg attgtacagc 480
acgcaagcat cgtgaatcca ggcagcgggg gagttgataa cgtgaagtgc gctggtacca 540
atacccccgt ccgtgcggtc accgaggcca gcactagccc ctcgaaatgc ccaggctacg 600
ttgctacgac cacgacgccg acgacgacca cgcccgaatt catccctgag accaccacct 660
cgccgcagcc cgtgatcaca acccagaaac ccaagcctct gtggaatttc aactgcacct 720
caattcagga gaggaagaac gacggtggcg actgcggaaa gcccgcctgc acaactctcc 780
tgaactgcgc gaatttcctc agctgcctct gctcaacctg cgccctctgc aggaaacgtt 840
gatcggcgtg 850

<210> SEQ ID NO 267
<211> LENGTH: 785
<212> TYPE: DNA
<213> ORGANISM: Artificial Sequence
<220> FEATURE:
<223> OTHER INFORMATION: Description of Artificial Sequence; note = synthetic construct

<400> SEQUENCE: 267
accagagcaa ctggcgctgt ctggactgtg cctccatggc cacccctcac ccacgatgct 60
cgagtgctga gcgacccagc cactcaagta gaggatgtcc gtgcactgac agtcccaggg 120
gttggtgtgg agccacacgt gggtgaggct cgggagacga gcgaacgcgc cgtcagggat 180
gctcttcagt tgattctggt taagactcaa ccgcctcaac tgagtgagtt tgtcaatgcc 240
acggggaagc tctgtgaact tgttgcagca catgtacagc tcctacagat tccccaggcg 300
gtcaaacacc ccaacaggaa gagcctgcag ctggttgcta tcaagagcca gacgagtcag 360
ctgggtgact ctgtcaaaca ccccggcggg gagagccgtc agctggttgt ttgagagata 420
cagagtagtc agttgcgtca gactgtcaaa cacgccgggc tcgagcttcg tgatctgatt 480
gacgtgcaaa tacagcactt gcgtggtggt ggggattcct gcaggcacag acgcgaggct 540
ttttttctga cagtgcactt ctgtccctga gcacgaacac tgcgagggac atgctaccgc 600
actttgtacc agggcgccaa aggcgaccag cgtggcgatc cacttgatcc acatgatggt 660
tggctcctgc aggccgagta gcggagagcg tgagagtgtt ggggagcgag agagcgagag 720
aggggacagt ggtggctgta gctggagctg ttgagagctg cagagccgag tcgctgtccc 780
cgcgt 785

<210> SEQ ID NO 268
<211> LENGTH: 710
<212> TYPE: DNA
<213> ORGANISM: Artificial Sequence
<220> FEATURE:
<223> OTHER INFORMATION: Description of Artificial Sequence; note = synthetic construct

<400> SEQUENCE: 268
accagagcac ttcacgttat caactccccc ataggggtgt ggattcacga tgcttgcgtg 60
ctgcacaatc cagttcttca gatagaggat gtccgaacac tcgcagtccc aggggttgtt 120
gaacagatag atgtgagtga ggctcttgag gttgtcaaag gcgcccctgg gaatgctctt 180
cagctggttg tctcgcagat tcagatgagt gagctgggtc agtttgtcaa acaccccaac 240
gggtagagcc gacaactggt ccgcatgcaa atacaactgc tgcagattca ccaggcggtc 300
aaacactccg tcgggaaggg cctgcagccg attgctctca agtccaatgt acgtgagctg 360
cgttagactg tcaaacacgc cgggctcgag cttcgtgatc tgattggtgt acaaatacag 420
cacttgcgtg gtggtgggga ttcccgtagg cacagatgcg aggcttttcc cactacaatc 480
cacagttgtc cctgagcacg aacactgcga gggacatgct accgcacttt gcaccagggc 540
gccaaaggcg accagcgtgg cgatccactt gatccacatg atggttggct cctgcagacc 600
gagtagcgga gagcgtgaga gtgttgggga gcgagagagc gagagagggg acagtggtgg 660
ctgtagctgg agctgttgag agctgcagag ccgagtcgct gtccccgcgt 710

<210> SEQ ID NO 269

<211> LENGTH: 713
<212> TYPE: DNA
<213> ORGANISM: Artificial Sequence
<220> FEATURE:
<223> OTHER INFORMATION: Description of Artificial Sequence; note = synthetic construct

<400> SEQUENCE: 269
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgcgatca gacaactgta tactgccata 240
gcagacgcct cacgtctgtg cctgcgggaa tccccaccga caggcagaac ctgtggttgt 300
acgacaatca gatcacgaag ctcgagcccg gggtgtttga cagactgaca gagcttactt 360
atttgaacct caataccaac cagctaacgg ctctaccgga gggggtgttt gagcggctgg 420
ggaatctgca ggagctgtac atgtgctgca acaagttcac agagcttccc cgtggcattg 480
acaaactcac ccggctgaag cagttgggtc tggaccagaa tcaactgaag agcatccctg 540
acggcgcgtt cgctcgtctc ccgagcctca cccacgtgtg gctccacacc aacccctggg 600
actgtcaatg cacggacatc ctctacttga gtggttgggt cgctcagcac tcgggcatcg 660
tgggtgaggg gtggccatgg aggcacagtc cagacagcgt caagtgctct ggt 713

<210> SEQ ID NO 270
<211> LENGTH: 418
<212> TYPE: DNA
<213> ORGANISM: Artificial Sequence
<220> FEATURE:
<223> OTHER INFORMATION: Description of Artificial Sequence; note = synthetic construct

<400> SEQUENCE: 270
acaatccagt tcttcagata gaggatgtcc gaacactcgc agtcccaggg gttgttcaac 60
agccagatgt gagtgaggct cttgaggttg tcaaaggcgc ccctgggaat gctcttcaac 120
tggttgtcgt tcaggcacag agaataaacc tgggtcagtt cgtcaaacaa cccagcggga 180
agagccgtca gtttgttgtt tttgagccac agcttctcta atttcacaag ctgatggaac 240
acgtctgcgg gaacggatga cagttggttt ccattcagat ccagtgttac gagctgggtg 300
agtttgtcaa acaccccagg gggaagagac accagctggt tcccccacag atgaagctcc 360
ctcaaattcg ccagactgtc aaacaccccg agctcgagct tcgtgatctg attgtcgt 418

<210> SEQ ID NO 271
<211> LENGTH: 641
<212> TYPE: DNA
<213> ORGANISM: Artificial Sequence
<220> FEATURE:
<223> OTHER INFORMATION: Description of Artificial Sequence; note = synthetic construct

<400> SEQUENCE: 271
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgcgatca gacaactgta tactgccata 240
gcagacgcct cacgtctgtg cctggaggaa tccccaccac cacgcgaggg ctgcatttgc 300
acaccaatca gatcacgaag ctcgagcccg gggtgtttga cagtctgacg gcactaactt 360
atttgggtct tggtggcaac cagctgacgg ctcttcccgt tggggtgttt gacaaactga 420
cccagctcaa tcatctgttt ctgaacaaca accagctgaa gagcgttccc aggggcgcct 480
ttgacaacct caagagcctc actcacatct ggctgtacaa caacccctgg gactgcgcct 540
gctcggacat cctgtatctc agtcgctgga tcggtcaaaa cgggggggaag ttggttaact 600 ctgcaggaaa ctttgacggc aacagtgctg tgtgctctgg t 641

<210> SEQ ID NO 272
<211> LENGTH: 715
<212> TYPE: DNA
<213> ORGANISM: Artificial Sequence
<220> FEATURE:
<223> OTHER INFORMATION: Description of Artificial Sequence; note = synthetic construct

<400> SEQUENCE: 272
accagagcac ttgacgctgt ctggactgtg cctccatggc caccccctcac ccacgatgct 60 cgagtgctga gcgacccagc cactcaagta gaggatgtcc gtgcattgac agtcccaggg 120
gttggtgtgg agccacacgt gggtgaggct cgggagacga gcgaacgcgc cgtcagggat 180
gctcttcagt tgattctggt ccagacccaa ctgcttcagc cgggtgagtt tgtcaaatgc 240
gccactgggc agctctgtga gcttcataca gcacaaaccc agatgctcca gattcaccag 300
gcgatcaaac acttcctcgg gtagagctgt cagctggttg ttacgaaggg tgagataagt 360
cagttgcgtt aactgtcaaa caccccggtc tcgagcttcg tgatttgatt gtcgttcaaa 420
tacagatact gcgtggtggt ggggattccc gcaggcacag acgcgaggct tttgctcaca 480
cagcgcactt ctgcccctga gcacgaacac tgcgagggac atgctaccgc actttgcacc 540
agggcgccaa aggcgaccag cgtggcgatc cacttgatcc acatgatggt tggctcctgt 600
aggccgagta gcggagagcg tgagagtgtt ggggagcgag agagcgagag aggggacagt 660
ggtggctgta gctggagctg ttgagagctg cagagccgag tcgctgtccc cgcgt 715

<210> SEQ ID NO 273
<211> LENGTH: 639
<212> TYPE: DNA
<213> ORGANISM: Artificial Sequence
<220> FEATURE:
<223> OTHER INFORMATION: Description of Artificial Sequence; note = synthetic construct

<400> SEQUENCE: 273
acgcggggac agcgactcgg catctgcagc tctcaacagc tccagctaca gccaccactg 60
atcccctctc tcgctctctc gctccccaac actctcacgc tctccgctac tcggcctgca 120
ggagccaacc atcatgtgga tcaagtggat cgccacgctg gtcgcctttg gcgccctggt 180
gcaaagtgcg gtagcatgtc cctcgcagtg ttcgtgctca gggacagaag tgaactgtgc 240
agggaaaagc ctcgcgtctg tgcctgcagg aatccccacc aatgcgcaga ttctgtattt 300
acacgacaat cagatcacga agctcgagcc cggggttttt gacagtctga cgcaactgac 360
tgttctgaat ctcgcaataa accagctgac ggctctaccc gtgggagtgt ttgaccgcct 420
ggtgaatctg gagcatctgg gtttgtgctg tatgaagctc acagagctgc ccagtggcgc 480
atttgacaaa ctcacccggc tgaagcagtt gggtctggac cagaatcaac tgaagagcat 540
ccctgacggc gcgttcgctc gtctcccgag cctcacccac gtgtggctcc acaccaaccc 600
ctgggactgt caatgcacgg acatcctcta cttgagtgg 639

<210> SEQ ID NO 274
<211> LENGTH: 565
<212> TYPE: DNA
<213> ORGANISM: Artificial Sequence
<220> FEATURE:
<223> OTHER INFORMATION: Description of Artificial Sequence; note = synthetic construct

<400> SEQUENCE: 274
accagagcac ttcacgttgt caactccccc atggccctgt agattcacga tgcttgcgtg 60
ctgcacaatc cagttcttca gatagaggat gtccgaacac tcgcagtccc agggttgttg 120
aacagataga tgtgagtgag gctcttgagg ttgtcaaagg cgcccctggg aatgctcttc 180
agctggttgt ctcgcagatt cagataagtg agctgggtca gtttgtcaaa caccccggtc 240
tcgagcttcg tgatttgatt gtcgttcaaa tacagcactt gcgtggtgct ggggattccc 300
gcaggcacag acgcgaggct tttgcttttg cagttcacag ttgtccctga gcacgaacac 360
tgcgagggac atgctaccgc actttgcacc agggcgccaa aggcgaccag cgtggcgatc 420
cacttgatcc acatgatggt tggctcctgc aggccgagta gcggagagcg tgagagtgtt 480
ggggagcgag agagcgagag aggggacagt ggtggctgta gctggagctg ttgagagctg 540
cagagccgag tcgctgtccc cgcgt 565

<210> SEQ ID NO 275
<211> LENGTH: 551
<212> TYPE: DNA
<213> ORGANISM: Artificial Sequence
<220> FEATURE:
<223> OTHER INFORMATION: Description of Artificial Sequence; note = synthetic construct

<400> SEQUENCE: 275
acaacaatca gatcacgaat ctcgagcccg gggtgtttga cagactcacc cagctcgtag 60
aactgaatct acgtgacaac catctgacat ccattcccgt aggtgtgttt gatcagctgg 120
tgaatctgaa ggagctgcat ttgtacggca accagctgac agctctaccc gttgggctgt 180
ttgacagagt cacccagctc gtaacactgg atctgaatgg aaaccaactg tcatccgttc 240
ccgcagacgt gttccatcag cttgtgaaat tagagaagct gtggctcaaa agcaacaaac 300
tgacggctct tcccgctggg ttgtttgacg aactgaccca ggtttattct ctgagtctga 360
acgacaacca gctgaagagc attcccaggg gcgcctttga caacctcaag agcctcactc 420
acatctggct gttcggcaac ccctgggact acgagtgttc ggacatcctc tatctgaaga 480
actggattgt gcagcacgca agcatcgtga atccaggcaa cgggggagtt gataacgtga 540
agtgctctgg t 551

<210> SEQ ID NO 276
<211> LENGTH: 572
<212> TYPE: DNA
<213> ORGANISM: Artificial Sequence
<220> FEATURE:
<223> OTHER INFORMATION: Description of Artificial Sequence; note = synthetic construct

<400> SEQUENCE: 276
accagagcag acagcctggc cctgctcttt ccctgcgtgc tggcccagcc agccgctgag 60
gtagaggatg tctgagcaag cacagtccca ggggttgttg tacagccaga tgtgagtgag 120
gctcttgagg ttgtcaaagg cgcccctggg aatgctcttc agctggttgg tgtgcagaac 180
caaatgtgtg agcttggtca gtttgtcaaa caccccaggg ggaagagaca ccagctggtc 240

-continued cccccacaga tgaagccccc tcaaattcgc cagaccgtca aacaccccgg gctcgagctt 300
cgtgatctga ttgttattca accacaggtt ctgcctgtcg gtggggattc ccgcaggcac 360
agacgagaag cgtttgttcc ggcagtccac agttgtctga tcgcacgaac actgcgaggg 420
acatgctacc gcactttgca ccagggcgcc aaaggcgacc agcgtggcga tccacttgat 480
ccacatgatg gttggctcct gcaggccgag taacggagag cgtgagagtg ttggggagcg 540
agagagcgag agaggggaca gtggtggctg ta 572

<210> SEQ ID NO 277
<211> LENGTH: 603
<212> TYPE: DNA
<213> ORGANISM: Artificial Sequence
<220> FEATURE:
<223> OTHER INFORMATION: Description of Artificial Sequence; note = synthetic construct

<400> SEQUENCE: 277
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgcacagg ggcatctgtg gaatgccaga 240
gcagaagaca cacgtctgtg cctgcgggaa tccccaccaa tgcgcagatt ctgtatttac 300
acgacaatca gatcacgaag ctcgagcccg gggtgtttga cagactgaca gagcttactt 360
atttgaacct caataccaac cagctaacgg ctctaccgga gggggtgttt gatcgcctgg 420
tggatctaga ggttctgagt ttgtgctgca acaagctcac agagctgccc agtggcgtgt 480
ttgacaaact tacccggctg aagcggttgg gtctggaccg gaatcaactg aagagcattc 540
ccaggggcgc ctttgacaac ctcaagagcc tcacccacgt gtggctccac accaacccct 600
ggg 603

<210> SEQ ID NO 278
<211> LENGTH: 651
<212> TYPE: DNA
<213> ORGANISM: Artificial Sequence
<220> FEATURE:
<223> OTHER INFORMATION: Description of Artificial Sequence; note = synthetic construct

<400> SEQUENCE: 278
acgcggggac agcgactcgg ctctgcagct ctcaacagct ccagctacag ccaccactgt 60
cccctctctc gctctctcgc tccccaacac tctcacgctc tccgctactc ggcttgcagg 120
agccaaccat catgtggatc aagtggatcg ccacgctggt cgcctttggc gccctggtgc 180
aaagtgcggt agcatgtccc tcgcagtgtt catgctcagg gacagatatt cactgtcatg 240
agagaagcct acggtctgtg cctgtgggaa tccccaccac cacgcagatc ctgcggctgt 300
acagaaatca gatcacgaag ctcgagctcg gggtgtttga cagtctgatg gaacttactg 360
aactctacct tcactacaac cagctgacga ctcttcccta cggggtgttt gaccgactgg 420
tgaatctgca gcagttggct ctgggaggta accagctgtc ggcgctccct gtcagaatgt 480
ttgataaact gactcagcta actactctga atttgtctga aaacaaactg acggctctac 540
ccgctggggt gtttgacaaa attgaccctg ctcgctggtc tgagtctgca caccaaccag 600
ctgaagagta ttcccagggg cgcctttgac aacctcaaga gcctcactca a 651

<210> SEQ ID NO 279

<211> LENGTH: 680
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 279
agcgtggtcg cggccgaggt acgcggggac agcgactcgg ctctgcagct ctcaacagct 60
ccagctacag ccaccactgt cccctctctc gctctctcgc tccccaacac tctcacgctc 120
tccgctactc ggcctgcagg agccaaccat catgtggatc aagtggatcg ccacgctggt 180
cgcctttggc gccctggtgc aaagtgcggt agcatgtccc tcgcagtgtt cgtgctcagg 240
gacagaagtg agctgtggga acaaaggcct agcgtctgtg cctccgggta tccccaccac 300
cacggaaaag ctggttttgt tcagcaatca gatcacaaag ctcgagcccg gagtgtttga 360
ccgcctggtg aatctgcaga agctgtggtt gaacagcaac cagctgacct ctctccccac 420
tggggtgttt gaccgcttgg ttaatctgca gacgctggat ttgcacaaca accagctgaa 480
gagcattccc aggggcgcct ttgacaacct caagagcctc actcacatct atctgttcaa 540
caacccctgg gactgcgagt gttcggacat cctctatctg aagaactgga ttgtgcagca 600
cgcaagcatc gtgaatccat cgggctatgg gggagttgat aacgttaagt mctctggtac 660
ctgcccgggc ggccgctcga 680

<210> SEQ ID NO 280
<211> LENGTH: 422
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 280
accaataccc ccgatccgtg cggtcaccga ggccagcact agcccctcga aatgcccagg 60
ctacgttgct acgaccacga cgccgacgac gaccacgccc gaattcatcc ctgagaccac 120
cacctcgccg cagcccgtga tcacaaccca gaaacccaag cctctgtgga atttcaactg 180
cacctcaatt caggagagga agaacgacgg tggcgactgc ggaaagcccg cctgcacaac 240
tctcctgaac tgcgcgaatt tcctcagctg cctctgctca acctgcgccc tctgcaggaa 300
acgttgatcg gcgtgcaaag gtcggggatg gcggtgggaa ggcgggcgcg gtggggtggg 360
ggtgtagtga acccctggga ctgcgagtgt tcggacatcc tctatctgaa gaactggatt 420
gt 422

<210> SEQ ID NO 281
<211> LENGTH: 575
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 281
accagagcag cgcgctgagt cggggtcaac aatataccat gaatcagccg ccctcaagac 60
tccagggtgc tgagagatcc agcggctgag gtacaggatg tctgaacagg cgcagtccca 120
ggggttgttg tacagccaga tgtgagtgag gctcttgagg ttatcaaagg cgcccctggg 180
aatgctcttc agttggttgt tactcagatc aacccgctgc agattcccga ggcggtcaaa 240
caccccgagc tcgagcttcg tgatctgatt tctgtacagc cgcaggatct gcgtggtggt 300
ggggattccc acaggcacag accgtaggct tctctcatga cagtgaatat ctgtccctga 360
gcatgaacac tgcgagggac atgctaccgc actttgcacc agggcgccaa aggcgaccag 420
cgtggcgatc cacttgatcc acatgatggt tggctcctgc aggccgagta gcggagagcg 480
tgagagtgtt ggggagcgag agagcgagag aggggacagt ggtggctgta gctggagctg 540
ttgagagctg cagagccgag tcgctgtccc tgcgt 575

<210> SEQ ID NO 282
<211> LENGTH: 638
<212> TYPE: DNA
<213> ORGANISM: Artificial Sequence
<220> FEATURE:
<223> OTHER INFORMATION: Description of Artificial Sequence; note = synthetic construct

<400> SEQUENCE: 282
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cttgctcagg gacaactgtg aactgtgata 240
gcagaagcct cgcgtctgtg cctggaggaa tccccaccac cacgcagtat ctgaatttgc 300
acgtcaatca gatcacgaag ctcgagcccg gggtgtttga ccgcctggtg aatctgcagc 360
ggctgtggtt gaacaacaac cagctgacct ctctccccgc tggggtgttt gacaaactca 420
cacagctcac tcatctggcc ctgcacaaca accagctgac gaccgttccc gagggcgcct 480
ttgacaacct caagagcctc actcacatct ggctgttgaa caacccctgg gactgcgagt 540
gttcggacat cctctatctg aagaactgga ttgtgcagca cgcaagcatc gtgaatccat 600
cgggccatgg gggagttgat aacgtgaagt gctctggt 638

<210> SEQ ID NO 283
<211> LENGTH: 802
<212> TYPE: DNA
<213> ORGANISM: Artificial Sequence
<220> FEATURE:
<223> OTHER INFORMATION: Description of Artificial Sequence; note = synthetic construct

<400> SEQUENCE: 283
acgcggggac agcgactcgg ctctgcagct ctcaacagct ccagctacag ccaccactgt 60
cccctctctc gctctctcgc tccccaacac tctcacgctc tccgctactc ggcccgcagg 120
agccaaccat catgtggatc aagtggatcg ccacgctggt cgcctttggc gccctggtgc 180
aaagtgcggt agcatgtccc tcgcagtgtt cgtgctcagg gacagatgtt caatgtgaca 240
ggagaagcct cgtgtctgtg cctgcgggaa tccctaccac cacgcgagtg ctgcatttgc 300
acaccaatca gatcacgaag ctcgagcccg gggtgtttga ccgcttggcg aatctgcaga 360
agctgtatct gtggggaaac cagctgtcgg ctctacccaa tggaattttc gacaaactca 420
cccagctcgt aacactggat ctgaatggaa accaactgtc atccgttccc gcagacgtgt 480
tccatcagct tgtgaaatta gagaagctgt ggctcaaaaa caacaaactg acggctcttc 540
ccgctgggtt gtttgacgaa ctgacccagg tttattctct gagtctgaac gacaaccagt 600
tgaagagcat cccgcatgga gcgttcgacc gtctcagctc cctcacccac gcctatttat 660
ttggcaaccc atgggattgc gagtgcaggg acattatgta cctcaggaac tgggtcgcag 720
accacacttc tattgtaatg cgctgggatg ggaaggccgt taacgacccc gactctgcca 780
agtgcgctgg tacctgcccg gg 802

<210> SEQ ID NO 284
<211> LENGTH: 721
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 284
accagcgcac ttggcagagt cggggtcgtt aacggccttc ccatcccagc gcattacaat 60
agaagtgtgg tctgcgaccc agttcctgag gtgcataatg tccctgcact cgcaatccca 120
tgggttgcca aataaatagg cgtgggtgag ggagctgaga cggtcgaacg ctccatgcgg 180
gatgctcttc aactggttct ttgacagatc taaatgctgc agcttcccca ggcggtcaaa 240
caatccctcg gaaagggcct gcagctggtt tctgtacaac tgaagattct tcagattggt 300
cagtttgtca aaaaccccga cggttacagc cgtcagctgg ttgccaccaa gttccagaga 360
agtcagttgc gtcagactgt caaacacccc gggctcgagc ttcgtgatct gattgctgga 420
caaacccagc acttgcgtgg tggtggggat tcccgcaggc acagacgcga ggcttttgct 480
cacacagcgc acttctgccc ctgagcacga acactgcgag ggacatgcta ccgcactttg 540
caccagggca ccaaaggcga ccagcgtggc gatccacttg atccacatga tggttggctc 600
ctgcaggccg agtaacggag agcgtgagag tgttggggag cgagagagcg agaaagggga 660
cagtggtggc tgtagctgga gctgttgaga gctgcagagc cgagtcgctg tccccgcgta 720
c 721

<210> SEQ ID NO 285
<211> LENGTH: 687
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 285
accagagcac ttcacgttat caactccccc atggcccgat ggattcacga tgcttgcgtg 60
ctgcacaatc cagttcttca gatagaggat gtccgaacac tcgcagtccc aggggttgtt 120
gaacagatag atgtgagtga ggctcttgag gttgtcaaag gcgcccctgg gaatgctctt 180
cagctggttg ttgttcagat ccagataagt gagctgggtc agtttgtcaa actgcccaac 240
gggtatggac gacagtcggt tcagatgcaa atacaactgt tgcagattga ccagtcggtc 300
aaacacccct cgggtagagc tgtcagctgg ttgttgtaca aacgcagctc cttcagattc 360
accaggcggt caaacacccc gggctcgagc ttcgtgatct gattgttatt caaccacagg 420
ttctgcctgt cggtggggat tcccgcaggc acagacgaga agcgtttgtt ccggcagtcc 480
acagttgtcc ctgagcacga acactgcgag ggacatgcta ccgcactttg caccagggcg 540
ccaaaggcga ccagcgtggc gatccacttg atccacatga tggttggctc ctgcaggccg 600
agtagcggag agcgtgagag tgttggggag cgagagaagc gagagagggg acagtggtgg 660
ctgtaactgg agctgttgag agctgca 687

<210> SEQ ID NO 286
<211> LENGTH: 592
<212> TYPE: DNA
<213> ORGANISM: Artificial Sequence
<220> FEATURE:
<223> OTHER INFORMATION: Description of Artificial Sequence; note = synthetic construct

<400> SEQUENCE: 286
actcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgcgatca gacaactgta taccgccata 240
gcagacgcct cacgtctgtg cctgcgggaa tccccaccga caggcagaac ctgtggttgt 300
acgacaatca gatcacgaag ctcgagcccg gggtgtttga ccgcctggtg aatccgcagg 360
agctgcgttt gtacaacaac cagctgacat ctctccccgc aggggtgttt gacaaactca 420
cccagctcgt aacactggat ctgaatggaa accaactgtc atccgttccc gcagacgtgt 480
tccatcagct tgtgaaatta gagaagctgt ggctcaaaaa caacaaactg acggctcttc 540
ccgctgggtt gtttgacgaa ctgacccagg tttattctct gagtctgaac ga 592

<210> SEQ ID NO 287
<211> LENGTH: 580
<212> TYPE: DNA
<213> ORGANISM: Artificial Sequence
<220> FEATURE:
<223> OTHER INFORMATION: Description of Artificial Sequence; note = synthetic construct

<400> SEQUENCE: 287
acacggggac agcgactcgg ctctgcagct ctcaacagct ccagctacag ccaccactgt 60
cccctctctc gctctctcgc tccccaacac tctcacgctc tccgctactc ggcctgctgg 120
agccaaccat catgtggatc aagtggatcg ccacgctggt cgcctttggc gccctggtgc 180
aaagtgcggt agcatgtccc tcgcagtgtt cgtgctcagg gacaactgtg gattgtagtg 240
ggaaaagcct cgcatctgtg cctacgggaa tccccaccac cacgcagtat ctgaatttgc 300
acgtcaatca gatcacgaag ctcgagcccg gggtgtttga ccgcctggtg aatctgcagc 360
atctgcattt gaacagcaac aagctaacag ctatacccac tggagtgttt gacaaactga 420
cccagctcac tcttctagaa ctgcaaaaca accagctgaa gagcattccc aggggcgcct 480
ttgacaacct cagagcctca ctcacatcta tctgtacaac aacccatggg attgcgagtg 540
cagggacatt atgtaacctc aggaactggg gtcgcaagac 580

<210> SEQ ID NO 288
<211> LENGTH: 643
<212> TYPE: DNA
<213> ORGANISM: Artificial Sequence
<220> FEATURE:
<223> OTHER INFORMATION: Description of Artificial Sequence; note = synthetic construct

<400> SEQUENCE: 288
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aagtgcggta gcatgtccct cgcagtgttc gtgctcaggg acatctgtgg attgccggag 240
cagaagacac gcgtctgtgc ctgcgggaat ccccaccacc acgcaagtgc tgggtttgtc 300
cagcaatcag atcacgaagc tcgagcccgg ggtgtttgat cgcctggtgc atctaaaaga 360

```
gctgttgatg tgctgcaata agctcacgga gctgccccgt ggcattgaga gactcaccca    420

tttgactcat ttagctctgg accaaaacca gttgaagagc gtcccgcatg gagcgttcga    480

ccgtctcagc tccctcaccc acgcctattt atttggcgac ccatgggatt gcgagtgcag    540

ggacattatg tacctcagga actgggtcgc agaccacact tctattgtaa tgcgctggga    600

tgggaaggcc gttaacgacc ccgactcagc gcgctgctct ggt                      643
```

<210> SEQ ID NO 289
<211> LENGTH: 766
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 289

```
accagagcac ttcacgttat caactccccc gctgcctgga ttcacgatgc ttgcatgctg     60

tacaatccag ttcttcagat agaggatgtc cgaacattcg cagtcccagg ggttgccgaa    120

cagccagatg tgagtgaggc tcttgaggtt gtcaaaggcg cccctgggaa tgctcttcag    180

ctggttggtg ctcagagtca ggcgagtgag ctgggtgagt ttgtcaaaca ccccaacggg    240

aagagccgtc agctggttaa cagcaaggtt cagataagtc agttgcgtca ggctgtcaaa    300

cacccccctcg ggtagagctg tcagctggtt gtcactcaga ctcagataag tgagttgtgt    360

cagtttgtga aatgctcctg agggaatatc ttttagctta ttcgaatgga gtttcagttc    420

agtcagtgcc gccagactgt caaacacccc tggctcgagc ttcgtgatct gattgatgta    480

cagccgcagg atcttcgtgg tggtggggat ttccgcaggc acagacgcca agcgtctctc    540

atgacagtta acatctgtcc ctgggcacga acactgcgag ggacatgcta ccgcactttg    600

caccagggcg ccaaaggcga ccagcgtggc gatccacttg atccacatga tggttggctc    660

ctgcaggccg agtagcggag agcgtgagag tgttggggag cgagagagtg agagaaggga    720

cagtggtggc tgtagctgga gctgttgaga gctgcaaagc cgaatc                   766
```

<210> SEQ ID NO 290
<211> LENGTH: 623
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 290

```
acataatgtc cctgcactcg caatcccatg ggttgccaaa taaataggcg tgggtgaggg     60

agctgagacg gtcgaacgct ccatgcggga tgctcttcaa ctggttttgg tccagagcta    120

aatgagtcaa tgggtgagtc tctcaatgcc acggggcagc tccgtgagct tattgcagca    180

catcaacagc tcttttagat gcaccaggct gtcaaacacc ccggcgggga gaactgtcaa    240

ctggttattg taaagatcca gtcgtgtcag ttgagtcagg cggtcaaaca ccccgggctc    300

gagcttcgtg agttgatttc tgtgcaaatg cagccatcgc gtggtggtgg ggattcccgc    360

aggcacagac gcgaggcttc tgccctcaca gcgcacttct gtccctgaac acgaacactg    420

cgagggacat gctaccgcac tttgcaccag ggcgccaaag gcgaccagcg tggcgatcca    480

cttgatccac atgatggttg gctcctgcag gccgagtagc ggagagcgtg agagtgttgg    540

ggagcgagag agcgagagag gggacagtgg tggctgtagc tggagctgtt gagagctgca    600

gagccgagtc gctgtccccg cgt                                            623
```

<210> SEQ ID NO 291
<211> LENGTH: 637
<212> TYPE: DNA
<213> ORGANISM: Artificial Sequence
<220> FEATURE:
<223> OTHER INFORMATION: Description of Artificial Sequence; note = synthetic construct

<400> SEQUENCE: 291
acgcgggaca gcgactcggc tctgcagctc tcaacagctc cagctacagc caccactgtc 60
ccctctctcg ctctctcgct ccccaacact ctcacgctct ccgctactcg gcctgcagga 120
gccaaccatc atgtggatca agtggatcgc cacgctggtc gcctttggcg ccctggtgca 180
aagtgcggta gcatgtccct cgcagtgttc ttgctcaggg acaactgtga actgtgatag 240
cagaagcctc gcgtctgtgc ctgggggaat ccccaccacc acgcaagtgc tgtatttgta 300
cgacaatcag atcacgaagc tcgagcccgg cgtgtttgac agtctgatgg aactgactga 360
actgaaactc cattcgaata agctaaaaga tattccctca ggagcatttc acaaactgac 420
acaactcact tatctgagtc tgtacaataa ccagctgaag agcattccca tgggcgcgtt 480
taacaacctc aagagcctca ctcacatcta tctgttcaac aacccctggg actgcgagtg 540
ttcggacatc ctctatctga agaactggat tgtgcagcat gcaagcatcg tgaatctacg 600
gggccatggg ggagttgata acgtgaagtg ctctggt 637

<210> SEQ ID NO 292
<211> LENGTH: 710
<212> TYPE: DNA
<213> ORGANISM: Artificial Sequence
<220> FEATURE:
<223> OTHER INFORMATION: Description of Artificial Sequence; note = synthetic construct

<400> SEQUENCE: 292
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgctcagg gacagatgtg aactgtgacg 240
ggaaacgctt cgcgtctgtg cctgcgggaa tccccgccac cacgcaagtg ctgtatttgt 300
acaccaataa gatcacgaag ctcgagcccg gcgtgtttga cagtctggcg gcactgactt 360
ttctgaacgt tggtgacaac cagctgacgg ctctacccga gggggtgttt gaccacctgg 420
tgaatctgca gcgggttgat ctgagtaaca accaactgaa ggcccttccc gaggggatat 480
ttggtcggct ggtgaatctg taacgcctgt atctgaatca gaaccagctg aagagcattc 540
ccaggggcgc ctttgacaac ctcaagagcc tcactcacat ctatctgttc aacaacccct 600
gggactgcga gtgttcggac atcctctatc tgaagaactg gattgtgcag cacgcaagca 660
tcgtgaatct agagggccat gggggagttg ataacgtgaa gtgctctggt 710

<210> SEQ ID NO 293
<211> LENGTH: 865
<212> TYPE: DNA
<213> ORGANISM: Artificial Sequence
<220> FEATURE:
<223> OTHER INFORMATION: Description of Artificial Sequence; note = synthetic construct

<400> SEQUENCE: 293
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgcccagg gacagatgtt aactgtcatg 240
agagacgctt ggcgtctgtg cctgcggaaa tccccaccac cacgaagatc ctgcggctgt 300
acatcaatca gatcacgaag ctcgagccag ggtgtttga cagtctgact gaactgacta 360
tcttggatct acgtaccaac cagctgcagg ctctacccac tttggtgttt gacagcctgg 420
tgaatctgca gaagctctat ttgagtggga atcagctgca ggctctacca gccggggtgt 480
ttgacaaact ttcccaactg acttttctgt ctttggatga aaataaacta actgctctcc 540
ccaacggggt gtttgacaag ctcacccagc tgaaggagtt gggtctggac cagaatcaac 600
tgaagagcat ttccgctgga gtgtttgaca aactgaccca gctcactcaa ctgggtctgt 660
gggacaacca gttgacgagc attcccaggg gcgcctttga caacctcaag agcctcactc 720
acatctatct gttcaacaac ccctgggact gcgcctgctc agacatccta tacctgagcc 780
actggggcaa atgggcacgc agacatagtg cagagaatgt cacttactac gtgctctggt 840
actgggccgg ggcggccgct cgaaa 865

<210> SEQ ID NO 294
<211> LENGTH: 398
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 294
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgctcagg gacagaagtg cactgtgcag 240
ggaaaagcct cgcgtctgtg cctgcgggaa tccccaccac cacgcagtat ctgaatttgc 300
acgtcaatca gatcacgaag ctcgagcccg ggtgtttga caaactgacc cagctcacta 360
atctgtatct gcacaacaac cagctgaaga gcattccc 398

<210> SEQ ID NO 295
<211> LENGTH: 644
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 295
atcagagcac ttgacgctgt ctggactgtg cctccatggc cacccctcac ccacgatgcc 60
cgagtgctga gcgacccagc cactcaagta gaggatgtcc gtgcactgac agtcccaggg 120
gttgttcaac agccagatgt gagtgaggct cttgaggttg tcaaaggcgc ccctgggaat 180
gctcttcagc tggttatacc tcagatccaa acgctgcaga ttctccagac ggccaaacac 240
tccatcggga agggcctgca ggtggtttgt aggcagagac agaactgtca gctgggtcag 300
actgtcaaac acgccgggct cgagattcgt gatctgattg ttgtacaaat tcaaaatctg 360
cacattggtg gggattcccg caggcacaga cgcgtgtctt ctgctgttgc aatccacaga 420
tgtccctgag cacgaacact gcgagggaca tgctaccgca ctttgcacca gggcgccaaa 480
ggcgaccagc gtggcgatcc acttgatcca catgatggtt ggctcctgca ggccgagtag 540
cggagagcgt gagagtgttg gggagcgaga gagcgagaga ggggacagtg gtggctgtag 600
ctggagctgt tgagagctgc agagccgagt cgctgtcccc gcgt 644

<210> SEQ ID NO 296
<211> LENGTH: 387
<212> TYPE: DNA
<213> ORGANISM: Artificial Sequence
<220> FEATURE:
<223> OTHER INFORMATION: Description of Artificial Sequence; note = synthetic construct

<400> SEQUENCE: 296
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgttcagg gacaactgtg gattgtagtg 240
ggaaaagcct cgcgtctttg cctgcgggaa tccccaccac cacgcactat ctgaatttga 300
acatgaatca gatcacgaag ctcgagcccg gggtgtttga ccgcctggtg aatctgcaga 360
agctgtggtt gaacagcaac cagctga 387

<210> SEQ ID NO 297
<211> LENGTH: 637
<212> TYPE: DNA
<213> ORGANISM: Artificial Sequence
<220> FEATURE:
<223> OTHER INFORMATION: Description of Artificial Sequence; note = synthetic construct

<400> SEQUENCE: 297
accagcgcac ttggcagagt cggggtcgtt aacggccttc ccatcccagc gcattacaat 60
agaagtgtgg tctgcgaccc agttcctgag gtacataatg tccctgcact cgcaatccca 120
tgggttgcca aataaatagg cgtgggtgag ggagctgaga cggtcgaacg ctccatgcgg 180
gatgctcttc aactggtttt ggtccagagc taaatgagtc aaatgggtga gtctctcaat 240
gccacggggc agctccgtga gcttattgca gcacatcaac agctctttta gatgcaccag 300
gcgatcaaac acttcctcgg gaagggcttg cagccggttg ccactcagag ccaaaagggt 360
cagctgggtc agactgtcaa acaccccggt ctcgagcttc gtgatctgat tgtcgttcaa 420
atacagcact cgcgtggtgg tggggattcc cgcaggcaca gacgcgaggc ttctgctatc 480
acagttcaca gttgtccctg agcaagaaca ctgcgaggga catgctaccg cactttgcac 540
cagggcgcca aaggcgacca gcgtggcgat ccacttgatc cacatgatgg ttggctcctg 600
caggccgagt agcggagagc gtgatagtgt tggggag 637

<210> SEQ ID NO 298
<211> LENGTH: 710
<212> TYPE: DNA
<213> ORGANISM: Artificial Sequence
<220> FEATURE:
<223> OTHER INFORMATION: Description of Artificial Sequence; note = synthetic construct

<400> SEQUENCE: 298
acgcggggac agcgactcgg ctctgcagct ctcagctact cggcctgcag gagccaacca 60
tcatgtggat caagtggatc gccacgctgg tcgcctttgg cgccctggtg caaagtgcgg 120
tagcatgtcc ctcgcagtgt tcgtgcgatc agacaactgt atactgccat agcagacgcc 180
tcacgtctgt gcctgcggga atccccaccg acaggcagaa cctgtggttg tacgacaatc 240
agatcacgaa gctcgagccc ggggtgtttg acagactgac ccagctcact caactgagtc 300
tgaatgacaa ccagctgaca gctctaccca atggaatttt cgacaaactc acccagctcg 360
taacactgga tctgagtgga aaccaactgt catccgttcc cgcagacgtg ttccatcagc 420
ttgtgaaatt agagaagctg tggctcaaaa acaacaaact gacggctctt cccgctgggt 480
tgtttgacga actgacccag gtttattctc tgagtctgaa cgacaaccaa ctgaagagca 540
ttcccagggg cgcctttgac aacctcaaga gcctcactca catctggctg ttcggcaacc 600
cctgggactg cgagtgttcg gacatcctct atctgaagaa ctggattgtg cagcacgcaa 660
gcatcgtgaa tccaggcaac gggggagttg ataacgtgaa gtgctctggt 710

<210> SEQ ID NO 299
<211> LENGTH: 566
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 299
acgcggggac agcgactcgg ctctgcagct ctcaacagct ccagctacag ccaccactgt 60
cccctctctc gctctctcgc tccccaacac tctcacgctc tccgctactc ggcctgcagg 120
agccaaccat catgtggatc aagtggatcg ccacgctggt cgcctttggc gccctggtgc 180
aaagtgcggt agcatgtccc tcgcagtgtt cgtgctcagg gacagatgtg aaatgtgatt 240
ggagacaact cgcgtctgtg cctgcgagaa tccccaccac cacgcaaagg ctgtggttga 300
acaacaatca gatcacgaag ctcgaccccg gggtgtttga caaactgacc cagctcactt 360
atctgaatct gcgagacaac cagctgacgg ctcttcccga gggcgccttt gacgacctca 420
agagcctcac tcacatctgg ctgtacagta acccctggga ctgcgagtgt tcggacatcc 480
tctatctgaa gaactggatt gtgcagcacg caggcatcgt gaatccacac ccctatgggg 540
gagttgataa cgtgaagtgc tctggt 566

<210> SEQ ID NO 300
<211> LENGTH: 350
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 300
gcatcaatca gatcacgaag ctcgagccag gggtgtttga cagcctgacg caactgactt 60
atctgaacct tgctgttaac cagctgacgg ctcttcccgt tggggtgttt gacgaactga 120
ccaaactcac tcatctggct ctgcacatca atcaactgaa gagcgtgccc aggggcgcct 180
ttgacaacct caagagcccc actcacatct ggctgtacga caacccctgg gactgtgcct 240
gttcagacat cctgtacctc agccgctgga tctctcagca cccaggaatc gtgagatcag 300
cagatgatgg ttggaacaga gtgaaccccg actcagcgcg ctgctctggt 350

<210> SEQ ID NO 301
<211> LENGTH: 419
<212> TYPE: DNA
<213> ORGANISM: Artificial Sequence
<220> FEATURE:

<223> OTHER INFORMATION: Description of Artificial Sequence; note =
synthetic construct

<400> SEQUENCE: 301
accagagcac ttggcagagt cggggtcgtt aacggccttc ccatcccagc gcattacaat 60
agaagtgtgg tctgcgaccc agttcctgag gtacataatg tccctgcact cgcaatccca 120
tgggttgctg gacagccaga tgttagtgag gctcttgagg ttgtcaaagg cgcccctggg 180
aatgctcttc agctggttgt tgtgcagata cagattagtg agctgggtca ggttgtcaaa 240
caccccggtg ggaacggtcg tcagctggtt tccccacaga tacagcttct gcagattcac 300
caagcggtca aacaccccag cggggagaga ggtcagctgg ttattgtaaa gatccagtcg 360
tgtcagttga gtcagactgt caaacacgcc gggctcgagc ttcgtgatct gattggtgt 419

<210> SEQ ID NO 302
<211> LENGTH: 554
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 302
acagaaatca gatcacgaag ctcgagctcg gggtgtttga cagcctggtg aaactgaagg 60
agctgtatct ggaccataac caactgcagg cgataccgcc cgctctgttt tacagtttga 120
ctgaactcac gcgactggaa ctggaagata accaactgaa gtctctgccg ccaggcatct 180
ttgacagact ggggaagctg atgtatttgc acctgcacga gaaccagttg acgactgttc 240
ccgccgggtt atttgaccgc ctggtgaatc tgcagaagct gtggttgaac agcaaccagc 300
tgacctctct ccccgctggt gtgtttgaca acctgaccca gcttagcata ctgaatatgc 360
acaccaacca gctgaagagc gttcccaggg gcgcctttga caacctcaag agcctcaccc 420
acgtgtggct ccacaccaac ccctgggact gcgagtgttc ggacatcctc tatctgaaga 480
actggattgt gcagcacgca agcatcgtga atccatcggg ctatggggga gttgataacg 540
tgaagtgctc tggt 554

<210> SEQ ID NO 303
<211> LENGTH: 200
<212> TYPE: DNA
<213> ORGANISM: Artificial Sequence
<220> FEATURE:
<223> OTHER INFORMATION: Description of Artificial Sequence; note =
synthetic construct

<400> SEQUENCE: 303
acttgacgct gtctggactg tgcctccatg gccacccctc acccacgatg cccgagtgct 60
gagcgaccca gccactcaag tagaggatgt ccgtgcactg acagtcccag gggttgccgt 120
acagccagat gtgagtgagg ctcttgaggt tgtcaaaggc gcccctggga atgctcttca 180
ggtggtttgt gtccagagcc 200

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence; note =
synthetic construct

<400> SEQUENCE: 304

Leu Leu Leu Leu Asn Gln Leu Leu Pro Gly Phe Asp
1 5 10

<210> SEQ ID NO 305
<211> LENGTH: 16
<212> TYPE: PRT
<213> ORGANISM: Artificial Sequence
<220> FEATURE:
<223> OTHER INFORMATION: Description of Artificial Sequence; note = synthetic construct

<400> SEQUENCE: 305

Lys Leu Thr Leu Thr Leu Leu Asn Gln Leu Ser Pro Gly Val Phe Asp
1 5 10 15

<210> SEQ ID NO 306
<211> LENGTH: 11
<212> TYPE: PRT
<213> ORGANISM: Artificial Sequence
<220> FEATURE:
<223> OTHER INFORMATION: Description of Artificial Sequence; note = synthetic construct

<400> SEQUENCE: 306

Leu Leu Leu Leu Asn Gln Leu Pro Gly Phe Asp
1 5 10

<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence; note = synthetic construct

<400> SEQUENCE: 307

Cys Pro Ser Arg Cys Ser Cys
1 5

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence; note = synthetic construct

<400> SEQUENCE: 308

Cys Pro Ala Gln Cys Ser Cys
1 5

<210> SEQ ID NO 309
<211> LENGTH: 7
<212> TYPE: PRT
<213> ORGANISM: Artificial Sequence
<220> FEATURE:
<223> OTHER INFORMATION: Description of Artificial Sequence; note = synthetic construct

<400> SEQUENCE: 309

Cys Pro Ser Gln Cys Leu Cys
1 5

<210> SEQ ID NO 310
<211> LENGTH: 7
<212> TYPE: PRT
<213> ORGANISM: Artificial Sequence
<220> FEATURE:
<223> OTHER INFORMATION: Description of Artificial Sequence; note = synthetic construct

<400> SEQUENCE: 310

Cys Pro Ser Gln Cys Pro Cys
1 5

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence; note = synthetic construct

<400> SEQUENCE: 311

Asn Gly Ala Thr Cys Lys Lys
1 5

<210> SEQ ID NO 312
<211> LENGTH: 7
<212> TYPE: PRT
<213> ORGANISM: Artificial Sequence
<220> FEATURE:
<223> OTHER INFORMATION: Description of Artificial Sequence; note = synthetic construct

<400> SEQUENCE: 312

Asn Glu Ala Leu Cys Lys Lys
1 5

<210> SEQ ID NO 313
<211> LENGTH: 11
<212> TYPE: PRT
<213> ORGANISM: Artificial Sequence
<220> FEATURE:
<223> OTHER INFORMATION: Description of Artificial Sequence; note = synthetic construct

<400> SEQUENCE: 313

Ser Gly Lys Pro Val Arg Ser Ile Ile Cys Pro
1 5 10

<210> SEQ ID NO 314
<211> LENGTH: 18
<212> TYPE: PRT
<213> ORGANISM: Artificial Sequence
<220> FEATURE:
<223> OTHER INFORMATION: Description of Artificial Sequence; note = synthetic construct

<400> SEQUENCE: 314

Ser Ser Lys Ala Val Leu Asp Val Thr Glu Glu Glu Ala Ala Glu Asp
1 5 10 15

Cys Val

<210> SEQ ID NO 315
<211> LENGTH: 18
<212> TYPE: PRT
<213> ORGANISM: Artificial Sequence
<220> FEATURE:
<223> OTHER INFORMATION: Description of Artificial Sequence; note = synthetic construct

<400> SEQUENCE: 315

Gln Ser Lys Ala Val Leu Glu Ile Thr Glu Lys Asp Ala Ala Ser Asp
1 5 10 15

Cys Val

<210> SEQ ID NO 316
<211> LENGTH: 276
<212> TYPE: PRT
<213> ORGANISM: Artificial Sequence
<220> FEATURE:
<223> OTHER INFORMATION: Description of Artificial Sequence; note = synthetic construct

<400> SEQUENCE: 316

```
Met Lys Phe Ala Leu Arg Gly Thr Cys Val Leu Leu Ala Leu Leu Leu
 1               5                  10                  15

Cys Cys Arg Asn Gly Lys Ala Cys Pro Ser Arg Cys Ser Cys Ser Gly
            20                  25                  30

Thr Lys Val Glu Cys Glu Gly Leu Thr Ser Val Pro Thr Gly Ile Pro
        35                  40                  45

Ala Gln Thr Thr Tyr Leu Asp Leu Cys Cys Asn Lys Leu Gln Ser Leu
    50                  55                  60

Pro His Gly Val Phe Asp Lys Leu Thr Ser Leu Thr Tyr Leu Asp Leu
65                  70                  75                  80

Gly Gly Asn Lys Phe Gln Ser Ile Pro His Gly Val Phe Asp Lys Leu
                85                  90                  95

Thr Ser Leu Thr Lys Leu Tyr Leu Cys Cys Asn Lys Phe Gln Ser Leu
            100                 105                 110

Pro His Gly Val Phe Asp Lys Leu Thr Lys Leu Thr Ile Leu Gly Leu
        115                 120                 125

Asp Lys Asn Gln Leu Lys Ser Val Pro Asp Gly Ile Phe Asp Arg Leu
    130                 135                 140

Thr Ser Leu Gln Lys Ile Trp Lys Asn Pro Trp Asp Cys Thr Cys Pro
145                 150                 155                 160

Gly Ile Arg Tyr Leu Ser Gln Trp Ile Asn Lys His Ser Gly Ile Ile
                165                 170                 175

Ile Lys Asp Gly Ser Val Asn Pro Asp Ser Ala Lys Cys Ser Gly Ser
            180                 185                 190

Gly Lys Pro Val Arg Ser Ile Ile Cys Pro Thr Thr Thr Thr Thr Thr
        195                 200                 205

Thr Thr Thr Thr Met Pro Thr Thr Thr Thr Leu Pro Thr Thr Thr Lys
    210                 215                 220

Met Ser Met Val Lys Val Pro Leu Val Pro Pro Glu Ala Phe Gly Arg
225                 230                 235                 240

Val Met Asn Ala Cys Ala Tyr Phe Pro Ser Tyr Ile Phe Leu His Leu
                245                 250                 255

Val His Gly Leu Ala Ala Val Pro Leu Val Tyr Leu Ile Cys His Ala
            260                 265                 270

Ser Gln Leu Leu
        275
```

<210> SEQ ID NO 317
<211> LENGTH: 283
<212> TYPE: PRT
<213> ORGANISM: Artificial Sequence
<220> FEATURE:
<223> OTHER INFORMATION: Description of Artificial Sequence; note = synthetic construct

<400> SEQUENCE: 317

```
Met Lys Phe Ala Leu Arg Gly Thr Cys Val Leu Leu Ala Leu Leu Leu
 1               5                  10                  15
```

```
Cys Cys Arg Asn Gly Lys Ala Cys Pro Ser Arg Cys Ser Cys Ser Gly
            20                  25                  30

Thr Glu Val Tyr Cys Gly Ser Arg Ser Leu Thr Asn Val Pro Ser Gly
        35                  40                  45

Ile Pro Ser Ser Ala Thr Arg Leu Gly Leu Glu Ser Asn Lys Phe Gln
    50                  55                  60

Ser Leu Pro His Gly Val Phe Asp Glu Leu Thr Gln Leu Thr Lys Leu
65                  70                  75                  80

Trp Leu Asn Asn Asn Gln Leu Gln Ser Leu Pro Ser Gly Val Phe Asp
                85                  90                  95

Gln Leu Ser Lys Leu Thr Gly Leu Gly Leu Gly Thr Asn Gln Leu Gln
            100                 105                 110

Ser Leu Pro Asn Gly Val Phe Asp Lys Leu Thr Lys Leu Thr Ala Leu
        115                 120                 125

Gly Leu Asp Thr Asn Gln Leu Lys Ser Val Pro Asp Gly Ile Phe Asp
    130                 135                 140

Arg Leu Thr Ser Leu Gln Lys Ile Tyr Leu Phe Ser Asn Pro Trp Asp
145                 150                 155                 160

Cys Thr Cys Pro Gly Ile Arg Tyr Leu Ser Glu Trp Ile Asn Lys His
                165                 170                 175

Ser Gly Val Val Val Asn Ala Tyr Gly Thr Ala Thr Pro Asp Ser Ala
            180                 185                 190

Lys Cys Ser Gly Ser Gly Lys Pro Val Arg Ser Ile Ile Cys Pro Thr
        195                 200                 205

Thr Thr Thr Thr Thr Thr Thr Thr Thr Thr Thr Met Pro Thr Thr Thr
    210                 215                 220

Thr Leu Pro Thr Thr Thr Lys Met Ser Met Val Lys Val Pro Leu Val
225                 230                 235                 240

Pro Pro Glu Thr Phe Gly Arg Val Met Asn Ala Cys Ala Tyr Phe Pro
                245                 250                 255

Ser Tyr Ile Phe Leu His Leu Val His Gly Leu Ala Ala Val Pro Leu
            260                 265                 270

Val Tyr Leu Val Cys His Ala Ser Gln Leu Leu
        275                 280


<210> SEQ ID NO 318
<211> LENGTH: 298
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 318

Met Trp Ile Lys Trp Ile Ala Thr Leu Val Ala Phe Gly Ala Leu Val
 1               5                  10                  15

Gln Ser Ala Val Ala Cys Pro Ala Gln Cys Ser Cys Ser Gly Thr Ser
            20                  25                  30

Val Asn Cys Gln Gly Arg Ser Leu Thr Ser Val Pro Ala Gly Ile Pro
        35                  40                  45

Thr Thr Thr Gln Asn Leu Asn Leu His Val Asn Gln Ile Thr Lys Leu
    50                  55                  60

Glu Pro Gly Val Phe Asp Ser Leu Thr Ala Leu Thr Phe Leu Asn Leu
65                  70                  75                  80

Gly Asn Asn Gln Leu Thr Ala Leu Ser Thr Gly Val Phe Asp Ser Leu
                85                  90                  95
```

-continued

```
Ala Asn Leu Gln Arg Leu Trp Leu Asn Asn Asn Gln Leu Thr Ser Leu
            100                 105                 110

Pro Thr Gly Val Phe Asp Lys Leu Thr Gln Leu Thr His Leu Val Leu
        115                 120                 125

Asp Thr Asn Gln Leu Lys Ser Ile Pro Arg Gly Ala Phe Asp Asn Leu
    130                 135                 140

Lys Ser Leu Thr Tyr Ile Tyr Leu Phe Asn Asn Pro Trp Asp Cys Ala
145                 150                 155                 160

Cys Ser Asp Ile Leu Tyr Leu Ser Arg Trp Ile Ser Gln His Pro Gly
                165                 170                 175

Val Pro Arg Thr Ala Asp Asp Asn Trp Thr Arg Val Val Pro Asp Ser
            180                 185                 190

Ala Arg Cys Ser Gly Thr Asn Thr Pro Val Arg Ala Val Thr Glu Ala
        195                 200                 205

Ser Thr Ser Pro Ser Lys Cys Pro Gly Tyr Val Ala Thr Thr Thr Thr
    210                 215                 220

Pro Thr Thr Thr Thr Pro Glu Ile Ile Pro Glu Thr Thr Thr Leu Pro
225                 230                 235                 240

Gln Pro Val Ile Thr Thr Gln Lys Pro Arg Ser Leu Met Asn Phe Asn
                245                 250                 255

Cys Ser Ser Ile Gln Glu Arg Lys Asn Asp Gly Gly Asp Cys Gly Lys
            260                 265                 270

Pro Ala Cys Thr Thr Leu Leu Asn Cys Ala Asn Phe Leu Ser Cys Leu
        275                 280                 285

Cys Ser Thr Cys Ala Leu Cys Lys Lys Arg
    290                 295


<210> SEQ ID NO 319
<211> LENGTH: 304
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 319

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Gly Lys Glu Ser
            20                  25                  30

Trp Ala Ala Gly Leu Gln Ala Thr Asn Cys Ala Gly Lys Gly Leu Ser
        35                  40                  45

Ser Val Pro Ala Gly Ile Pro Asp Asn Thr Gln Ala Leu Ser Val Gly
    50                  55                  60

Ser Asn Arg Ile Glu Ser Leu Pro Glu Gly Val Phe Asp Arg Leu Val
65                  70                  75                  80

Asn Leu Gln Trp Leu Ser Leu Asp Ser Asn Gln Leu Lys Ala Leu Pro
                85                  90                  95

Ala Trp Val Phe Asp Lys Leu Thr Gln Leu Thr Gly Leu Asp Leu Asn
            100                 105                 110

Arg Asn Gln Leu Gln Ala Leu Pro Thr Gly Met Phe Asp Arg Leu Gly
        115                 120                 125

Asn Leu Gln Arg Phe Asp Leu Ser Arg Asn Gln Leu Lys Ser Val Thr
    130                 135                 140

Arg Gly Ala Phe Asp Asn Leu Lys Ser Leu Thr His Ile Trp Leu Tyr
145                 150                 155                 160
```

```
Gly Asn Pro Trp Asp Cys Gln Cys Thr Asp Ile Leu Tyr Leu Ser Gly
                165                 170                 175

Trp Val Ala Gln His Ser Gly Ile Val Arg Gly Asn Trp Asp Gly Ser
            180                 185                 190

Ser Tyr Ala Val Asn Pro Asp Ser Ala Lys Cys Ser Gly Thr Asn Thr
        195                 200                 205

Pro Val Arg Ala Val Thr Glu Ala Ser Thr Ser Pro Ser Lys Cys Pro
    210                 215                 220

Gly Tyr Val Ala Thr Thr Thr Thr Pro Thr Thr Thr Thr Pro Glu Phe
225                 230                 235                 240

Ile Pro Glu Thr Thr Thr Ser Pro Gln Pro Val Ile Thr Thr Gln Lys
                245                 250                 255

Pro Lys His Leu Met Asn Phe Asn Cys Thr Ser Ile Arg Lys Asn Asp
            260                 265                 270

Gly Gly Asp Cys Gly Lys Pro Ala Cys Thr Thr Leu Leu Asn Cys Ala
        275                 280                 285

Asn Phe Leu Ser Cys Leu Cys Ser Thr Cys Ala Leu Cys Arg Lys Arg
    290                 295                 300


<210> SEQ ID NO 320
<211> LENGTH: 294
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 320

Met Met Gly Pro Val Leu Ala Ala Cys Leu Leu Ile Ile Leu Ser Thr
 1               5                  10                  15

Ala Trp Ile Ser Gln Ala Asn Gly Ala Thr Cys Lys Lys Asp Gly Gly
            20                  25                  30

Val Cys Thr Cys Asn Asp Asn Thr Lys Ser Val Asp Cys Ser Ser Lys
        35                  40                  45

Gly Leu Thr Val Ile Pro Ser Asn Ile Pro Thr Asp Thr Asp Asn Leu
    50                  55                  60

Lys Leu Asp Tyr Asn Lys Leu Ser Ser Leu Pro Ser Lys Ala Phe His
65                  70                  75                  80

His Leu Ser Lys Leu Thr Tyr Leu Ser Leu Ser Thr Asn Gln Leu Gln
                85                  90                  95

Thr Leu Pro Pro Gly Val Phe Asp His Leu Val Gly Thr Leu Tyr Leu
            100                 105                 110

Asn Asn Asn Gln Leu Gln Arg Leu Pro Glu Gly Val Phe Asp Asn Leu
        115                 120                 125

Ala Lys Leu Thr Arg Leu Glu Leu Asn Ile Asn Gln Leu Arg Ser Val
    130                 135                 140

Pro Asn Gly Ala Phe Asp Tyr Leu Ser Asn Ile Lys Thr Leu Trp Leu
145                 150                 155                 160

Asn Asp Asn Pro Trp Asp Cys Ser Cys Asn Asp Ile Leu Tyr Leu Ala
                165                 170                 175

Lys Trp Leu Ala Thr Asn Leu Glu Arg His Ala Gly Ala Asn Cys Asp
            180                 185                 190

Gln Ser Ser Lys Ala Val Leu Asp Val Thr Glu Glu Glu Ala Ala Glu
        195                 200                 205

Asp Cys Val Tyr Pro Asn Thr Thr Thr Ala Ile Pro Thr Thr Ile Ile
    210                 215                 220
```

```
Thr Thr Leu Ala Ser Ser Asn Asp Asp Asp Ile Pro Glu Leu Pro Val
225                 230                 235                 240

Pro Gln Glu Asn Phe Gln Lys Phe Leu Gly Tyr Gln Glu Pro Asp His
                245                 250                 255

Leu Pro Thr Gln Pro Gln Cys Leu Met Ser Ile Ser Gly Tyr Leu Gly
            260                 265                 270

Leu Met Met Ser Leu Val Leu Thr Ser Ala Ala Ile Leu Tyr Val Ile
        275                 280                 285

His Phe Leu Lys Lys Ala
    290
```

<210> SEQ ID NO 321
<211> LENGTH: 297
<212> TYPE: PRT
<213> ORGANISM: Artificial Sequence
<220> FEATURE:
<223> OTHER INFORMATION: Description of Artificial Sequence; note = synthetic construct

<400> SEQUENCE: 321

```
Met Met Gly Pro Val Leu Ala Ala Cys Leu Leu Ile Ile Leu Ser Thr
 1               5                  10                  15

Ala Trp Ile Ser Gln Ala Asn Glu Ala Leu Cys Lys Lys Asp Gly Gly
            20                  25                  30

Val Cys Ser Cys Asn Asn Asn Lys Asn Ser Val Asp Cys Ser Ser Lys
        35                  40                  45

Arg Leu Thr Ala Ile Pro Ser Asn Ile Pro Thr Asp Thr Glu Asn Leu
    50                  55                  60

Lys Leu Asp Tyr Asn Lys Leu Ser Ser Leu Pro Ser Lys Ala Phe His
65                  70                  75                  80

Ser Leu Ser Lys Leu Thr Tyr Leu Ser Leu Thr Gly Asn Lys Leu Gln
                85                  90                  95

Thr Leu Pro Pro Gly Val Phe Asp His Leu Val Gly Thr Leu Asn Leu
            100                 105                 110

Asn Lys Asn Gln Leu Gln Ser Leu Pro Pro Arg Val Phe Asp Ser Leu
        115                 120                 125

Thr Lys Leu Thr Tyr Leu Ser Leu Arg Asn Asn Gln Leu Arg Ser Val
    130                 135                 140

Pro Asn Arg Ala Phe Asp Ser Leu Ser Asn Leu Asn Leu Leu Tyr Leu
145                 150                 155                 160

Arg Ser Asn Pro Trp Asp Cys Ser Cys Lys Asp Ile Leu Tyr Leu Arg
                165                 170                 175

Asp Trp Ile Asp Asp Asn Lys Asp Lys Val Thr Gly Ala Gln Asp Ala
            180                 185                 190

Ala Cys Gly Asp Gln Gln Ser Lys Ala Val Leu Glu Ile Thr Glu Lys
        195                 200                 205

Asp Ala Ala Ser Asp Cys Val Ser Pro Asn Thr Thr Thr Ala Ile Pro
    210                 215                 220

Ile Gly Thr Met Thr Pro Ala Ser Val Ile Tyr Asp Asp Ile His Glu
225                 230                 235                 240

Ile Lys Val Pro Gln Glu Asn Phe Gln Lys Phe Leu Gly Tyr Gln Glu
                245                 250                 255

Pro Asp His Leu Pro Thr Gln Pro Gln Cys Leu Met Ser Ile Ser Gly
            260                 265                 270

Tyr Leu Gly Leu Met Met Ser Leu Met Leu Thr Ser Ala Ala Ile Leu
        275                 280                 285
```

Tyr Val Phe His Phe Leu Lys Lys Ala
290 295

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence; note = synthetic construct

<400> SEQUENCE: 322
tggtgataac ctcaaggtgc t 21

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence; note = synthetic construct

<400> SEQUENCE: 323
cagagatgat gggtccggt 19

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence; note = synthetic construct

<400> SEQUENCE: 324
ggcaagtgag acactggttc 20

<210> SEQ ID NO 325
<211> LENGTH: 22
<212> TYPE: DNA
<213> ORGANISM: Artificial Sequence
<220> FEATURE:
<223> OTHER INFORMATION: Description of Artificial Sequence; note = synthetic construct

<400> SEQUENCE: 325
tcttgagaaa gtggaagacg ta 22

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence; note = synthetic construct

<400> SEQUENCE: 326
cacgaggatt gcacgtgaag a 21

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence; note = synthetic construct

<400> SEQUENCE: 327
ttccacctcg aggaagatga 20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence; note = synthetic construct

<400> SEQUENCE: 328
ggcaaaatgt tggacggtgt 20

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence; note = synthetic construct

<400> SEQUENCE: 329
ggcgtgacat atgaggtaaa c 21

<210> SEQ ID NO 330
<211> LENGTH: 19
<212> TYPE: DNA
<213> ORGANISM: Artificial Sequence
<220> FEATURE:
<223> OTHER INFORMATION: Description of Artificial Sequence; note = synthetic construct

<400> SEQUENCE: 330
ctcggctctg cagctctca 19

<210> SEQ ID NO 331
<211> LENGTH: 19
<212> TYPE: DNA
<213> ORGANISM: Artificial Sequence
<220> FEATURE:
<223> OTHER INFORMATION: Description of Artificial Sequence; note = synthetic construct

<400> SEQUENCE: 331
ctccgctact cggcctgca 19

<210> SEQ ID NO 332
<211> LENGTH: 21
<212> TYPE: DNA
<213> ORGANISM: Artificial Sequence
<220> FEATURE:
<223> OTHER INFORMATION: Description of Artificial Sequence; note = synthetic construct

<400> SEQUENCE: 332
gatgaagcga agacagacgt g 21

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence; note = synthetic construct

<400> SEQUENCE: 333
gatgaagcga agacagacgt g 21

VARIABLE LYMPHOCYTE RECEPTORS

The application claims the benefit of U.S. provisional Application 60/573,563, filed May 21, 2004, which is incorporated herein by reference in its entirety.

This invention was made with government support under NIH/NIAID Grant AI39816 and HG02526-01 and NSF Grants MCB-0317460 and IBN-0321461. The government has certain rights in the invention.

BACKGROUND OF THE INVENTION

Adaptive immune responses in jawed vertebrates are initiated when antigens are recognized by specific lymphocyte receptors. Antigen receptor diversity is generated via recombination of variable, diversity and joining gene segments in the immunoglobulin (Ig) and T cell receptor (TCR) gene loci. This combinatorial rearrangement generates vast repertoires of antibodies against unprocessed antigens and of TCRs that recognize antigen fragments presented within the cusp of major histocompatibility complex (MHC) class I and II molecules. Clonally diverse lymphocytes thus form the cornerstone of vertebrate adaptive immunity in the form of Ig bearing B cells and TCR bearing T cells that differentiate from stem cell precursors within primary hematopoietic tissues and the thymus. Cardinal elements of this recombinatorial immune system are conserved in all jawed vertebrates and the multigene TCR and Ig loci are remarkably complex even in the most basal gnathostome representatives, sharks, skates, and rays (Rast et al., 1997; Flajnik and Kasahara, 2001; Flajnik, 2002).

There is also abundant evidence for adaptive immunity in the jawless vertebrates, lamprey and hagfish, the only surviving descendents from the early vertebrate radiation (Forey and Janvier, 1993). Humoral and cell mediated types of immunologic responses have been reported for these agnathans. For example, lampreys produce specific circulating agglutinins in response to primary antigenic stimulation, make higher agglutinin levels after booster immunization (Finstad and Good, 1964; Marchalonis and Edelman, 1968; Litman et al., 1970; Pollara et al., 1970; Good et al., 1972; Hagen et al., 1985), reject second set skin allografts at an accelerated rate (Finstad et al., 1964; Perey et al., 1968; Good et al., 1972; Fujii and Hayakawa, 1983) and exhibit delayed type hypersensitivity reactions (Finstad and Good, 1964; Good et al., 1972). Agnathan adaptive immune responses have been attributed to cells that morphologically resemble the lymphocytes found in the lympho-hematopoietic tissues and blood of jawed vertebrates (Finstad and Good, 1964; Finstad et al., 1964; Perey et al., 1968; Cooper, 1971; Piavis and Hiatt, 1971; Good et al., 1972; Kilarski and Plytycz, 1981; Zapata et al., 1981; Fujii, 1982; Fujii and Hayakawa, 1983; Ardavin and Zapata, 1987; Mayer et al., 2002a). Like their mammalian counterparts, lamprey lymphocytes are more irradiation sensitive than other blood cell types (Good et al., 1972), aggregate and proliferate in response to antigenic stimulation (Finstad and Good, 1964; Cooper, 1971; Piavis and Hiatt, 1971), and express transcription factors that are involved in mammalian lymphocyte differentiation, such as PU.1/Spi-B and Ikaros (Haire et al., 2000; Shintani et al., 2000; Anderson et al., 2001; Mayer et al., 2002b). Surprisingly, however, Ig, TCR, and MHC genes have not been previously identified in jawless vertebrates or in the genome sequence of the invertebrate urochordate *Ciona intestinalis* (Azumi et al., 2003). The present invention relates to a novel lymphocyte receptor and nucleic acids that encode a novel lymphocyte receptor.

SUMMARY OF THE INVENTION

In accordance with the purposes of this invention, as embodied and broadly described herein, this invention, in one aspect, relates to polypeptides comprising a novel lymphocyte receptor or fragments thereof. The invention further relates to nucleic acids that encode the lymphocyte receptors or fragments. Further provided are methods of making and using the polypeptides and nucleic acids. Such uses include a broad range of purification, therapeutic and diagnostic methods.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1*a* shows a light scatter analysis of blood leukocytes before and after immunostimulation with antigen/mitogen cocktail. FIG. 1*b* shows sorted immunostimulated leukocytes: small lymphocytes (R1) large lymphocytes (R2) or myeloid cells (R3). Wright-Giemsa stain, 100×. Scale bar=10 μm. FIG. 1*c* shows virtual Northern blots of VLR and GAPDH (control). Amplified cDNA from tissues or sorted cells from hematopoietic organs and blood of immunostimulated and unstimulated larvae are shown. FIG. 1*d* shows a VLR stick model: signal peptide, N-terminal LRR, nine LRRs, connecting peptide, C-terminal LRR, threonine-proline rich stalk, GPI-anchor and hydrophobic tail (Clone 12.26, 417 residues, AY577974). FIG. 1*e* shows the cell surface expression of epitope-tagged VLR and FcγRIIb (control) expressed in mouse thymoma cells, treated with (+PLC) or without (−PLC) bacterial GPI-phospholipase C. FIG. 1*f* shows a 3D model of VLR diversity region viewed in two rotations (clone 12.26).

FIG. 2 shows a survey of VLR diversity in two lamprey larvae. Alignment of 20 diversity regions PCR amplified from lymphocytes. PCR primers were located in regions conserved in all VLR sequences: signal peptide 5' to LRRNT and near 3' of LRRCT. Donor animals and clone numbers are indicated. The locations of LRR motifs are also indicated. Black: 100% identity; gray: 60-99%; white: 60%. Sequences 1.3-2.10 correspond herein to SEQ ID NOs:1-20, respectively.

FIG. 4(*a*) shows blots of three lampreys (blood DNA #10, 12; carcass #13) Only animal 13 showed a polymorphic BamHI pattern. FIG. 4*b* shows a genome spread of erythrocytes pooled from 10 lampreys. Pulse-filed blot hybridization shows matching patterns for both probes, with an additional 350 kb NotI N-terminal band corresponding to a 5' gVLR duplication.

FIG. 5*a* shows motifs identified in a 57 kb gVLR contig (AY577941) melded from clones PAC16 (44 kb) and PAC3 (33 kb) that overlap over 20 kb. Dashed lines represent PAC inserts; red bars indicate N-terminal and C-terminal probes. FIG. 5*b* that PAC4 (58 kb, AY577942) aligns with the gVLR contig over 11.7 kb (nt 45,882-57,609). Cassettes of 1-3 LRRs are positioned in forward or reverse orientations: eight in the gVLR contig and 17 in PAC4. FIG. 5*c* shows LR-PCR analysis of the gVLR. DNA from blood (#10) or body carcass (#13) amplified with primers gVLR.F1+gVLR.R1 (indicated in FIG. 5*a* and FIG. 5*e*). PAC16 amplicon served as control. The ~20 kb band corresponds to the germline VLR and the ~8 kb band corresponds to mature VLRs. FIG. 5*d* shows lymphocyte specific rearrangement of mature VLRs. LR-PCR from sorted pools of 100 lymphocytes or erythrocytes. The ~14 kb band corresponds to the germline VLR and the ~1 kb band corresponds to mature VLRs that were amplified only from lymphocyte DNA. FIG. 5*e* shows an illustration of an 8 kb mature VLR amplicon.

FIG. 7 shows an ORF of a representative VLR (cDNA clone LyEST2913, AY578059). The start methionine is at nt 118-120 and the stop codon at nt 937-939. Nucleotide sequence conserved in exons 2 and 4 of the germline VLR are colored red; the diverse 5' LRRCT corresponding to exon 3 is colored green. Structural motifs are indicated above the protein sequence; GPI cleavage site is colored blue. The amino acid sequence shown corresponds to SEQ ID NO:43, and the nucleic acid sequence shown corresponds to SEQ ID No:156.

FIG. 9 shows the evolutionarily conserved agnathan VLRs. VLR amino acid sequences representing the Inshore hagfish (*Eptatretus burgeri*), Pacific hagfish (*E. stoutii*), Sea lamprey (*Petromyzon marinus*; GenBank accession AY577946), American brook lamprey (*Lampetra appendix*) and Northern brook lamprey (*Ichthyomyzon fossor*). Blue shade: 100% identity; yellow: 60-99%; green: 40-59%; red: hydrophobic tail region.

FIG. 11A shows the Pacific hagfish VLR-A. FIG. 11B shows the Inshore hagfish VLR-A. FIG. 11C shows the Pacific hagfish VLR-B. FIG. 11D shows the Inshore hagfish VLR-B. Sequence of inserts from four BAC clones, with uncaptured gaps marked. Location of VLR germline genes and flanking cassettes, in reverse or forward orientation, is indicated in kilobases (graphics are out of scale). GenScan gene predictions indicated in blue: an unrelated LRR gene upstream from the Pacific hagfish germline VLR-A gene and two flanking transposase ORFs in the Inshore hagfish VLR-A and Pacific hagfish VLR-B loci.

FIG. 12A shows a schematic presentation of germline and mature VLR genes of Pacific hagfish and Sea lamprey. Colored bars indicate coding regions; size in nucleotides; positions of PCR primers (Table 5) used to amplify hagfish VLR are indicated by arrows ad labeled F (forward) R (reverse). FIG. 12B shows Pacific hagfish VLRs PCR amplified from lymphocyte-like transcripts (RT-PCR) or blood genomic DNA. Agarose gel image; molecular weight marker indicated on the left (kilobases); position of germline and mature VLR amplicons indicated on the right. FIG. 12C shows the phylogenetic analysis of agnathan VLRs. Neighbor Joining tree of hagfish and lamprey VLR proteins (same sequences as in FIG. 9); bootstrap values are indicated. Scale bar represents 10% amino acid divergence. FIG. 12D shows a model for the evolution of agnathan VLR.

DETAILED DESCRIPTION

Figure 1:
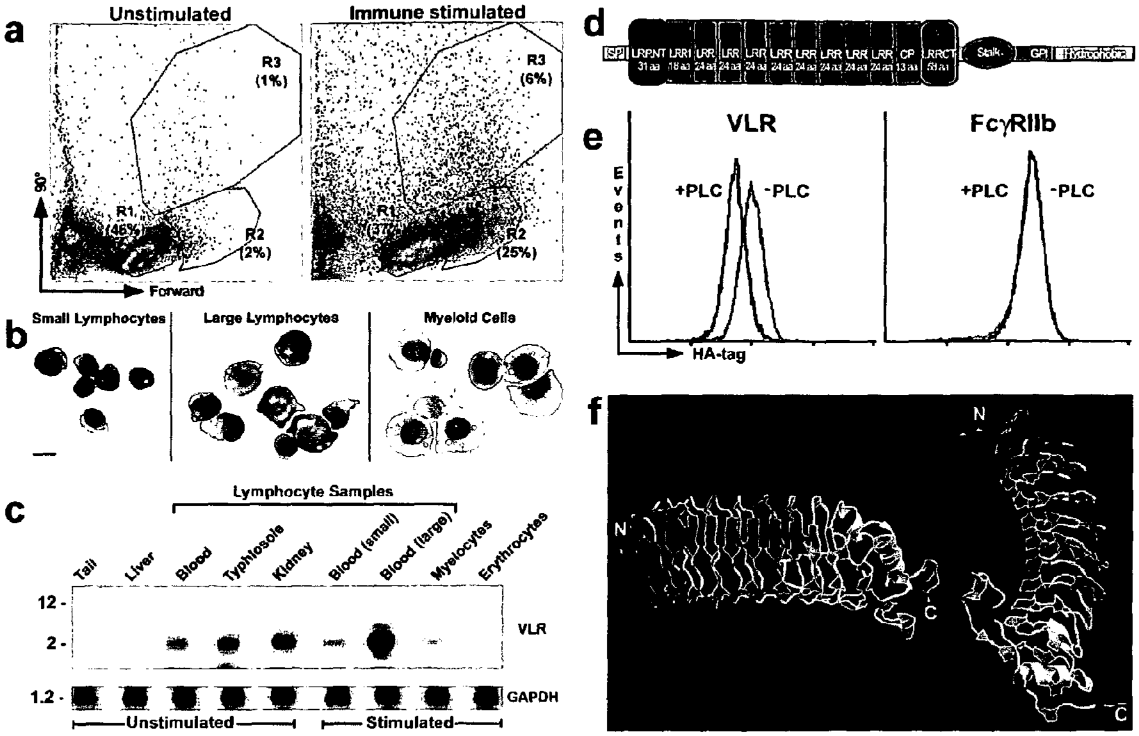
FIG. 1 shows lamprey leukocytes and VLRs.

A lymphocentric search was initiated for primordial elements of the vertebrate immune system in the sea lamprey, *Petromyzon marinus*, a modern representative of the oldest vertebrates. An earlier analysis of transcripts expressed by lymphocyte-like cells from lamprey hematopoietic tissues identified several homologs of immune system molecules (Mayer et al., 2002a; Uinuk-Ool et al., 2002; Uinuk-Ool et al., 2003), but none of the cardinal Ig superfamily receptor elements employed by jawed vertebrates for specific adaptive immunity were identified. Reasoning that activated lymphoblasts present in the blood stream were more likely to express the genes involved in adaptive responses, the present study began with a survey of the transcriptome of blood lymphocytes from immunostimulated lamprey larvae. This search revealed a novel type of highly variable lymphocyte receptors which are described here.

The present invention may be understood more readily by reference to the following detailed description of preferred embodiments of the invention and the Examples included therein and to the figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms “a,” “an” and “the” include plural referents unless the context clearly dictates otherwise. Thus, for example, reference to “a pharmaceutical carrier” includes mixtures of two or more such carriers, and the like.

Ranges may be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint.

“Optional” or “optionally” means that the subsequently described event or circumstance may or may not occur, and that the description includes instances where said event or circumstance occurs and instances where it does not.

As used herein, “polypeptide,” “protein,” and “peptide” are used interchangeably to refer to amino acid sequences.

The invention relates to a variable lymphocyte receptor (VLR), which is a polypeptide capable of somatic rearrangement, which comprises 1-12 leucine rich repeats and which can function in adaptive immunity.

The invention provides an isolated polypeptide comprising an N-terminal leucine rich repeat (LRRNT), one or more leucine rich repeats (LRRs) (referred to herein as the internal LRRs), a C-terminal leucine rich repeat (LRRCT), and a connecting peptide, wherein the connecting peptide comprises an alpha helix. The length of the polypeptide can comprise as few as about 130 amino acids or as many as about 225 amino acids. Examples of the general structure and specific sequences of the polypeptides and encoding nucleic acids are shown in figures Furthermore numerous examples of various regions (including the signal peptide, LRRNT, LRR, LRRCT, connecting peptide, stalk and hydrophobic tails) can be found in figures.

Optionally the connecting peptide is located on the N-terminal side of the LRRCT, and more specifically located between the internal LRR and the LRRCT. The connecting peptide can be linked to an internal LRR and the LRRCT. Thus disclosed herein are polypeptides comprising a LRRNT, one or more internal LRRs, a connecting peptide, and a LRRCT, in that order. Also disclosed are polypeptides, wherein the internal LRR region between the LRRNT and the LRRCT comprises 1, 2, 3, 4, 5, 6, 7, 8, or 9 leucine rich repeats, with LRR1 located adjacent to or close to the LRRNT. As used herein LRRs 1, 2, 3, 4, 5, 6, 7, 8, or 9 are considered to run from the LRRNT to the LLRCT consecutively. Thus disclosed herein are polypeptides comprising a LRRNT, 1, 1-2, 1-3, 1-4, 1-5, 1-6, 1-7, 1-8, or 1-9 LRRs, a connecting peptide, and a LRRCT, in that order.

Leucine rich repeats (LRRs) are short sequence motifs typically involved in protein to protein interactions, wherein the LRRs comprise multiple leucine residues. LRRs contain leucine or other aliphatic residues, for example, at positions 2, 5, 7, 12, 16, 21, and 24. However, it is understood and herein contemplated that the leucine or other aliphatic residues can occur at other positions in addition to or in the place of residues at positions 2, 5, 7, 12, 16, 21, and 24. For example, a leucine can occur at position 3 rather than position 2. It is also understood that structurally, the motifs form β-sheet structures. Thus, for example, a disclosed polypeptide comprising a LRRNT, 5 LRR, a LRRCT, and a connecting peptide would comprise 7 β-sheet structures and the alpha helix of the connecting peptide.

It is understood that the length and sequence of each LRR can vary from the other LRRs in the polypeptide as well as from the LRRNT and LRRCT. For example, one embodiment of the present invention are polypeptides comprising a LRRNT, 1-9 LRR, a connecting peptides, and a LRRCT, wherein the first internal LRR is LRR1, and wherein LRR1 comprises less than about 20 amino acids. Also disclosed are polypeptides, wherein LRR1 comprises about 18 amino acids. Optionally, the polypeptide further comprises LRR2-9, wherein LRR2-9 are less than about 25 amino acids each. Also disclosed are polypeptides, wherein LRR2-9 comprise about 24 amino acids each. LRR1-9 can be the same or different from each other in a given polypeptide both in length and in specific amino acid sequence.

The terminal LRRs, designated LRRNT and LRRCT, are typically longer than each internal LRR. The LRRNT and LRRCT comprise invariant regions (regions that have little variation relative to the rest of the polypeptide as compared to similar variable lymphocyte receptors). The variable regions provide the receptors with specificity, but the invariant regions and general structural similarities across receptors help maintain the protective immunity functions. The polypeptide can comprise an LRRNT, wherein the LRRNT comprises less than about 40 amino acids. Thus the LRRNT optionally comprises the amino acid sequence CPSQCSC (SEQ ID NO: 157), CPSRCSC (SEQ ID NO: 307), CPAQCSC (SEQ ID NO: 308), CPSQCLC (SEQ ID NO: 309), CPSQCPC (SEQ ID NO: 310), NGATCKK (SEQ ID NO: 311), or NEALCKK (SEQ ID NO: 312) in the presence or absence of one or more conservative amino acid substitutions. Also disclosed are polypeptides comprising a LRRCT, wherein the LRRCT is less than about 60 amino acids, and optionally 40-60 amino acids in length. In particular, specifically disclosed are polypeptides, wherein the LRRCT comprises the amino acid sequence TNTPVRAVTEASTSPSKCP (SEQ ID NO:158), SGKPVRSIICP (SEQ ID NO: 313), SSKAVLDVTEEEAAEDCV (SEQ ID NO: 314), or QSKAVLEITEKDAASDCV (SEQ ID NO: 315) in the presence or absence of conservative amino acid substitutions.

As with all peptides, polypeptides, and proteins, it is understood that substitutions in the amino acid sequence of the LRRCT and LRRNT can occur that do not alter the nature or function of the peptides, polypeptides, or proteins. Such substitutions include conservative amino acid substitutions and are discussed in greater detail below.

The disclosed compositions can also comprise a connecting peptide. Typically such peptides are short peptides less than 15 amino acids in length and comprise an alpha helix. Thus, for example, specifically disclosed are connecting peptides of 10, 11, 12, 13, 14, and 15 amino acids in length comprising an alpha helix. It is understood that the connecting peptide serves to link structural components of the polypeptide. It is further understood that the connecting peptide of the polypeptide can be linked to the LRRCT.

The polypeptides of the invention can comprise soluble or membrane bound forms. Many mechanisms exist that allow a polypeptide to be soluble or membrane bound. For example, a polypeptide missing a transmembrane domain can be secreted directly by a cell. Alternatively, a polypeptide can comprise a glycosyl-phosphatidyl-inositol (GPI) anchor which maintains the polypeptide on a membrane surface. Therefore, disclosed herein are polypeptides comprising a GPI anchor. Other mechanisms for maintaining a polypeptide bound to a surface are known in the art. For example, the polypeptide may be bound to a hydrophobic layer through single or multi-pass transmembrane regions that form covalent interactions with the lipid bilayer of the membrane. Alternatively, the polypeptide may be bound to the surface through noncovalent interactions with surface proteins.

The polypeptides of the invention can be surface bound polypeptides. Trafficking to the cell surface can be conducted by means of a signal peptide which provides a indicator to the intracellular transport machinery to deliver the polypeptide to the surface of a cell. Thus it is a further embodiment of the invention that the polypeptides of the invention comprise a signal peptide of the N-terminal of the polypeptide.

It is understood and herein contemplated that the polypeptides can comprise a hydrophobic tail.

The polypeptide can comprise a stalk region. The stalk region comprises a threonin-proline rich region and is optionally present in the membrane bound form of the polypeptide, along with the GPI anchor and the hydrophobic tail.

Examples of polypeptides of the invention include those comprising amino acid sequences of SEQ ID NOs: 1-43, 45-52, 54, 56, 60-65, 68-72, 75, 77-78, 81-119, 122-125, 129-132, 134-144, and 146-155. Sequences include GenBank Accession Numbers AY577941-AY578059 and CK988414-CK988652. Those sequences comprising the amino acid sequences of SEQ ID NOs:1-20 represent examples of full length VLRs. The sequence comprising the amino acid sequence of SEQ ID NO:43 is an example of a full length VLR with the signal peptide. Additional full length VLRs and fragments thereof comprising the amino acid sequences can be found in the figures Based on the structure taught herein for the polypeptides of the invention, it will be understood that these sequences are examples of a genus of polypeptides. It is understood that the invention includes full length VLRs and fragments thereof.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polypeptide is disclosed and discussed and a number of modifications that can be made to a number of polypeptides are discussed, specifically contemplated is each and every combination and permutation of polypeptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The polypeptides of the invention have a desired function. The polypeptides as described herein selectively bind an antigen or an agent, much as an antibody selectively binds an antigen or agent. The polypeptides optionally are variable lymphocyte receptors (naturally occurring or non-naturally occurring) or fragments or variants thereof. The term “variable lymphocyte receptors” is used herein in a broad sense and, like the term “antibody” includes various versions having various specificities. The polypeptides are tested for their desired activity using the in vitro assays described herein, or by analogous methods, after which their therapeutic, diagnostic or other purification activities are tested according to known testing methods.

The polypeptide of the invention can bind an extracellular agent (e.g., a pathogen) or antigen. Agents or antigens can include but are not limited to peptides, polypeptides, lipids, glycolipids, and proteins. Agents or antigens can originate from a variety of sources including but not limited to pathogenic organisms. The binding to an agent or antigen is understood to be selective. By “selectively binding” or “specifically binding” is meant that is binds one agent or antigen to the partial or complete exclusion or other antigens or agents. By “binding” is meant a detectable binding at least about 1.5 times the background of the assay method. For selective or specific binding such a detectable binding can be detected for a given antigen or agent but not a control antigen or agent. Thus, disclosed are polypeptides that selectively bind, for example, a viral, bacterial, fungal, or protozoan antigen or agent.

Thus specifically disclosed are polypeptides, wherein the polypeptide binds an agent, wherein the agent is a pathogenic agent. Also disclosed are polypeptides of the invention that selectively binds a pathogenic agent, wherein the pathogen is a virus. Many viruses are known to exist. Thus, the virus can be selected from the group of viruses consisting of Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed are polypeptides of the invention, wherein the pathogen is a bacterium. Many bacteria are known to exist. Specifically contemplated and herein disclosed are polypeptides that selectively bind a pathogen, wherein the pathogen is a bacterium selected from the list of bacteria consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetii*, other Rickettsial species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species.

Also disclosed are polypeptides of the invention that selectively bind a pathogen, wherein the pathogen is a protozoan or other parasite. Many parasitic infections are known to exist. Specifically contemplated and herein disclosed are polypeptides that selectively bind a pathogen, wherein the pathogen is a parasitic infection selected from the group consisting of *Toxoplasma gondii, Plasmodium falciparum, Plasmodium vivax, Plasmodium malariae*, other *Plasmodium* species, *Trypanosoma brucei, Trypanosoma cruzi, Leishmania major*, other *Leishmania* species, *Schistosoma mansoni*, other *Schistosoma* species, and *Entamoeba histolytica.*

Also disclosed are polypeptides of the invention that selectively bind a pathogen, wherein the pathogen is a fungus. Many fungi are known to exist. Specifically contemplated and herein disclosed are polypeptides, wherein the pathogen is a fungi selected from the group fungi consisting of *Candida albicans, Cryptococcus neoformans, Histoplama capsulatum, Aspergillus fumigatus, Coccidiodes immitis, Paracoccidiodes brasiliensis, Blastomyces dermitidis, Pneomocystis carnii, Penicillium marneffi*, and *Alternaria alternata.*

The polypeptide of can also selectively bind to toxins. Herein "toxins" refer to any chemical or biological agent that effectively destroys any cell that it (the toxin) contacts. Notable examples of toxins include ricin, pertussis toxin, sarin, bacterial endotoxin, toxic shock syndrome toxin 1, cholera toxin, and snake venom toxins. Thus, specifically discloses are polypeptides that bind to a toxin.

The polypeptides described herein can be modified and varied so long as the desired function is maintained. It is understood that one way to define any known variants and derivatives or those that might arise, of the disclosed genes and proteins herein is through defining the variants and derivatives in terms of homology to specific known sequences. For example SEQ ID NO: 1 sets forth a particular amino acid sequence of the polypeptide encoded by any number of nucleic acids of the invention. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | Ala A |
| allosoleucine | AIle |
| arginine | Arg R |
| asparagine | Asn N |
| aspartic acid | Asp D |
| cysteine | Cys C |
| glutamic acid | Glu E |
| glutamine | Gln Q |
| glycine | Gly G |
| histidine | His H |
| isolelucine | Ile I |
| leucine | Leu L |
| lysine | Lys K |
| phenylalanine | Phe F |
| proline | Pro P |
| pyroglutamic acidp | pGlu |
| serine | Ser S |
| threonine | Thr T |
| tyrosine | Tyr Y |
| tryptophan | Trp W |
| valine | Val V |

TABLE 2

| Amino Acid Substitutions<br>Original Residue Exemplary Conservative Substitutions, others are known in the art. |
|---|
| Ala; Ser |
| Arg; Lys; Gln |
| Asn; Gln; His |
| Asp; Glu |
| Cys; Ser |
| Gln; Asn, Lys |
| Glu; Asp |
| Gly; Pro |
| His; Asn; Gln |
| Ile; Leu; Val |
| Leu; Ile; Val |
| Lys; Arg; Gln; |
| Met; Leu; Ile |
| Phe; Met; Leu; Tyr |
| Ser; Thr |
| Thr; Ser |
| Trp; Tyr |
| Tyr; Trp; Phe |
| Val; Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

As used herein, the term "variable lymphocyte receptor" or "variable lymphocyte receptors" can also refer to polypeptides that have been modified to have reduced immunogenicity when administered to a subject. For example, human amino acid sequences may be inserted within or added to the polypeptide to make a version less immunogenic to a human subject, much like antibodies are humanized. Many non-human variable lymphocyte receptors (e.g., those derived from lampreys, mice, rats, or rabbits) can be naturally antigenic in humans, and thus can give rise to undesirable immune responses when administered to humans. Therefore, the use of modified polypeptides in the methods of the invention can serve to lessen the chance that a polypeptide administered to a human will evoke an undesirable immune response.

Modification techniques can involve the use of recombinant DNA technology to manipulate the DNA sequence encoding one or more polypeptide regions of the variable lymphocyte receptor molecule. Accordingly, the humanized form of the variable lymphocyte receptor (or a fragment thereof) is a chimeric variable lymphocyte receptor, preferably the antigen (agent)-binding portion of the variable lymphocyte receptor) which contains a portion of an antigen (agent) binding site from a non-human (donor) variable lymphocyte receptor integrated into human (recipient) amino acid sequence.

It is understood that the nucleic acids that can encode those protein sequences, variants and fragments thereof are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Humanized variable lymphocyte receptors can also contain amino acid sequences which are found neither in the recipient variable lymphocyte receptor nor in the imported human sequences.

The polypeptides of the invention can also used to make fusion proteins. The polypeptides can serve a targeting function in the fusion protein. Thus the polypeptide of the invention can be conjugated to or otherwise linked by recombinant engineering to a second moiety. The second moiety can comprise a toxin, for example, if cell killing is desired. Thus, for example, the polypeptide that selectively binds a protozoan can target the protozoan and the toxin moiety of the fusion protein can kill the cell. Similarly, the polypeptide of the invention can perform a delivery function. Thus the second moiety can be a therapeutic agent.

The polypeptide of the invention can be linked to a detectable tag. A "detectable tag" is any tag that can be visualized with imaging or detection methods, in vivo or in vitro. The detectable tag can be a radio-opaque substance, radiolabel, a chemoluminescent label, a fluorescent label, or a magnetic label. The detectable tag can be selected from the group consisting of gamma-emitters, beta-emitters, and alpha-emitters, gamma-emitters, positron-emitters, X-ray-emitters and fluorescence-emitters. Suitable fluorescent compounds include fluorescein sodium, fluorescein isothiocyanate, phycoerythrin, and Texas Red sulfonyl chloride, Allophycocyanin (APC), Cy5-PE, CY7-APC, and Cascade yellow.

Suitable radioisotopes for labeling include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18.

Optionally the detectable tag can be visualized using histochemical techniques, ELISA-like assays, confocal microscopy, fluorescent detection, cell sorting methods, nuclear magnetic resonance, radioimmunoscintigraphy, X-radiography, positron emission tomography, computerized axial tomography, magnetic resonance imaging, and ultrasonography.

Alternatively, the polypeptide can be biotintylated and a subsequent detectable label like a fluorescently labeled strepavidin can be used to indirectly detect the polypeptide. Biotin is detected by any one of several techniques known in the art. For example, the biotin is detectable by binding with a fluorescence-labeled avidin and the avidin is labeled with a phycoerythrin or a catenated fluorescent label to increase the signal associate with each binding event.

Optionally the polypeptide is bound to a solid support such as a slide, a culture dish, a multiwell plate, column, chip, array or stable beads. An "array" includes one or more multiwell arraying means such as microplates or slides.

Optionally the polypeptide is bound to a mobile solid support, e.g., beads, which can be sorted using cell sorting technology. "Mobile solid support" refers to a set of distinguishably labeled microspheres or beads. Preferably, the microspheres are polystyrene-divinylbenzene beads. Sets of microspheres marked with specific fluorescent dyes and having specific fluorescent profiles can be obtained commercially, for example, from Luminex Corporation (Austin, Tex.).

The invention also provides a plurality of polypeptides of the invention. Optionally the LRRs of the polypeptides are highly variable across polypeptides. Thus, the plurality can include polypeptides with different binding specificities, based on the variability of the internal LRRs.

Also provided are kits that include a container with polypeptides of the invention or a stable or mobile solid support with polypeptides of the invention. Optionally the polypeptides are bound to the solid support or the kit. Optionally the kit contains the polypeptides the sold support, and a linking means for binding the polypeptide to the solid support.

The invention provides isolated nucleic acids that encode the polypeptides of the invention. One example of such a nucleic acid comprises the nucleotide sequence of SEQ ID NO:156, the ORF of a representative VLR. Other examples of nucleic acids that encode VLRs or fragments thereof include SEQ ID NO:44, SEQ ID NO:53-55, SEQ ID NO:57-59, SEQ ID NO:66-67, SEQ ID NO:73-74, SEQ ID NO:76, SEQ ID NOs:79-80, and SEQ ID NOs:172-302. There are a variety of sequences related to the VLR gene having Genbank Accession Numbers AY57791-AY578059, AY964719-AY964931, AY965520-AY965612, AY965658-AY965681, and CK988414-CK988652. These sequences are herein incorporated by reference in their entireties as well as for individual subsequences (regions or fragments) contained therein.

Such nucleic acid sequences are provided by way of example of the genus of nucleic acids and are not intended to be limiting. Also provided are expression vectors comprising these nucleic acids, wherein the nucleic acids are operably linked to an expression control sequence. Further provided are cultured cells comprising the expression vectors. Such expression vectors and cultured cells can be used to make the polypeptides of the invention.

There are a variety of molecules disclosed herein that are nucleic acid based, including for example the nucleic acids that encode, for example VLR or fragments or variants thereof. The disclosed nucleic acids are made up of nucleotides, nucleotide analogs, or nucleotide substitutes.

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to $—O[(CH_2)_nO]_m CH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to U.S. Pat. Nos. 3,687,808; 4,469,863; 4,476,301; 5,023,243; 5,177,196; 5,188,897; 5,264,423; 5,276,019; 5,278,302; 5,286,717;

5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. *Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med.* Chem. Let., 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochem. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Disclosed are compositions including primers and probes, which are capable of interacting with the VLR gene, or comparable genes. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner.

The size of the primers or probes for interaction with the VLR gene in certain embodiments can be any size that supports the desired enzymatic manipulation of the primer, such as DNA amplification or the simple hybridization of the probe or primer. A typical VLR primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The polypeptides and nucleic acids of the invention can be used in a variety of techniques. For example, the polypeptides can be used to detect a selected agent, to block the activity of a selected agent, to purify an agent, as an imaging tool, and as a therapeutic agent.

Provided herein are methods of detecting an agent in a sample, comprising the steps of contacting the sample with the polypeptide, under conditions in which the polypeptide can bind to the agent in the sample, and detecting the polypeptide bound to the agent in the sample. The bound polypeptide indicates the agent in the sample. Detection methods are well known in the art. For example, the polypeptide can be labeled with a detectable tag as described above. The diction method can be used to note the presence or absence of an agent in the sample. The detection method, however, can be further combined with quantification methods. In vitro assay methods include colorometric assays such as ELISA that allow the quantification of the agent based on a comparison to a control sample or samples of known agent quantity which can be used to establish an amount relative to a standard. The methods can also include radiometric assays that allow for quantification based on emitted radiation and fluorescent assays or any means of visualization and quantification described above.

The sample can be any sample to be tested including any biologic sample. Samples can include fluid samples (like water, blood, urine, etc.), tissue samples, culture samples, cellular samples, etc.

The polypeptides of the invention may also be used to block the activity of any agent to which it binds, comparable to a blocking antibody. Thus also disclosed are methods of blocking the activity of an agent, comprising contacting the agent with the polypeptide of the invention under conditions for the polypeptide to bind the agent. The binding of the polypeptide to the agent blocks the activity of the agent. The contacting step can be in vivo or in vitro. Thus, for example, to reduce contamination of a sample, a polypeptide that binds a toxin can be added to the sample and block the toxin activity.

The polypeptides of the invention may also be used to promote the activity of an agent to which it binds, comparable to an agonistic antibody. Thus also disclosed are methods of promoting the activity of an agent, comprising contacting the agent with the polypeptide of the invention under conditions for the polypeptide to bind the agent. The binding of the polypeptide to the agent promotes the activity of the agent.

The polypeptides disclosed herein can be used to determine the function of a gene with unknown function. Thus, disclosed herein are methods of using the disclosed polypeptides in protein knock-down assays. For example, the disclosed polypeptides can be expressed in the cytoplasm of a cell which comprises a gene of unknown function. When the RNA transcript is being translated in the cytoplasm of the cell, the disclosed polypeptides can bind the protein product of the gene question. By monitoring the effect the loss of protein expression has on the cell, the proteins function can be determined. Thus, specifically disclosed are polypeptides specific for a gene product of unknown function. Also are methods of determining the function of a gene comprising introducing a polypeptide specific for the protein product of the gene into the cytoplasm of a cell expressing the gene and monitoring the effect due to the loss of protein product of the gene with unknown function.

The polypeptides of the invention can also be used in imaging methods. For example, the invention provides an imaging method comprising administering to a subject an effective amount of the polypeptide and detecting the localization of the bound polypeptide in the subject. Examples of imaging methods are described above.

The invention also provides methods of purification. Disclosed herein are methods of purifying an agent from a sample comprising contacting the sample with a polypeptide under conditions for the polypeptide to bind the agent and form a polypeptide/agent complex; and isolating the agent from the polypeptide/agent complex. For example, the polypeptide can be bound to a column and the sample can be passed through the column under conditions that allow the agent in the sample to bind to the bound polypeptide. The agent can subsequently be eluted from the column in a desired eluant. The purification methods would be useful as research methods and as commercial methods. For example, such a method would be useful in removing contaminants from pharmacological compounds.

The polypeptides can also be used in therapeutic methods. For example, provided herein is a method of reducing or preventing a pathogenic effect in a subject comprising administering to the subject an effective amount of a polypeptide that binds a pathogen. Also provided is a method of blocking or promoting the activity of an agent so as to reduce deleterious effects or promote positive effects.

Provided herein are composition comprising the polypeptides or nucleic acids of the invention and a pharmaceutically acceptable carrier. The compositions of the invention can also be administered in vivo. The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, “topical intranasal administration” means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as “stealth” and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

By "pharmaceutically acceptable" is meant a material that is not biologically or otherwise undesirable, i.e., the material may be administered to a subject, along with the polypeptide of the invention, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the variable lymphocyte receptor, which matrices are in the form of shaped articles, e.g., films, liposomes or microparticles. It will be apparent to those persons skilled in the art that certain carriers may be more preferable depending upon, for instance, the route of administration and concentration of variable lymphocyte receptor being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously, for example. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any contraindications. Dosage can vary, and can be administered in one or more dose administrations daily, for one or several days.

The variable lymphocyte receptors and variable lymphocyte receptor fragments and variants of the invention can also be administered to patients or subjects as a nucleic acid preparation (e.g., DNA or RNA) that encodes the variable lymphocyte receptor or variable lymphocyte receptor fragment or variant, such that the patient's or subject's own cells take up the nucleic acid and produce and secrete the encoded variable lymphocyte receptor or variable lymphocyte receptor fragment.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver nucleic acids into cells (e.g., a plasmid), or as part of a general strategy to deliver genes, e.g., as part of recombinant retrovirus or adenovirus (Ram et al. *Cancer Res.* 53:83-88, (1993)). As used herein, plasmid or viral vectors are agents that transport the disclosed nucleic acids, such as VLR into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

A retrovirus is an animal virus belonging to the virus family of Retroviridae, including any types, subfamilies, genus, or tropisms. Retroviral vectors, in general, are described by Verma, I. M., Retroviral vectors for gene transfer. *In Microbiology*-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Mourner, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, Cell 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970);

Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Molecular genetic experiments with large human herpesviruses have provided a means whereby large heterologous DNA fragments can be cloned, propagated and established in cells permissive for infection with herpesviruses (Sun et al., *Nature genetics* 8: 33-41, 1994; Cotter and Robertson, *Curr Opin Mol Ther* 5:633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA > 220 kb and to infect cells that can stably maintain DNA as episomes.

Other useful systems include, for example, replicating and host-restricted non-replicating vaccinia virus vectors.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via VLRs, antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). These techniques can be used for a variety of other specific cell types. Vehicles such as "stealth" and other antibody or VLR conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273:113 (1978)). The immediate early promoter of the human cytomegalovirus is conveniently obtained as a HindIII E restriction fragment (Greenway, P. J. et al., *Gene* 18:355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78:993 (1981)) or 3' (Lusky, M. L., et al., *Mol. Cell. Bio.* 3:1108 (1983)) to the transcription unit. Furthermore, enhancers can be within an intron (Banerji, J. L. et al., *Cell* 33:729 (1983)) as well as within the coding sequence itself (Osborne, T. F., et al., *Mol. Cell. Bio.* 4:1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hygromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1:327 (1982)), mycophenolic acid, (Mulligan, R. C. and Berg, P. *Science* 209:1422 (1980)) or hygromycin, (Sugden, B. et al., *Mol. Cell. Biol.* 5:410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

In the methods described above which include the administration and uptake of exogenous DNA into the cells of a subject (i.e., gene transduction or transfection), the nucleic acids of the present invention can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof) of the invention. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these or other commonly used gene transfer methods.

As one example, if the antibody-encoding nucleic acid of the invention is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

The invention further provides a method of making a polypeptide of the invention comprising culturing a cell comprising a vector comprising a nucleic acid that encodes the polypeptide and purifying the polypeptide from the cell or from the medium. Further provided are methods of making a polypeptide of the invention using protein synthesis techniques.

Also disclosed are methods of screening for one or more variable lymphocyte receptors in a subject comprising identifying in the subject one or more polypeptides comprising an N-terminal leucine rich repeat (LRRNT), one or more leucine rich repeats (LRRs), a C-terminal leucine rich repeat (LRRCT), and a connecting peptide, wherein the connecting peptide comprises an alpha helix.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Variable Lymphocyte Receptors in Sea Lamprey Analysis of Transcripts from Immunostimulated Blood Lymphocytes In order to survey the transcriptome of activated lymphocytes, lamprey larvae were stimulated by intraperitoneal injections of an antigen/mitogen cocktail, including live *E. coli* bacteria, sheep erythrocytes, phytohemagglutinin and pokeweed mitogen, two to four times at weekly intervals. The fraction of large lymphocytes among peripheral blood leukocytes three days after the second booster stimulation was 13-fold greater than in unstimulated individuals, and the fraction of myeloid cells was also 6-fold greater (FIG. 1*a*). Compared to the small blood lymphocytes, the large lymphocytes were nearly double in size, had extensive azurophilic cytoplasm and featured prominent nucleoli (FIG. 1*b*). These cells were sorted and used to construct cDNA libraries enriched in messages of activated lymphocytes by subtraction against cDNA from lamprey activated myeloid cells or erythrocytes.

Figure 6:
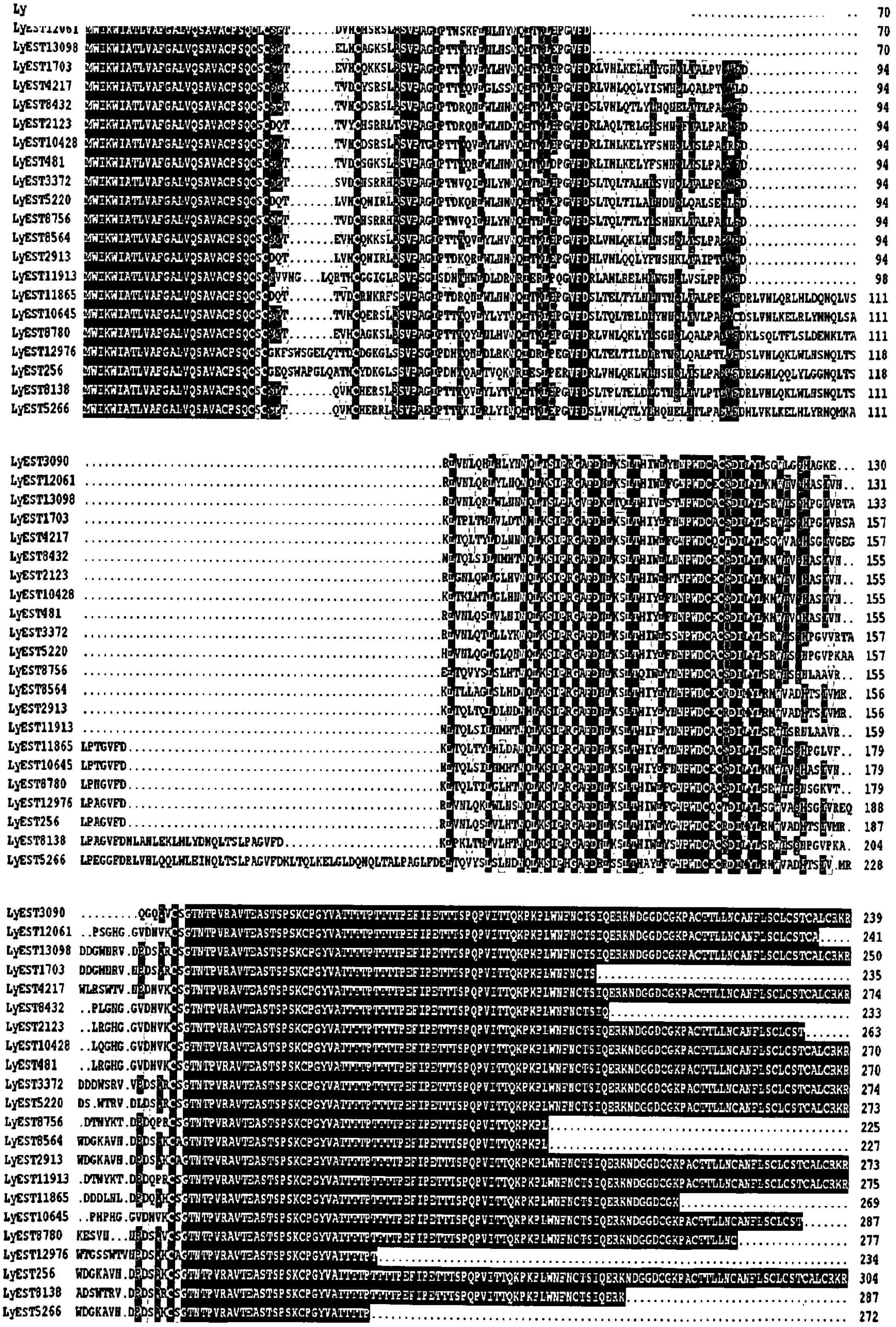
FIG. 6 shows the multiple alignment of 22 VLR proteins predicted from EST clones (single pass 5' sequence, some incomplete C-termini). Black: full identity; yellow 80-99%; green: 60-79%; white<60%. The amino acid sequences for LyEST3090-LyEST5266 correspond to SEQ ID NOs:21-42, respectively.

The most abundant group of sequences identified among 1,507 clones from the subtracted libraries predicted 319 proteins with variable numbers of diverse leucine-rich repeat (LRR) motifs, that clustered with a set of 52 LRR-containing expressed sequence tags (EST) from a survey of unstimulated lymphocyte transcripts. After purging the 3' end sequences, a set of 239 uniquely diverse LRR proteins were identified, 22 of which encoded most or all of the open reading frames (ORF) of 239-304 aa (FIG. 6). These lamprey proteins were provisionally named variable lymphocyte receptors (VLR) because each of these 239 sequences was unique and their transcripts were found to be expressed predominantly by lymphocytes (FIG. 1*c*). Lymphocytes from hematopoietic tissues showed highest VLR levels in unstimulated animals, and immune stimulation resulted in enhanced VLR transcription by the large blood lymphocytes. The basic composition of these VLRs included a conserved signal peptide, N-terminal LRR (LRRNT), a variable number of diverse LRRs, a connecting peptide followed by a C-terminal LRR (LRRCT) and a conserved C-terminus composed of a threonine- and praline rich stalk, a generic glycosyl-phosphatidyl-inositol (GPI)-anchor site and a hydrophobic tail (FIG. 1*d* and FIG. 7). When a retroviral construct encoding an epitope tagged VLR was transfected into a mammalian cell line, immunofluorescence analysis confirmed the cell surface localization of the protein, and treatment with bacterial GPI-specific phospholipase C significantly reduced the level of cell surface expression (FIG. 1*e*) and released VLR protein into the supernatant. The longest VLR sequence consisting of 11 LRRs was threaded on the crystal structure coordinates of related LRR proteins to generate a 3-dimensional structural model (Schwede et al., 2000). The model provides a concave solenoid structure in which nine β-sheets are capped on both ends by the LRRNT and LRRCT (FIG. 1*f*), similar to the model predicted for Toll-like receptor (TLR) ectodomains (Bell et al., 2003).

The VLR Repertoire is Highly Diverse in Individual Lampreys

Figure 8:
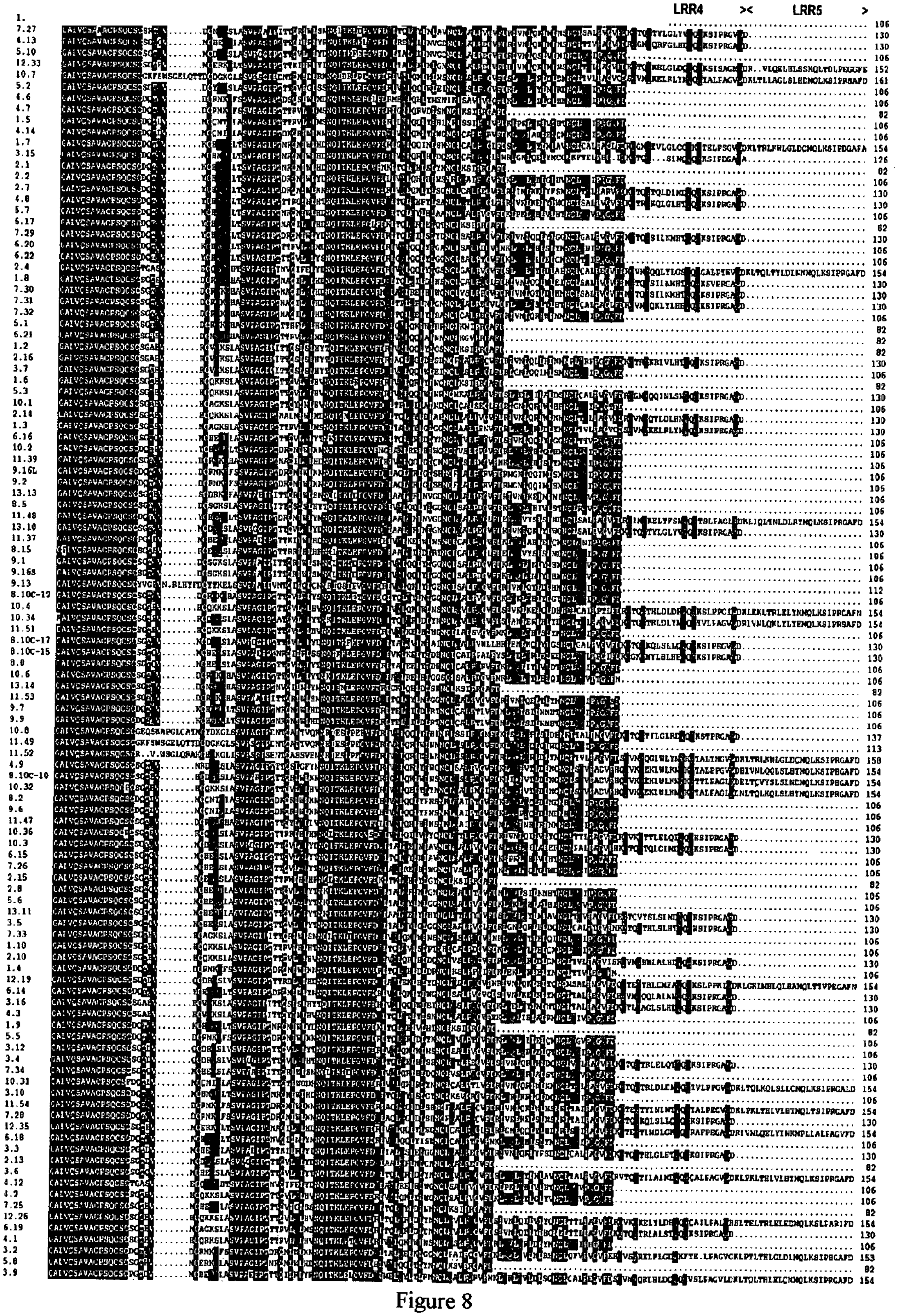
FIG. 8 shows the multiple alignment of 112 VLR diversity regions PCR amplified from 13 lampreys. Genomic and RT-PCR clones from immunostimulated and unstimulated lampreys. Unstimulated animals: animal designated #1-4 (N=41), sorted single lymphocytes from animal designated #8 (N=4) and clones from a pool of 10 cells from animal designated #8. 10C (N=4); Immune stimulated animals: from animals designated #5-7 (N=27) and sorted single lymphocytes from animal designated #9 (N=8) including one isolate with two VLRs (9.16S, 9.16L); Mature VLRs: larval genomic DNA extracted from blood designated #10-13 (N=28) or carcass (#11, 13). Black: 80-100% identity; yellow 60-79%; green: 40-59%; white <40%. From the top of the alignment, the amino acid sequence for 1.1 corresponds to SEQ ID NO:13, amino acid sequences 7.27-4.7 correspond to SEQ ID NOs:45-52, amino acid sequence 1.5 corresponds to SEQ ID NO:12, amino acid sequence 4.14 corresponds to SEQ ID NO:54, amino acid sequence 1.7 corresponds to SEQ ID NO:8, amino acid sequence 3.15 corresponds to SEQ ID NO:56, amino acid sequence 2.1 corresponds to SEQ ID NO:5, amino acid sequence 2.2 corresponds to 10, amino acid sequence 2.7 corresponds to SEQ ID NO:11, amino acid sequences 4.8-6.22 correspond to SEQ ID NOs:60-65, amino acid sequences 2.4 corresponds to SEQ ID NO:3, amino acid sequence 1.8 corresponds to SEQ ID NO:2, amino acid sequences 7.3-6.21 correspond to SEQ ID NOs:68-72, amino acid sequence 1.2 corresponds to SEQ ID NO:5, amino acid sequence 2.14 corresponds to SEQ ID NO:6, amino acid sequence 3.7 corresponds to SEQ ID NO:75, amino acid sequence 1.6 corresponds to SEQ ID NO:7, amino acid sequence 5.3 corresponds to SEQ ID NO:77, amino acid sequence 10.1 corresponds to SEQ ID NO:78, amino acid sequence 2.14 corresponds to SEQ ID NO:4, amino acid sequence 1.3 corresponds to SEQ ID NO:1, amino acid sequences 6.16-7.26 correspond to SEQ ID NOs:81-119, amino acid sequence 2.15 corresponds to SEQ ID NO:14, amino acid sequence 2.8 corresponds to SEQ ID NO:17, amino acid sequences 5.6-7.33 correspond to SEQ ID NOs: 122-125, amino acid sequence 1.10 corresponds to SEQ ID NO:19, amino acid sequence 2.10 corresponds to SEQ ID NO:20, amino acid sequence 1.4 corresponds to SEQ ID NO:15, amino acid sequences 12.19-4.3 correspond to SEQ ID NOs:129-132, amino acid sequence 1.9 corresponds to SEQ ID NO:16, amino acid sequences 5.5-3.3 correspond to SEQ ID NOs:134-144, amino acid sequence 2.13 corresponds to SEQ ID NO:18, and amino acid sequences 3.6-3.9 correspond to SEQ ID NOs:146-155.
Figure 8:
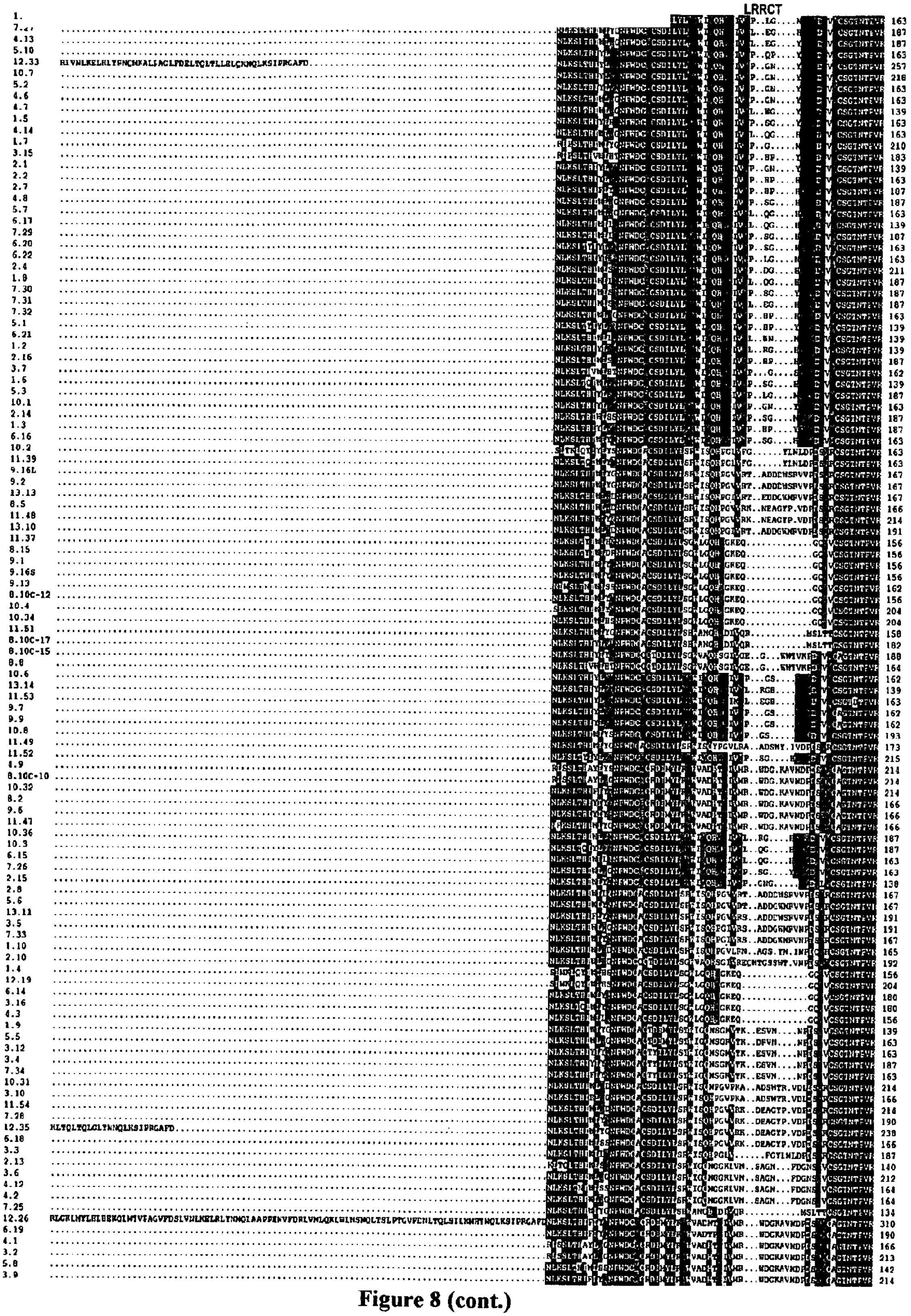

The VLR diversity was surveyed in individual lampreys by RT-PCR. Blood leukocytes mRNA from three immunostimulated and four unstimulated larvae was amplified with primers flanking the VLRs diversity region. Sequencing of ~10 clones per animal yielded 69 unique VLRs and only two identical clones from one individual. Variable sequences of 20 VLRs from two animals illustrate the protein diversity (FIG. 2; entire set included in FIG. 3 and FIG. 8). The size variation, 134-214 aa, is primarily due to differences in number of LRR modules. Each sequence contains an LRRNT, an 18 aa LRR1, 1-9 LRRs almost invariably 24 aa long, a 13 aa connecting peptide and C-terminal LRRCT; the LRRNTs have 30-38 aa and the LRRCTs 48-58 aa. While regions of pronounced sequence diversity are evident for each LRR motif, the first seven residues in LRRNT and the last 20 residues in LRRCT are nearly invariant.

To assess VLRs diversity at the level of individual lymphocytes RT-PCR with primers flanking the whole ORF was used. Single cell isolates were sorted from the blood of an immunostimulated and an unstimulated larvae. Analysis of the PCR products obtained from six single cell reactions from the unstimulated animal and seven reactions from the immunostimulated larva showed that 12 of the 13 lymphocytes expressed a single VLR (FIG. 3), and five of six VLR clones from a control pool of 10 unstimulated cells were unique. One cell isolate yielded two VLRs (9.16S, 9.16L), but the possibility that this isolate contained two lymphocytes cannot be excluded. Three of the VLRs had in-frame stop codons predicting truncated proteins. Interestingly, combinations of identical VLRs were identified among five lymphocytes from the immunostimulated larva (9.1=9.16S; 9.2=9.16L; 9.7=9.9). The analysis of blood samples from three additional immunostimulated larvae (#5-7) revealed only unique VLRs (N=27). These findings are indicative of monoallelic expression of the diverse VLRs, and provide preliminary evidence for clonal expansion of VLR-bearing lymphocytes.

Complexity of the VLR Locus

Figure 4:
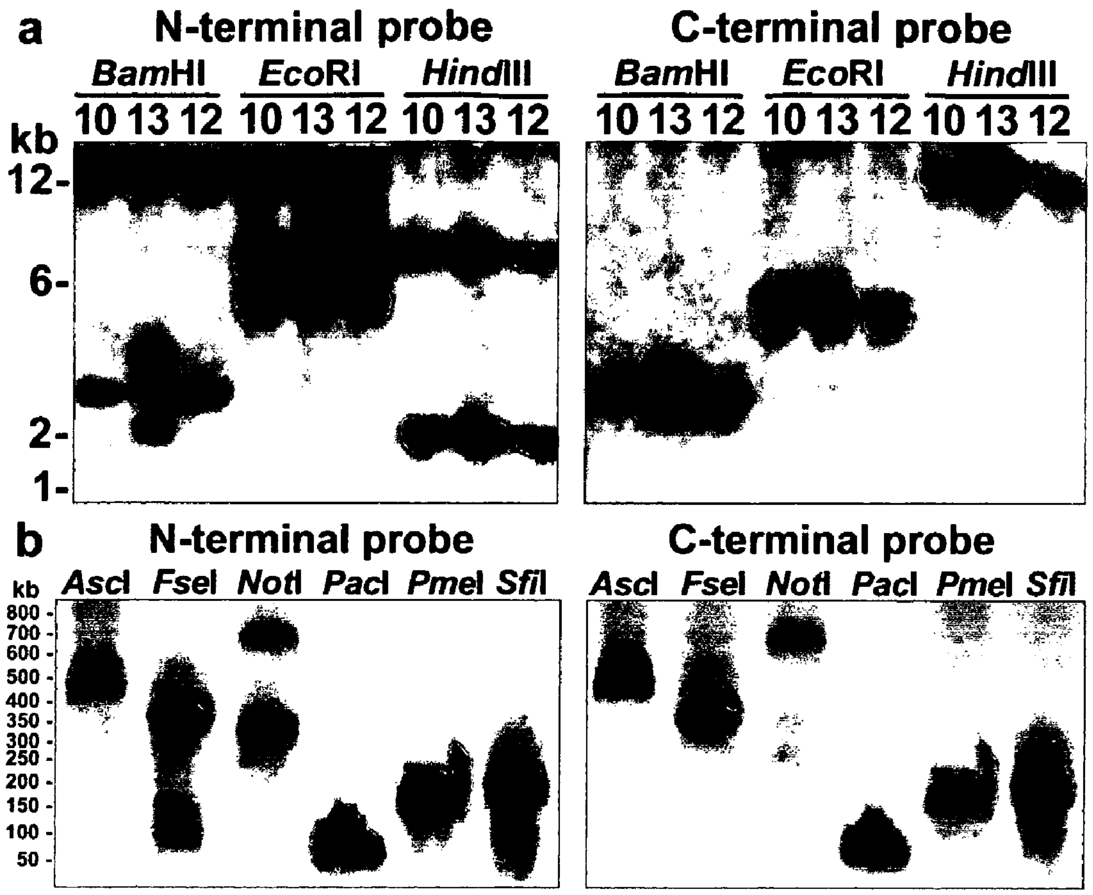
FIG. 4 shows VLR genome blots of restriction-enzyme digested DNA that were hybridized with VLR N-terminal or C-terminal probes.
Figure 5:
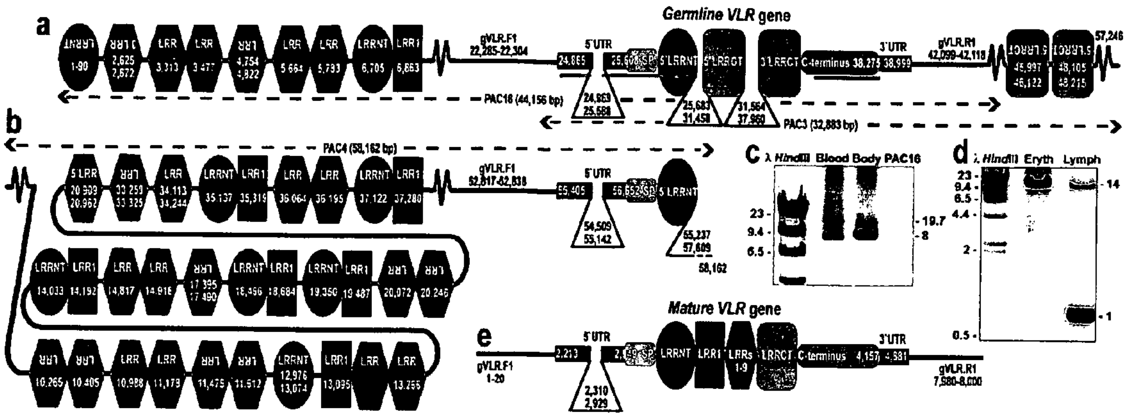
FIG. 5 shows the genomic organization of the VLR locus.

Genome blot hybridization with a conserved C-terminal probe revealed a single band (FIG. 4*a*). The N-terminal probe, consisting of the conserved 5' UTR and signal peptide, reacted with 2-3 bands depending upon the restriction enzyme employed, except for an individual whose blot showed 2 additional BamHI bands. In addition, a genomic pulse-field CHEF blot revealed a single hybridization band with the C-terminal probe in all six digests, whereas the N-terminal probe produced a matching pattern with one additional 350 kb NotI band (FIG. 4*b*). These findings indicate a single VLR locus, with the N-terminus and C-terminus of the germline VLR gene (gVLR) contained within 100-150 kb of the genome (FIG. 4*b*; PacI digest). To further characterize the locus, these probes were used to screen a large insert sea lamprey P1 bacterial artificial chromosome (PAC) library constructed from erythrocyte DNA of one adult. In an analysis of five PACs that hybridized with both probes, a single 14 kb VLR gene (gVLR) amplicon was identified by long range PCR (LR-PCR) using the ORF-flanking primers. Restriction-enzyme analysis of the PCR products revealed identical EcoRI bands and two allelic BamHI patterns. PAC clones representing the two gVLR alleles were sequenced, PAC3 and PAC16 with 33 and 44 kb inserts respectively. Their sequences overlapped a 20 kb region containing the gVLR; PAC16 extended 25 kb upstream from the gVLR and PAC3 extended 18 kb downstream. The overlap region between PACs 3 and 16 was nearly identical, except for short deletions in the gVLR of PAC16 (24, 43 and 78 bp). These sequences were therefore melded into a gVLR contig preserving the slightly longer sequence of PAC3 (FIG. 5*a*).

The gVLR in the PAC3/16 contig consist of 4 exons. The first contains part of the 5' UTR; exon 2 contains the rest of the 5' UTR, a signal peptide and the 5' half of LRRNT; exon 3 encodes the 5' half of LRRCT, and exon 4 encodes the 3' half of LRRCT, the C-terminus and 3' UTR. Canonical eukaryotic splice sites were identified only in the 5' UTR intron, while other exon/intron boundaries in the gVLR were determined by alignment to cDNA sequences. Notably, the gVLR sequence did not contain a 3' LRRNT, LRR1 or any of the 24 aa LRRs. Upstream from this gVLR, six cassettes of variable LRR modules were identified, singlet or doublet, including LRRNT, LRR1 and LRR positioned either in forward or reverse orientation. These LRR cassettes spanned the first 6 kb of the contig, while two diverse 5' LRRCT cassettes were located 7 kb downstream from the gVLR.

Another clone, PAC4, hybridized only with the N-terminal probe but it was found to encode multiple LRRs that were identified by PCR with LRRNT and LRR1 consensus primers. The entire insert was 58 kb long (FIG. 5*b*), and the sequence overlapped 11.7 kb of the gVLR contig with minor gaps (four gaps of 210-738 bp in PAC4 and eight gaps of 25-55 bp in the PAC3/16 contig). The overlap extended into the intervening sequence between gVLR exons 2 and 3, but the 553 bp terminal sequence of PAC4 was unique. Seventeen cassettes of 1-3 diverse LRR modules, 30 in total, were encoded in a 31 kb region in PAC4 located 15 kb upstream from the partial gVLR. Comparison of the PAC3/16 gVLR contig and PAC4 sequences revealed additional 1-5 kb regions with >90% identity, but these were disrupted by unrelated sequences. PAC4 could represent either a duplication of ~12 kb, encompassing the 5' flank and about half of the gVLR, or a highly divergent VLR allele. To distinguish between these possibilities the pattern of genomic hybridization was compared with the N-terminal probe (FIG. 4*a*) to the map of restriction sites in the gVLRs from these PAC inserts. The blot pattern and restriction map were compatible for all fragments except for a 5.7 kb HindIII fragment from PAC4 that was different than the 2 kb band in the blot (FIG. 4*a*). In view of such limited variability amongst three blotted genomes and the genome from the PAC library, PAC4 seems unlikely to represent a polymorphic gVLR allele. Limited VLR allelic variation would be consistent with other evidence of low allelic diversity even in microsatellite loci (Bryan et al., 2003), indicating the sea lamprey populations in the North American Great Lakes and other landlocked populations are highly inbred. The analysis thus indicates the single lamprey gVLR locus harbors an additional copy of the N-terminal half of the gVLR.

Somatic gVLR Rearrangement Generates Diverse Mature VLRs

Figure 3:
FIG. 3 shows an assessment of VLR protein diversity in 13 individual larvae. Genetic distance dendrogram of 112 VLR diversity regions from cDNA and genomic PCR clones. Larvae numbers and clone numbers (e.g., 6.20=donor 6, clone 20) are indicated in red for immunostimulated (N=27) and green for unstimulated (N=41) donors. Asterisk (*) indicates clones derived from single cell isolates (N=12), including two VLRs from one isolate (9.16S, 9.16L); and clones derived from a control 10-cell pool are denoted 10C (N=4). Mature VLR sequences derived from genomic DNA are in blue (N=28; blood #10, 12; carcass #11, 13). The mean diversity for the entire set is 1.36±0.03, ranging 0.28-0.54 within the groups of sequences from 13 individuals.

When larval DNA samples were analyzed by PCR amplification with primers flanking the VLR diversity region, six unique intron-less VLR ORFs were obtained (FIG. 3, animals #10, 12). In accordance with this intriguing finding, PCR amplification of larval DNA samples with the ORFflanking primers produced VLR clones of 1.5-2 kb including the 5' UTR intron, revealing unique sequence in 13 of 14 clones (#10, 11). Because these genomic PCR clones contained uninterrupted VLR ORFs, they were provisionally named mature VLRs to distinguish them from the 'incomplete' germline VLR. Sequence analysis indicated that these mature VLRs should generate 1-1.3 kb polymorphic EcoRI bands hybridizing with the N-terminal probe, but these bands were observed only in a lymphocyte DNA blot (FIG. 4*c* to be included). These observations indicate that lamprey DNA samples extracted from pelleted blood erythrocytes or whole larval bodies contain mature VLRs, but only copies of the germline VLR are sufficiently abundant to be detected in DNA blots from these samples.

To address this enigma it was theorized that somatic gene rearrangement in lamprey lymphocytes generated the small mature VLRs, replacing non-coding DNA from the germline gVLR with diverse LRRs from the upstream and downstream cassettes. To test this hypothesis primers were designed for PCR amplification across the germline gVLR, including ~3 kb of upstream and ~3 kb of downstream flanks (FIG. 5*a*). LR-PCR amplification from larval DNA samples yielded a minor band of ~20 kb, similar to the gVLR amplicon from PAC16 plasmid, plus an additional prominent band of ~8 kb (FIG. 5*c*). Sequence analysis of the 8 kb amplicons from two larval samples revealed 9 of 10 clones encoding unique mature VLRs (FIG. 3), the flanks of which were identical to those of the gVLR (FIG. 5*d*). Altogether 28 unique mature VLRs were identified among the PCR products from four larval DNA samples. Lymphocyte DNA was most likely the template for these mature VLRs, as a small fraction of the pelleted erythrocytes or whole larval bodies used to extract these DNA samples. Apparently, the shorter templates of lymphocyte mature VLRs were preferentially amplified during the LR-PCR. A similar PCR bias was observed when amplifying with primers that flanked the gVLR ORF, resulting in two amplicons, the 1.5-2 kb of mature VLRs and the 14 kb gVLRs.

The search for lymphocyte receptors that could trigger adaptive immune responses in lampreys thus identifies a system of variable lymphocyte receptors that is entirely different from the Ig and TCR of jawed vertebrates. The VLRs consist of multiple LRR modules and an invariant stalk region that is attached to the lymphocyte plasma membrane via a GPI-anchor. The flanking tips of the N-terminal and C-terminal LRRs are invariant and the remarkable VLR diversity is contributed by variation in number and sequences of the intervening LRRs. The potential VLR diversity is vast, with 345 out of 354 unique sequences, and only three pairs of identical VLRs from immunostimulated lymphocytes and three other nearly identical VLRs. The VLRs thus endow this agnathan representative with a diverse repertoire of lymphocyte receptors.

These highly diverse VLRs serve a role in recognition of pathogens. Proteins featuring diverse LRR modules are cardinal innate immune receptors of animals and plants due to their propensity to interact with an extraordinary vast array of ligands. Animal TLRs are implicated in recognition of conserved epitopes on viruses, bacteria, fungi and protozoa, activating signal transduction cascades that culminate in inflammatory responses (Beutler, 2004). CD14, a GPI-anchored LRR protein that is also found in a soluble form, binds bacterial lipopolysaccharide and phospholipids to form a signaling complex with the TLR4 receptor (Landmann, 2000). Yet another mammalian family of cytosolic LRR proteins, the NBS-LRRs, recognize intracellular pathogens (Chamaillard et al., 2003). Plant disease resistance genes are members of large multigene families including hundreds of NBS-LRR proteins, LRR-receptorlike kinases and LRR-receptor-like proteins, many of which have been shown to be involved in specific activation of anti-pathogen responses (Jones et al., 2004). Antigen-binding VLRs with their remarkable diversity mediate the adaptive immune responses observed in lampreys. The GPI-anchorage of VLRs to the surface of lymphocytes allow GPI-specific phospholipase release of these receptors (Ikezawa 2002), endowing VLRs with dual functionality both as surface receptors and humoral agglutinins in an anticipatory immune system.

Sequencing genomic PAC clones a germline gVLR consisting of 4 exons that encoded only the signal peptide, 5' LRRNT, 5' LRRCT, 3' LRRCT and the C-terminus was identified. The gVLR lacked diversity LRR modules except for a 5' LRRCT, indicating that without modification it could not encode the highly diverse VLR messages. However, multiple diverse LRR cassettes were found upstream and downstream from the gVLR, and these could be available for insertion into the gVLR to assemble mature VLR genes. To test the hypothesis that mature VLRs are generated through somatic replacement of non-coding DNA in the germline gVLR with upstream and downstream LRR cassettes, LR-PCR was used to detect the presence of both germline and mature VLR genes. The expected product of ~20 kb from the gVLR was obtained from genomic DNA of two lampreys and in addition, the predicted 8 kb amplicon from mature VLRs, that was found to encode a diverse set of mature VLRs. Moreover, in a few cases candidate LRR donors could be identified among the gVLR neighboring cassettes based on identity to VLR sequences, and the highly conserved sequences in the gVLR 5' LRRNT and 3' LRRCT could potentially serve as anchoring regions for a gene conversion process. VLRs are generated by a mechanism of somatic DNA rearrangement.

Non-meiotic DNA rearrangements are known from other systems. For example, rearrangement of genes encoding surface components is a strategy used by several pathogens to evade immune recognition during chronic infection. Antigenic variation in the pilin of *Neisseria gonorrhoeae* involves non-reciprocal recombination between the pilE locus and multiple silent pilS copies (Hamrick, 2001), and antigenic variation in Lyme disease *Borrelia* spirochaetes is generated by gene conversion between an array of 15 silent cassettes and the vlsE expression site (Wang et al., 2003). Also the protozoan *Trypanosoma brucei* alternate expression of their variant surface coat glycoprotein by repeated DNA rearrangements (Donelson, 2003), as well as the malaria parasite *Plasmodium falciparum* and the intestinal dweller *Giardia lamblia* that frequently switch among multiple surface antigen genes. In the evolutionary arms race between hosts and parasites, vertebrates adopted a similar strategy to combat infectious disease by somatic rearrangement of germline receptors. Diverse lymphocyte antigen receptors are assembled via the cut-and-paste activity of the paired transposase-like RAG1 and RAG2 in gnathostomes (Schluter et al., 1999) and via an as yet uncharacterized mechanism in agnatha.

Features of the lamprey VLR system bear analogy to the Ig and TCR of jawed vertebrate lymphocytes, with two notable differences. First, lamprey VLRs consist of LRR modules whereas gnathostome antigen receptors consist of Ig domains. Lampreys immunity underwent a gradual evolutionary process, replacing the ancestral germline encoded diversity of LRR receptors with a system of variable lymphocyte LRR receptors that are somatically diversified versions of their germline VLR gene. In contrast, Ig domains as core components of jawed vertebrates recombinatorial lymphocyte receptors is an intriguing untraceable evolutionary drift from their predecessors, since no Ig superfamily member has yet been shown to play a role in any type of immune recognition of pathogens or allografts in animals other than the jawed vertebrates (Kaufman, 2002). Second, no evidence for the existence of MHC molecules in the lamprey has been found. In jawed vertebrates polymorphic MHC molecules are essential for efficient presentation of antigen peptides to T-cells, whereas inbred MHC homozygotes appear to suffer from impaired disease resistance (Penn et al., 2002; Grimholt et al., 2003). Since lampreys thrive as an inbred population in the Great Lakes, this indicates their VLR system may have evolved to function independent of polymorphic components.

Animals

Larvae (8-13 cm long) of the sea lamprey were from tributaries to Lake Michigan (Lamprey Services, Ludington, Mich.), or tributaries to Lake Huron (Hammond Bay Biological Station, Millersburg, Mich.). Larvae for immunostimulation were sedated (100 mg/l MS222; Sigma) and injected intraperitoneally with 75 μl 0.67×PBS containing: 107 *E. coli* BL21 (DE3), 107 sheep erythrocytes, 50 μg phytohemagglutinin and 25 μg pokeweed mitogen (Sigma). Immunostimulation was repeated 2 or 4 times at weekly intervals and cells were collected 3-4 days after last immunization. Blood was drained from tail-severed larvae, diluted 1:1 with 0.57×PBS and 30 mM EDTA. Buffy coat leukocytes were collected after 5 min centrifugation at 50 g. Cells were sorted using MoFlo cytometer as described (Mayer et al., 2002a).

Subtracted Immunostimulated Lymphocyte cDNA Libraries

Super SMART PCR cDNA Synthesis (BD Biosciences) was used with mRNA from large blood lymphocytes, myeloid cells and erythrocytes sorted from larvae immunostimulated 4 times at weekly intervals. Activated lymphocyte cDNA was subtracted in 2 reactions against cDNA of myeloid cells or erythrocytes (PCR-Select, BD Biosciences). Subtracted products were cloned in pGEM-T Easy (Promega) and 1,507 sequences were analyzed.

TABLE 3

PCR primers

| Primer (10 pmloe/μl) | Sequence (5'-3') | Position (cDNA clone) | Position (gVLR contig) |
|---|---|---|---|
| Slit.F | CTCGGCTCTGCAGCTCTCA (SEQ ID NO: 159) | 2-20 (LRR-2913) | 24872-24890 |
| LRR.F1 | TGGCGCCCTGGTGCAAAGT (SEQ ID NO: 160) | 153-171" | 25643-25661 |
| Slit.R | GAACACTGCGAGGGACATG (SEQ ID NO: 161) | 179-197" | 25669-25687 |
| Dis_LRR.F | AAAAGATCTTGTCCCTCGCAGTGTTC (SEQ ID NO: 162) | 181-197" | |
| LRR.R1 | ACGGACGGGGGTATTGGTA (SEQ ID NO: 163) | 633-651" | 37969-37987 |

TABLE 3-continued

| PCR primers | | | |
|---|---|---|---|
| Primer (10 pmloe/μl) | Sequence (5'-3') | Position (cDNA clone) | Position (gVLR contig) |
| LRR_C.F1 | ATCCCTGAGACCACCACCT (SEQ ID NO: 164) | 739-757" | 38075-38093 |
| LRR_C.R1 | CACGCCGATCAACGTTTCCT (SEQ ID NO: 165) | 928-947" | 38264-38283 |
| Dis_LRR.R1 | AAAGTCGACACGCCGATCAACGTTTC (SEQ ID NO: 166) | 930-946" | |
| LRR_C.R2 | CCGCCATCCCCGACCTTTG (SEQ ID NO: 167) | 948-966" | 38302-38284 |
| gVLR.F1 | CCGGTTGGACACTAGTGTTG (SEQ ID NO: 168) | | 22285-22304 |
| gVLR.R1 | GTGCCATTGGGATCAGTGGT (SEQ ID NO: 169) | | 42099-42118 |
| GAPDH.F | GAACATCGGCATCAATGGGT (SEQ ID NO: 170) | 71-90 (PmGAPDH) | |
| GAPDH.R | GAGGCCTTATCGATGGTGGT (SEQ ID NO: 171) | 366-385" | |

VLR RT-PCR

Buffy coat leukocytes from unstimulated larvae (#1-4), or immunostimulated twice at one week intervals (#5-7), were pelleted 5 min at 300 g. First strand cDNA was primed with 50 ng random hexamers (Superscript III; Invitrogen). VLR diversity regions were amplified with Expand High Fidelity (Roche) using LRR.F1+LRR.R1 (Table 3). Thermal cycling was as follows: 94° C. 1 min, then 35 cycles of 94° C. 30 sec, 59° C. 30 sec, 72° C. 1 min. Per animal 10-12 clones were sequenced.

VLR Single Cell RT-PCR

Single lymphocytes, or a 10-cell pool, from buffy coats of unstimulated larva (#8), and one immunostimulated twice at one week interval (#9), were sorted into 0.2 ml TRIzol (Invitrogen). First strand cDNA was primed with LRR_C.R2. VLRs were amplified by 2 rounds of nested PCR, first Slit.F+LRR_C.R2 using Advantage II (BD Biosciences) then LRR_N.F1+LRR_C.R1 using Expand High Fidelity. Cycling parameters were: 94° C. 1 min, then 40 cycles of 94° C. 30 sec, 60° C. 30 sec, 72° C. 1 min. Colony PCR with vector primers revealed a single size insert in 6 colonies from each of the 12 cells, 3 of which were sequenced. Colonies from cell 9.16 revealed 2 sizes and 3 short and 3 long inserts were sequenced. From the pool of 10 unstimulated cells 6 clones were sequenced.

Genomic DNA and Genomic PCR

Genomic DNA was isolated from ⅓ whole larval body, erythrocytes from 0.25 ml blood pelleted for 5 min at 50 g, or 107 sorted lymphocytes. PCR was from 400 ng gDNA using Expand Long Template (Roche). VLR diversity regions were amplified from larvae #10 and 12, using LRR.F1+LRR.R1. Mature VLRs were amplified from animals #10 and 11, using Slit.F+LRR_C.R2, or LRR_N.F1+LRR_C.R1. Amplification across the gVLR was from animals #10 and 13, with gVLR.F1+gVLR.R1. The 8 kb band was cloned in pCR-XL (Invitrogen) and sequenced with: M13.Forward, M13.Reverse, Slit.F and LRR_C.R2.

Virtual Northern and DNA Blots

Virtual Northern was prepared as recommended (Super SMART manual). Twenty cycleamplified cDNA was from larval tail, liver and sorted lymphocytes from blood, typhlosole and kidneys of unstimulated animals, or small and large blood lymphocytes, myeloid cells and erythrocytes sorted from blood of larvae immunostimulated 4 times at weekly intervals.

Genomic DNA from larvae #10, 12 and 13, 10 μg per lane, was digested with BamHI, EcoRI or HindIII (Roche); 5 μg lymphocyte DNA was digested with EcoRI. For the pulse-field CHEF blot, erythrocytes from 10 larvae were embedded in agarose, and 20 μg DNA per lane were digested with AscI, FseI, NotI, PacI, PmeI, or SfiI.

The following 32P-labeled probes were used: VLR N-terminal probe, 196 bp, PCR amplified from clone LRR-2913 using Slit.F+Slit.R, and C-terminal probe, 208 bp, amplified with LRR_C.F1+LRR_C.R1; GAPDH probe, 314 bp, amplified from clone PmGAPDH using GAPDH.F+GAPDH.R.

PAC Library and Clones

Arrayed sea lamprey PAC library in pCYPAC6 (AF133437) was constructed from erythrocyte DNA of one Lake Michigan adult using partial MboI digests. The 6×104 clones had 65 kb average inserts with 1-2 fold genome coverage. Library was screened using both N-terminal and Cterminal probes. Plasmids of positive clones were EcoRI digested, blotted and hybridized either with the N-terminal or C-terminal probes. Five PACs hybridized with both probes (2, 3, 15, 16, 17) and 5 PACs hybridized only with the N-terminal probe (4, 9, 14, 35, 42, 43).

The gVLR was amplified with Expand Long Template from plasmids of PACs 2, 3, 15, 16 and 17 using Slit.F+LRR_C.R2. All PCR products were of 14 kb, with 2 sets of BamHI patterns (PACs 2, 3 and 15-17). PACs 3, 4 and 16 were sequenced at McGill University (Quebec, Canada).

VLR GPI-Anchor

A VLR insert, LRRNT to stop codon, was amplified from clone LRR-2913 with Expand High Fidelity using Dis_LRR.F+Dis_LRR.R1 and fused to Igκ signal peptide and Hemagglutinin epitope in pDisplay (Invitrogen). Surface localization and VLR GPI-anchor were analyzed in BW1547 cells, or controls expressing mFcγRIIb. Cells were treated with 1 unit/ml bacterial GPIspecific phospholipase C (Sigma) 45 min at 30° C. Surface staining of epitope tagged proteins was with anti-HA-tag mAb 12CA5.

Sequence Analysis

Sequence variability was estimated using MEGA 2.1 UPGMA (Kumar et al., 2001). GPI-anchor site was identified via: http://129.194.185.165/dgpi/. SWISS-MODEL VLR 3D structure was via: http://cubic.bioc.columbia.edu/predictprotein/submit_meta.html. Residues 22-319 from clone 12.26 were threaded on crystal coordinates of CD42a (1m10.pdb) and NOGO-66 receptor (1p8t.pdb).

Example 2

Variable Lymphocyte Receptors in Hagfish

Cyclostome VLR Homologs

Two distinct types of VLR, VLR-A and VLR-B, were identified among expressed sequence tags from 12,000 leukocyte cDNA clones of the Inshore hagfish, *Eptatretus burgeri* (Suzuki et al., 2004B). Matching VLR were then cloned by RT-PCR from transcripts of lymphocyte-like cells of the Pacific hagfish, *E. stoutii*. FIG. 9 depicts an alignment of the amino acid sequences of hagfish VLR-A and VLR-B, the Sea lamprey VLR (*Petromyzon marinus*) and VLRs of two non-parasitic lampreys, American brook lamprey (*Lampetra appendix*) and Northern brook lamprey (*Ichthyomyzon fossor*). These VLR share similar structural domains: a signal peptide (SP), N-terminal LRR (LRRNT), 18-residue LRR1 followed by a variable number of 24-residue LRRs, a 13-residue connecting peptide (CP) and C-terminal LRR (LRRCT). At the beginning of the C-terminus the lamprey VLR and hagfish VLR-B have a threonine/proline-rich region, but this region is not well conserved in the hagfish VLR-A. All VLR proteins end with a hydrophobic tail region that is required for modification of the protein to add a glycosyl-phosphatidyl-inositol (GPI) cell surface membrane anchor. Like the sea lamprey VLR, hagfish VLR-A was predicted to be a GPI-anchored protein although no ωcleavage site was identified (DGPI http://129.194.185.165/dgpi/); the C-terminal hydrophobicity profile for VLR-B is also predictive of GPI modification.

Figure 13:
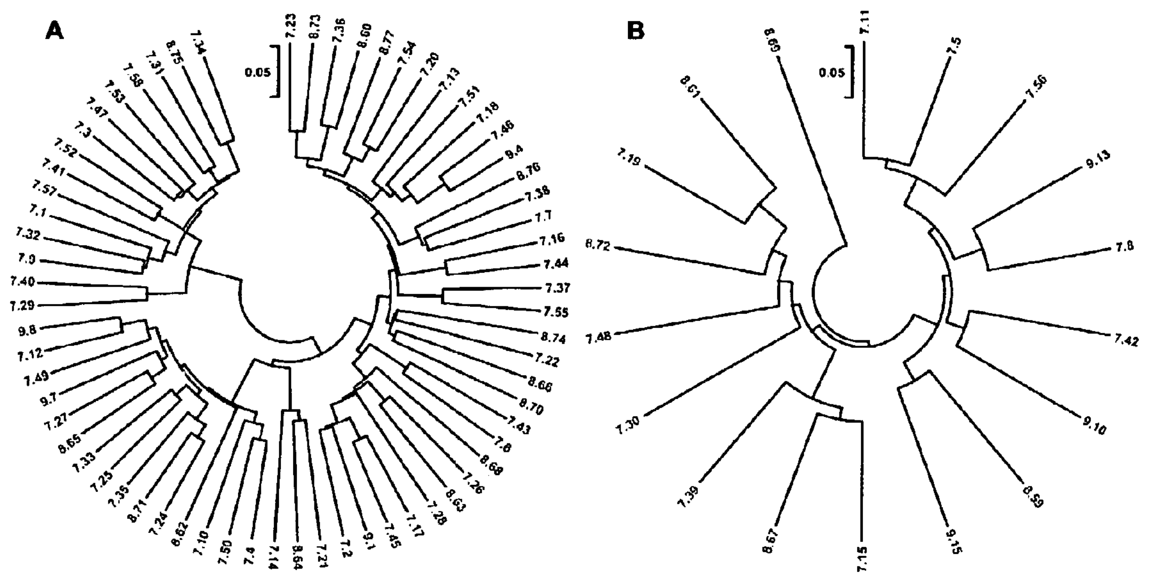
FIG. 13 shows the Genetic distance among Inshore hagfish VLR diversity regions (LRRNT to LRRCT). Proteins were predicted from leukocyte cDNA clones, or mature VLR amplicons from genomic DNA of three animals. Scale bars represent 5% amino acid divergence. A. VLR-A (N=66). B. VLR-B (N=18). Red: hagfish #7; green: #8; blue: genomic mature VLR from hagfish #9.

Transcripts of hagfish VLR are abundant in lymphocyte-like cells, but not in myeloid cells or erythrocytes sorted by their light scatter characteristics. VLR-A transcript levels were ~3-fold higher than VLR-B levels in blood leukocyte samples. Both VLR types of the Pacific hagfish are highly heterogeneous (FIGS. 10A and B), exhibiting variable numbers of the 24-residue LRR modules and pronounced LRR sequence diversity. Comparable diversity was observed for VLR-A (N=66) and VLR-B (N=18) sequences from Inshore hagfish (FIG. 13). Interestingly, five clusters of 2-4 VLR-A clones that were identical or differed by only 1-2 residues were found among the 40 transcripts from hagfish #5 (marked by asterisks in FIG. 10A), that was given four weekly injections of an antigen and mitogen cocktail. The finding that 30% of the VLR-A transcripts from this hagfish consisted of clusters of related sequences indicates clonal expansion of VLR-A bearing lymphocytes. The clones with 1-2 amino acid substitutions reflect additional VLR diversification through somatic hypermutation.

The dataset of unique sequence Pacific hagfish VLR-A (N=130) reveals 2-6 copies per transcript of the 24-residue LRRs (N=527; average 4). In the VLR-B dataset (N=69) there are 1-6 copies of the 24-residue LRRs (N=195; average 2.8), while in the set of 129 Sea lamprey VLR (19; GenBank accessions AY577943-AY578059) there were 1-9 copies of 24-residue LRRs (N=325; average 2.5). The individual components of these VLR, except for LRRNT and LRRCT that were too diverse among the species for reliable alignment (Table 4; 328 LRR1 domains, 328 CP domains, and 1,047 single domains of the 24-residue LRRs) were then analyzed separately in a Neighbor Joining phylogenetic tree.

TABLE 4

Components of unique hagfish and Sea lamprey VLR

| | Unique LRR motifs | | | |
|---|---|---|---|---|
| | LRR1 (18 aa) | CP (13 aa) | Diversity LHR (24 aa) | Diversity LRR consensus* |
| Es_VLR-A | 77/130 (59%) | 71/130 (55%) | 477/527 (90%) | -L--L--L-L--NqL--1P-G-FD (SEQ ID NO: 304) |
| Es_VLR-B | 68/69 (98%) | 46/69 (67%) | 190/195 (97%) | KLT-Lt-L-L--NqL-S-P-GvFD (SEQ ID NO: 305) |
| Pm_VLR | 68/129 (53%) | 36/129 (28%) | 269/325 (83%) | -L--L--L-L--NQL---P-G-FD (SEQ ID NO: 306) |

*Consensus-capital letters: 80-100% identity; small letters: 60-79%

The clusters were nearly exclusively of the same type and species origin, i.e., Pacific hagfish VLR-A, VLR-B or Sea lamprey VLR clustering. There were no instances of identical LRR domains between the different VLR types. However, a large portion of the LRR1 and CP domains within hagfish VLR-A and lamprey VLR clusters were identical (Table 4). In contrast, the LRR1 domains in hagfish VLR-B were 98% unique; the sets of 24-residue LRRs also consisted predominantly of unique sequences: 97% were unique in hagfish VLR-B, 90% in VLR-A and 83% in the Sea lamprey VLR. This remarkably high degree of diversity is especially remarkable given that consensus sequences derived for each of the 24-residue LRR types share at least 10 framework residues.

Hagfish VLR Genes

Figure 11:
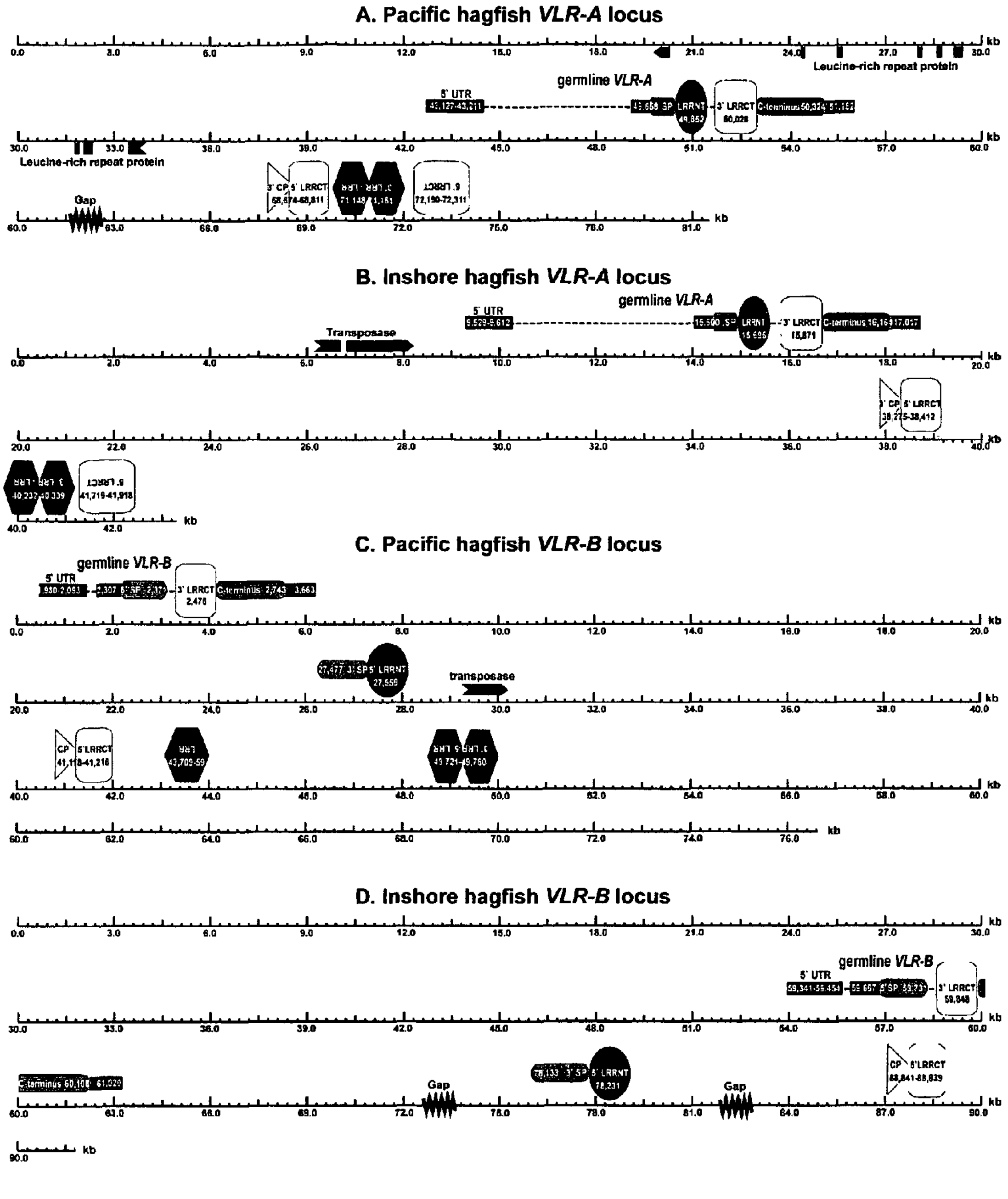
FIG. 11 shows the hagfish VLR gene loci.
Figure 12:
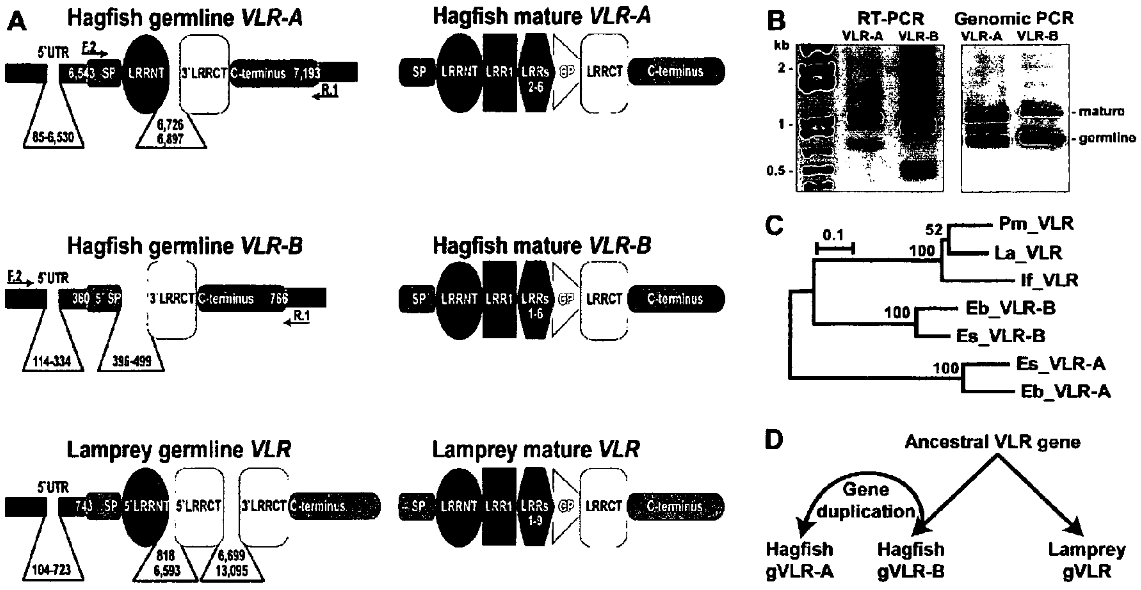
FIG. 12 shows the Agnathan VLR genes, transcripts and phylogeny.

Genomic organization of the Pacific and Inshore hagfish VLR loci was determined from sequences of large insert genomic clones isolated from bacterial artificial chromosome (BAC) libraries, one BAC for each VLR type (FIG. 11). Only one copy of each of the gVLRs was identified in hagfish genomes. The sequences and organization of the loci are nearly identical in both species and fairly conserved between gVLR-A and gVLR-B. Hagfish gVLR begin with a 5' untranslated region (UTR) that is followed by two coding regions (FIG. 12A). As in the Sea lamprey gVLR, the 5' UTR is split by an intron, 6.4 kb long in the Pacific hagfish gVLR-A and 220 bp in gVLR-B. The first coding region in the hagfish gVLR encodes the signal peptide and an LRRNT domain in gVLR-A and only residues 1-13 of the 23-residue signal peptide in gVLR-B. Next, there are short intervening sequences of 171 and 211 bp for gVLR-A and gVLR-B, respectively. The second coding region consists of the 3' end of LRRCT and the C-terminus, as in the Sea lamprey gVLR, except that the lamprey region coding for the 5' end of LRRCT is missing. The hagfish gVLR are compact, 671 bp from start-to-stop codons in gVLR-A and 410 bp in gVLR-B.

Figure 10:
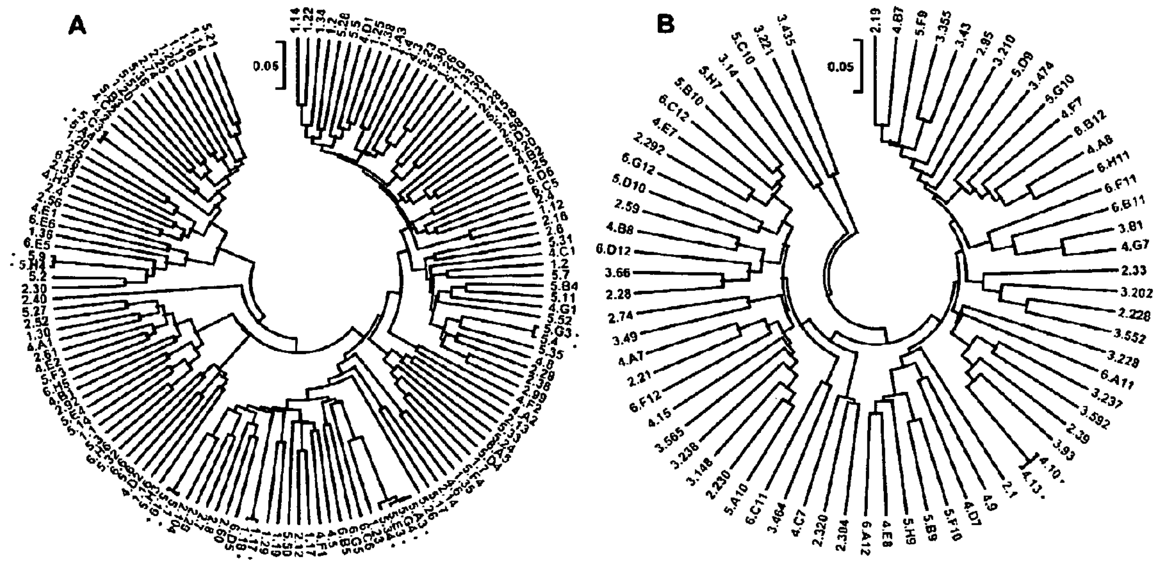
FIG. 10 shows the genetic distance among Pacific hagfish VLR diversity regions (LRRNT to LRRCT). Proteins predicted form PCR amplified lymphocyte-like cDNA clones, or blood genomic PCR amplicons from five animals. Scale bars represent 5% amino acid divergence. A. VLR-A (N=139). B. VLR-B (N=70). Green: unstimulated; red: immunostimulated; blue: genomic mature VLR; asterisk-related sequences.

The hagfish gVLR loci harbor cassettes encoding diverse LRR motifs located ~20-40 kb downstream from the germline genes (FIG. 11). In the VLR-A locus there is a cassette encoding 6-8 terminal residues of a diverse CP domain and a 5' LRRCT that includes a 4-residue identical overlap with the gVLR-A 3' LRRCT. Farther downstream there is a cassette of two diverse LRRs positioned in reverse orientation relative to the gVLR-A and then an inverted incomplete 5' LRRCT. In the gVLR-B locus, there is a cassette encoding residues 7-23 of the signal peptide and a 5' LRRNT, then a diverse CP domain and 5' LRRCT, one inverted LRR and, farther downstream, another inverted LRR cassette consisting of the 12-terminal residues and 8-proximal residues of LRRs. No other diverse LRR modules were identified in flanking DNA spanning ~50 kb upstream and ~70 kb downstream from the gVLRs. However, diverse LRR elements likely exist elsewhere in the genome to provide missing components of the mature VLR genes identified in samples of genomic PCR amplicons from lymphocyte-like cells: 35 unique mature VLR-A and 38 VLR-B sequences from two animals (FIG. 10). Thus, the hagfish mature VLR genes must be assembled through somatic recombination, as is the case for lamprey.

Germline VLR genes in hagfish lymphocyte-like cells are actively transcribed prior to gene rearrangement. PCR amplicons of VLR-A germline transcripts are ~0.7 kb long and ~0.5 kb for VLR-B (FIG. 12B, RT-PCR; position of PCR primers indicated in FIG. 12A) while the larger amplicons correspond to transcripts from the rearranged mature VLR genes, ~1.1 and ~0.8 kb for VLR-A and VLR-B respectively. The corresponding PCR amplicons from blood genomic DNA are ~0.7 kb for the germline genes and ~1.1 kb for the mature VLR-A and VLR-B genes (FIG. 12B, genomic PCR). In transcripts from germline and mature VLR genes, the 5' intron is spliced out to yield RT-PCR products shorter than the corresponding genomic PCR amplicons (see VLR-B in FIG. 12B; gVLR-A amplicons do not include the 6.4 kb intron). However, the intervening sequences between the coding exons are retained in the germline transcripts because they lack consensus eukaryotic splice sites. The germline transcription may be required for gVLR rearrangement, as is the case in mammalian antibody class switch recombination for which germline switch region transcription is obligatory (Bottaro et al., 1994; Hein et al., 1998).

VLR Phylogeny

A phylogenetic analysis of the agnathan VLR proteins reveals three distinct clusters respectively composed by lamprey VLR, hagfish VLR-A and VLR-B sequences (FIG. 12C). The hagfish VLR-B and lamprey VLR cluster in a separate branch from that with the hagfish VLR-A. The same tree topology was seen when only the VLR diversity regions, LRRNT to LRRCT or LRR1 to CP, were aligned. Hence, either the hagfish VLR-A arose by duplication of the ancestral gene (FIG. 12D) or the lamprey lost their VLR-A ortholog after the split between the hagfish and lamprey lineages, dating 499±38 Myr ago in the Cambrian period (Hedges et al., 2001). It is also possible that a lamprey VLR-A ortholog exists, but was not detected in >18,000 cDNA sequences derived from lamprey lymphocyte-like cells (Pancer et al., 2004) because it is expressed at very low levels or in non-lymphoid cells.

The presence of VLRs in both of the extant cyclostome orders is indicative of strong evolutionary pressure for vertebrates to develop an anticipatory molecular recognition system. The analysis indicates that, within less than 40 million years in the Cambrian, two radically different systems evolved in agnathans and gnathostomes in which either LRR or Ig gene fragments undergo recombinatorial assembly to generate diverse repertoires of lymphocyte receptors. This evolutionary scenario raises many intriguing questions, one of which concerns the issue of whether the two adaptive immune strategies represent convergent evolution or if one was ancestral to the other. Whether VLRs were forerunner vertebrate immune receptors or the rearranging VLRs and Igs evolved independently will become certain only with an unambiguous resolution of the phylogenetic relationships among the groups of living and extinct jawless and jawed vertebrates (Mallatt et al., 2003; Meyer et al., 2003). In this regard, however, the presence of VLRs in both orders of contemporary agnathans lends additional molecular evidence favoring a monophyletic origin of cyclostomes.

Animals.

Live specimens of Pacific hagfish *Eptatretus stoutii* (30-60 cm long) were purchased form Marinus Scientific (Long Beach, Calif.) and maintained for two months at 12° C. in artificial sea water (Oceanic System, Dallas, Tex.). Larvae (15-20 cm long) of the American brook lamprey (*Lampetra appendix*) and Northern brook lamprey (*Ichthyomyzon fossor*), were from tributaries to the Great Lakes (Lamprey Services, Ludington, Mich.).

Hagfish were sedated by immersion for 15 min in 0.5 gr/liter MS222 (Sigma, St. Louis, Mo.) buffered to pH=7 before intraperitoneal injection with an antigen/mitogen cocktail in 0.5 ml hagfish PBS (per litter: 28 gr NaCl, 0.2 gr KCL, 1.44 gr $Na_2HPO_4$, 0.24 gr $KH_2PO_4$, pH=7.4, 1 osmole). The cocktail contained $10^9$ live *E. coli* TG1 bacteria, $10^9$ sheep erythrocytes (Colorado Serum Company, Denver, Colo.) and 100 μg each phytohemagglutinin and pokeweed mitogen (Sigma). Immune stimulation was repeated at weekly intervals and four days after the fourth stimulation blood was collected with a syringe from the tail blood sinus and diluted 1:1 with hagfish PBS containing 30 mM EDTA. Buffy coat leukocytes collected after 5 min centrifugation at 50×g were sorted by their light scatter characteristics as described (Newton et al., 1994; Raison et al., 1994) using a MoFlo cytometer (Cytomation, Fort Collins, Colo.).

Hagfish VLR.

Inshore hagfish *Eptatretus burgeri* VLR homologs were identified using lamprey VLR as BLAST queries against the database of expressed sequence tags from leukocyte RNA of unstimulated animals #7, 8 (Suzuki et al., 2004B). Clones with significant matches were sequenced on both strands: 64 VLR-A and 15 VLR-B cDNA clones. For the Pacific hagfish, unseparated blood cells and buffy coat leukocytes from three unstimulated individuals (#1-3, 6), and buffy coat leukocytes from two immunostimulated animals (#4, 5) were used for extraction of blood genomic DNA and leukocyte RNA. Extraction of RNA was with TRIzol Reagent (Invitrogen, Carlsbad, Calif.) and PolyA RNA was selected with Dynabeads mRNA purification Kit (Dynal Biotech, Lake Success, N.Y.). First strand cDNA synthesis was primed with 20 pmoles of the HgVLRA.F1 (Table 5) for VLR-A, or HgVLRB.F1 for VLR-B, using Superscript III First Strand cDNA Synthesis kit (Invitrogen), and the products were column purified (QIAquick PCR purification; QIAGEN, Valencia, Calif.).

TABLE 5

| VLR PCR primers | | | |
|---|---|---|---|
| Name | Sequence 5'-3' | Position in cDNA clone | Position in Eb_gVLR Contig |
| HgVLRA.F1 | TGGTGATAACCTCAAGGTGCT (SEQ ID NO: 322) | 35-55 (Eb7VLRA.21) | 9597-9614 |
| HgVLRA.F2 | CAGAGATGATGGGTCCGGT (SEQ ID NO: 323) | 60-78 (Eb7VLRA.21) | 15509-15527 |
| HgVLRA.R1 | GGCAAGTGAGACACTGGTTC (SEQ ID NO: 324) | 1023-1042 (Eb7VLRA.21) | 16166-16185 |
| HgVLRA.R2 | TCTTGAGAAAGTGGAAGACGTA (SEQ ID NO: 325) | 995-1016 Eb7VLRA.21) | 16138-16159 |
| HgVLRB.F1 | CACGAGGATTGGACGTGAAGA (SEQ ID NO: 326) | 49-69 (Eb7VLRB.15) | 59421-59441 |
| HgVLRB.F2 | TTCCACCTCGAGGAAGATGA (SEQ ID NO: 327) | 93-112 (Eb7VLRB.15) | 59677-59696 |
| HgVLRB.R1 | GGCAAAATGTTGGACGGTGT (SEQ ID NO: 328) | 866-885 (Eb7VLRB.15) | 60116-60135 |
| HgVLRB.R2 | GGCGTGACATATGAGGTAAAC (SEQ ID NO: 329) | 826-846 (Eb7VLRLB.15) | 60076-60096 |
| Slit.F | CTCGGCTCTGCAGCTCTCA (SEQ ID NO: 330) | 1-19 (LaVLR.2) | |
| LRR_N.F1 | CTCCGCTACTCGGCCTGCA (SEQ ID NO: 331) | 1-19 (IfVLR.15) | |
| VLR_3UT.R | GATGAAGCGAAGACAGACGTG (SEQ ID NO: 332) | 1607-1627 (LaVLR.2) | |
| VLR_3UT.R | GATGAAGCGAAGACAGACGTG (SEQ ID NO: 333) | 1405-1425 (IfVLR.15) | |

VLRs were then PCR amplified using Expand High Fidelity PCR (Roche Applied Science, Indianapolis, Ind.), from the cDNA or from genomic DNA, in 50 μl reactions containing: 1 μl each of the sets of forward and reverse primers (F1 or F2 and R1 or R2) at 10 pmole/μl, 5 μl 10× buffer, 36.25 μl DDW, 5 μl cDNA or genomic DNA (250 ng) and 0.75 μl Expand enzyme. Reactions were amplified using one cycle of 94° C. 1 min, then 35 cycles of 94° C. 30 sec, 58° C. 30 sec and 72° C. 1 min, and a final 7 min elongation at 72° C. Products were column purified, cloned in pCRII-TOPO (Invitrogen) and the inserts were sequenced. For the Pacific hagfish, 109 VLR-A RT-PCR clones were sequenced (four contained in-frame stop codons), and 36 genomic mature VLR-A amplicons (two contained in-frame stop codons). For VLR-B, 37 RT-PCR clones were sequenced (one contained an in-frame stop codon), and 38 genomic mature VLR-B amplicons (four contained in-frame stop codons). Liver genomic DNA from Inshore hagfish #9 (Suzuki et al., 2004B) was used for PCR cloning and sequencing mature VLRs: 4 mature VLR-A amplicons (two contained in-frame stop codons) and 3 mature VLR-B amplicons.

Non-Parasitic Lamprey VLR

First strand cDNA was synthesized as above using the reverse primer VLR__3UT.R (Sea lamprey 3' UTR primer, Table 5). For the American brook lamprey the forward primer was Slit.F (Sea lamprey 5' UTR primer), and for the Northern brook lamprey LRR_N.F1 (another Sea lamprey 5' UTR primer). In total 13 unique VLR clones of the American brook lamprey and seven of the Northern brook lamprey were sequenced.

BAC Libraries and Clones.

An Inshore hagfish BAC library (Suzuki et al., 2004A) was screened by PCR using VLR primers as above (F1 or F2 and R1 or R2). The Pacific hagfish BAC library (VMRC23) was constructed from EcoRI partial digests of erythrocyte DNA from a single specimen in the vector pCCBACE1 (Epicentre Technologies, Madison Wis.). This library consists of ~184,000 recombinants and encompasses ~5× coverage of the hagfish genome. The entire library was screened by hybridization with 5' and 3' VLR-A and VLR-B probes and positive clones were authenticated by PCR. One BAC for each VLR type from the Pacific and Inshore hagfish were sequenced at ~10× coverage and assembled into contigs (Macrogen, Seoul, Korea). In case of incomplete sequence of the inserts only portions containing the gVLR and LRR cassettes were included with uncaptured gaps in the contigs: Eb_gVLR-A, 43,362 bp; Eb_gVLR-B, 92,072 bp; Es_gVLR-A, 81,648 bp; Es_gVLR-B, 76,730 bp.

Sequence Analysis

Neighbor Joining and UPGMA trees were constructed with the pairwise deletion option using the programs from MEGA 3 Molecular Evolutionary Genetics Analysis (Kumar et al., 2004). Prediction of genes in the BAC inserts was accomplished by using local BLAST downloaded from ftp://ftp.ncbi.nlm.nih.gov/blast/executables/ and the GenScan server: genes.mit.edu/GENSCAN.html.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Anderson M K, Sun X, Miracle A L, Litman G W and Rothenberg E V (2001) Evolution of hematopoiesis: Three members of the PU.1 transcription factor family in a cartilaginous fish, Raja eglanteria. *Proc. Natl. Acad. Sci. USA* 98:553-8

Ardavin C F and Zapata A (1987) Ultrastructure and changes during metamorphosis of the lympho-hemopoietic tissue of the larval anadromous sea lamprey *Petromyzon marinus. Dev. Comp. Immunol.,* 11:79-93

Azumi K et al., Genomic analysis of immunity in a Urochordate and the emergence of the vertebrate immune system: "waiting for Godot". *Immunogenetics* 55: 570-81, 2003

Bell, J K., Mullen, G E D., Leifer, C A. Mazzoni, A., Davies, D R. and Segal, D M. Leucine-rich repeats and pathogen recognition in Toll-like receptors. *Trends in Immunology* 2003, 24: 528-533.

Beutler, B. Innate immunity: an overview. *Molecular Immunology* 40 (2004) 845-859.

Bryan, M. B., Libants, S. V., Warrillow, J. A., Li, W. and Scribner, K. T. Polymorphic microsatellite markers for the landlocked sea lamprey, *Petromyzon marinus. Conservation Genetics* 4:113-116, 2003

Bottaro, A., Lansford, R., Xu, L., Zhang, J., Rothman, P. & Alt, F. W. (1994) *EMBO J.* 13, 665-674.

Chamaillard, M., Girardin, S E., Viala, J. and Philpott, D J. Nods, Nalps and Naip: intracellular regulators of bacterial-induced inflammation. *Cellular Microbiology* (2003) 5: 581-592.

Cooper A J (1971) Ammocoete lymphoid cell populations in vitro. *In: 4th Leukocyte Culture Conference*. O. R. McIntyre (Ed). New York Appleton Century-Crofts, pp. 137-47

Donelson J E. Antigenic variation and the African trypanosome genome. *Acta Trop.* 2003, 85: 391-404.

Finstad J and Good R A (1964) The evolution of the immune response. III. Immunologic responses in the lamprey. *J. Exp. Med.,* 120:1151-67

Finstad J, Papermaster B W and Good R A (1964) Evolution of the immune response. II. Morphologic studies of the thymus and organized lymphoid tissue. *Lab Invest.,* 13:490-512

Flajnik M F and Kasahara M (2001) Comparative genomics of the MHC: glimpses into the evolution of the adaptive immune system. *Immunity* 15:351-62

Flajnik M F (2002) Comparative analyses of immunoglobulin genes: surprises and portents. *Nat. Rev. Immunol,* 2:688-98

Forey P L and Janvier P (1993) Agnathans and the origin of jawed vertebrates. *Nature* 361:129-134

Fujii T (1982) Electron microscopy of the leukocytes of the typhlosole in ammocoetes, with special attention to the antibody-producing cells. *J. Morphol.,* 173:87-100

Fujii T and Hayakawa I (1983) A histological and electron-microscopic study of the cell types involved in rejection of skin allografts in ammocoetes. *Cell Tissue Res.,* 231:301-12

Good, R. A., Finstad, J. & Litman, G. W. in *The biology of lampreys II: Immunology* (Eds Hardisty, M. V. & Potter, I. C.) 405-432 (Academic Press, London 1972).

Grimholt U, Larsen S, Nordmo R, Midtlyng P, Kjoeglum S, Storset A, Saebo S, Stet R J. MHC polymorphism and disease resistance in Atlantic salmon (*Salmo salar*); facing pathogens with single expressed major histocompatibility class I and class II loci. *Immunogenetics.* 55:210-9, 2003

Hagen M, Filosa M F and Youson J H (1985) The immune response in adult sea lamprey (*Petromyzon marinus* L.): the effect of temperature. *Comp. Biochem. Physiol,* 82:207-10

Haire R N, Miracle A L, Rast J P and Litman G W (2000) Members of the Ikaros gene family are present in early representative vertebrates. *J. Immunol.,* 165:306-12

Hamrick T S, Dempsey J A, Cohen M S, Cannon J G. Antigenic variation of gonococcal pilin expression in vivo: analysis of the strain FA1090 pilin repertoire and identification of the pilS gene copies recombining with pilE during experimental human infection. *Microbiology* 2001, 147: 839-49.

Hedges, S. B. (2001) in *Major events in early vertebrate evolution, Systematics Association special vol. 61: Molecular evidence for the early history of living vertebrates*, ed Ahlberg, P. E. (Taylor & Francis, London), pp. 119-134.

Hein, K., Lorenz, M. G., Siebenkotten, G., Perry, K., Christine, R. & Radbruch, A (1998) *J. Exp. Med.* 188, 2369-2374.

Ikezawa, H. Glycosylphosphatidylinositol (GPI)-Anchored Proteins. *Biol. Pharm. Bull.* 25:409-417 (2002)

Jones, D. A. and Takemoto, D. Plant innate immunity—direct and indirect recognition of general and specific pathogen-associated molecules. *Current Opinion in Immunology* 2004, 16:48-62

Kaufman J (2002) The origins of the adaptive immune system: whatever next? *Nat. Immunol.,* 3:1124-5

Kilarski W and Plytycz B (1981) The presence of plasma cells in the lamprey (Agnatha). *Dev. Comp. Immunol,* 5:361-6

Kumar, S., Tamura, K., Jakobsen, I. B. and Nei, M. (2001) MEGA2: Molecular Evolutionary Genetics Analysis software, Arizona State University, Tempe, A R Laird D J, De Tomaso A W, Cooper M D and Weissman I L (2000) 50 million years of chordate evolution: seeking the origins of adaptive immunity. *Proc. Natl. Acad. Sci., USA* 97:6924-6

Kumar, S., Tamura, K. & Nei, M. (2004) *Brief. Bioinform.* 5, 150-163.

Landmann, R., Müller, B. and Zimmerli, W. CD 14, new aspects of ligand and signal diversity. Microbes and Infection, 2, 2000, 295-304.

Litman G W, Frommel D, Finstad F J, Howell J, Pollara B W and Good R A (1970) The evolution of the immune response. VIII. Structural studies of the lamprey immunoglobulin. *J. Immunol,* 105:1278-85

Mallatt, J. & Chen, J. Y. (2003) *J. Morphol.* 258, 1-31.

Marchalonis J J and Edelman G M (1968) Phylogenetic origins of antibody structure. 3. Antibodies in the primary immune response of the sea lamprey, *Petromyzon marinus. J. Exp. Med.,* 127:891-914

Mayer W E, Uinuk-Ool T, Tichy H, Gartland L A, Klein J and Cooper M D (2002 a) Isolation and characterization of lymphocyte-like cells from a lamprey. *Proc. Natl. Acad. Sci., USA* 99:14350-5

Mayer W E, O'Huigin C, Tichy H, Terzic J and Saraga-Babic M (2002 b) Identification of two Ikaros-like transcription factors in lamprey. *Scand. J. Immunol,* 55:162-70

Meyer, A. & Zardoya, R. (2003) *Annu. Rev. Ecol. Evol. Syst.* 34, 311-338.

Newton, R. A., Raftos, D. A., Raison, R. L. & Geczy, C. L. (1994) *Dev. Comp. Immunol.* 18, 295-303.

Pancer, Z., Mayer, W. E., Klein, J. & Cooper, M. D. (2004) *Proc. Natl. Acad. Sci. USA* 101, 13273-13278.

Penn D J, Damjanovich K, Potts W K. MHC heterozygosity confers a selective advantage against multiple-strain infections. *Proc Natl Acad Sci* 99:11260-42002, 2002

Perey D Y, Finstad J, Pollara B and Good R A (1968) Evolution of the immune response. VI. First and second set skin homograft rejections in primitive fishes. *Lab. Invest.,* 19:591-7

Piavis G W and Hiatt J L (1971) Blood cell lineage in the sea lamprey *Petromyzon marinus* (Pisces: Petromyzontidae). *Copeia* 4:722-8

Pollara B, Litman G W, Finstad J, Howell J and Good R A (1970) The evolution of the immune response. VII. Antibody to human "O" cells and properties of the immunoglobulin in lamprey. *J. Immunol,* 105:738-45

Raison, R. L., Coverley, J., Hook, J. W., Towns, P., Weston, K. M. & Raftos, D. A (1994) *Immunol Cell Biol.* 72, 326-332.

Rast, J. P., Michele K. Anderson, M. K., Strong, S. J., Luer, C, Litman, R. T., and Litman, G. W. α, β, g, and δ T Cell Antigen Receptor Genes Arose Early in Vertebrate Phylogeny. *Immunity,* 6:1-11, 1997.

Schluter S F, Bernstein R M, Bernstein H and Marchalonis J J (1999) 'Big Bang' emergence of the combinatorial immune system. *Dev. Comp. Immunol.,* 23:107-11

Schwede, T., Diemand, A. Guex, N. and Peitsch, M. V. Protein structure computing in the genomic era. *Research in Microbiology* 151:107-112 (2000)

Shintani S, Terzic J, Sato A, Saraga-Babic M, O'hUigin C, Tichy H and Klein J (2000) Do lampreys have lymphocytes? The Spi evidence. *Proc. Natl. Acad. Sci., USA* 97:7417-22

Suzuki, T., Ota, T., Fujiyama, A. & Kasahara, M. (2004A) *Genes Genet. Syst.* 79, 251-253.

Suzuki, T., Shin-I, T., Kohara, Y. & Kasahara, M. (2004B) *Dev. Comp. Immunol.* 28, 993-1003.

Uinuk-Ool T, Mayer W E, Sato A, Dongak R, Cooper M D and Klein J (2002) Lamprey lymphocyte-like cells express homologs of genes involved in immunologically relevant activities of mammalian lymphocytes. *Proc. Natl. Acad. Sci., USA* 99:14356-61

Uinuk-Ool T S, Mayer W E, Sato A, Takezaki N, Benyon L, Cooper M D and Klein J (2003) Identification and characterization of a TAP-family gene in the lamprey. *Immunogenetics* 55:38-48

Wang D, Botkin D J, Norris S J. Characterization of the vls antigenic variation loci of the Lyme disease spirochaetes *Borrelia garinii* Ip90 and *Borrelia afzelii* ACAI. *Mol. Microbiol.* 2003, 47: 1407-17.

Zapata A, Ardavin C F, Gomariz R P and Leceta J (1981) Plasma cells in the ammocoete of *Petromyzon marinus. Cell Tissue Res.,* 221:203-8.

What is claimed is:

1. An isolated polypeptide comprising an N-terminal leucine rich repeat (LRRNT), one or more leucine rich repeats (LRRs), a C-terminal leucine rich repeat (LRRCT), and a connecting peptide, wherein the connecting peptide comprises an alpha helix and wherein the isolated polypeptide is a variable lymphocyte receptor (VLR) or, wherein the VLR selectively binds an antigen and wherein the VLR can function in an adaptive immunity and can be generated by somatic rearrangement.

2. The polypeptide of claim 1, wherein the connecting peptide is linked to the LRRCT.

3. The polypeptide of claim 1, further comprising a stalk region and a glycosyl-phosphatidyl-inositol anchor.

4. The polypeptide of claim 3, further comprising a hydrophobic tail.

5. The polypeptide of claim 3, wherein the stalk region comprises a threonine-proline rich region.

6. The polypeptide of claim 1, further comprising a signal peptide.

7. The polypeptide of claim 1, wherein there are 1-9 LRRs, with LRR1 adjacent to the LRRNT.

8. The polypeptide of claim 7, wherein LRR1 comprises less than about 20 amino acids.

9. The polypeptide of claim 7, wherein LRR1 comprises about 18 amino acids.

10. The polypeptide of claim 7, wherein each of LRR 2-9 comprises less than about 25 amino acids.

11. The polypeptide of claim 1, wherein the LRRNT comprises less than about 40 amino acids.

12. The polypeptide of claim 11, wherein the LRRNT comprises the amino acid sequence of SEQ ID NO: 157.

13. The polypeptide of claim 11, wherein the LRRNT comprises the amino acid sequence of SEQ ID NO: 157 with one or more conservative amino acid substitutions.

14. The polypeptide of claim 1, wherein the LRRCT comprises less than about 60 amino acids.

15. The polypeptide of claim 14, wherein the LRRCT comprises the amino acid sequence of SEQ ID NO:158.

16. The polypeptide of claim 14, wherein the LRRCT comprises the amino acid sequence of SEQ ID NO: 158 with one or more conservative amino acid substitutions.

17. The polypeptide of claim 1, wherein the connecting peptide comprises less than about 15 amino acids.

18. The polypeptide of claim 1, wherein the LRRs differ in amino acid sequence from each other and from the LRRNT and the LRRCT.

19. The polypeptide of claim 1, wherein the polypeptide is about 130 to about 225 amino acids in length.

20. The polypeptide of claim 1, wherein the antigen is a pathogen.

21. The polypeptide of claim 20, wherein the pathogen is a bacterium.

22. The polypeptide of claim 1, wherein the antigen is a toxin.

23. The polypeptide of claim 1, wherein the polypeptide is bound to a solid support.

24. The polypeptide of claim 23, wherein the solid support is a mobile solid support.

25. The polypeptide of claim 23, wherein the solid support is a column.

26. The polypeptide of claim 23, wherein the solid support is a chip.

27. The polypeptide of claim 23, wherein the solid support is a multiwell plate.

28. A plurality of the polypeptides of claim 1, wherein the LRRs are highly variable across polypeptides.

29. The plurality of polypeptides of claim 28, wherein the plurality is bound to a solid support.

30. The plurality of polypeptide of claim 28, wherein the solid support is a mobile solid support.

31. The plurality of polypeptide of claim 28, wherein the solid support is a column.

32. The plurality of polypeptide of claim 28, wherein the solid support is a chip.

33. The plurality of polypeptide of claim 28, wherein the solid support is a multiwell plate.

* * * * *

UNITED STATES PATENT AND TRADEMARK OFFICE

CERTIFICATE OF CORRECTION

PATENT NO. : 8,039,588 B2
APPLICATION NO. : 11/568601
DATED : October 18, 2011
INVENTOR(S) : Pancer et al.

It is certified that error appears in the above-identified patent and that said Letters Patent is hereby corrected as shown below:

Column 381, line 7, “(VLR) or, wherein” should read
--(VLR), wherein--
Column 382, line 31, “of polypeptide” should read
--of polypeptides--
Column 382, line 33, “of polypeptide” should read
--of polypeptides--
Column 382, line 35, “of polypeptide” should read
--of polypeptides--
Column 382, line 37, “of polypeptide” should read
--of polypeptides--

Signed and Sealed this
Twentieth Day of December, 2011

David J. Kappos
*Director of the United States Patent and Trademark Office*